(12) United States Patent
Ichiyanagi et al.

(10) Patent No.: US 10,934,530 B2
(45) Date of Patent: Mar. 2, 2021

(54) AMADORIASE HAVING IMPROVED SPECIFIC ACTIVITY

(71) Applicant: Kikkoman Corporation, Noda (JP)

(72) Inventors: Atsushi Ichiyanagi, Noda (JP); Airi Komatsuzaki, Noda (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 15/563,054

(22) PCT Filed: Apr. 4, 2016

(86) PCT No.: PCT/JP2016/061043
§ 371 (c)(1),
(2) Date: Sep. 29, 2017

(87) PCT Pub. No.: WO2016/159384
PCT Pub. Date: Oct. 6, 2016

(65) Prior Publication Data
US 2018/0371429 A1 Dec. 27, 2018

(30) Foreign Application Priority Data
Apr. 3, 2015 (JP) .................................. 2015-077112

(51) Int. Cl.
C12N 9/06 (2006.01)
C12Q 1/26 (2006.01)
G01N 33/72 (2006.01)
C12Q 1/28 (2006.01)

(52) U.S. Cl.
CPC ............. *C12N 9/0032* (2013.01); *C12Q 1/26* (2013.01); *C12Y 105/03* (2013.01); *G01N 33/72* (2013.01); *G01N 33/723* (2013.01); *C12Q 1/28* (2013.01); *G01N 2333/805* (2013.01)

(58) Field of Classification Search
CPC .................................................. C12N 9/0032
See application file for complete search history.

(56) References Cited

U.S. PATENT DOCUMENTS

| | | | |
|---|---|---|---|
| 5,370,990 | A | 12/1994 | Staniford et al. |
| 7,070,948 | B1 | 7/2006 | Sakaue et al. |
| 2006/0240501 | A1 | 10/2006 | Ebinuma |
| 2008/0113381 | A1 | 5/2008 | Matsuoka et al. |
| 2008/0233605 | A1 | 9/2008 | Taniguchi et al. |
| 2011/0003361 | A1 | 1/2011 | Kurosawa et al. |
| 2011/0195444 | A1 | 8/2011 | Hirao et al. |
| 2014/0234886 | A1 | 8/2014 | Aisaka et al. |
| 2015/0118700 | A1 | 4/2015 | Ichiyanagi et al. |
| 2016/0123999 | A1 | 5/2016 | Ogawa et al. |
| 2016/0138073 | A1 | 5/2016 | Ogawa |
| 2016/0274129 | A1 | 9/2016 | Ichiyanagi |

FOREIGN PATENT DOCUMENTS

| | | |
|---|---|---|
| JP | 05-033997 B2 | 5/1993 |
| JP | 11-127895 A | 5/1999 |
| JP | 2001-095598 A | 4/2001 |
| JP | 2003-235585 A | 8/2003 |
| JP | 2004-275013 A | 10/2004 |
| JP | 2004-275063 A | 10/2004 |
| JP | 2010-035469 A | 2/2010 |
| JP | 2010-057474 A | 3/2010 |
| JP | 2011-229526 A | 11/2011 |
| JP | 2014-183786 A | 10/2014 |
| WO | WO 97/13872 A1 | 4/1997 |
| WO | WO 2004/038034 A1 | 5/2004 |
| WO | WO 2004/104203 A1 | 12/2004 |
| WO | WO 2005/049857 A1 | 6/2005 |
| WO | WO 2008/108385 A1 | 9/2008 |
| WO | WO 2010/041419 A1 | 4/2010 |
| WO | WO 2010/041715 A1 | 4/2010 |
| WO | WO 2011/015325 A1 | 2/2011 |
| WO | WO 2013/162035 A1 | 10/2013 |
| WO | WO 2015/005257 A1 | 1/2015 |
| WO | WO 2015/005258 A1 | 1/2015 |
| WO | WO 2015/060431 A1 | 4/2015 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

International Search Report dated May 24, 2016, in PCT/JP2016/061043.

Ferri et al., "Cloning and Expression of Fructosyl-amine Oxidase from Marine Yeast *Pichia* Species N1-1," Mar. Biotechnol., 2004, 6:625-632.

Ferri et al., "Isolation and characterization of a fructosyl-amine oxidase from an *Arthrobacter* sp.," Biotechnology Letters, 2005, 27:27-32.

Fujiwara et al., "Alteration of Substrate Specificity of Fructosyl-Amino Acid Oxidase from *Ulocladium* sp. JS-103," Journal of Bioscience and Bioengineering, 2006, 102(3):241-243.

Fujiwara et al., "Alteration of substrate specificity of fructosyl-amino acid oxidase from *Fusarium oxysporum*," Appl. Microbiol. Biotechnol., 2007, 74:813-819.

(Continued)

*Primary Examiner* — Richard G Hutson
(74) *Attorney, Agent, or Firm* — Foley & Lardner LLP

(57) ABSTRACT

This invention provides an amadoriase having improved specific activity on a glycated substrate, compared with conventional amadoriase. Provided is an amadoriase comprising a substitution of the amino acid at the position corresponding to position 64 of the amino acid sequence as shown in SEQ ID NO: 1 with an amino acid selected from the group consisting of glycine, serine, methionine, leucine, threonine, valine, and isoleucine, a method for measurement of HbA1c, and a reagent kit for measurement of HbA1c using such amadoriase. Such method and kit for measurement enable rapid, simple, and accurate quantification of HbA1c.

14 Claims, 10 Drawing Sheets
Specification includes a Sequence Listing.

(56) References Cited

OTHER PUBLICATIONS

Hirokawa et al., "Molecular cloning and expression of novel fructosyl peptide oxidases and their application for the measurement of glycated protein," Biochemical and Biophysical Research Communications, 2003, 311:104-111.
Hirokawa et al., "Recombinant *Agrobacterium* AgaE-like Protein with Fructosyl Amino Acid Oxidase Activity," Biosci. Biotechnol. Biochem., 2002, 66(11):2323-2329.
Jeppsson et al., "Approved IFCC Reference Method for the Measurement of $HbA_{1c}$ in Human Blood," Clin. Chem. Lab. Med., 2002, 40(1):78-89.
Kim et al., "Motif-Based Search for a Novel Fructosyl Peptide Oxidase from Genome Databases," Biotechnology and Bioengineering, Jun. 15, 2010, 106(3):358-366.
Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.
Yoshida et al., "Primary structures of fungal fructosyl amino acid oxidases and their application to the measurement of glycated proteins," Eur. J. Biochem., 1996, 242:499-505.
Database UniProt [Online] Oct. 13, 2009, "RecName: Full=DAO domain-containing protein {ECO:0000259|Pfam:PF01266};", XP055711479, retrieved from EBI accession No. UNIPROT:C7Z4C9.
Office Action dated Jul. 9, 2020 in EP 16773264.3.

\* cited by examiner

| | | | | | | | | | | | |
|---|---|---|---|---|---|---|---|---|---|---|---|
| Co | 399 | EEMAYQ | WRWRPG | -GDDAL | KSRRA | APPKDLA | DMPGWKHDPKL | ------ | - | 437 |
| Et | 399 | QEMAGA | WRWRPG | -GDDAL | RSQRG | APAKDLA | EMPGWKHDAHL | ------ | - | 437 |
| Py | 397 | ADLAQA | WRWRPG | -GDDAL | QSRRA | APAKDLA | DMPGWNHD-ESPRAKL | --- | - | 440 |
| Ar | 400 | DDLAHA | WRWRPG | QQGDDAL | KSRRA | APAKDLA | DMPGWNHDGDSGNATSGTSSE | | | 449 |
| Cc | 397 | EDLAEA | WRWRPG | GSGDDAL | KSRRA | APAKDLA | DMPGWKHD-DVVKSKL | --- | - | 440 |
| Nv | 399 | DDLAES | WRWRPG | QGGDDAL | RKSRR- | APAKDLA | DLPGWKHDQDSESR- | ---- | - | 441 |
| Cn | 399 | EDLAEA | WRWRPG | GSGDDAL | -SRRR | APAKDLA | DMPGWNHDEPSDDMDVKDVA | | | 448 |
| Pn | 395 | DDSVFK | WRWRPG | GSSGDDAL | ARKS- | APARDLA | DMPGWNHD--KPRANL | --- | - | 437 |
| An | 399 | SVFKDA | WRWRPG | SGGDDAL | KSRRR | APAKDLA | DMPGWRNEAKM | ------ | - | 438 |
| En | 399 | DDLAHA | WRWRPG | SGGDDAL | KSRRR | APARDLA | DMPGWRNEAKM | ------ | - | 438 |
| Ui | 397 | QDLAGA | WRWRPG | GTGDDAL | KSRRA | ARAKDLA | DMPGWNHDGEAPRAKL | --- | - | 441 |
| Pj | 399 | QDLAGA | WRWRPG | -GDDAL | KSKRS | APAKDLA | EMPGWKHDAKL | ------ | - | 437 |

| | | |
|---|---|---|
| Co | 437 | ------------------------------ (SEQ ID NO: 1) |
| Et | 437 | ------------------------------ (SEQ ID NO: 145) |
| Py | 440 | --HKL------------------------- (SEQ ID NO: 113) |
| Ar | 452 | ------------------------------ (SEQ ID NO: 115) |
| Cc | 440 | ------------------------------ (SEQ ID NO: 117) |
| Nv | 441 | --VSLASVKIGENIGEKVVEDGARVGVKVLA (SEQ ID NO: 54) |
| Cn | 477 | ------------------------------ (SEQ ID NO: 149) |
| Pn | 437 | ------------------------------ (SEQ ID NO: 38) |
| An | 438 | ------------------------------ (SEQ ID NO: 147) |
| En | 438 | ------------------------------ (SEQ ID NO: 119) |
| Ui | 441 | ------------------------------ (SEQ ID NO: 121) |
| Pj | 437 | ------------------------------ (SEQ ID NO: 123) |

Fig. 2-1

| | | | | | | | | | | | | |
|---|---|---|---|---|---|---|---|---|---|---|---|---|
| Co | 1 | MTSNRADTRV | IVGGT | GSSTALHL | VRSGYAPAN | ITVLDT | FEIP | SAQS | 50 |
| Et | 1 | MAHSRASTKV | VVGGT | GSSTALHL | LRSGYTPSN | ITVLDD | VYKP | PSLQS | 50 |
| Py | 1 | MAASRAKTTK | VVGGT | GSSTALHL | LRSGYTPSN | ITVLDD | YTPP | IPSAQS | 50 |
| Ar | 1 | MAPSRAKTKS | VVGGT | GSSTALHL | VRSGYTPSA | ITVLDD | TYPP | IPSAQS | 50 |
| Cc | 1 | MAPTRANTKV | IVGGT | GSSTALHL | LRAGYYPSN | ITVLDD | TYPP | IPSAQS | 50 |
| Nv | 1 | MPPSRANTKT | VVGGT | MGSSTALHL | VRSGYTPSN | ITVLDD | TLPP | IPSAQS | 50 |
| Cn | 1 | MAPSRANTKS | VV--- | -GSSTALHL | LRAGYTPSN | ITVLDD | AYPP | IPSAQS | 50 |
| Pn | 1 | MTP-RANTKL | -V--- | -GSSTALHL | LRAGYTPSN | ITVLDD | TCPP | IPSAQS | 49 |
| An | 1 | MAP-RRANTK | SVV-- | -MGSSTALHL | VRAGYTPSN | ITVLDD | TYPP | IPSAQS | 49 |
| En | 1 | MAPNRANTKK | VVVV- | -MGSSTALHL | LRSGYTPSN | ITVLDT | TYPP | IPSAQS | 50 |
| Ui/Pj | 1 | MAHSRESTKW | VIVGGT | MGSSTALHL | IRSGYTPSN | ITVLDV | YPP | PSLQS | 50 |

| | | | | | | | | | | | | |
|---|---|---|---|---|---|---|---|---|---|---|---|---|
| Co | 51 | AGHDLNKIMG | IRLRNKVDL | QMSLEARQM | WKEDEL | FQKPFFHN | TGRMDCEHT | 100 |
| Et | 51 | AGHDLNKIMG | -RLRNGPDL | QLLEESL | DMWQRDEL | LFRDPYFHQ | NVGM-DCSSS | 100 |
| Py | 51 | AGNDLNKIMG | -RLRNKVDL | QLLEARDM | WREDEL | FKRPFFHN | TGRLDCAHG | 100 |
| Ar | 51 | AGNDLNKIMG | -RLRNPKDL | QLLEARDM | WCHDDAL | FKRPYFHN | TGRLDCEGT | 100 |
| Cc | 51 | AGNDLNKIMG | -RLRNKVDL | QLLEARQM | WRNDDEL | FKKPFFHN | TGRMDCAHG | 100 |
| Nv | 51 | AGNDLNKIMS | -RLRNVDL | ALLEARQM | WNEDDEV | FKKPFFHN | TGRLDCESS | 100 |
| Cn | 51 | AGNDLNKIMG | -R-LNPDL | QYLEARDL | WKNDPPL | FKKPFFHK | TGRLDVSST | 100 |
| Pn | 50 | AGNDLNKIMG | -R-LKDL | QLSLEAR-L | WTEDDDL | FKEYFYHN | VGM-DVSST | 99 |
| An | 50 | AGYDLNKIFG | -R-LLPDL | QLLEAL | WKND-L | FKPFPFHN | TGRLDCAHG | 99 |
| En | 51 | AGNDLNKIMG | -RLRNKVDL | QLLEARQM | WKNDDEP | FKPFPFHN | TGRLDCSSS | 100 |
| Ui/Pj | 51 | AGYDLNKIMS | IRLRNGPDL | QLSLEAL | WKND-P | FKPFFHN | VGMLDCSSS | 100 |

| | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| Co | 399 | E | E | M | A | Y | Q | W | R | W | R | P | G | - | G | D | A | L | K | S | R | R | A | A | P | P | A | K | D | L | A | D | M | P | G | W | K | H | D | P | K | L | - | - | - | - | - | - | - | - | 437 |
| Et | 399 | Q | E | M | A | G | A | W | R | W | R | P | G | - | G | D | D | A | L | R | S | R | R | G | A | P | A | K | D | L | A | E | M | P | G | W | K | H | D | A | H | L | - | - | - | - | - | - | - | - | 437 |
| Py | 397 | A | D | L | A | H | A | W | R | W | R | P | G | I | G | D | D | A | L | Q | S | R | R | A | A | P | A | K | D | L | A | D | M | P | G | W | N | H | D | - | E | S | P | R | A | K | L | - | - | - | 440 |
| Ar | 400 | E | D | L | A | Q | A | W | R | W | R | P | G | Q | G | D | D | A | L | K | S | R | R | A | A | P | A | K | D | L | A | D | M | P | G | W | N | H | D | - | D | V | K | S | K | L | - | - | - | - | 449 |
| Cc | 397 | D | D | L | A | E | A | W | R | W | R | P | G | Q | G | D | D | A | L | K | S | R | R | A | A | P | A | K | D | L | A | D | M | P | G | W | K | H | D | - | D | V | K | S | K | L | - | - | - | - | 440 |
| Nv | 399 | D | D | L | A | E | S | W | R | W | R | P | G | S | G | G | D | A | L | K | S | R | R | A | A | P | A | K | D | L | A | D | L | P | G | W | N | H | D | - | D | V | K | S | K | L | - | - | - | - | 441 |
| Cn | 399 | E | D | L | A | E | S | W | R | W | R | P | G | S | G | S | D | A | L | K | S | R | R | A | A | P | A | K | D | L | A | D | M | P | G | W | K | H | D | - | D | V | K | S | K | L | - | - | - | - | 449 |
| Pn | 395 | D | D | L | A | H | A | W | R | W | R | P | G | S | G | G | D | A | L | K | S | - | R | R | A | A | P | A | K | D | L | A | D | M | P | G | W | N | H | D | - | D | E | P | S | D | D | M | D | V | K | D | V | A | 477 |
| An | 399 | S | V | F | K | D | A | W | R | W | R | P | G | G | G | G | D | A | L | K | S | - | R | R | A | A | P | A | K | D | L | A | D | M | P | G | W | N | H | D | - | - | K | P | R | A | N | L | - | - | - | 437 |
| En | 399 | S | V | F | K | D | A | W | R | W | R | P | G | S | G | D | D | A | L | K | S | R | R | A | A | P | A | K | D | L | A | D | M | P | G | W | R | N | E | A | K | M | - | - | - | - | - | - | - | - | 438 |
| Ui | 397 | D | D | L | A | H | A | W | R | W | R | P | G | T | G | D | D | A | L | K | S | - | R | R | A | R | A | P | A | K | D | L | A | D | M | P | G | W | R | N | E | A | K | M | - | - | - | - | - | - | - | - | 438 |
| Pj | 399 | Q | D | L | A | G | A | W | R | W | R | P | G | - | G | D | D | A | L | K | S | K | R | S | A | P | A | K | D | L | A | E | M | P | G | W | K | H | D | A | K | L | - | - | - | - | - | - | - | - | 437 |

| | | |
|---|---|---|
| Co | 437 | (SEQ ID NO: 1) |
| Et | 437 | (SEQ ID NO: 145) |
| Py | 440 | (SEQ ID NO: 113) |
| Ar | 450 | (SEQ ID NO: 115) |
| Cc | 440 | (SEQ ID NO: 117) |
| Nv | 441 | (SEQ ID NO: 54) |
| Cn | 449 HKL - - - - - - - - - - - - - - - - - - - - - - - - - - - - | (SEQ ID NO: 149) |
| Pn | 437 VSLASVKIGENIGEKVVEDGARVGVKVLA | (SEQ ID NO: 38) |
| An | 438 | (SEQ ID NO: 147) |
| En | 438 | (SEQ ID NO: 119) |
| Ui | 441 | (SEQ ID NO: 121) |
| Pj | 437 | (SEQ ID NO: 123) |

AMADORIASE HAVING IMPROVED SPECIFIC ACTIVITY

TECHNICAL FIELD

The present invention relates to an amadoriase having improved specific activity, a method for measurement of hemoglobin A1c in a sample using the same, and a reagent kit for measurement comprising an amadoriase.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, hemoglobin A1c (HbA1c) has drawn attention as a glycemic control marker significant for diagnosis of diabetic patients and control of conditions in the field of clinical diagnosis of diabetes mellitus. HbA1c is a protein comprising glucose bound to the α-amino group at the N-terminal (amino-terminal) valine (Val) residue of the hemoglobin "β chain." The blood HbA1c level reflects the average blood glucose level for a given period of time in the past, and the measured value thereof serves as a significant indicator for diagnosis and control of diabetes conditions.

Several types of enzymatic methods involving the use of amadoriases have heretofore been known as methods for rapidly and simply measuring HbA1c.

Enzymes that oxidize iminodiacetic acid or a derivative thereof (also referred to as an "Amadori compound") in the presence of oxygen to catalyze a reaction to generate glyoxylic acid or α-ketoaldehyde, amino acid or peptide, and hydrogen peroxide are collectively referred to as "amadoriases." Amadoriases are known to be useful for measuring HbA1c by an enzymatic method. An example of a substrate that is known to be oxidized by amadoriases is α-fructosyl-valyl-histidine (hereafter referred to as "αFVH").

Amadoriases have been found in bacteria, yeast, and fungi. For example, amadoriases derived from the genera *Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium*, and *Arthrobacter* have been reported (e.g., Patent Documents 1 and 6 to 15 and Non-Patent Documents 1 to 9). These genera may be referred to as the genera *Coniochaeta* etc. in this description. In some of the aforementioned documents, an amadoriase may also be referred to as, for example, ketoamine oxidase, fructosyl amino acid oxidase, fructosyl peptide oxidase, or fructosyl amine oxidase.

As a method for rapidly and readily measuring HbA1c with the use of various types of amadoriases as described above, a method in which HbA1c is degraded with a cleavage enzyme such as a protease or peptidase (hereafter referred to as "protease(s) or the like"), and a particular target substance released from the β-chain amino terminus of HbA1c is quantified with the use of amadoriases as described above is known (e.g., Patent Documents 1 to 7).

Specifically, a method in which HbA1c is degraded with a particular protease or the like, αFVH is released from the β-chain amino terminus thereof, and the released αFVH is quantified has been known. At present, such method is a major technique for measuring HbA1c by an enzymatic method.

According to a further method for measurement of HbA1c involving the use of amadoriases, HbA1c is digested using a Glu-C protease, α-fructosyl hexapeptide comprising 6 amino acids including valine at the glycated β-chain amino terminus (α-fructosyl-valyl-histidyl-leucyl-threonyl-prolyl-glutamic acid, hereafter referred to as "αF6P") is released, and the released αF6P is then quantified (e.g., Patent Documents 16 to 18). This method for measurement of HbA1c by an enzymatic method is defined by the International Federation of Clinical Chemistry and Laboratory Medicine (IFCC) (Non-Patent Document 10).

In the method for measurement of HbA1c involving the use of amadoriases, however, it is indispensable to perform a process comprising digesting HbA1c with a protease or peptidase (hereafter, referred to as a "protease or the like"), so as to release a glycated peptide including valine at the β-chain amino terminus thereof. Accordingly, it is always necessary to include a protease or the like in the reagent kit for measurement of a glycated peptide derived from HbA1c; however, such inclusion is not preferable for the reasons described below.

First, proteases that can be used are limited. When, for example, αF6P derived from HbA1c is to be assayed, proteases that can be used are limited to those that cleave HbA1c on the C terminal side of the glutamic acid residue, such as Glu-C protease. Further, a protease and the like is capable of protein hydrolysis and, therefore, enzymes which are proteins are also hydrolyzed by the protease or the like. As such, amadoriases will also be hydrolyzed by a protease and inactivated, and, as a result, the reaction consuming a glycated peptide and oxygen to generate hydrogen peroxide will be inhibited. In order to address such problem, it is possible to increase the amount of amadoriases and to complete the measurement before amadoriases are completely inactivated. However, an increased amount of amadoriases will lead a protease or the like to preferentially hydrolyze amadoriases rather than HbA1c, which is intrinsically not preferable.

When measuring HbA1c by allowing an amadoriase to react with a glycated peptide and quantifying the resulting hydrogen peroxide, hydrogen peroxide may be quantified using a peroxidase. In such a case, the peroxidase will also be hydrolyzed by the protease or the like and inactivated, which is not preferable.

As another aspect, when measuring HbA1c using enzymes, it is commonplace to use an automated analyzer. In such a case, a single sample is simultaneously subjected to analysis of various biomarkers including HbA1c. Since each biomarker is analyzed using an enzyme or antibody, upon contamination of a protease or the like, the enzyme or antibody contained in the biomarker reagent may be hydrolyzed. In such a case, biomarkers other than HbA1c may not be accurately analyzed. Accordingly, it is intrinsically preferable that a reagent to be mounted on an automated analyzer be free from a protease or the like.

Due to the reasons above, an amadoriase that can directly oxidize the HbA1c β-chain to generate hydrogen peroxide, and a method of measuring HbA1c using such amadoriase was needed. In addition, there is a need for practical methods and reagent kits that enable quantification of HbA1c within a short period of time. In order to realize such methods and kits, an amadoriase having sufficient specific activity is needed.

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: WO 2004/38034
Patent Document 17: WO 2008/108385
Patent Document 18: WO 2013/162035
Patent Document 19: WO 2015/005257

Non-Patent Documents

Non-Patent Document 1: Biochem. Biophys. Res. Commun. 311, 104-11, 2003
Non-Patent Document 2: Biotechnol. Bioeng. 106, 358-66, 2010
Non-Patent Document 3: J. Biosci. Bioeng. 102, 241-3, 2006
Non-Patent Document 4: Appl. Microbiol. Biotechnol. 74, 813-9, 2007
Non-Patent Document 5: Eur. J. Biochem. 242, 499-505, 1996
Non-Patent Document 6: Mar. Biotechnol. 6, 625-32, 2004
Non-Patent Document 7: Biosci. Biotechnol. Biochem. 66, 1256-61, 2002
Non-Patent Document 8: Biosci. Biotechnol. Biochem. 66, 2323-29, 2002
Non-Patent Document 9: Biotechnol. Letters 27, 27-32, 2005
Non-Patent Document 10: Jeppsson J O, et al, Approved IFCC reference method for the measurement of HbA1c in human blood, Clin. Chem. Lab. Med. 40, 78-89, 2002

SUMMARY OF THE INVENTION

Objects to be Attained by the Invention

It is an object of the present invention to provide an amadoriase having improved specific activity on α-fructosyl octapeptide (αF8P), compared with conventional amadoriase, a method for measurement of HbA1c using such amadoriase, and a reagent kit comprising such amadoriase having improved specific activity.

Means for Attaining the Object

The present inventors have conducted concentrated studies in order to attain the above objects. As a result, they discovered that a modified amadoriase produced via introduction of amino acid substitution into the amadoriase derived from the genus *Coniochaeta* or the like has improved specific activity on αF8P, compared with a conventional amadoriase. This has led to the completion of the present invention.

Specifically, the present invention encompasses the following.

[1] An amadoriase selected from the group consisting of the following (i) to (iv):

(i) an amadoriase comprising an amino acid sequence in which, when the amino acid sequence is aligned with the amino acid sequence as shown in SEQ ID NO: 1, the amino acid at the position corresponding to position 64 of the amino acid sequence as shown in SEQ ID NO: 1 is an amino acid selected from the group consisting of glycine, serine, methionine, leucine, threonine, valine, and isoleucine and having activity on glycated peptide;

(ii) an amadoriase comprising an amino acid sequence in which, when the amino acid sequence is aligned with the amino acid sequence as shown in SEQ ID NO: 1, the amino acid at the position corresponding to position 64 of the amino acid sequence as shown in SEQ ID NO: 1 is an amino acid selected from the group consisting of glycine, serine, methionine, leucine, threonine, valine, and isoleucine and having activity on α-fructosyl-valyl-histidyl-leucyl-threonyl-prolyl-glutamyl-glutamyl-lysine (αF8P);

(iii) the amadoriase as defined in (i) or (ii) consisting of an amino acid sequence comprising substitution, deletion, or addition of 1 or several amino acids at positions other than those corresponding to position 64 of the amino acid sequence as shown in SEQ ID NO: 1 and having activity on glycated peptide or αF8P; and (iv) the amadoriase as defined in (i) or (ii) comprising an amino acid sequence having 70% or higher sequence identity with the amino acid sequence as shown in SEQ ID NO: 1 over the full length and having 90% or higher sequence identity between the amino acid sequence of a homologous region consisting of amino acids at positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of the amino acid sequence as shown in SEQ ID NO: 1 and the amino acid sequence of the homologous region in corresponding positions of the amadoriase and having activity on glycated peptide or αF8P.

[2] The amadoriase according to [1], comprising an amino acid sequence having substitution of 1 or more amino acid residues at a position (or positions) corresponding to the position(s) selected from the group consisting of (z) and (a) to (h) below, when the amino acid sequence is aligned with the amino acid sequence as shown in SEQ ID NO: 1:

(z) position 99 in SEQ ID NO: 1;
(a) position 62 in SEQ ID NO: 1;
(b) position 63 in SEQ ID NO: 1;
(c) position 102 in SEQ ID NO: 1;
(d) position 106 in SEQ ID NO: 1;
(e) position 110 in SEQ ID NO: 1;
(f) position 113 in SEQ ID NO: 1;
(g) position 355 in SEQ ID NO: 1; and
(h) position 419 in SEQ ID NO: 1.

[3] The amadoriase according to [2], wherein
(z) the amino acid at a position corresponding to position 99 in SEQ ID NO: 1 is serine;
(a) the amino acid at a position corresponding to position 62 in SEQ ID NO: 1 is alanine, aspartic acid, asparagine, glutamine, glutamic acid, glycine, valine, leucine, isoleucine, cysteine, serine, methionine, threonine, or proline;
(b) the amino acid at a position corresponding to position 63 in SEQ ID NO: 1 is alanine, histidine, or glycine;
(c) the amino acid at a position corresponding to position 102 in SEQ ID NO: 1 is lysine;
(d) the amino acid at a position corresponding to position 106 in SEQ ID NO: 1 is alanine, lysine, or arginine;
(e) the amino acid at a position corresponding to position 110 in SEQ ID NO: 1 is phenylalanine, histidine, leucine, or tyrosine;
(f) the amino acid at a position corresponding to position 113 in SEQ ID NO: 1 is lysine or arginine;
(g) the amino acid at a position corresponding to position 355 in SEQ ID NO: 1 is serine; and/or
(h) the amino acid at a position corresponding to position 419 in SEQ ID NO: 1 is lysine.

[4] The amadoriase according to any of [1] to [3], comprising an amino acid sequence having substitution of 1 or 2 amino acid residue(s) at position(s) corresponding to the position (i) or (j) in the amino acid sequence as shown in SEQ ID NO: 1, when the amino acid sequence is aligned with the amino acid sequence as shown in SEQ ID NO: 1:
(i) position 68 in SEQ ID NO: 1; or
(j) position 356 in SEQ ID NO: 1.

[5] The amadoriase according to [4], wherein
(i) the amino acid at a position corresponding to position 68 in SEQ ID NO: 1 is asparagine; and/or
(j) the amino acid at a position corresponding to position 356 in SEQ ID NO: 1 is threonine.

[6] The amadoriase according to any of [1] to [5], comprising an amino acid sequence having substitution of 1 or more amino acid residues at a position (or positions) corresponding to the position(s) of the amino acid sequence as shown in SEQ ID NO: 1 selected from the group consisting of (i) to (xiv) below:
(i) position 262;
(ii) position 257;
(iii) position 249;
(iv) position 253;
(v) position 337;
(vi) position 340;
(vii) position 232;
(viii) position 129;
(ix) position 132;
(x) position 133;
(xi) position 44;
(xii) position 256;
(xiii) position 231; and
(xiv) position 81,
and wherein, optionally, the 3 amino acid residues from the carboxyl terminus of the amadoriase may be deleted.

[7] The amadoriase according to any of [1] to [6], which has specific activity on αF8P of 0.1 U/mg or greater.
[8] The amadoriase according to any of [1] to [7], which has specific activity on αF8P of 1 U/mg or greater.
[9] The amadoriase according to any of [1] to [8], which has specific activity on αF8P of 4 U/mg or greater. [10] The amadoriase according to any of [1] to [9], which is derived from the genus *Coniochaeta, Eupenicillium, Pyrenochaeta,* *Arthrinium, Curvularia, Neocosmospora, Cryptococcus, Phaeosphaeria, Aspergillus, Emericella, Ulocladium,* or *Penicillium*.

[11] The amadoriase according to any of [1] to [10], which is derived from *Coniochaeta* sp., *Eupenicillium terrenum, Pyrenochaeta* sp., *Arthrinium* sp., *Curvularia clavata, Neocosmospora vasinfecta, Cryptococcus neoformans, Phaeosphaeria nodorum, Aspergillus nidulans, Emericella nidulans, Ulocladium* sp., *Penicillium janthinelum,* or *Penicillium chrysogenum*.

[12] An amadoriase selected from the group consisting of (i), (ii), and (iv) below:
(i) an amadoriase comprising the amino acid sequence as shown in SEQ ID NO: 211 or 213;
(ii) the amadoriase as defined in (i), consisting of an amino acid sequence comprising substitution, deletion, or addition of 1 or several amino acids at positions other than positions corresponding to positions 64, 99, 62, 63, 102, 106, 110, 113, 355, 419, 68, and 356 of the amino acid sequence as shown in SEQ ID NO: 1 and having activity on αF8P; and
(iv) the amadoriase as defined in (i) or (ii) comprising an amino acid sequence having 70% or higher sequence identity with the amino acid sequence as shown in SEQ ID NO: 1 over the full length and having 90% or higher sequence identity between the amino acid sequence of a homologous region consisting of amino acids at positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of the amino acid sequence as shown in SEQ ID NO: 1 and the amino acid sequence of the homologous region in corresponding positions of the amadoriase and having activity on αF8P.

[13] The amadoriase according to any of [1] to [12], comprising an amino acid sequence having substitution of 1 or more amino acid residue(s) at a position (or positions) corresponding to a position (or positions) selected from the group consisting of (l) to (q) below, when the amino acid sequence is aligned with the amino acid sequence as shown in SEQ ID NO: 1:
(l) position 67 in SEQ ID NO: 1;
(m) position 72 in SEQ ID NO: 1;
(n) position 76 in SEQ ID NO: 1;
(o) position 96 in SEQ ID NO: 1;
(p) position 109 in SEQ ID NO: 1; and
(q) position 116 in SEQ ID NO: 1.

[14] The amadoriase according to [13], wherein
(l) the amino acid at a position corresponding to position 67 in SEQ ID NO: 1 is histidine;
(m) the amino acid at a position corresponding to position 72 in SEQ ID NO: 1 is serine;
(n) the amino acid at a position corresponding to position 76 in SEQ ID NO: 1 is alanine or phenylalanine;
(o) the amino acid at a position corresponding to position 96 in SEQ ID NO: 1 is glutamic acid;
(p) the amino acid at a position corresponding to position 109 in SEQ ID NO: 1 is arginine or lysine; and/or
(q) the amino acid at a position corresponding to position 116 in SEQ ID NO: 1 is arginine.

[15] A reagent kit for measurement of hemoglobin A1c comprising the amadoriase according to any of [1] to [14].

[16] A method for measurement of hemoglobin A1c in a sample involving the use of the amadoriase according to any of [1] to [14].

The present specification encompasses the contents described in the description and/or drawings of Japanese Patent Application No. 2015-077112, which is a priority document of the present application.

Effects of the Invention

The present invention can provide an amadoriase having high specific activity on αF8P that enables quantification of HbA1c to be performed rapidly, simply, accurately, and satisfactorily. With the use of such amadoriase, quantification of HbA1c can be performed within a short period of time, sensitivity for a direct measurement of HbA1c can be improved, the amount of an amadoriase to be formulated can be reduced, and tests can be performed rapidly.

BRIEF DESCRIPTION OF THE DRAWINGS

FIG. 1-1 is a first diagram showing amino acid sequence identity among various known amadoriases. In addition to Co (*Coniochaeta* sp.), Et (*Eupenicillium terrenum*), Py (*Pyrenochaeta* sp.), Ar (*Arthrinium* sp.), Cc (*Curvularia clavata*), and Nv (*Neocosmospora vasinfecta*), Cn (*Cryptococcus neoformans*), Pn (*Phaeosphaeria nodorum*), An (*Aspergillus nidulans*), En (*Emericella nidulans*), Ul (*Uloclladium* sp.), and Pj (*Penicillium janthinelum*) were aligned.

FIG. 1-2 is a continuation from FIG. 1-1.
FIG. 1-3 is a continuation from FIG. 1-2.
FIG. 1-4 is a continuation from FIG. 1-3.
FIG. 1-5 is a continuation from FIG. 1-4.
FIG. 2-1 is a second diagram showing amino acid sequence identity and similar amino acids among various known amadoriases. In addition to Co, Et, Py, Ar, Cc, and Nv, Cn, Pn, An, En, Ul, and Pj were aligned.
FIG. 2-2 is a continuation from FIG. 2-1.
FIG. 2-3 is a continuation from FIG. 2-2.
FIG. 2-4 is a continuation from FIG. 2-3.
FIG. 2-5 is a continuation from FIG. 2-4.

EMBODIMENTS FOR CARRYING OUT THE INVENTION

The present invention is described in detail as follows.
(Glycated Protein and Hemoglobin A1c)

The term "glycated protein" used herein refers to a protein glycated non-enzymatically. Glycated proteins exist in vivo and ex vivo. Examples of glycated proteins existing in vivo include glycated hemoglobin and glycated albumin in the blood. In particular, glycated hemoglobin comprising glycated valine at the β-chain amino terminus of hemoglobin is referred to as hemoglobin A1c (HbA1c). Examples of glycated proteins existing ex vivo include foods and drinks, such as liquid flavors, and infusion solutions in which a protein or peptide exists together with sugar.
(Glycated Peptide and Fructosyl Peptide)

The term "glycated peptide" used herein refers to a non-enzymatically-glycated peptide derived from a glycated protein. Peptides that are directly and non-enzymatically glycated, products of degradation of glycated proteins by a protease or the like, and products of glycation of (poly) peptides constituting glycated proteins are included in glycated peptides. A "glycated peptide" is also referred to as a "fructosyl peptide." Regarding glycated proteins, examples of amino groups in the glycated peptide side chain include an amino terminal α-amino group and a ε-amino group in the lysine side chain within a peptide. In the present invention, more specifically, the glycated peptide is an α-glycated peptide (α-fructosyl peptide). An α-glycated peptide is released and formed from a glycated protein having a glycated N-terminal α-amino acid by an arbitrary means, such as limited degradation with a protease or the like. When the glycated protein of interest is hemoglobin A1c (HbA1c), for example, the α-glycated peptide is a glycated peptide cleaved from the HbA1c β-chain having the glycated N terminus. The HbA1c β-chain composed of 146 amino acids also falls under an α-glycated peptide.

According to an embodiment of the present invention, the target substance to which the amadoriase of the present invention acts on is HbA1c and more specifically, is the β-chain of HbA1c. According to another embodiment, the target substance to which the amadoriase of the present invention acts on is αF8P cleaved from the HbA1c β-chain and, more specifically, is α-fructosyl-valyl-histidyl-leucyl-threonyl-prolyl-glutamyl-glutamyl-lysine. According to another embodiment, the target substance to which the amadoriase of the present invention acts on is αFVH (α-fructosyl-valyl-histidine), αFV (α-fructosyl valine), or αF6P. Likewise, an α-glycated peptide substrate having a chain longer than those described above is within the scope of the target substance.
(Amadoriase)

An amadoriase is also referred to as ketoamine oxidase, fructosyl amino acid oxidase, fructosyl peptide oxidase, or fructosyl amine oxidase, and it is an enzyme that oxidizes iminodiacetic acid or a derivative thereof (Amadori compound) in the presence of oxygen to catalyze a reaction to generate glyoxylic acid or α-ketoaldehyde, amino acid or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria.

The amadoriase of the present invention acts directly on HbA1c. In the present specification, the phrase an amadoriase acts directly on HbA1c as used herein refers to the amadoriase acting on the fructosyl group at the N-terminus of the HbA1c β-chain in the presence of oxygen, and generating 2-keto-D-glucose, hydrogen peroxide, and hemoglobin β-chain. This however does not exclude the amadoriase acting on fructosyl peptides derived from the HbA1c β-chain, such as αF8P, or α-fructosyl peptides comprising shorter chains. That is, according to one embodiment, the amadoriase of the present invention not only acts directly on HbA1c but also has reactivity to fructosyl peptides derived from the HbA1c β-chain, such as αF8P or an α-fructosyl peptide having a shorter chain.
(Modified Amadoriase)

The present invention provides a modified amadoriase having reactivity with αF8P and capable of acting directly on HbA1c, which is produced based on a wild-type amadoriase comprising the amino acid sequence as shown in SEQ ID NO: 1, SEQ ID NO: 38, SEQ ID NO: 40, SEQ ID NO: 54, SEQ ID NO: 62, SEQ ID NO: 89, or SEQ ID NO: 99. In the present specification, the terms "modified amadoriase" and "amadoriase variant" are used interchangeably and refer to amadoriases which comprise an amino acid sequence derived from the amino acid sequence of a wild-type amadoriase having substitutions, deletions, or additions of some amino acids. The term "addition(s)" used in this context encompasses "insertion(s)."

Further, the present invention provides a modified amadoriase having reactivity with αF8P and capable of acting directly on HbA1c, which is produced based on a wild-type amadoriase comprising the amino acid sequence as shown in SEQ ID NO: 113, SEQ ID NO: 115, SEQ ID NO: 117, SEQ ID NO: 119, SEQ ID NO: 121, SEQ ID NO: 123, SEQ ID NO: 145, or SEQ ID NO: 149.

Further, based on findings of the present invention, a modified amadoriase that acts directly on HbA1c can be obtained from other wild-type amadoriases derived from the genus *Coniochaeta* or the like.

The modified amadoriase of the present invention can comprise a further mutation that alters other properties of the enzyme, provided that the modified amadoriase retains activity to αF8P and acts directly on HbA1c.

(Modified Amadoriase Based on Amadoriase Derived from *Coniochaeta* sp. NISL 9330)

According to an embodiment, the amadoriase of the present invention is a modified amadoriase that acts directly on HbA1c, which is prepared from the amadoriase derived from the genus *Coniochaeta* comprising the amino acid sequence as shown in SEQ ID NO: 1.

An amadoriase comprising an amino acid sequence exhibiting high sequence identity with the amino acid sequence as shown in SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 137, SEQ ID NO: 139, SEQ ID NO: 165, SEQ ID NO: 167, SEQ ID NO: 169, SEQ ID NO: 171, SEQ ID NO: 173, SEQ ID NO: 133, SEQ ID NO: 135, SEQ ID NO: 175, SEQ ID NO: 189, SEQ ID NO: 177, SEQ ID NO: 179, SEQ ID NO: 143, SEQ ID NO: 181, SEQ ID NO: 183, SEQ ID NO: 187, SEQ ID NO: 191, SEQ ID NO: 141, SEQ ID NO: 185, SEQ ID NO: 199, SEQ ID NO: 203, SEQ ID NO: 209, SEQ ID NO: 211, or SEQ ID NO: 213 (e.g., sequence identity of 50% or higher, preferably 60% or higher, 70% or higher, 75% or higher, or 80% or higher, more preferably 85% or higher, further preferably 90% or higher, 95% or higher, or 98% or higher, and most preferably 99% or higher) and having activity on αF8P can act directly on HbA1c. For example, CFP-T7-H38 comprising the amino acid sequence as shown in SEQ ID NO: 211 and CFP-DH3 comprising the amino acid sequence as shown in SEQ ID NO: 213 have improved specific activities on αF8P than an amadoriase having the amino acid sequence as shown in SEQ ID NO: 209 and an amadoriase having the amino acid sequence as shown in SEQ ID NO: 203 and act directly on HbA1c.

An amadoriase comprising an amino acid sequence derived from the amino acid sequence as shown in SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 137, SEQ ID NO: 139, SEQ ID NO: 165, SEQ ID NO: 167, SEQ ID NO: 169, SEQ ID NO: 171, SEQ ID NO: 173, SEQ ID NO: 133, SEQ ID NO: 135, SEQ ID NO: 175, SEQ ID NO: 189, SEQ ID NO: 177, SEQ ID NO: 179, SEQ ID NO: 143, SEQ ID NO: 181, SEQ ID NO: 183, SEQ ID NO: 187, SEQ ID NO: 191, SEQ ID NO: 141, SEQ ID NO: 185, SEQ ID NO: 199, SEQ ID NO: 203, SEQ ID NO: 209, SEQ ID NO: 211, or SEQ ID NO: 213 by modification, mutation, deletion, substitution, addition, and/or insertion of 1 or several amino acids and having activity on αF8P can act directly on HbA1c. The term "1 or several amino acids" used herein refers to 1 to 15, preferably 1 to 10, more preferably 1 to 5, still more preferably 1 to 4, further preferably 1 to 3, and still further preferably 1 or 2 amino acids, when the full-length amino acid sequence comprises more than 400 amino acids. Also, the term "1 or several amino acids" refers to 1 to 10, preferably 1 to 7, more preferably 1 to 5, still more preferably 1 to 4, further preferably 1 to 3, and still further preferably 1 or 2 amino acids, when the full-length amino acid sequence comprises 200 to 400 amino acids. The term "1 or several amino acids" refers to 1 to 5, preferably 1 to 4, more preferably 1 to 3, and further preferably 1 or 2 amino acids, when the full-length amino acid sequence comprises 40 to less than 200 amino acids. The term "1 or several amino acids" refers to 1 or 2 amino acids, when the full-length amino acid sequence comprises less than 40 amino acids.

An amadoriase which is encoded by a nucleotide sequence which hybridizes under stringent conditions to a sequence complementary to the nucleotide sequence as shown in SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 138, SEQ ID NO: 140, SEQ ID NO: 166, SEQ ID NO: 168, SEQ ID NO: 170, SEQ ID NO: 172, SEQ ID NO: 174, SEQ ID NO: 134, SEQ ID NO: 136, SEQ ID NO: 176, SEQ ID NO: 190, SEQ ID NO: 178, SEQ ID NO: 180, SEQ ID NO: 144, SEQ ID NO: 182, SEQ ID NO: 184, SEQ ID NO: 188, SEQ ID NO: 192, SEQ ID NO: 142, SEQ ID NO: 186, SEQ ID NO: 200, SEQ ID NO: 204, SEQ ID NO: 210, SEQ ID NO: 212, or SEQ ID NO: 214 and has activity on αF8P can act directly on HbA1c. Stringent hybridization conditions are described in, for example, Sambrook et al., Molecular Cloning, Vol. 2 (Cold Spring Harbor Laboratory Press) or Current Protocols in Molecular Biology (Frederick, M. Ausubel et al. (ed.), 1987). Under stringent conditions, for example, hybridization is carried out by conducting incubation with the use of a hybridization solution (50% formamide, 6 to 10×SSC (0.15 to 1.5 M NaCl, 15 mM sodium citrate, pH 7.0), 5×Denhardt solution, 1% SDS, 10% dextran sulfate, 10 µg/ml denatured salmon sperm DNA, and 50 mM phosphate buffer (pH 7.5)) at about 42° C. to about 50° C., followed by washing with 0.1×SSC and 0.1% SDS at about 65° C. to about 70° C. Under other stringent conditions, hybridization is carried out with the use of, for example, a hybridization solution of 50% formamide, 5×SSC (0.15 M NaCl, 15 mM sodium citrate, pH 7.0), 1×Denhardt solution, 1% SDS, 10% dextran sulfate, 10 µg/ml denatured salmon sperm DNA, and 50 mM phosphate buffer (pH 7.5).

The variant according to the present invention may be obtained from amadoriases derived from other organism species, such as the genus *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium,* or *Arthrobacter,* provided that the conditions concerning substrate specificity and/or amino acid sequences described in the claims are satisfied.

A modified amadoriase obtained from the amadoriase derived from *Coniochaeta* sp. NISL 9330 (SEQ ID NO: 1) may comprise 1 or a plurality of amino acid substitutions at positions described below. The term "1 or a plurality of amino acid substitutions" used with regard to the modified amadoriase refers to substitution of 1, 2, 3, 4, 5, 6, 7, 8, 9, 10, 11, 12, 13, 14, 15, 16, 17, 18, 19, or 20 amino acids, such as substitution of 1, 2, 3, 4, 5, 6, 7, 8, 9, 10, 11, or 12 amino acids. According to an embodiment, the term "1 or a plurality of amino acid substitutions" used with regard to the modified amadoriase refers to substitution of 1, 2, 3, 4, 5, 6, 7, 8, 9, or 10 amino acids:

(a) arginine at position 62;
(b) leucine at position 63;
(c) glutamic acid at position 102;
(d) aspartic acid at position 106;
(e) glutamine at position 110;
(f) alanine at position 113;
(g) alanine at position 355;
(h) alanine at position 419;
(i) aspartic acid at position 68;
(j) alanine at position 356;
(k) arginine at position 64; and
(l) histidine at position 99.

In the amadoriase derived from *Coniochaeta* sp. NISL 9330 (SEQ ID NO: 1), preferably, (a) arginine at position 62 can be substituted with alanine, asparagine, aspartic acid, glutamine, glutamic acid, glycine, valine, leucine, isoleucine, cysteine, serine, methionine, threonine, or proline. Preferably, (b) leucine at position 63 is substituted with histidine, alanine, or glycine. Preferably, (c) glutamic acid at position 102 is substituted with lysine. Preferably, (d) aspartic acid at position 106 is substituted with alanine, lysine, or arginine. Preferably, (e) glutamine at position 110 is substituted with leucine, tyrosine, phenylalanine, or histidine. Preferably, (f) alanine at position 113 is substituted with lysine or arginine. Preferably, (g) alanine at position 355 is substituted with serine. Optionally, (h) alanine at position 419 may be substituted with lysine. Optionally, (i) aspartic acid at position 68 may be substituted with asparagine. Optionally, (j) alanine at position 356 may be substituted with threonine. In the present invention, (k) arginine at position 64 is substituted with glycine, serine, methionine, leucine, threonine, valine, or isoleucine. In an embodiment of the present invention, (l) histidine at position 99 is substituted with serine.

Optionally, the amadoriase derived from *Coniochaeta* sp. NISL 9330 can further comprise 1 or more amino acid substitutions at positions described below:
(l) position 67 in SEQ ID NO: 1;
(m) position 72 in SEQ ID NO: 1;
(n) position 76 in SEQ ID NO: 1;
(o) position 96 in SEQ ID NO: 1;
(p) position 109 in SEQ ID NO: 1; and
(q) position 116 in SEQ ID NO: 1.

Optionally, the amino acid at the position corresponding to (l) position 67 in SEQ ID NO: 1 can be histidine. Optionally, the amino acid at the position corresponding to (m) position 72 in SEQ ID NO: 1 can be serine. Optionally, the amino acid at the position corresponding to (n) position 76 in SEQ ID NO: 1 can be alanine or phenylalanine. Optionally, the amino acid at the position corresponding to (o) position 96 in SEQ ID NO: 1 can be glutamic acid. Optionally, the amino acid at the position corresponding to (p) position 109 in SEQ ID NO: 1 can be arginine or lysine. Optionally, the amino acid at the position corresponding to (q) position 116 in SEQ ID NO: 1 can be arginine.

A modified amadoriase obtained from the amadoriase derived from *Phaeosphaeria nodorum* (PnFX, SEQ ID NO: 38) can comprise 1 or a plurality of amino acid substitutions at positions described below:
(a) serine at position 62;
(b) leucine at position 63;
(c) lysine at position 102;
(d) aspartic acid at position 106;
(e) glycine at position 110;
(f) alanine at position 113;
(g) alanine at position 351;
(h) serine at position 416;
(i) aspartic acid at position 68;
(j) alanine at position 352;
(k) arginine at position 64; and
(l) histidine at position 99.

In the amadoriase derived from *Phaeosphaeria nodorum* (SEQ ID NO: 38), (a) serine at position 62 may, optionally, not be substituted. Alternatively, (a) serine at position 62 may be substituted with alanine, aspartic acid, asparagine, glutamine, glutamic acid, glycine, valine, leucine, isoleucine, cysteine, methionine, threonine, or proline. Preferably, (b) leucine at position 63 is substituted with histidine, alanine, or glycine. Optionally, (c) lysine at position 102 need not be substituted. Preferably, (d) aspartic acid at position 106 is substituted with lysine, alanine, or arginine. Preferably, (e) glycine at position 110 is substituted with leucine, tyrosine, phenylalanine, or histidine. Preferably, alanine at position 113 is substituted with lysine or arginine. Preferably, alanine at position 351 is substituted with serine. Optionally, (h) serine at position 416 may be substituted with lysine. Optionally, (i) aspartic acid at position 68 may be substituted with asparagine. Optionally, (j) alanine at position 352 may be substituted with threonine. Preferably, (k) arginine at position 64 may be substituted with glycine, serine, methionine, leucine, threonine, valine, or isoleucine. In an embodiment of the present invention, (l) histidine at position 99 is substituted with serine.

Optionally, the amadoriase derived from *Phaeosphaeria nodorum* can further comprise 1 or more amino acid substitutions at positions described below:
(l) position 67 of SEQ ID NO: 38;
(m) position 72 of SEQ ID NO: 38;
(n) position 76 of SEQ ID NO: 38;
(o) position 96 of SEQ ID NO: 38;
(p) position 109 of SEQ ID NO: 38; and
(q) position 116 of SEQ ID NO: 38.

Optionally, the amino acid at (l) position 67 of SEQ ID NO: 38 can be histidine. Optionally, the amino acid at (m) position 72 of SEQ ID NO: 38 can be serine. Optionally, the amino acid at (n) position 76 of SEQ ID NO: 38 can be alanine or phenylalanine. Optionally, the amino acid at (o) position 96 of SEQ ID NO: 38 can be glutamic acid. Optionally, the amino acid at (p) position 109 of SEQ ID NO: 38 can be arginine or lysine. Optionally, the amino acid at (q) position 116 of SEQ ID NO: 38 can be arginine.

A modified amadoriase obtained from the amadoriase derived from *Neocosmospora vasinfecta* (NvFX, SEQ ID NO: 54) can comprise 1 or a plurality of amino acid substitutions at positions described below:
(a) arginine at position 62;
(b) leucine at position 63;
(c) glutamic acid at position 102;
(d) glycine at position 106;
(e) glutamic acid at position 110;
(f) lysine at position 113;
(g) serine at position 355;
(h) alanine at position 420;
(i) aspartic acid at position 68;
(j) alanine at position 356;
(k) arginine at position 64; and
(l) serine at position 99.

In the amadoriase derived from *Neocosmospora vasinfecta* (SEQ ID NO: 54), preferably, (a) arginine at position 62 may be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Preferably, (c) glutamic acid at position 102 is substituted with lysine. Preferably, (d) glycine at position 106 is substituted with lysine, alanine, or arginine. Preferably, (e) glutamic acid at position 110 is substituted with leucine, tyrosine, phenylalanine, or histidine. Optionally, lysine at position 113 need not be substituted or may be substituted with arginine. Optionally, serine at position 355 need not be substituted. Optionally, (h) alanine at position 420 may be substituted with lysine. Optionally, (i) aspartic acid at position 68 may be substituted with asparagine. Optionally, (j) alanine at position 356 may be substituted with threonine. Preferably, (k) arginine at position 64 can be substituted with glycine, serine, methionine, leucine, threonine, valine, or isoleucine.

Optionally, the amadoriase derived from *Neocosmospora vasinfecta* can further comprise 1 or more amino acid substitutions at positions described below:
(l) position 67 of SEQ ID NO: 54;
(m) position 72 of SEQ ID NO: 54;
(n) position 76 of SEQ ID NO: 54;
(o) position 96 of SEQ ID NO: 54;
(p) position 109 of SEQ ID NO: 54; and
(q) position 116 of SEQ ID NO: 54.

Optionally, the amino acid at (l) position 67 of SEQ ID NO: 54 can be histidine. Optionally, the amino acid at (m) position 72 of SEQ ID NO: 54 may remain serine. Optionally, the amino acid at (n) position 76 of SEQ ID NO: 54 can be alanine or phenylalanine. Optionally, the amino acid at (o) position 96 of SEQ ID NO: 54 can be glutamic acid. Optionally, the amino acid at (p) position 109 of SEQ ID NO: 54 can remain arginine or it can be lysine. Optionally, the amino acid at (q) position 116 of SEQ ID NO: 54 can be arginine.

A modified amadoriase obtained from the amadoriase derived from *Aspergillus nidulans* (AnFX, SEQ ID NO: 62) can comprise 1 or a plurality of amino acid substitutions at positions described below:
(a) arginine at position 61;
(b) leucine at position 62;
(c) glutamic acid at position 101;
(d) glycine at position 105;
(e) lysine at position 109;
(f) serine at position 112;
(g) alanine at position 355;
(h) alanine at position 420;
(i) aspartic acid at position 67;
(j) asparagine at position 356;
(k) arginine at position 63; and
(l) serine at position 98.

In the amadoriase derived from *Aspergillus nidulans* (SEQ ID NO: 62), preferably, (a) arginine at position 61 may be substituted with alanine, aspartic acid, asparagine, glutamine, glutamic acid, glycine, valine, leucine, isoleucine, cysteine, serine, methionine, threonine, or proline. Preferably, (b) leucine at position 62 is substituted with histidine, alanine, or glycine. Preferably, (c) glutamic acid at position 101 is substituted with lysine. Preferably, (d) glycine at position 105 is substituted with lysine, alanine, or arginine. Preferably, (e) lysine at position 109 is substituted with leucine, tyrosine, phenylalanine, or histidine. Preferably, serine at position 112 is substituted with lysine or arginine. Preferably, alanine at position 355 is substituted with serine. Optionally, (h) alanine at position 420 may be substituted with lysine. Optionally, (i) aspartic acid at position 67 may be substituted with asparagine. Optionally, (j) asparagine at position 356 may be substituted with threonine. Preferably, (k) arginine at position 63 may be substituted with glycine, serine, methionine, leucine, threonine, valine, or isoleucine.

Optionally, the amadoriase derived from *Aspergillus nidulans* can further comprise 1 or more amino acid substitutions at positions described below:
(l) position 66 of SEQ ID NO: 62;
(m) position 71 of SEQ ID NO: 62;
(n) position 75 of SEQ ID NO: 62;
(o) position 95 of SEQ ID NO: 62;
(p) position 108 of SEQ ID NO: 62; and
(q) position 115 of SEQ ID NO: 62.

Optionally, the amino acid at (l) position 66 of SEQ ID NO: 62 can be histidine. Optionally, the amino acid at (m) position 71 of SEQ ID NO: 62 can be serine. Optionally, the amino acid at (n) position 75 of SEQ ID NO: 62 can be alanine or phenylalanine. Optionally, the amino acid at (o) position 95 of SEQ ID NO: 62 can be glutamic acid. Optionally, the amino acid at (p) position 108 of SEQ ID NO: 62 can be arginine or lysine. Optionally, the amino acid at (q) position 115 of SEQ ID NO: 62 can be arginine. The same applies to the amadoriase derived from *Aspergillus nidulans* (SEQ ID NO: 147).

A modified amadoriase obtained from the amadoriase derived from *Eupenicillium terrenum* (SEQ ID NO: 40 or 145) can comprise 1 or a plurality of amino acid substitutions at positions described below:
(a) arginine at position 62;
(b) leucine at position 63;
(c) glutamic acid at position 102;
(d) asparagine at position 106;
(e) lysine at position 110;
(f) threonine at position 113;
(g) alanine at position 355;
(h) glycine at position 419;
(i) aspartic acid at position 68;
(j) asparagine at position 356;
(k) arginine at position 64; and
(l) serine at position 99.

In the amadoriase derived from *Eupenicillium terrenum* (EFP-T5 as shown in SEQ ID NO: 40 or SEQ ID NO: 145), preferably, (a) arginine at position 62 can be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Preferably, (c) glutamic acid at position 102 is substituted with lysine. Preferably, (d) asparagine at position 106 is substituted with lysine, alanine, or arginine. Preferably, (e) lysine at position 110 is substituted with leucine, tyrosine, phenylalanine, or histidine. Preferably, threonine at position 113 is substituted with lysine or arginine. Preferably, alanine at position 355 is substituted with serine. Optionally, (h) glycine at position 419 may be substituted with lysine. Optionally, (i) aspartic acid at position 68 may be substituted with asparagine. Optionally, (j) asparagine at position 356 may be substituted with threonine. Preferably, (k) arginine at position 64 can be substituted with glycine, serine, methionine, leucine, threonine, valine, or isoleucine.

Optionally, the amadoriase derived from *Eupenicillium terrenum* (EFP-T5) can further comprise 1 or more amino acid substitutions at positions described below:
(l) position 67 of SEQ ID NO: 40;
(m) position 72 of SEQ ID NO: 40;
(n) position 76 of SEQ ID NO: 40;
(o) position 96 of SEQ ID NO: 40;
(p) position 109 of SEQ ID NO: 40; and
(q) position 116 of SEQ ID NO: 40.

Optionally, the amino acid at (l) position 67 of SEQ ID NO: 40 can be histidine. Optionally, the amino acid at (m)

position 72 of SEQ ID NO: 40 may remain serine. Optionally, the amino acid at (n) position 76 of SEQ ID NO: 40 can be alanine or phenylalanine. Optionally, the amino acid at (o) position 96 of SEQ ID NO: 40 can be glutamic acid. Optionally, the amino acid at (p) position 109 of SEQ ID NO: 40 can be arginine or lysine. Optionally, the amino acid at (q) position 116 of SEQ ID NO: 40 may remain arginine.

The same applies to the amadoriase derived from *Eupenicillium terrenum* (SEQ ID NO: 145).

A modified amadoriase obtained from fructosyl amino acid oxidase derived from *Cryptococcus neoformans* (SEQ ID NO: 89 or 149) can comprise 1 or a plurality of amino acid substitutions at positions described below:
  (a) arginine at position 62;
  (b) isoleucine at position 63;
  (c) glutamic acid at position 102;
  (d) serine at position 106;
  (e) serine at position 110;
  (f) alanine at position 113;
  (g) alanine at position 355;
  (h) alanine at position 420;
  (i) aspartic acid at position 68;
  (j) asparagine at position 356;
  (k) arginine at position 64; and
  (l) histidine at position 99.

In the fructosyl amino acid oxidase derived from *Cryptococcus neoformans* (CnFX, SEQ ID NO: 89 or 149), preferably, (a) arginine at position 62 may be substituted with alanine, aspartic acid, asparagine, glutamine, glutamic acid, glycine, valine, leucine, isoleucine, cysteine, serine, methionine, threonine, or proline. Preferably, (b) isoleucine at position 63 can be substituted with histidine, alanine, or glycine. Preferably, (c) glutamic acid at position 102 is substituted with lysine. Preferably, (d) serine at position 106 is substituted with lysine, alanine, or arginine. Preferably, (e) serine at position 110 is substituted with leucine, tyrosine, phenylalanine, or histidine. Preferably, alanine at position 113 is substituted with lysine or arginine. Preferably, alanine at position 355 is substituted with serine. Optionally, alanine at position 420 may be substituted with lysine. Optionally, (i) aspartic acid at position 68 may be substituted with asparagine. Optionally, (j) asparagine at position 356 may be substituted with threonine. Preferably, (k) arginine at position 64 can be substituted with glycine, serine, methionine, leucine, threonine, valine, or isoleucine. In an embodiment of the present invention, (l) histidine at position 99 is substituted with serine.

Optionally, the amadoriase derived from *Cryptococcus neoformans* can further comprise 1 or more amino acid substitutions at positions described below:
  (l) position 67 of SEQ ID NO: 89 or 149;
  (m) position 72 of SEQ ID NO: 89 or 149;
  (n) position 76 of SEQ ID NO: 89 or 149;
  (o) position 96 of SEQ ID NO: 89 or 149;
  (p) position 109 of SEQ ID NO: 89 or 149; and
  (q) position 116 of SEQ ID NO: 89 or 149.

Optionally, the amino acid at (l) position 67 of SEQ ID NO: 89 or 149 can be histidine. Optionally, the amino acid at (m) position 72 of SEQ ID NO: 89 or 149 may remain serine. Optionally, the amino acid at (n) position 76 of SEQ ID NO: 89 or 149 can be alanine or phenylalanine. Optionally, the amino acid at (o) position 96 of SEQ ID NO: 89 or 149 can be glutamic acid. Optionally, the amino acid at (p) position 109 of SEQ ID NO: 89 or 149 can be arginine or lysine. Optionally, the amino acid at (q) position 116 of SEQ ID NO: 89 or 149 can be arginine.

A modified amadoriase obtained from ketoamine oxidase derived from *Pyrenochaeta* sp. (SEQ ID NO: 113) can comprise 1 or a plurality of amino acid substitutions at positions described below:
  (a) arginine at position 62;
  (b) leucine at position 63;
  (c) lysine at position 102;
  (d) aspartic acid at position 106;
  (e) alanine at position 110;
  (f) threonine at position 113;
  (g) alanine at position 353;
  (h) alanine at position 418;
  (i) aspartic acid at position 68;
  (j) alanine at position 354;
  (k) arginine at position 64; and
  (l) histidine at position 99.

In the ketoamine oxidase derived from *Pyrenochaeta* sp. (SEQ ID NO: 113), preferably, (a) arginine at position 62 can be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Optionally, (c) lysine at position 102 need not be substituted. Preferably, (d) aspartic acid at position 106 is substituted with lysine, alanine, or arginine. Preferably, (e) alanine at position 110 is substituted with leucine, tyrosine, phenylalanine, or histidine. Preferably, threonine at position 113 is substituted with lysine or arginine. Preferably, alanine at position 353 is substituted with serine. Optionally, (h) alanine at position 418 may be substituted with lysine. Optionally, (i) aspartic acid at position 68 may be substituted with asparagine. Optionally, (j) alanine at position 354 may be substituted with threonine. Preferably, (k) arginine at position 64 can be substituted with glycine, serine, methionine, leucine, threonine, valine, or isoleucine. In an embodiment of the present invention, (l) histidine at position 99 is substituted with serine.

Optionally, the amadoriase derived from *Pyrenochaeta* sp. can further comprise 1 or more amino acid substitutions at positions described below:
  (l) position 67 of SEQ ID NO: 113;
  (m) position 72 of SEQ ID NO: 113;
  (n) position 76 of SEQ ID NO: 113;
  (o) position 96 of SEQ ID NO: 113;
  (p) position 109 of SEQ ID NO: 113; and
  (q) position 116 of SEQ ID NO: 113.

Optionally, the amino acid at (l) position 67 of SEQ ID NO: 113 can be histidine. Optionally, the amino acid at (m) position 72 of SEQ ID NO: 113 may remain serine. Optionally, the amino acid at (n) position 76 of SEQ ID NO: 113 can be alanine or phenylalanine. Optionally, the amino acid at (o) position 96 of SEQ ID NO: 113 can be glutamic acid. Optionally, the amino acid at (p) position 109 of SEQ ID NO: 113 can be arginine or lysine. Optionally, the amino acid at (q) position 116 of SEQ ID NO: 113 can be arginine.

A modified amadoriase obtained from ketoamine oxidase derived from *Arthrinium* sp. (SEQ ID NO: 115) can comprise 1 or a plurality of amino acid substitutions at positions described below:
  (a) arginine at position 62;
  (b) leucine at position 63;
  (c) lysine at position 102;
  (d) alanine at position 106;
  (e) glutamine at position 110;
  (f) threonine at position 113;
  (g) alanine at position 356;
  (h) alanine at position 421;

(i) aspartic acid at position 68;
(j) alanine at position 357;
(k) arginine at position 64; and
(l) glycine at position 99.

In the ketoamine oxidase derived from *Arthrinium* sp. (SEQ ID NO: 115), preferably, (a) arginine at position 62 can be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Optionally, (c) lysine at position 102 need not be substituted. Preferably, (d) alanine at position 106 may be substituted with lysine or arginine, or it may remain alanine. Preferably, (e) glutamine at position 110 is substituted with leucine, tyrosine, phenylalanine, or histidine. Preferably, threonine at position 113 is substituted with lysine or arginine. Preferably, alanine at position 356 is substituted with serine. Optionally, (h) alanine at position 421 may be substituted with lysine. Optionally, (i) aspartic acid at position 68 may be substituted with asparagine. Optionally, (j) alanine at position 357 may be substituted with threonine. Preferably, (k) arginine at position 64 can be substituted with glycine, serine, methionine, leucine, threonine, valine, or isoleucine. In an embodiment of the present invention, (l) glycine at position 99 is substituted with serine.

Optionally, the amadoriase derived from *Arthrinium* sp. can further comprise 1 or more amino acid substitutions at positions described below:
  (l) position 67 of SEQ ID NO: 115;
  (m) position 72 of SEQ ID NO: 115;
  (n) position 76 of SEQ ID NO: 115;
  (o) position 96 of SEQ ID NO: 115;
  (p) position 109 of SEQ ID NO: 115; and
  (q) position 116 of SEQ ID NO: 115.

Optionally, the amino acid at (l) position 67 of SEQ ID NO: 115 can be histidine. Optionally, the amino acid at (m) position 72 of SEQ ID NO: 115 may remain serine. Optionally, the amino acid at (n) position 76 of SEQ ID NO: 115 can be alanine or phenylalanine. Optionally, the amino acid at (o) position 96 of SEQ ID NO: 115 can be glutamic acid. Optionally, the amino acid at (p) position 109 of SEQ ID NO: 115 can be arginine or lysine. Optionally, the amino acid at (q) position 116 of SEQ ID NO: 115 can be arginine.

A modified amadoriase obtained from ketoamine oxidase derived from *Curvularia clavata* (SEQ ID NO: 117) can comprise 1 or a plurality of amino acid substitutions at positions described below:
  (a) arginine at position 62;
  (b) leucine at position 63;
  (c) glutamic acid at position 102;
  (d) aspartic acid at position 106;
  (e) alanine at position 110;
  (f) alanine at position 113;
  (g) alanine at position 353;
  (h) alanine at position 418;
  (i) aspartic acid at position 68;
  (j) alanine at position 354;
  (k) arginine at position 64; and
  (l) histidine at position 99.

In the ketoamine oxidase derived from *Curvularia clavata* (SEQ ID NO: 117), preferably, (a) arginine at position 62 can be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Preferably, (c) glutamic acid at position 102 is substituted with lysine. Preferably, (d) aspartic acid at position 106 is substituted with lysine, alanine, or arginine. Preferably, (e) alanine at position 110 is substituted with leucine, tyrosine, phenylalanine, or histidine. Preferably, alanine at position 113 is substituted with lysine or arginine. Preferably, alanine at position 353 is substituted with serine. Optionally, (h) alanine at position 418 may be substituted with lysine. Optionally, (i) aspartic acid at position 68 may be substituted with asparagine. Optionally, (j) alanine at position 354 may be substituted with threonine. Preferably, (k) arginine at position 64 may be substituted with glycine, serine, methionine, leucine, threonine, valine, or isoleucine. In an embodiment of the present invention, (l) histidine at position 99 is substituted with serine.

Optionally, the amadoriase derived from *Curvularia clavata* can further comprise 1 or more amino acid substitutions at positions described below:
  (l) position 67 of SEQ ID NO: 117;
  (m) position 72 of SEQ ID NO: 117;
  (n) position 76 of SEQ ID NO: 117;
  (o) position 96 of SEQ ID NO: 117;
  (p) position 109 of SEQ ID NO: 117; and
  (q) position 116 of SEQ ID NO: 117.

Optionally, the amino acid at (l) position 67 of SEQ ID NO: 117 can be histidine. Optionally, the amino acid at (m) position 72 of SEQ ID NO: 117 may remain serine. Optionally, the amino acid at (n) position 76 of SEQ ID NO: 117 can be alanine or phenylalanine. Optionally, the amino acid at (o) position 96 of SEQ ID NO: 117 can be glutamic acid. Optionally, the amino acid at (p) position 109 of SEQ ID NO: 117 can be arginine or lysine. Optionally, the amino acid at (q) position 116 of SEQ ID NO: 117 can be arginine.

A modified amadoriase obtained from ketoamine oxidase (Cc95FX, SEQ ID NO: 99) having 95% amino acid sequence identity with ketoamine oxidase derived from *Curvularia clavata* (SEQ ID NO: 117) can comprise 1 or a plurality of amino acid substitutions at positions described below:
  (a) arginine at position 62;
  (b) leucine at position 63;
  (c) glutamic acid at position 102;
  (d) aspartic acid at position 106;
  (e) alanine at position 110;
  (f) alanine at position 113;
  (g) alanine at position 353;
  (h) serine at position 418;
  (i) aspartic acid at position 68;
  (j) alanine at position 354;
  (k) arginine at position 64; and
  (l) histidine at position 99.

In the ketoamine oxidase (SEQ ID NO: 99) having 95% amino acid sequence identity with ketoamine oxidase derived from *Curvularia clavata* (SEQ ID NO: 117), preferably, (a) arginine at position 62 can be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Preferably, (c) glutamic acid at position 102 is substituted with lysine. Preferably, (d) aspartic acid at position 106 is substituted with lysine, alanine, or arginine. Preferably, (e) alanine at position 110 is substituted with leucine, tyrosine, phenylalanine, or histidine. Preferably, alanine at position 113 is substituted with lysine or arginine. Preferably, alanine at position 353 is substituted with serine. Optionally, (h) serine at position 418 may be substituted with lysine. Optionally, (i) aspartic acid at position 68 may be substituted with asparagine. Optionally, (j) alanine at position 354 may be substituted with threonine. Preferably, (k) arginine at position 64 can be substituted with glycine, serine, methionine, leucine, threonine, valine, or isoleucine. In an embodiment of the present invention, (l) histidine at position 99 is substituted with serine.

Optionally, the amadoriase derived from *Curvularia clavata* (Cc95FX) can further comprise 1 or more amino acid substitutions at positions described below:
  (l) position 67 of SEQ ID NO: 99;
  (m) position 72 of SEQ ID NO: 99;
  (n) position 76 of SEQ ID NO: 99;
  (o) position 96 of SEQ ID NO: 99;
  (p) position 109 of SEQ ID NO: 99; and
  (q) position 116 of SEQ ID NO: 99.

Optionally, the amino acid at (l) position 67 of SEQ ID NO: 99 can be histidine. Optionally, the amino acid at (m) position 72 of SEQ ID NO: 99 may remain serine. Optionally, the amino acid at (n) position 76 of SEQ ID NO: 99 can be alanine or phenylalanine. Optionally, the amino acid at (o) position 96 of SEQ ID NO: 99 can be glutamic acid. Optionally, the amino acid at (p) position 109 of SEQ ID NO: 99 can be arginine or lysine. Optionally, the amino acid at (q) position 116 of SEQ ID NO: 99 can be arginine.

A modified amadoriase obtained from fructosyl peptide oxidase derived from *Emericella nidulans* (SEQ ID NO: 119) can comprise 1 or a plurality of amino acid substitutions at positions described below:
  (a) arginine at position 61;
  (b) leucine at position 62;
  (c) glutamic acid at position 101;
  (d) lysine at position 105;
  (e) arginine at position 109;
  (f) serine at position 112;
  (g) alanine at position 355;
  (h) alanine at position 420;
  (i) aspartic acid at position 67;
  (j) asparagine at position 356;
  (k) arginine at position 63; and
  (l) serine at position 98.

In the fructosyl peptide oxidase derived from *Emericella nidulans* (SEQ ID NO: 119), preferably, (a) arginine at position 61 can be substituted with alanine, aspartic acid, asparagine, glutamine, glutamic acid, glycine, valine, leucine, isoleucine, cysteine, serine, methionine, threonine, or proline. Preferably, (b) leucine at position 62 is substituted with histidine, alanine, or glycine. Preferably, (c) glutamic acid at position 101 is substituted with lysine. Optionally, (d) lysine at position 105 need not be substituted, or it can be substituted with alanine or arginine. Preferably, (e) arginine at position 109 is substituted with leucine, tyrosine, phenylalanine, or histidine. Preferably, serine at position 112 is substituted with lysine or arginine. Preferably, alanine at position 355 is substituted with serine. Optionally, (h) alanine at position 420 may be substituted with lysine. Optionally, (i) aspartic acid at position 67 may be substituted with asparagine. Optionally, (j) asparagine at position 356 may be substituted with threonine. Preferably, (k) arginine at position 63 can be substituted with glycine, serine, methionine, leucine, threonine, valine, or isoleucine.

Optionally, fructosyl peptide oxidase derived from *Emericella nidulans* can further comprise 1 or more amino acid substitutions at positions described below:
  (l) position 66 of SEQ ID NO: 119;
  (m) position 71 of SEQ ID NO: 119;
  (n) position 75 of SEQ ID NO: 119;
  (o) position 95 of SEQ ID NO: 119;
  (p) position 108 of SEQ ID NO: 119; and
  (q) position 115 of SEQ ID NO: 119.

Optionally, the amino acid at (l) position 66 of SEQ ID NO: 119 can be histidine. Optionally, the amino acid at (m) position 71 of SEQ ID NO: 119 can be serine. Optionally, the amino acid at (n) position 75 of SEQ ID NO: 119 can be alanine or phenylalanine. Optionally, the amino acid at (o) position 95 of SEQ ID NO: 119 can be glutamic acid. Optionally, the amino acid at (p) position 108 of SEQ ID NO: 119 can be arginine or lysine. Optionally, the amino acid at (q) position 115 of SEQ ID NO: 119 can be arginine.

A modified amadoriase obtained from fructosyl amino acid oxidase derived from *Ulocladium* sp. (SEQ ID NO: 121) can comprise 1 or a plurality of amino acid substitutions at positions described below:
  (a) arginine at position 62;
  (b) leucine at position 63;
  (c) lysine at position 102;
  (d) aspartic acid at position 106;
  (e) alanine at position 110;
  (f) alanine at position 113;
  (g) alanine at position 353;
  (h) alanine at position 418;
  (i) aspartic acid at position 68;
  (j) alanine at position 354;
  (k) arginine at position 64; and
  (l) histidine at position 99.

In the fructosyl amino acid oxidase derived from *Ulocladium* sp. (SEQ ID NO: 121), preferably, (a) arginine at position 62 can be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Optionally, (c) lysine at position 102 need not be substituted. Preferably, (d) aspartic acid at position 106 is substituted with lysine, alanine, or arginine. Preferably, (e) alanine at position 110 is substituted with leucine, tyrosine, phenylalanine, or histidine. Preferably, alanine at position 113 is substituted with lysine or arginine. Preferably, alanine at position 353 is substituted with serine. Optionally, (h) alanine at position 418 may be substituted with lysine. Optionally, (i) aspartic acid at position 68 may be substituted with asparagine. Optionally, (j) alanine at position 354 may be substituted with threonine. Preferably, (k) arginine at position 64 can be substituted with glycine, serine, methionine, leucine, threonine, valine, or isoleucine. In an embodiment of the present invention, (l) histidine at position 99 is substituted with serine.

Optionally, the amadoriase derived from *Ulocladium* sp. can further comprise 1 or more amino acid substitutions at positions described below:
  (l) position 67 of SEQ ID NO: 121;
  (m) position 72 of SEQ ID NO: 121;
  (n) position 76 of SEQ ID NO: 121;
  (o) position 96 of SEQ ID NO: 121;
  (p) position 109 of SEQ ID NO: 121; and
  (q) position 116 of SEQ ID NO: 121.

Optionally, the amino acid at (l) position 67 of SEQ ID NO: 121 can be histidine. Optionally, the amino acid at (m) position 72 of SEQ ID NO: 121 may remain serine. Optionally, the amino acid at (n) position 76 of SEQ ID NO: 121 can be alanine or phenylalanine. Optionally, the amino acid at (o) position 96 of SEQ ID NO: 121 can be glutamic acid. Optionally, the amino acid at (p) position 109 of SEQ ID NO: 121 can be arginine or lysine. Optionally, the amino acid at (q) position 116 of SEQ ID NO: 121 can be arginine.

A modified amadoriase obtained from fructosyl amino acid oxidase derived from *Penicillium janthinellum* (SEQ ID NO: 123) can comprise 1 or a plurality of amino acid substitutions at positions described below:
(a) arginine at position 62;
(b) leucine at position 63;
(c) glutamic acid at position 102;
(d) serine at position 106;
(e) lysine at position 110;
(f) aspartic acid at position 113;
(g) alanine at position 355;
(h) serine at position 419;
(i) aspartic acid at position 68;
(j) asparagine at position 356;
(k) arginine at position 64; and
(l) serine at position 99.

In the fructosyl amino acid oxidase derived from *Penicillium janthinellum* (SEQ ID NO: 123), preferably, (a) arginine at position 62 can be substituted with alanine, aspartic acid, asparagine, glutamine, glutamic acid, glycine, valine, leucine, isoleucine, cysteine, serine, methionine, threonine, or proline. Preferably, (b) leucine at position 63 is substituted with histidine, alanine, or glycine. Preferably, (c) glutamic acid at position 102 is substituted with lysine. Preferably, (d) serine at position 106 is substituted with lysine, alanine, or arginine. Preferably, (e) lysine at position 110 is substituted with leucine, tyrosine, phenylalanine, or histidine. Preferably, aspartic acid at position 113 is substituted with lysine or arginine. Preferably, alanine at position 355 is substituted with serine. Optionally, (h) serine at position 419 may be substituted with lysine. Optionally, (i) aspartic acid at position 68 may be substituted with asparagine. Optionally, (j) asparagine at position 356 may be substituted with threonine. The same applies to fructosyl amino acid oxidase derived from *Penicillium chrysogenum*. Preferably, (k) arginine at position 64 can be substituted with glycine, serine, methionine, leucine, threonine, valine, or isoleucine.

Optionally, the amadoriase derived from *Penicillium janthinellum* can further comprise 1 or more amino acid substitutions at positions described below:
(l) position 67 of SEQ ID NO: 123;
(m) position 72 of SEQ ID NO: 123;
(n) position 76 of SEQ ID NO: 123;
(o) position 96 of SEQ ID NO: 123;
(p) position 109 of SEQ ID NO: 123; and
(q) position 116 of SEQ ID NO: 123.

Optionally, the amino acid at (l) position 67 of SEQ ID NO: 123 can be histidine. Optionally, the amino acid at (m) position 72 of SEQ ID NO: 123 may remain serine. Optionally, the amino acid at (n) position 76 of SEQ ID NO: 123 can be alanine or phenylalanine. Optionally, the amino acid at (o) position 96 of SEQ ID NO: 123 can be glutamic acid. Optionally, the amino acid at (p) position 109 of SEQ ID NO: 123 may remain arginine, or it can be lysine. Optionally, the amino acid at (q) position 116 of SEQ ID NO: 123 can be arginine.

According to an embodiment, the amadoriase of the present invention that acts directly on hemoglobin A1c may preferably:
recognize the β chain of hemoglobin A1c as a substrate,
oxidize the β chain of hemoglobin A1c and generates hydrogen peroxide,
have an optimal pH range between pH 6 and 8,
have an operable pH range between pH 5 and 9,
have an operable temperature between 25° C. and 40° C., and
have a molecular weight according to SDS-PAGE of about 45 to 55 KDa (e.g., about 48 to 50 KDa).

Amadoriases exhibiting no activity on HbA1c at all are excluded from the scope of the amadoriase variant or the modified amadoriase according to the present invention.
(Obtaining a Gene Encoding an Amadoriase)

In order to obtain a gene encoding the amadoriases described above (hereinafter, also referred to as merely "amadoriase gene"), gene cloning methods can be employed. For example, chromosomal DNA or mRNA can be extracted from a microorganism fungus body or various cells having an ability to produce an amadoriase by a conventional technique, such as a method described in "Current Protocols in Molecular Biology" (WILEY Interscience, 1989). In addition, cDNA can be synthesized using mRNA as the template. A chromosomal DNA or cDNA library can be made using the chromosomal DNA or cDNA obtained in such a manner.

Subsequently, DNA including the entire sequence of a target amadoriase gene can be obtained by a method of synthesizing an appropriate probe DNA based on the amino acid sequence of the aforementioned amadoriase and selecting an amadoriase gene from a chromosomal DNA or cDNA library using the probe DNA. Alternatively, an appropriate primer DNA may be produced based on the aforementioned amino acid sequence, a DNA including the target gene fragment encoding the amadoriase gene may be amplified by using an appropriate polymerase chain reaction (PCR) technique, such as the 5' RACE or 3' RACE method, and the resulting DNA fragments may then be linked.

A preferable example of a gene encoding an amadoriase thus obtained is an amadoriase gene derived from the genus *Coniochaeta* (JP 2003-235585 A).

Other preferable examples include amadoriase genes derived from the genus *Phaeosphaeria*, amadoriase genes derived from the genus *Neocosmospora*, amadoriase genes derived from the genus *Aspergillus*, amadoriase genes derived from the genus *Cryptococcus*, amadoriase genes derived from the genus *Curvularia*, and amadoriase genes derived from the genus *Eupenicillium*.

Such amadoriase genes are preferably linked to various vectors according to a conventional technique from the viewpoint of handleability. For example, a DNA encoding an amadoriase gene can be obtained by subjecting a recombinant plasmid pKK223-3-CFP-T7 including DNA encoding an amadoriase gene derived from a strain of *Coniochaeta* sp. NISL9330 (WO 2007/125779) to extraction and purification using the GenElute Plasmid Miniprep Kit (Sigma-Aldrich). A person skilled in the art would be able to obtain DNA of amadoriase genes derived from other organisms in a similar manner using conventional techniques. More specifically, DNA encoding an amadoriase gene can be obtained by culturing *E. coli* strains carrying the recombinant plasmid pUTE100K'-EFP-T5 including DNA encoding an amadoriase gene derived from a strain of *Eupenicillium terrenum* ATCC 18547 (WO 2007/125779) and extracting and purifying the recombinant plasmid pUTE100K'-EFP-T5 including DNA encoding an amadoriase gene from the cells using the GenElute Plasmid Miniprep Kit. Also, DNA encoding an amadoriase gene can be obtained by culturing *E. coli* strains carrying the recombinant plasmid pET22b-AnFX including DNA encoding an amadoriase gene derived from a strain of *Aspergillus nidulans* FGSC A26 (WO 2012/018094) and extracting and purifying the recombinant plasmid pET22b-AnFX including DNA encoding an amadoriase gene therefrom with the use of the GenElute Plasmid Miniprep Kit. DNA encoding an amadoriase gene can be obtained by culturing E. coli strains carrying the recombinant plasmid pET22b-CnFX including DNA encoding an amadoriase gene derived from a strain of Cryptococcus neoformans (WO 2012/018094) and extracting and purifying the recombinant plasmid pET22b-CnFX including DNA encoding an amadoriase gene therefrom with the use of the GenElute Plasmid Miniprep Kit. DNA encoding an amadoriase gene can be obtained by culturing E. coli strains carrying the recombinant plasmid pET22b-NvFX including DNA encoding an amadoriase gene derived from a strain of Neocosmospora vasinfecta (WO 2012/018094) and extracting and purifying the recombinant plasmid pET22b-NvFX including DNA encoding an amadoriase gene therefrom with the use of the GenElute Plasmid Miniprep Kit.

(Vector)

Vectors that can be used in the present invention are not limited to the aforementioned plasmid vectors. For example, any other vectors known in the art, such as bacteriophage or cosmid vectors, can be used. Specifically, for example, pBluescriptII SK+(manufactured by Stratagene Corporation) is preferable.

(Mutation of Amadoriase Gene)

Mutation of an amadoriase gene can be performed by any known method depending on an intended form of mutation. More specifically, a method of bringing a chemical mutagen into contact with and allowing to act on an amadoriase gene or recombinant DNA comprising such gene integrated therein, an ultraviolet irradiation method, a genetic engineering technique, a method of making full use of a protein engineering technique, or various other methods can be extensively used.

Examples of chemical mutagens used in the aforementioned mutation include hydroxylamine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used, and such conditions are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the aforementioned drug at the concentration of 0.5 M to 12 M. The ultraviolet irradiation may be also performed according to a conventional technique as described above (Gendai Kagaku, pp. 24-30, June, 1989).

As the method of making full use of the protein engineering technique, in general, a technique known as site-specific mutagenesis can be used. Examples include the Kramer method (Nucleic Acids Res., 12, 9441, 1984; Methods Enzymol., 154, 350, 1987; Gene, 37, 73, 1985), the Eckstein method (Nucleic Acids Res., 13, 8749, 1985; Nucleic Acids Res., 13, 8765, 1985; Nucleic Acids Res, 14, 9679, 1986), and the Kunkel method (Proc. Natl. Acid. Sci. U.S.A., 82, 488, 1985; Methods Enzymol., 154, 367, 1987).

A technique known as a general PCR technique can also be used (Technique, 1, 11, 1989). In addition to the conventional genetic mutation technique, the modified amadoriase genes of interest can be directly synthesized by an organic synthesis method or an enzyme synthesis method.

The nucleotide sequences of DNAs encoding the amadoriase genes obtained by the aforementioned methods may be determined or verified by, for example, using a multi-capillary DNA analysis system, Applied Biosystems 3130x Genetic Analyzer (Life Technologies).

(Transformation/Transduction)

The amadoriase genes obtained as described above are integrated into a vector such as a bacteriophage vector, a cosmid vector, or a plasmid vector used in transformation of a procaryotic or eucaryotic cell by a conventional technique, and a host corresponding to each vector can be transformed or transduced by a conventional technique. For example, a microorganism belonging to the genus Escherichia, such as the obtained recombinant DNA, is used as the host to transform a strain of E. coli K-12, and preferably a strain of E. coli JM109 or E. coli DH5α (manufactured by Takara Bio Inc.), or such microorganism is transduced into such strain. Thus, transformed or transduced strains of interest can be obtained.

(Amino Acid Sequence Homology, Identity, or Similarity)

The amino acid sequence homology, identity, or similarity can be calculated by a program such as maximum matching or search homology of GENETYX (manufactured by GENETYX), a program such as maximum matching or multiple alignment of DNASIS Pro (manufactured by Hitachi Solutions, Ltd.), or a program such as multiple alignment of CLUSTALW. In order to calculate amino acid sequence identity, two or more amadoriases may be aligned, and the positions of identical amino acids in such two or more amadoriases may be determined. The identical regions in amino acid sequences can be determined based on such information. The percent identity of two or more amino acid sequences is determined by subjecting two or more amino acid sequences to alignment using the algorithm such as Blosum62 by designating the total number of amino acids in the aligned region as the denominator and the number of identical amino acids relative to the total number as the numerator. If no identity is found in parts of the two or more amino acid sequences, for example, an amino acid sequence comprises at its C terminus an additional sequence in which no identity is observed, in general, such regions cannot be aligned. Accordingly, such regions are not used for calculation of the percent identity.

Also, positions of similar amino acids in two or more amadoriases can be inspected. For example, a plurality of amino acid sequences can be subjected to alignment with the use of CLUSTALW. In such a case, Blosum62 is used as the algorithm and a plurality of amino acid sequences are subjected to alignment. Amino acids determined to be similar as a result of alignment may be referred to as "similar amino acids." In the variant of the present invention, amino acid substitution can be carried out between such similar amino acids. Through such alignment, amino acid sequences composed of the identical amino acids or similar amino acids among a plurality of amino acid sequences can be investigated. Based on such information, homologous regions (conserved regions) in the amino acid sequences can be determined.

The term "homologous region(s)" used herein refers to region(s) consisting of identical or similar amino acids at corresponding positions in the reference amadoriase and in the amadoriase being compared, when two or more amadoriases are aligned, wherein the region(s) consists of 3 or more, 4 or more, 5 or more, 6 or more, 7 or more, 8 or more, 9 or more, or 10 or more continuous amino acids. For example, FIG. 1 shows the alignment of amadoriases exhibiting sequence identity of 74% or higher over the full-length amino acid sequences. In such sequences, the region of positions 10 to 32 with reference to the sequence of the amadoriase derived from Coniochaeta sp. as shown in SEQ ID NO: 1 consists of identical or similar amino acids, and such region is considered to be a homologous region. Similarly, regions of positions 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the sequence of the amadoriase derived from *Coniochaeta* sp. as shown in SEQ ID NO: 1 can be homologous regions.

Preferably, the homologous region of an amadoriases is composed of amino acid sequences of positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from *Coniochaeta* sp. as shown in SEQ ID NO: 1.

More preferably, the homologous region of an amadoriases is composed of amino acid sequences of positions 11 to 18, 20 to 32, 50 to 52, 54 to 58, 266 to 268, 270 to 273, 277 to 286, and 370 to 383 with reference to the sequence of the amadoriase derived from *Coniochaeta* sp. as shown in SEQ ID NO: 1.

When the full-length amino acid sequence of the amadoriase variant of the present invention is aligned with that of the amadoriase comprising the amino acid sequence as shown in SEQ ID NO: 1, the sequence identity is 50% or higher, preferably 60% or higher, 70% or higher, 71% or higher, 72% or higher, 73% or higher, 74% or higher, 75% or higher, 80% or higher, or 85% or higher, more preferably 90% or higher or 95% or higher, and most preferably 99% or higher, and such amadoriase variant has high reactivity with αF8P. In addition, the amino acid sequence in the homologous region of the amadoriase variant according to the present invention exhibits 80%, preferably 85% or higher, 90%, 91%, 92%, 93%, 94%, 95%, or 98%, and further preferably 99% or higher sequence identity with the amino acid sequence in the homologous region of SEQ ID NO: 1.

According to an embodiment, the homologous region of an amadoriase is, with reference to the amadoriase sequence as shown in SEQ ID NO: 211 or 213, a region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431; preferably a region consisting of amino acids at positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410; and more preferably a region consisting of amino acids at positions 11 to 18, 20 to 32, 50 to 52, 54 to 58, 266 to 268, 270 to 273, 277 to 286, and 370 to 383.

According to an embodiment of the present invention, the amadoriase is (i) or (ii) below:

(i) an amadoriase comprising an amino acid sequence derived from the amino acid sequence as shown in SEQ ID NO: 211 or 213 by substitution, deletion, or addition of 1 or several amino acids; or (ii) the amadoriase as defined in (i), wherein the amadoriase comprises an amino acid sequence having 70% or higher, 71% or higher, 72% or higher, 73% or higher, 74% or higher, 75% or higher, 80% or higher, or 85% or higher sequence identity with the amino acid sequence as shown in SEQ ID NO: 211 or 213 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 211 or 213 and the amino acid sequence of the homologous region in corresponding positions of the amadoriase. According to an embodiment, the amadoriase of the present invention comprises an amino acid sequence exhibiting 95% or higher sequence identity between the amino acid sequence of the homologous region as defined in (ii) above and the amino acid sequence of the homologous region in corresponding positions of the amadoriase.

In addition to or independent of the substitutions described above, the amadoriase according to an embodiment of the present invention comprises 1 or more amino acid substitutions at positions corresponding to (i) and (ii) below in the amino acid sequence as shown in SEQ ID NO: 1:

(i) position 68; or
(ii) position 356.

In addition to the substitutions described above, the amadoriase according to an embodiment of the present invention comprises 1 or more amino acid substitutions at positions corresponding to the positions selected from the group consisting of (i) to (xiv) in the amino acid sequence as shown in SEQ ID NO: 1:

(i) position 262;
(ii) position 257;
(iii) position 249;
(iv) position 253;
(v) position 337;
(vi) position 340;
(vii) position 232;
(viii) position 129;
(ix) position 132;
(x) position 133;
(xi) position 44;
(xii) position 256;
(xiii) position 231; and
(xiv) position 81.

In addition to the substitutions described above, the amadoriase according to another embodiment of the present invention may optionally lack 3 amino acid residues from the carboxyl terminus.

In addition to the substitutions described above, the amadoriase according to an embodiment of the present invention may comprise 1 or more amino acid substitutions at positions corresponding to the positions selected from the group consisting of (l) to (q) in the amino acid sequence as shown in SEQ ID NO: 1:

(l) position 67 in SEQ ID NO: 1;
(m) position 72 in SEQ ID NO: 1;
(n) position 76 in SEQ ID NO: 1,
(o) position 96 in SEQ ID NO: 1,
(p) position 109 in SEQ ID NO: 1, and
(q) position 116 in SEQ ID NO: 1.

Optionally, the amino acid at the position corresponding to (l) position 67 in SEQ ID NO: 1 can be histidine. Optionally, the amino acid at the position corresponding to (m) position 72 in SEQ ID NO: 1 can be serine. Optionally, the amino acid at the position corresponding to (n) position 76 in SEQ ID NO: 1 can be alanine or phenylalanine. Optionally, the amino acid at the position corresponding to (o) position 96 in SEQ ID NO: 1 can be glutamic acid. Optionally, the amino acid at the position corresponding to (p) position 109 in SEQ ID NO: 1 can be arginine. Optionally, the amino acid at the position corresponding to (q) position 116 in SEQ ID NO: 1 can be arginine.

(Identifying a Corresponding Position in an Amino Acid Sequence)

When an amino acid at a particular position in the reference amino acid sequence corresponds to an amino acid at a particular position in another similar amino acid sequence, in the present invention, such amino acid is referred to as a corresponding amino acid, and the position of such amino acid is referred to as the corresponding position. For convenience, explanations are provided with reference to the amino acid sequence of the amadoriase derived from the genus *Coniochaeta* as shown in SEQ ID NO: 1. In this case, the term "corresponding position" in an amino acid sequence refers to a position in an amino acid sequence of an amadoriase derived from another organism species corresponding to a particular position in the amino acid sequence of the amadoriase derived from the genus *Coniochaeta* as shown in SEQ ID NO: 1.

A method of identifying a "corresponding position" in an amino acid sequence may be also performed by comparing amino acid sequences using a known algorithm such as a Lipman-Pearson method to assign maximum identity to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. Homologous positions are considered to exist in the same positions in the three-dimensional structures, and amino acid residues at such homologous positions are expected to exert similar effects in terms of specificity of the amadoriase of interest.

In the present invention, the term "the position corresponding to position 64 in the amino acid sequence as shown in SEQ ID NO: 1" refers to a position corresponding to position 64 in the amadoriase sequence as shown in SEQ ID NO: 1, when the amino acid sequence of the target amadoriase is aligned and compared with that of the amino acid sequence of the amadoriase sequence as shown in SEQ ID NO: 1. Such position can be identified by the method in "Identifying a corresponding position in an amino acid sequence" above.

The same applies to "the position corresponding to position 62 in the amino acid sequence as shown in SEQ ID NO: 1," "the position corresponding to position 63 in the amino acid sequence as shown in SEQ ID NO: 1," "the position corresponding to position 102 in the amino acid sequence as shown in SEQ ID NO: 1," "the position corresponding to position 106 in the amino acid sequence as shown in SEQ ID NO: 1," "the position corresponding to position 110 in the amino acid sequence as shown in SEQ ID NO: 1," "the position corresponding to position 113 in the amino acid sequence as shown in SEQ ID NO: 1," "the position corresponding to position 355 in the amino acid sequence as shown in SEQ ID NO: 1," "the position corresponding to position 419 in the amino acid sequence as shown in SEQ ID NO: 1," "the position corresponding to position 68 in the amino acid sequence as shown in SEQ ID NO: 1," "the position corresponding to position 356 in the amino acid sequence as shown in SEQ ID NO: 1," and "the position corresponding to position 99 in the amino acid sequence as shown in SEQ ID NO: 1."

The amino acid at "the position corresponding to position 64 in the amino acid sequence as shown in SEQ ID NO: 1" is arginine at position 64 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl amino acid oxidase derived from *Ulocladium* sp., the fructosyl amino acid oxidase derived from *Penicillium janthinellum*, and the fructosyl peptide oxidase derived from *Phaeosphaeria nodorum*, and it is arginine at position 63 in the case of the fructosyl peptide oxidase derived from *Emericella nidulans* and the fructosyl amino acid oxidase derived from *Aspergillus nidulans*.

The amino acid at "the position corresponding to position 62 in the amino acid sequence as shown in SEQ ID NO: 1" is arginine at position 62 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl amino acid oxidase derived from *Ulocladium* sp., and the fructosyl amino acid oxidase derived from *Penicillium janthinellum*, it is serine at position 62 in the case of the fructosyl peptide oxidase derived from *Phaeosphaeria nodorum*, it is arginine at position 61 in the case of the fructosyl peptide oxidase derived from *Emericella nidulans*, and it is arginine at position 61 in the case of the fructosyl amino acid oxidase derived from *Aspergillus nidulans*.

The amino acid at "the position corresponding to position 63 in the amino acid sequence as shown in SEQ ID NO: 1" is leucine at position 63 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl peptide oxidase derived from *Phaeosphaeria nodorum*, the fructosyl amino acid oxidase derived from *Ulocladium* sp., and the fructosyl amino acid oxidase derived from *Penicillium janthinellum*, it is isoleucine at position 63 in the case of the fructosyl amino acid oxidase derived from *Cryptococcus neoformans*, and it is leucine at position 62 in the case of the fructosyl amino acid oxidase derived from *Aspergillus nidulans* and the fructosyl peptide oxidase derived from *Emericella nidulans*.

The amino acid at "the position corresponding to position 102 in the amino acid sequence as shown in SEQ ID NO: 1" is glutamic acid at position 102 in the case of the amadoriase derived from *Eupenicillium terrenum*, the ketoamine oxidase derived from *Curvularia clavata*, the ketoamine oxidase derived from *Neocosmospora vasinfecta*, the fructosyl amino acid oxidase derived from *Cryptococcus neoformans*, and the fructosyl amino acid oxidase derived from *Penicillium janthinellum*, it is lysine at position 102 in the case of the ketoamine oxidase derived from *Pyrenochaeta* sp., the ketoamine oxidase derived from *Arthrinium* sp., the fructosyl peptide oxidase derived from *Phaeosphaeria nodorum*, and the fructosyl amino acid oxidase derived from *Ulocladium* sp., and it is glutamic acid at position 101 in the case of the fructosyl peptide oxidase derived from *Emericella nidulans* and the fructosyl amino acid oxidase derived from *Aspergillus nidulans*.

The amino acid at "the position corresponding to position 106 in the amino acid sequence as shown in SEQ ID NO: 1" is asparagine at position 106 in the case of the amadoriase derived from *Eupenicillium terrenum*, it is aspartic acid at position 106 in the case of the ketoamine oxidase derived from *Pyrenochaeta* sp., the ketoamine oxidase derived from *Curvularia clavata*, the fructosyl peptide oxidase derived from *Phaeosphaeria nodorum*, and the fructosyl amino acid oxidase derived from *Ulocladium* sp., it is alanine at position 106 in the case of the ketoamine oxidase derived from *Arthrinium* sp., it is glycine at position 106 in the case of the ketoamine oxidase derived from *Neocosmospora vasinfecta*, it is serine at position 106 in the case of the fructosyl amino acid oxidase derived from *Cryptococcus neoformans* and the fructosyl amino acid oxidase derived from *Penicillium janthinellum*, it is lysine at position 105 in the case of the fructosyl peptide oxidase derived from *Emericella nidulans*, and it is glycine at position 105 in the case of the fructosyl amino acid oxidase derived from *Aspergillus nidulans*.

The amino acid at "the position corresponding to position 110 in the amino acid sequence as shown in SEQ ID NO: 1" is lysine at position 110 in the case of the amadoriase derived from *Eupenicillium terrenum* and the fructosyl amino acid oxidase derived from *Penicillium janthinellum*, it is alanine at position 110 in the case of the ketoamine oxidase derived from *Pyrenochaeta* sp., the ketoamine oxidase derived from *Curvularia clavata*, and the fructosyl amino acid oxidase derived from *Ulocladium* sp., it is glutamine at position 110 in the case of the ketoamine oxidase derived from *Arthrinium* sp., it is glutamic acid at position 110 in the case of the ketoamine oxidase derived from *Neocosmospora vasinfecta*, it is serine at position 110 in the case of the fructosyl amino acid oxidase derived from *Cryptococcus neoformans*, it is glycine at position 110 in the case of the fructosyl peptide oxidase derived from *Phaeosphaeria nodorum*, it is arginine at position 109 in the case of the fructosyl peptide oxidase derived from *Emericella nidulans*, and it is lysine at position 109 in the case of the fructosyl amino acid oxidase derived from *Aspergillus nidulans*.

The amino acid at "the position corresponding to position 113 in the amino acid sequence as shown in SEQ ID NO: 1" is threonine at position 113 in the case of the amadoriase derived from *Eupenicillium terrenum*, the ketoamine oxidase derived from *Pyrenochaeta* sp., and the ketoamine oxidase derived from *Arthrinium* sp., it is alanine at position 113 in the case of the ketoamine oxidase derived from *Curvularia clavata*, the fructosyl amino acid oxidase derived from *Cryptococcus neoformans*, the fructosyl peptide oxidase derived from *Phaeosphaeria nodorum*, and the fructosyl amino acid oxidase derived from *Ulocladium* sp., it is lysine at position 113 in the case of the ketoamine oxidase derived from *Neocosmospora vasinfecta*, it is serine at position 112 in the case of the fructosyl amino acid oxidase derived from *Aspergillus nidulans* and the fructosyl peptide oxidase derived from *Emericella nidulans*, and it is aspartic acid at position 113 in the case of the fructosyl amino acid oxidase derived from *Penicillium janthinellum*.

The amino acid at "the position corresponding to position 355 in the amino acid sequence as shown in SEQ ID NO: 1" is alanine at position 355 in the case of the amadoriase derived from *Eupenicillium terrenum*, the fructosyl amino acid oxidase derived from *Cryptococcus neoformans*, the fructosyl amino acid oxidase derived from *Aspergillus nidulans*, the fructosyl peptide oxidase derived from *Emericella nidulans*, and the fructosyl amino acid oxidase derived from *Penicillium janthinellum*, it is alanine at position 353 in the case of the ketoamine oxidase derived from *Pyrenochaeta* sp., the ketoamine oxidase derived from *Curvularia clavata*, and the fructosyl amino acid oxidase derived from *Ulocladium* sp., it is alanine at position 356 in the case of the ketoamine oxidase derived from *Arthrinium* sp., it is serine at position 355 in the case of the ketoamine oxidase derived from *Neocosmospora vasinfecta*, and it is alanine at position 351 in the case of the fructosyl peptide oxidase derived from *Phaeosphaeria nodorum*.

The amino acid at "the position corresponding to position 419 in the amino acid sequence as shown in SEQ ID NO: 1" is glycine at position 419 in the case of the amadoriase derived from *Eupenicillium terrenum*, it is alanine at position 418 in the case of the ketoamine oxidase derived from *Pyrenochaeta* sp., the ketoamine oxidase derived from *Curvularia clavata*, and the fructosyl amino acid oxidase derived from *Ulocladium* sp., it is alanine at position 421 in the case of the ketoamine oxidase derived from *Arthrinium* sp., it is alanine at position 420 in the case of the ketoamine oxidase derived from *Neocosmospora vasinfecta*, the fructosyl amino acid oxidase derived from *Cryptococcus neoformans*, and the fructosyl peptide oxidase derived from *Emericella nidulans*, it is serine at position 416 in the case of the fructosyl peptide oxidase derived from *Phaeosphaeria nodorum*, it is serine at position 419 in the case of the fructosyl amino acid oxidase derived from *Penicillium janthinellum*, and it is alanine at position 420 in the case of the fructosyl amino acid oxidase derived from *Aspergillus nidulans*.

The amino acid at "the position corresponding to position 68 in the amino acid sequence as shown in SEQ ID NO: 1" is aspartic acid at position 68 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl peptide oxidase derived from *Phaeosphaeria nodorum*, the fructosyl amino acid oxidase derived from *Ulocladium* sp., and the fructosyl amino acid oxidase derived from *Penicillium janthinellum*, and it is aspartic acid at position 67 in the case of the fructosyl peptide oxidase derived from *Emericella nidulans* and the fructosyl amino acid oxidase derived from *Aspergillus nidulans*.

The amino acid at "the position corresponding to position 356 in the amino acid sequence as shown in SEQ ID NO: 1" is asparagine at position 356 in the case of the amadoriase derived from *Eupenicillium terrenum*, it is alanine at position 354 in the case of the ketoamine oxidase derived from *Pyrenochaeta* sp., it is alanine at position 357 in the case of the ketoamine oxidase derived from *Arthrinium* sp., it is alanine at position 354 in the case of the ketoamine oxidase derived from *Curvularia clavata*, it is alanine at position 356 in the case of the ketoamine oxidase derived from *Neocosmospora vasinfecta*, it is asparagine at position 356 in the case of the fructosyl amino acid oxidase derived from *Cryptococcus neoformans*, it is alanine at position 352 in the case of the fructosyl peptide oxidase derived from *Phaeosphaeria nodorum*, it is asparagine at position 356 in the case of the fructosyl amino acid oxidase derived from *Aspergillus nidulans*, it is asparagine at position 356 in the case of the fructosyl peptide oxidase derived from *Emericella nidulans*, it is alanine at position 354 in the case of the fructosyl amino acid oxidase derived from *Ulocladium* sp., and it is asparagine at position 356 in the case of the fructosyl amino acid oxidase derived from *Penicillium janthinellum*.

The amino acid at "the position corresponding to position 99 in the amino acid sequence as shown in SEQ ID NO: 1" is serine at position 99 in the case of the amadoriase derived from *Eupenicillium terrenum*, it is histidine at position 99 in the case of the ketoamine oxidase derived from *Pyrenochaeta* sp., it is glycine at position 99 in the case of the ketoamine oxidase derived from *Arthrinium* sp., it is histidine at position 99 in the case of the ketoamine oxidase derived from *Curvularia clavata*, it is serine at position 99 in the case of the ketoamine oxidase derived from *Neocosmospora vasinfecta*, it is histidine at position 99 in the case of the fructosyl amino acid oxidase derived from *Cryptococcus neoformans*, it is histidine at position 99 in the case of the fructosyl peptide oxidase derived from *Phaeosphaeria nodorum*, it is serine at position 98 in the case of the fructosyl amino acid oxidase derived from *Aspergillus nidulans*, it is serine at position 98 in the case of the fructosyl peptide oxidase derived from *Emericella nidulans*, it is histidine at position 99 in the case of the fructosyl amino acid oxidase derived from *Ulocladium* sp., and it is serine at position 99 in the case of the fructosyl amino acid oxidase derived from *Penicillium janthinellum*.

The amadoriase variant of the present invention may be a single variant or a multiple variant comprising two or more amino acid substitutions. The present inventors found that an amadoriase resulting from substitution of the amino acid at the position corresponding to positions 64 of the amino acid sequence as shown in SEQ ID NO: 203 with glycine (SEQ ID NO: 213) and an amadoriase resulting from substitution of the amino acid at the position corresponding to positions 64 of the amino acid sequence as shown in SEQ ID NO: 209 with glycine (SEQ ID NO: 211) surprisingly exhibits improved specific activity on αF8P. These amadoriases are considered to have enhanced activity on HbA1c as well. These findings were particularly surprising in view of the fact that, regarding an amadoriase comprising the amino acid sequence as shown in SEQ ID NO: 163, amadoriases in which the amino acid at position 64 was substituted with alanine, glutamic acid, or histidine had reduced (lowered) activity on αF6P.

In the present description, mutations at these positions (at positions 64, 62, 63, 102, 106, 110, 113, 355, 419, as well as positions 68 and 356) may also be referred to as "mutations that alter substrate specificity of an amadoriase" or "amino acid substitutions that alter substrate specificity of an amadoriase."

According to an embodiment, the specific activity (U/mg) of the amadoriase of the present invention on αF8P is 0.1 U/mg or greater, 0.2 U/mg or greater, 0.3 U/mg or greater, 0.4 U/mg or greater, 0.5 U/mg or greater, 0.6 U/mg or greater, 0.7 U/mg or greater, 0.8 U/mg or greater, or 0.9 U/mg or greater, such as 1 U/mg or greater. Such amadoriase can comprise 1 or more, 2 or more, 3 or more, 4 or more, 5 or more, 6 or more, 7 or more, 8 or more, 9 or more, or 10 or more amino acid substitutions that alter substrate specificity. Such amadoriase of the present invention acts directly on HbA1c and can be used for the method for measurement of HbA1c according to the present invention.

According to an embodiment, the amadoriase of the present invention having improved specific activity (U/mg) on αF8P can result from substitution of, when the amino acid sequence thereof is aligned with the amino acid sequence as shown in SEQ ID NO: 1, 1 or more, 2 or more, 3 or more, 4 or more, 5 or more, 6 or more, 7 or more, 8 or more, 9 or more, 10 or more, 11 or more, or 12 or more (e.g., 10) amino acids at positions corresponding to the positions selected from (a) to (l) below:

(a) position 62 in SEQ ID NO: 1;
(b) position 63 in SEQ ID NO: 1;
(c) position 102 in SEQ ID NO: 1;
(d) position 106 in SEQ ID NO: 1;
(e) position 110 in SEQ ID NO: 1;
(f) position 113 in SEQ ID NO: 1;
(g) position 355 in SEQ ID NO: 1;
(h) position 419 in SEQ ID NO: 1;
(i) position 68 in SEQ ID NO: 1;
(j) position 356 in SEQ ID NO: 1;
(k) position 64 in SEQ ID NO: 1; and
(l) position 99 in SEQ ID NO: 1.

In the case of the fructosyl peptide oxidase derived from *Phaeosphaeria nodorum* (SEQ ID NO: 38), the amino acid at "the position corresponding to position 62 in the amino acid sequence as shown in SEQ ID NO: 1" is serine at position 62. From the perspective of the amino acid sequence as shown in SEQ ID NO: 1, this can be recognized as the amino acid at the position corresponding to arginine at position 62 being serine, i.e., equivalent to the amino acid being substituted with serine. Accordingly, a naturally occurring amadoriase comprising an amino acid sequence in which the amino acid at the position corresponding to arginine at position 62 in the amino acid sequence as shown in SEQ ID NO: 1 is serine, such as the fructosyl peptide oxidase derived from *Phaeosphaeria nodorum* (SEQ ID NO: 38) is also, for the sake of convenience, encompassed within the scope of an amadoriase comprising amino acid substitution at a position corresponding to (a) arginine at position 62 in SEQ ID NO: 1, when the amino acid sequence is aligned with the amino acid sequence as shown in SEQ ID NO: 1, in the present specification.

According to an embodiment, the amadoriase of the present invention having improved specific activity (U/mg) on αF8P can comprise 1 or more, 2 or more, 3 or more, 4 or more, 5 or more, 6 or more, 7 or more, 8 or more, 9 or more, 10 or more, or 11 or more (e.g., 12, 11, or 10) amino acids at positions corresponding to the positions in the amino acid sequence as shown in SEQ ID NO: 1 selected from the group consisting of (a) to (l) below:

(a) the amino acid at a position corresponding to position 62 in SEQ ID NO: 1 is alanine, aspartic acid, asparagine, glutamine, glutamic acid, glycine, valine, leucine, isoleucine, cysteine, serine, methionine, threonine, or proline;

(b) the amino acid at a position corresponding to position 63 in SEQ ID NO: 1 is alanine, histidine, or glycine;

(c) the amino acid at a position corresponding to position 102 in SEQ ID NO: 1 is lysine;

(d) the amino acid at a position corresponding to position 106 in SEQ ID NO: 1 is alanine, lysine, or arginine;

(e) the amino acid at a position corresponding to position 110 in SEQ ID NO: 1 is leucine, tyrosine, phenylalanine, or histidine;

(f) the amino acid at a position corresponding to position 113 in SEQ ID NO: 1 is lysine or arginine;

(g) the amino acid at a position corresponding to position 355 in SEQ ID NO: 1 is serine;

(h) the amino acid at a position corresponding to position 419 in SEQ ID NO: 1 is lysine;

(i) the amino acid at a position corresponding to position 68 in SEQ ID NO: 1 is asparagine;

(j) the amino acid at a position corresponding to position 356 in SEQ ID NO: 1 is threonine;

(k) the amino acid at a position corresponding to position 64 in SEQ ID NO: 1 is glycine, serine, methionine, leucine, threonine, valine, or isoleucine; and (l) the amino acid at a position corresponding to position 99 in SEQ ID NO: 1 is serine.

(Auxiliary Substitution)

It has been reported that, when the amino acid at the position corresponding to position 60 in the amino acid sequence as shown in SEQ ID NO: 1 is serine, substitution thereof with glycine renders the amadoriase, which did not exhibit activity on αFVH prior to substitution, to exhibit activity on αFVH after substitution (see JP 2010-35469 A and WO 2012/018094). When an amadoriase used in the present invention comprises serine at the position corresponding to position 60 in the amadoriase sequence of SEQ ID NO: 1, accordingly, such serine may be substituted with glycine in advance. Alternatively, a wild-type amadoriase comprising a sequence in which the amino acid at the position corresponding to position 60 in the sequence of SEQ ID NO: 1 is glycine may be used to introduce mutations into positions corresponding to positions 64, 62, 63, 102, 106, 110, 113, 355, and 419 and positions 68 and 356 of SEQ ID NO: 1. Unless specified otherwise, an amadoriase comprising a sequence in which the amino acid at a position corresponding to position 60 in the sequence as shown in SEQ ID NO: 1 is glycine is encompassed within the scope of the amadoriase variant of the present invention. In the case of the amadoriase derived from *Aspergillus nidulans*, for example, the amino acid at position 59 in SEQ ID NO: 147 that corresponds to position 60 in SEQ ID NO: 1 is serine in the wild-type amadoriase. An amadoriase having this serine substituted with glycine (i.e., SEQ ID NO: 62) may be used as a basis amadoriase to obtain a variant of the present invention. The same applies to the amadoriase derived from *Penicillium janthinellum* (Pj) (SEQ ID NO: 123).

(Additional Auxiliary Substitutions-Mutations that Improve Surfactant Resistance)

The present inventors have confirmed that surfactant resistance of an amadoriase can be improved via substitution of amino acid residues of the amadoriase. The amadoriase of the present invention can, optionally, further comprise such amino acid substitution(s).

Examples of amino acid substitutions that can improve surfactant resistance include those at positions corresponding to the amino acids (1) to (14) below in the amino acid sequence as shown in SEQ ID NO: 1:

(1) substitution of asparagine at position 262 with, for example, histidine;

(2) substitution of valine at position 257 with, for example, cysteine, serine, or threonine;

(3) substitution of glutamic acid at position 249 with, for example, lysine or arginine;

(4) substitution of glutamic acid at position 253 with, for example, lysine or arginine;

(5) substitution of glutamine at position 337 with, for example, lysine or arginine;

(6) substitution of glutamic acid at position 340 with, for example, proline;

(7) substitution of aspartic acid at position 232 with, for example, lysine or arginine;

(8) substitution of aspartic acid at position 129 with, for example, lysine or arginine;

(9) substitution of aspartic acid at position 132 with, for example, lysine or arginine;

(10) substitution of glutamic acid at position 133 with, for example, alanine, methionine, lysine, or arginine;

(11) substitution of glutamic acid at position 44 with, for example, proline;

(12) substitution of glycine at position 256 with, for example, lysine or arginine;

(13) substitution of glutamic acid at position 231 with, for example, lysine or arginine;

(14) substitution of glutamic acid at position 81 with, for example, lysine or arginine.

It is sufficient that an amadoriase variant exhibiting improved surfactant resistance comprises at least one of the amino acid substitutions described above. An amadoriase variant may comprise a plurality of amino acid substitutions. For example, an amadoriase variant may comprise 1, 2, 3, 4, 5, 6, 7, 8, 9, 10, 11, 12, 13, or 14 of the amino acid substitutions described above.

In the present invention, the term "the position corresponding to position 44 in the amino acid sequence as shown in SEQ ID NO: 1" is the position corresponding to position 44 in the amadoriase sequence as shown in SEQ ID NO: 1, when the target amino acid sequence of an amadoriase is compared with the amino acid sequence of the amadoriase as shown in SEQ ID NO: 1. This can be specified by the aforementioned method.

The same applies to "the position corresponding to position 81 in the amino acid sequence as shown in SEQ ID NO: 1," "the position corresponding to position 133 in the amino acid sequence as shown in SEQ ID NO: 1," "the position corresponding to position 253 in the amino acid sequence as shown in SEQ ID NO: 1," "the position corresponding to position 256 in the amino acid sequence as shown in SEQ ID NO: 1," "the position corresponding to position 257 in the amino acid sequence as shown in SEQ ID NO: 1," "the position corresponding to position 262 in the amino acid sequence as shown in SEQ ID NO: 1," "the position corresponding to position 337 in the amino acid sequence as shown in SEQ ID NO: 1," "the position corresponding to position 340 in the amino acid sequence as shown in SEQ ID NO: 1," "the position corresponding to position 129 in the amino acid sequence as shown in SEQ ID NO: 1," "the position corresponding to position 132 in the amino acid sequence as shown in SEQ ID NO: 1," "the position corresponding to position 231 in the amino acid sequence as shown in SEQ ID NO: 1," "the position corresponding to position 232 in the amino acid sequence as shown in SEQ ID NO: 1," and "the position corresponding to position 249 in the amino acid sequence as shown in SEQ ID NO: 1."

Specifically, the amino acid at "the position corresponding to position 44 in the amino acid sequence as shown in SEQ ID NO: 1" is lysine at position 44 in the case of the amadoriase derived from *Eupenicillium terrenum*, it is proline at position 44 in the case of the ketoamine oxidase derived from *Pyrenochaeta* sp., it is proline at position 44 in the case of the ketoamine oxidase derived from *Arthrinium* sp., it is proline at position 44 in the case of the ketoamine oxidase derived from *Curvularia clavata*, it is proline at position 44 in the case of the ketoamine oxidase derived from *Neocosmospora vasinfecta*, it is leucine at position 44 in the case of the fructosyl amino acid oxidase derived from *Cryptococcus neoformans*, it is proline at position 44 in the case of the fructosyl peptide oxidase derived from *Phaeosphaeria nodorum*, it is proline at position 43 in the case of the fructosyl amino acid oxidase derived from *Aspergillus nidulans*, it is proline at position 43 in the case of the fructosyl peptide oxidase derived from *Emericella nidulans*, it is proline at position 44 in the case of the fructosyl amino acid oxidase derived from *Ulocladium* sp., and it is proline at position 44 in the case of the fructosyl amino acid oxidase derived from *Penicillium janthinelum*.

The amino acid at "the position corresponding to position 81 in the amino acid sequence as shown in SEQ ID NO: 1" is asparagine at position 81 in the case of the amadoriase derived from *Eupenicillium terrenum*, it is glutamic acid at position 81 in the case of the ketoamine oxidase derived from *Pyrenochaeta* sp., it is histidine at position 81 in the case of the ketoamine oxidase derived from *Arthrinium* sp., it is glutamic acid at position 81 in the case of the ketoamine oxidase derived from *Curvularia clavata*, it is asparagine at position 81 in the case of the ketoamine oxidase derived from *Neocosmospora vasinfecta*, it is asparagine at position 81 in the case of the fructosyl amino acid oxidase derived from *Cryptococcus neoformans*, it is glutamic acid at position 81 in the case of the fructosyl peptide oxidase derived from *Phaeosphaeria nodorum*, it is asparagine at position 80 in the case of the fructosyl amino acid oxidase derived from *Aspergillus nidulans*, it is asparagine at position 80 in the case of the fructosyl peptide oxidase derived from *Emericella nidulans*, it is glutamic acid at position 81 in the case of the fructosyl amino acid oxidase derived from *Ulocladium* sp., and it is asparagine at position 81 in the case of the fructosyl amino acid oxidase derived from *Penicillium janthinelum*.

The amino acid at "the position corresponding to position 133 in the amino acid sequence as shown in SEQ ID NO: 1" is glutamic acid at position 133 in the case of the amadoriase derived from *Eupenicillium terrenum*, it is glutamic acid at position 133 in the case of the ketoamine oxidase derived from *Pyrenochaeta* sp., it is alanine at position 133 in the case of the ketoamine oxidase derived from *Arthrinium* sp., it is glutamic acid at position 133 in the case of the ketoamine oxidase derived from *Curvularia clavata*, it is alanine at position 133 in the case of the ketoamine oxidase derived from *Neocosmospora vasinfecta*, it is glutamic acid at position 133 in the case of the fructosyl amino acid oxidase derived from *Cryptococcus neoformans*, it is glutamic acid at position 131 in the case of the fructosyl peptide oxidase derived from *Phaeosphaeria nodorum*, it is glutamic acid at position 132 in the case of the fructosyl amino acid oxidase derived from *Aspergillus nidulans*, it is glutamic acid at position 132 in the case of the fructosyl peptide oxidase derived from *Emericella nidulans*, it is lysine at position 133 in the case of the fructosyl amino acid oxidase derived from *Ulocladium* sp., and it is aspartic acid at position 133 in the case of the fructosyl amino acid oxidase derived from *Penicillium janthinelum*.

The amino acid at "the position corresponding to position 253 in the amino acid sequence as shown in SEQ ID NO: 1" is alanine at position 253 in the case of the amadoriase derived from *Eupenicillium terrenum*, it is alanine at position 251 in the case of the ketoamine oxidase derived from *Pyrenochaeta* sp., it is glutamic acid at position 253 in the case of the ketoamine oxidase derived from *Arthrinium* sp., it is glutamic acid at position 251 in the case of the ketoamine oxidase derived from *Curvularia clavata*, it is valine at position 253 in the case of the ketoamine oxidase derived from *Neocosmospora vasinfecta*, it is glutamic acid at position 253 in the case of the fructosyl amino acid oxidase derived from *Cryptococcus neoformans*, it is arginine at position 249 in the case of the fructosyl peptide oxidase derived from *Phaeosphaeria nodorum*, it is alanine at position 253 in the case of the fructosyl amino acid oxidase derived from *Aspergillus nidulans*, it is alanine at position 253 in the case of the fructosyl peptide oxidase derived from *Emericella nidulans*, it is glutamic acid at position 251 in the case of the fructosyl amino acid oxidase derived from *Ulocladium* sp., and it is glutamine at position 253 in the case of the fructosyl amino acid oxidase derived from *Penicillium janthinelum*.

The amino acid at "the position corresponding to position 256 in the amino acid sequence as shown in SEQ ID NO: 1" is asparagine at position 256 in the case of the amadoriase derived from *Eupenicillium terrenum*, it is aspartic acid at position 254 in the case of the ketoamine oxidase derived from *Pyrenochaeta* sp., it is glycine at position 256 in the case of the ketoamine oxidase derived from *Arthrinium* sp., it is asparagine at position 254 in the case of the ketoamine oxidase derived from *Curvularia clavata*, it is glycine at position 256 in the case of the ketoamine oxidase derived from *Neocosmospora vasinfecta*, it is glutamic acid at position 256 in the case of the fructosyl amino acid oxidase derived from *Cryptococcus neoformans*, it is asparagine at position 252 in the case of the fructosyl peptide oxidase derived from *Phaeosphaeria nodorum*, it is asparagine at position 256 in the case of the fructosyl amino acid oxidase derived from *Aspergillus nidulans*, it is asparagine at position 256 in the case of the fructosyl peptide oxidase derived from *Emericella nidulans*, it is asparagine at position 254 in the case of the fructosyl amino acid oxidase derived from *Ulocladium* sp., and it is aspartic acid at position 256 in the case of the fructosyl amino acid oxidase derived from *Penicillium janthinelum*.

The amino acid at "the position corresponding to position 257 in the amino acid sequence as shown in SEQ ID NO: 1" is valine at position 257 in the case of the amadoriase derived from *Eupenicillium terrenum*, it is threonine at position 255 in the case of the ketoamine oxidase derived from *Pyrenochaeta* sp., it is cysteine at position 257 in the case of the ketoamine oxidase derived from *Arthrinium* sp., it is valine at position 255 in the case of the ketoamine oxidase derived from *Curvularia clavata*, it is cysteine at position 257 in the case of the ketoamine oxidase derived from *Neocosmospora vasinfecta*, it is cysteine at position 257 in the case of the fructosyl amino acid oxidase derived from *Cryptococcus neoformans*, it is serine at position 253 in the case of the fructosyl peptide oxidase derived from *Phaeosphaeria nodorum*, it is threonine at position 257 in the case of the fructosyl amino acid oxidase derived from *Aspergillus nidulans*, it is threonine at position 257 in the case of the fructosyl peptide oxidase derived from *Emericella nidulans*, it is valine at position 255 in the case of the fructosyl amino acid oxidase derived from *Ulocladium* sp., and it is valine at position 257 in the case of the fructosyl amino acid oxidase derived from *Penicillium janthinelum*.

The amino acid at "the position corresponding to position 262 in the amino acid sequence as shown in SEQ ID NO: 1" is aspartic acid at position 262 in the case of the amadoriase derived from *Eupenicillium terrenum*, it is asparagine at position 260 in the case of the ketoamine oxidase derived from *Pyrenochaeta* sp., it is histidine at position 262 in the case of the ketoamine oxidase derived from *Arthrinium* sp., it is asparagine at position 260 in the case of the ketoamine oxidase derived from *Curvularia clavata*, it is histidine at position 262 in the case of the ketoamine oxidase derived from *Neocosmospora vasinfecta*, it is asparagine at position 262 in the case of the fructosyl amino acid oxidase derived from *Cryptococcus neoformans*, it is asparagine at position 258 in the case of the fructosyl peptide oxidase derived from *Phaeosphaeria nodorum*, it is aspartic acid at position 262 in the case of the fructosyl amino acid oxidase derived from *Aspergillus nidulans*, it is aspartic acid at position 262 in the case of the fructosyl peptide oxidase derived from *Emeri-

*cella nidulans*, it is asparagine at position 260 in the case of the fructosyl amino acid oxidase derived from *Ulocladium* sp., and it is aspartic acid at position 262 in the case of the fructosyl amino acid oxidase derived from *Penicillium janthinelum*.

The amino acid at "the position corresponding to position 337 in the amino acid sequence as shown in SEQ ID NO: 1" is lysine at position 337 in the case of the amadoriase derived from *Eupenicillium terrenum*, it is lysine at position 335 in the case of the ketoamine oxidase derived from *Pyrenochaeta* sp., it is glutamine at position 338 in the case of the ketoamine oxidase derived from *Arthrinium* sp., it is threonine at position 335 in the case of the ketoamine oxidase derived from *Curvularia clavata*, it is lysine at position 337 in the case of the ketoamine oxidase derived from *Neocosmospora vasinfecta*, it is lysine at position 337 in the case of the fructosyl amino acid oxidase derived from *Cryptococcus neoformans*, it is lysine at position 333 in the case of the fructosyl peptide oxidase derived from *Phaeosphaeria nodorum*, it is asparagine at position 337 in the case of the fructosyl amino acid oxidase derived from *Aspergillus nidulans*, it is asparagine at position 337 in the case of the fructosyl peptide oxidase derived from *Emericella nidulans*, it is threonine at position 335 in the case of the fructosyl amino acid oxidase derived from *Ulocladium* sp., and it is lysine at position 337 in the case of the fructosyl amino acid oxidase derived from *Penicillium janthinelum*.

The amino acid at "the position corresponding to position 340 in the amino acid sequence as shown in SEQ ID NO: 1" is glutamic acid at position 340 in the case of the amadoriase derived from *Eupenicillium terrenum*, it is glutamic acid at position 338 in the case of the ketoamine oxidase derived from *Pyrenochaeta* sp., it is glutamic acid at position 341 in the case of the ketoamine oxidase derived from *Arthrinium* sp., it is glutamic acid at position 338 in the case of the ketoamine oxidase derived from *Curvularia clavata*, it is proline at position 340 in the case of the ketoamine oxidase derived from *Neocosmospora vasinfecta*, it is glutamic acid at position 340 in the case of fructosyl amino acid oxidase derived from *Cryptococcus neoformans*, it is lysine at position 336 in the case of the fructosyl peptide oxidase derived from *Phaeosphaeria nodorum*, it is glutamic acid at position 340 in the case of the fructosyl amino acid oxidase derived from *Aspergillus nidulans*, it is glutamic acid at position 340 in the case of the fructosyl peptide oxidase derived from *Emericella nidulans*, it is glutamic acid at position 338 in the case of the fructosyl amino acid oxidase derived from *Ulocladium* sp., and it is glutamic acid at position 340 in the case of the fructosyl amino acid oxidase derived from *Penicillium janthinelum*.

The amino acid at "the position corresponding to position 129 in the amino acid sequence as shown in SEQ ID NO: 1" is glutamic acid at position 129 in the case of the amadoriase derived from *Eupenicillium terrenum*, it is aspartic acid at position 129 in the case of the ketoamine oxidase derived from *Pyrenochaeta* sp., it is aspartic acid at position 129 in the case of the ketoamine oxidase derived from *Arthrinium* sp., it is aspartic acid at position 129 in the case of the ketoamine oxidase derived from *Curvularia clavata*, it is aspartic acid at position 129 in the case of the ketoamine oxidase derived from *Neocosmospora vasinfecta*, it is serine at position 129 in the case of the fructosyl amino acid oxidase derived from *Cryptococcus neoformans*, it is aspartic acid at position 127 in the case of the fructosyl peptide oxidase derived from *Phaeosphaeria nodorum*, it is glutamic acid at position 128 in the case of the fructosyl amino acid oxidase derived from *Aspergillus nidulans*, it is glutamic acid at position 128 in the case of the fructosyl peptide oxidase derived from *Emericella nidulans*, it is aspartic acid at position 129 in the case of the fructosyl amino acid oxidase derived from *Ulocladium* sp., and it is glutamic acid at position 129 in the case of the fructosyl amino acid oxidase derived from *Penicillium janthinelum*.

The amino acid at "the position corresponding to position 132 in the amino acid sequence as shown in SEQ ID NO: 1" is aspartic acid at position 132 in the case of the amadoriase derived from *Eupenicillium terrenum*, it is aspartic acid at position 132 in the case of the ketoamine oxidase derived from *Pyrenochaeta* sp., it is aspartic acid at position 132 in the case of the ketoamine oxidase derived from *Arthrinium* sp., it is aspartic acid at position 132 in the case of the ketoamine oxidase derived from *Curvularia clavata*, it is glutamic acid at position 132 in the case of the ketoamine oxidase derived from *Neocosmospora vasinfecta*, it is aspartic acid at position 132 in the case of the fructosyl amino acid oxidase derived from *Cryptococcus neoformans*, it is aspartic acid at position 130 in the case of the fructosyl peptide oxidase derived from *Phaeosphaeria nodorum*, it is aspartic acid at position 131 in the case of the fructosyl amino acid oxidase derived from *Aspergillus nidulans*, it is aspartic acid at position 131 in the case of the fructosyl peptide oxidase derived from *Emericella nidulans*, it is aspartic acid at position 132 in the case of the fructosyl amino acid oxidase derived from *Ulocladium* sp., and it is aspartic acid at position 132 in the case of the fructosyl amino acid oxidase derived from *Penicillium janthinelum*.

The amino acid at "the position corresponding to position 231 in the amino acid sequence as shown in SEQ ID NO: 1" is glutamic acid at position 231 in the case of the amadoriase derived from *Eupenicillium terrenum*, it is glutamic acid at position 229 in the case of the ketoamine oxidase derived from *Pyrenochaeta* sp., it is glutamic acid at position 231 in the case of the ketoamine oxidase derived from *Arthrinium* sp., it is glutamic acid at position 229 in the case of the ketoamine oxidase derived from *Curvularia clavata*, it is glutamic acid at position 231 in the case of the ketoamine oxidase derived from *Neocosmospora vasinfecta*, it is glutamic acid at position 231 in the case of the fructosyl amino acid oxidase derived from *Cryptococcus neoformans*, it is histidine at position 227 in the case of the fructosyl peptide oxidase derived from *Phaeosphaeria nodorum*, it is glutamic acid at position 231 in the case of the fructosyl amino acid oxidase derived from *Aspergillus nidulans*, it is glutamic acid at position 231 in the case of the fructosyl peptide oxidase derived from *Emericella nidulans*, it is glutamine at position 229 in the case of the fructosyl amino acid oxidase derived from *Ulocladium* sp., and it is glutamic acid at position 231 in the case of the fructosyl amino acid oxidase derived from *Penicillium janthinelum*.

The amino acid at "the position corresponding to position 232 in the amino acid sequence as shown in SEQ ID NO: 1" is aspartic acid at position 232 in the case of the amadoriase derived from *Eupenicillium terrenum*, it is aspartic acid at position 230 in the case of the ketoamine oxidase derived from *Pyrenochaeta* sp., it is glutamic acid at position 232 in the case of the ketoamine oxidase derived from *Arthrinium* sp., it is aspartic acid at position 230 in the case of the ketoamine oxidase derived from *Curvularia clavata*, it is glutamic acid at position 232 in the case of the ketoamine oxidase derived from *Neocosmospora vasinfecta*, it is glycine at position 232 in the case of the fructosyl amino acid oxidase derived from *Cryptococcus neoformans*, it is glutamic acid at position 228 in the case of the fructosyl peptide oxidase derived from *Phaeosphaeria nodorum*, it is glutamic acid at position 232 in the case of the fructosyl amino acid oxidase derived from *Aspergillus nidulans*, it is glutamic acid at position 232 in the case of the fructosyl peptide oxidase derived from *Emericella nidulans*, it is aspartic acid at position 230 in the case of the fructosyl amino acid oxidase derived from *Ulocladium* sp., and it is aspartic acid at position 232 in the case of the fructosyl amino acid oxidase derived from *Penicillium janthinelum*.

The amino acid at "the position corresponding to position 249 in the amino acid sequence as shown in SEQ ID NO: 1" is lysine at position 249 in the case of the amadoriase derived from *Eupenicillium terrenum*, it is lysine at position 247 in the case of the ketoamine oxidase derived from *Pyrenochaeta* sp., it is histidine at position 249 in the case of the ketoamine oxidase derived from *Arthrinium* sp., it is glutamic acid at position 247 in the case of the ketoamine oxidase derived from *Curvularia clavata*, it is glutamic acid at position 249 in the case of the ketoamine oxidase derived from *Neocosmospora vasinfecta*, it is glutamic acid at position 249 in the case of the fructosyl amino acid oxidase derived from *Cryptococcus neoformans*, it is glutamic acid at position 245 in the case of the fructosyl peptide oxidase derived from *Phaeosphaeria nodorum*, it is alanine at position 249 in the case of the fructosyl amino acid oxidase derived from *Aspergillus nidulans*, it is alanine at position 249 in the case of the fructosyl peptide oxidase derived from *Emericella nidulans*, it is serine at position 247 in the case of the fructosyl amino acid oxidase derived from *Ulocladium* sp., and glutamine at position 249 in the case of the fructosyl amino acid oxidase derived from *Penicillium janthinelum*.

In the present description, mutations at the positions described above (at positions 44, 133, 253, 257, 262, 337, 340, 249, 232, 129, 132, 256, 231, and 81) are also referred to as "mutations that improve surfactant resistance of an amadoriase" or "amino acid substitutions that improve surfactant resistance of an amadoriase." According to an embodiment, the amadoriase of the present invention can further comprise a mutation that improves surfactant resistance, in addition to mutations that alter substrate specificity.

(Further Auxiliary Deletion-Deletion of 3 Amino Acid Residues from the Carboxyl Terminus)

In the past, the present inventors reported that heat stability of an amadoriase can be improved by deletion of 3 amino acid residues from the carboxyl terminus of the amadoriase (see WO 2013/100006, all of the contents as disclosed therein are incorporated herein by reference in their entirety). According to an embodiment, the amadoriase of the present invention may further involve deletion of 3 amino acid residues from the carboxyl terminus, in addition to the substitution described above.

(Position Corresponding to Deletion at the Carboxyl Terminus)

The "positions corresponding to 3 amino acid residues from the carboxyl terminus of the amino acid sequence as shown in SEQ ID NO: 1" refers to the positions corresponding to 3 amino acid residues from the carboxyl terminus in the amino acid sequence as shown in SEQ ID NO: 1, when the amino acid sequence of an amadoriase is compared with the amino acid sequence of the amadoriase as shown in SEQ ID NO: 1. In the amadoriase derived from the genus *Coniochaeta*, the sequence of the 3 residues at these positions consist of proline at position 435, lysine at position 436, and leucine at position 437. The amino acid sequence at positions corresponding thereto can be identified on the basis of FIG. 1 in which the amino acid sequences are aligned in the manner described above.

Specifically, 3 amino acids at the carboxyl terminus are alanine at position 435, histidine at position 436, and leucine at position 437 in the case of the amadoriase derived from *Eupenicillium terrenum*, alanine at position 438, lysine at position 439, and leucine at position 440 in the case of the ketoamine oxidase derived from *Pyrenochaeta* sp., histidine at position 450, lysine at position 451, and leucine at position 452 in the case of the ketoamine oxidase derived from *Arthrinium* sp., serine at position 438, lysine at position 439, and leucine at position 440 in the case of the ketoamine oxidase derived from *Curvularia clavata*, alanine at position 435, asparagine at position 436, and leucine at position 437 in the case of the fructosyl peptide oxidase derived from *Phaeosphaeria nodorum*, alanine at position 436, lysine at position 437, and methionine at position 438 in the case of the fructosyl amino acid oxidase derived from *Aspergillus nidulans*, alanine at position 436, lysine at position 437, and methionine at position 438 in the case of the fructosyl peptide oxidase derived from *Emericella nidulans*, alanine at position 439, lysine at position 440, and leucine at position 441 in the case of the fructosyl amino acid oxidase derived from *Ulocladium* sp., and alanine at position 435, lysine at position 436, and leucine at position 437 in the case of the fructosyl amino acid oxidase derived from *Penicillium janthinelum*.

In the present description, a deletion of the amino acid residues from the carboxyl terminus in an amadoriase is also referred to as a "deletion that improves heat stability of an amadoriase." According to an embodiment, the amadoriase of the present invention can further comprise a deletion that improves heat stability, in addition to a mutation that alters substrate specificity and a mutation that improves surfactant resistance.

(Production of Amadoriase)

In order to produce the amadoriase obtained as described above using a strain having the ability to produce such amadoriase, the strain may be cultured by a conventional solid culture method, although liquid culture is preferable.

Thus, the present invention provides a method for producing an amadoriase comprising a step of culturing a strain capable of producing an amadoriase under conditions where the amadoriase protein can be expressed and a step of isolating an amadoriase from a culture product or culture solution. In such method, a host cell transformed with a vector comprising a gene encoding the amadoriase of the present invention can be used. In the present specification, conditions where the amadoriase protein can be expressed refers to conditions in which an amadoriase gene is transcribed and translated, and a polypeptide encoded by such gene is produced.

Examples of media to culture the aforementioned strains include media prepared by adding 1 or more inorganic salts selected from among, for example, sodium chloride, monopotassium phosphate, dipotassium phosphate, magnesium sulfate, magnesium chloride, ferric chloride, ferric sulfate, and manganese sulfate to 1 or more nitrogen sources, such as a yeast extract, tryptone, peptone, a meat extract, a corn steep liquor, and a leaching solution of soybean or wheat bran, and adequately adding saccharine materials, vitamins, and the like thereto, where necessary.

Further, a substrate with which the amadoriase can react or a compound similar thereto, such as a glycated protein, including a glycated amino acid, a glycated peptide, a degradation product of glycated protein, glycated hemoglobin, or glycated albumin, may be added to the media, so as to increase the amount of the target enzyme to be produced.

It is appropriate to adjust the initial pH of the media to 7 to 9. Culture is preferably performed at 20° C. to 42° C., and more preferably at about 25° C. to 37° C. for 4 to 24 hours, and further preferably at about 25° C. to 37° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove solid content, and nucleic acid is removed with the aid of streptomycin sulfate, protamine sulfate, or manganese sulfate, according to need. Ammonium sulfate, alcohol, acetone, or the like is added thereto, so as to fractionate the solution, and sediments are then collected to obtain the crude enzymes of the amadoriases.

The purified amadoriase enzyme preparation can be obtained from the crude enzyme of the aforementioned amadoriase by a method appropriately selected from: gel filtration methods using Sephadex, Superdex, or Ultrogel; adsorption-elution methods using ion exchange carriers, hydrophobic carriers, or hydroxyapatite; electrophoretic methods using polyacrylamide gels, etc.; sedimentation methods such as sucrose density-gradient centrifugation; affinity chromatographic methods; and fractionation methods using a molecular sieve membrane, a hollow-fiber membrane, etc. Alternatively, the aforementioned methods can adequately be performed in combination. The amadoriase of interest can thus be obtained.

(Reactivity of the Amadoriase of the Present Invention on HbA1c)

The amadoriase obtained by the means described above can act directly on HbA1c as a result of mutation in the amino acid sequence caused by genetic modification or other means.

The amadoriase according to an embodiment of the present invention has improved specific activity on αF8p, compared with an amadoriase before modification.

When the specific activity (U/mg) of an amadoriase before modification on αF8P is designated as 1, the specific activity of the modified amadoriase according to the present invention can be 1.1 or higher, 1.2 or higher, 1.3 or higher, 1.4 or higher, 1.5 or higher, 1.6 or higher, 1.7 or higher, or 1.75 or higher.

Examples of amadoriases having improved specific activity according to the present invention include CFP-T7-H38 and CFP-DH3. Such amadoriases have improved reactivity with αF8P, compared with existing amadoriases (conventional amadoriases). Accordingly, such amadoriases enable rapid measurement of HbA1c without the use of proteases and thus are highly useful at the industrial level. In addition, the amadoriase according to the present invention can be used for measurement of αF8P generated upon treatment of HbA1c with Lys-C protease or the like, and thus highly useful at the industrial level.

(Method of Measuring Activity of Amadoriase)

The activity of an amadoriase can be measured by various methods. An example of the method of measuring the activity of an amadoriase as used herein is described below.

Examples of major methods for measuring the enzyme activity of the amadoriase of the present invention include a method of measuring the amount of hydrogen peroxide generated by enzyme reactions and a method of measuring the amount of oxygen consumed in enzyme reactions. An example of the method of measuring the amount of hydrogen peroxide is described below.

For measurement of the activity of the amadoriase of the present invention, unless specified otherwise, αF8P is used as the substrate. αFV, αFVH, αF6P, HbA1c, or the like can also be used as a substrate where necessary. Regarding enzyme titer, unless specified otherwise, the amount of enzyme needed to generate 1 μmol of hydrogen peroxide per minute, when carrying out measurement using αF8P as the substrate, is defined as 1 U.

Further, specific activity (U/mg) is enzyme titer (U) per mg of an enzyme. When the specific activity of a particular enzyme on αF8P is 0.1 U/mg or greater, for example, the amount of an enzyme may be increased 10-fold, to achieve an enzyme titer that is the same as the enzyme titer of an enzyme having specific activity of 1 U/mg.

When the amadoriase "has reactivity with αF8P" herein, specific activity thereof on αF8P (U/mg) may be 0.1 U/mg or greater, 0.2 U/mg or greater, 0.3 U/mg or greater, 0.4 U/mg or greater, 0.5 U/mg or greater, 0.6 U/mg or greater, 0.7 U/mg or greater, 0.8 U/mg or greater, or 0.9 U/mg or greater, such as 1 U/mg or greater, 2 U/mg or greater, 3 U/mg or greater, or 4 U/mg or greater, unless specified otherwise.

The amadoriase according to an embodiment of the present invention has specific activity (U/mg) of 0.1 U/mg or greater, 0.5 U/mg or greater, 1 U/mg or greater, 2 U/mg or greater, 3 U/mg or greater, 4 U/mg or greater, 5 U/mg or greater, or 6 U/mg or greater on αF8P.

In one embodiment, the amadoriase according to the present invention has the specific activity as described above as well as surfactant tolerance. Surfactant tolerance can be evaluated by measuring the residual activity after treatment with a surfactant, compared with the activity before treatment with a surfactant. The residual activity can be represented in terms of (%) indicating the ratio of activity after the surfactant treatment relative to the activity before the surfactant treatment (regarded as 100). The residual activity (%) of the amadoriase having surfactant tolerance according to the present invention can be 5% or higher, 10% or higher, 15% or higher, 20% or higher, 25% or higher, 30% or higher, 35% or higher, 40% or higher, 50% or higher, 60% or higher, 70% or higher, 80% or higher, 90% or higher, 95% or higher, or 99% or higher after the surfactant treatment.

A glycated peptide, such as αFV or αFVH, synthesized and purified with reference to the method of, for example, Sakaue et al. can be used (see JP 2001-95598 A). Upon treatment of glycated hemoglobin (HbA1c) with endoproteinase Glu-C, for example, α-glycated hexapeptide derived from the β chain subunit of glycated hemoglobin (HbA1c) (i.e., fructosyl Val-His-Leu-Thr-Pro-Glu) is released (Clin. Chem., 43, 1994-1951, 1997), and it can be used as an αF6P substrate. Also, αF8P and αF6P provided as synthetic substrates (manufactured by Peptide Institute, Inc.) can be used.

A: Preparation of Reagents (Preparation Example of Reagent Used for Measuring Activity of Amadoriase on αF8P, αF6P, αFVH, or αFV)

(Reagent 1) 0.1 M Phosphate Buffer (pH 6.5) Containing 5 U/Ml Peroxidase and 0.49 mM 4-aminoantipyrine Peroxidase (5.0 kU, manufactured by Kikkoman Corporation) and 100 mg of 4-aminoantipyrine (manufactured by Wako Pure Chemical Industries, Ltd.) are dissolved in a 0.1 M potassium phosphate buffer (pH 6.5), and the volume of the solution is fixed to 1,000 ml.

(Reagent 2) 15 mM TOOS Solution 500 mg of TOOS (N-ethyl-N-(2-hydroxy-3-sulfopropyl)-m-toluidine sodium, manufactured by Dojindo Laboratories) is dissolved in ion-exchange water, and the volume of the solution is fixed to 100 ml.

(Reagent 3) Substrate Solution (30 mM; Final Concentration: 1 mM)

αF8P (334 mg, manufactured by Peptide Institute, Inc.), αF6P (257.1 mg, manufactured by Peptide Institute, Inc.), αFVH (124.9 mg, manufactured by Kikkoman Corporation), or αFV (83.8 mg, manufactured by Kikkoman Corporation) is dissolved in ion-exchange water, and the volume of the solution is fixed to 10 ml.

B: Method for Measurement of Activity (Example of Method for Measurement of Activity of Amadoriase on αF8P, αF6P, αFVH, or αFV)

Reagent 1 (2.7 ml), 100 μl of Reagent 2, and 100 μl of an enzyme solution are mixed, and the mixture is preliminarily heated at 37° C. for 5 minutes. Subsequently, 100 μl of Reagent 3 is added, the resultant is thoroughly mixed, and the absorbance at 555 nm is then measured using a spectrophotometer (U-3010A, manufactured by Hitachi High-Technologies) with the elapse of time to determine the change in absorbance per minute (ΔAs) at 555 nm. A control solution is prepared in the manner as described above, except that 100 μl of ion-exchange water is added instead of 100 μl of Reagent 3, and the change in absorbance per minute (ΔA0) at 555 nm thereof is determined. The number of micromoles of hydrogen peroxide generated per minute at 37° C. is calculated using the equation shown below in terms of the unit of activity (U) in the enzyme solution.

$$\text{Activity (U/ml)} = \{(\Delta As - \Delta A0) \times 3.0 \times df\}/(39.2 \times 0.5 \times 0.1)$$

ΔAs: the change in absorbance of the reaction solution per minute

ΔA0: the change in absorbance of the control solution per minute 39.2: millimole absorbance index of quinoneimine dye generated by the reaction ($mM^{-1} \cdot cm^{-1}$)

0.5: number of moles of quinoneimine dye generated by 1 mol of hydrogen peroxide df: dilution factor (Example of Method of Quantification of Heat-Treated HbA1c)

Reagents for measurement of HbA1c described below are prepared.

Sample: HbA1c Solution

The certified reference material for measurement of HbA1c, JCCRM-423 (Reference Material Institute for Clinical Chemistry Standards)

Total hemoglobin concentration: 133 g/l

Three HbA1c concentration levels (NGSP levels: about 5.6%, about 7.7%, and about 10.5%)

Reagent A1: Sample Pre-Treatment Solution 5.0% n-dodecyl-β-D-maltoside (Dojindo Laboratories)

Reagent A2: Sample Pre-Treatment Solution 5.0% n-tetradecyl-β-D-maltoside (Sigma-Aldrich Co. LLC.)

Reagent B: Leucodye, Peroxidase Solution 150 mM potassium phosphate buffer (pH 6.5)

0.30 mM N-(carboxymethylaminocarbonyl)-4,4'-bis(dimethylamino)diphenylamine sodium (DA-64, Wako Pure Chemical Industries, Ltd.)

15 U/ml peroxidase (Kikkoman Corporation)

Reagent C1: Amadoriase Solution 120 mM potassium phosphate buffer (pH 6.5)

120 U/ml amadoriase of the present invention.

(Example of Method for Measurement of Activity of Amadoriase on HbA1c)

A sample diluted 30 fold with Reagent A1 or Reagent A2 (also referred to as a "sample diluent" herein) is incubated at high temperature for a given period of time, for example, at 98° C. for 2 minutes, 25 μl of the sample diluent is added to 50 μl of Reagent B, the resultant is incubated at 37° C. for 5 minutes, 25 μl of Reagent C1 is added thereto, and quantification of hydrogen peroxide generated upon oxidation of the HbA1c β-chain amino terminus is allowed to proceed at 37° C. for 5 minutes. When hydrogen peroxide is generated in the solution, a leucodye develops color by the action of peroxidase, and the absorbance of light at 751 nm increases. On the basis of the results attained depending on the HbA1c concentration in the sample, the HbA1c concentration in the sample (i.e., the NGSP level) and a difference in the absorbance of light at 751 nm before and after hydrogen peroxide quantification (ΔA) can be plotted on a chart.

ΔA is calculated in accordance with the equation below.

$$\Delta A = (\text{absorbance 5 minutes after the addition of Reagent } C1) - (\text{absorbance immediately before the addition of Reagent } C1 \times 0.75)$$

According to the example above, the volume of the reaction solution is increased 1.33 fold with the addition of Reagent C1. Accordingly, the value attained by multiplying the absorbance immediately before the addition of Reagent C1 by 0.75 is regarded as the absorbance immediately after the addition of Reagent C1.

(Example of Method for Quantification of Acid-Treated HbA1c)

Reagents for measurement of HbA1c having the compositions described below are prepared and HbA1c is measured with the use of Bio Majesty JCA-BM1650 (JEOL Ltd.).

Sample: HbA1c Solution

The certified reference material for measurement of HbA1c, JCCRM-423 (Reference Material Institute for Clinical Chemistry Standards)

Total hemoglobin concentration: 133 g/l

Three HbA1c concentration levels (NGSP levels: about 5.6%, about 7.7%, and about 10.5%)

Reagent D: Sample Pre-Treatment Solution 8.3% n-dodecyl-β-D-maltoside (Dojindo Laboratories) or polyoxyethylene (20) cetyl ether (Brij58, Wako Pure Chemical Industries, Ltd.)

0.1 M hydrochloric acid

Reagent E: Leucodye Solution 30 mM Tris-potassium phosphate buffer (pH 9.0)

290 mM potassium phosphate buffer (pH 6.5)

0.16 mM N-(carboxymethylaminocarbonyl)-4,4'-bis(dimethylamino)diphenylamine sodium (DA-64, Wako Pure Chemical Industries, Ltd.)

Reagent F1: Peroxidase, amadoriase solution 100 mM potassium phosphate buffer (pH 6.5)

40 U/ml peroxidase (Kikkoman Corporation)

180 U/ml amadoriase of the present invention (e.g., CFP-T7-H35)

A sample diluted 30 fold with Reagent D (25 μl) is added to 125 μl of Reagent E, the mixture is incubated at 37° C. for 5 minutes, 50 μl of Reagent F1 is added thereto, and quantification of hydrogen peroxide generated upon oxidation of the HbA1c β-chain amino terminus is allowed to proceed at 37° C. for 5 minutes.

For example, ΔA can be calculated in accordance with the equation below.

ΔA=(absorbance 5 minutes after the addition of Reagent F1)−(absorbance immediately before the addition of Reagent F1×0.75)

(Example of Method of Quantification of Surfactant-Treated HbA1c)

Reagents for measurement of HbA1c having the compositions described below are prepared and HbA1c is measured with the use of Bio Majesty JCA-BM1650 (JEOL Ltd.).

Sample: HbA1c Solution

The certified reference material for measurement of HbA1c, JCCRM-423 (Reference Material Institute for Clinical Chemistry Standards)

Total hemoglobin concentration: 133 g/l

Three HbA1c concentration levels (NGSP levels: about 5.6%, about 7.7%, and about 10.5%)

Reagent G1: Sample Pre-Treatment Solution
    0.80% tetradecyltrimethylammonium bromide (Tokyo Chemical Industry Co., Ltd.)

Reagent G2: Sample Pre-Treatment Solution
    0.70% hexadecyltrimethylammonium bromide (Tokyo Chemical Industry Co., Ltd.)

Reagent H1: Leucodye Solution
    120 mM MOPS-NaOH buffer (pH 6.5)
    1.6% n-dodecyl-β-D-maltoside (Dojindo Laboratories)
    0.16 mM N-(carboxymethylaminocarbonyl)-4,4'-bis(dimethylamino)diphenylamine sodium (DA-64, Wako Pure Chemical Industries, Ltd.)

Reagent H2: Leucodye Solution
    120 mM PIPES-NaOH buffer (pH 6.5)
    1.6% n-dodecyl-β-D-maltoside (Dojindo Laboratories)
    0.16 mM N-(carboxymethylaminocarbonyl)-4,4'-bis(dimethylamino)diphenylamine sodium (DA-64, Wako Pure Chemical Industries, Ltd.)

Reagent I1: Peroxidase, amadoriase solution
    100 mM MOPS-NaOH buffer (pH 6.5)
    40 U/ml peroxidase (Kikkoman Corporation)
    160 U/ml amadoriase of the present invention (e.g., CFP-DH2)

Reagent I2: Peroxidase, Amadoriase Solution
    100 mM PIPES-NaOH buffer (pH 6.5)
    40 U/ml peroxidase (Kikkoman Corporation)
    160 U/ml amadoriase of the present invention A sample diluted 25 fold with Reagent G1 (25 μl) is added to 125 μl of Reagent H1, the mixture is incubated at 37° C. for 5 minutes, 50 μl of Reagent I1 is added thereto, and quantification of hydrogen peroxide generated upon oxidation of the HbA1c β-chain amino terminus is allowed to proceed at 37° C. for 5 minutes. When the sample is diluted 25 fold with Reagent G2, 25 μl of the diluted sample is added to 125 μl of Reagent H2, the mixture is incubated at 37° C. for 5 minutes, 50 μl of Reagent I2 is added thereto, and quantification of hydrogen peroxide generated upon oxidation of the HbA1c β-chain amino terminus is allowed to proceed at 37° C. for 5 minutes.

For example, ΔA can be calculated in accordance with the equation below.

ΔA=(absorbance 5 minutes after the addition of Reagent I1 or I2)−(absorbance immediately before the addition of Reagent I1 or I2×0.75)

(Measurement of HbA1c)

HbA1c oxidase (amadoriase) is allowed to react with the sample containing HbA1c. The duration of the reaction may be, for example, 5 seconds or longer, 10 seconds or longer, 20 seconds or longer, 30 seconds or longer, or 1 minute or longer to shorter than 180 minutes, shorter than 150 minutes, shorter than 120 minutes, shorter than 60 minutes, shorter than 50 minutes, shorter than 40 minutes, shorter than 30 minutes, shorter than 20 minutes, shorter than 15 minutes, shorter than 10 minutes, or shorter than 5 minutes. For example, the duration may be 0.5 minutes to less than 120 minutes, 0.5 minutes to less than 60 minutes, 1 minute to less than 30 minutes, 1 minute to less than 20 minutes, 1 minute to less than 15 minutes, 1 minute to less than 10 minutes, or 1 minute to less than 5 minutes. If the duration of the reaction is too short, HbA1c in the sample cannot be sufficiently measured and measurement cannot be performed satisfactorily. If the duration of the reaction is too long, in contrast, the duration of measurement is prolonged, and measurement efficiency becomes poor. In addition thereto, the sample and the reagent are exposed to the measurement conditions for a long period of time, and this disadvantageously causes problems such as degradation or denaturation of the substrate in the sample or components of the reagent. In microassay systems, in particular, the sample may be dehydrated with the elapse of time, the volume of the sample may be decreased, and a change in concentrations may occur, which may cause errors. By allowing HbA1c oxidase to react with the sample for 0.5 to 60 minutes, and preferably 1 to 50 minutes, 1 to 40 minutes, 1 to 30 minutes, 1 to 20 minutes, 1 to 15 minutes, 1 to 10 minutes, or 1 to 5 minutes, HbA1c can be measured rapidly and satisfactorily. While the reaction temperature may vary depending on the optimal temperature for the enzyme being used, it is, for example, from 20° C. to 45° C., and a temperature that is generally employed for an enzymatic reaction can adequately be selected.

The preferable amount of an amadoriase to be used in the present invention may vary depending on the amount of the substrate contained in the sample solution. For example, the amadoriase may be added, so as to adjust the final concentration of the amadoriase to 0.1 to 50 U/ml, and preferably 0.2 to 10 U/ml in the solution. The pH level is preferably adjusted to an adequate level for the reaction with the use of a buffer by taking the optimal pH level for the amadoriase into consideration, although the pH level is not particularly limited, provided that the amadoriase is capable of reaction. For example, the pH level is preferably 3 to 11, and particularly preferably 5 to 9, such as 6 to 8.

In the method of measurement according to the present invention, it is preferable to use various types of buffers, according to need, in order to adjust and/or maintain the pH level for the purpose of stabilization of an enzyme or a reagent or improvement in reactivity. Examples of buffers that can be used include N-[tris(hydroxymethyl)methyl]glycine, phosphate, acetate, carbonate, tris(hydroxymethyl)-aminomethane, borate, citrate, dimethyl glutamate, Tricine, HEPES, MES, Bis-Tris, ADA, PIPES, ACES, MOPSO, BES, MOPS, TES, DIPSO, TAPSO, POPSO, HEPPSO, EPPS, Tricine, Bicine, TAPS, phthalate, and tartrate. In addition, solubilizers, stabilizers, reaction-improving agents, or, as HbA1c denaturation agents, surfactants (e.g., n-octyl-β-D-glucoside, n-octyl-β-D-thioglucoside, n-dodecyl-β-D-maltoside, n-tetradecyl-β-D-maltoside, n-octyl-β-D-maltoside, 1-dodecylpyridinium salt, hexadecyltrimethylammonium salt, tetradecyltrimethylammonium salt, dodecyltrimethylammonium salt, triton X-100, Brij 35, Brij 58, Tween 80, cholate, n-heptyl-β-D-thioglucoside, 3-oxatridecyl-α-D-mannoside, n-nonyl-β-D-thiomaltoside, n-decyl-β-D-maltoside, n-undecyl-β-D-maltoside, trehalose C8, trehalose C10, trehalose C12, trehalose C14, trehalose C16, BIGCHAP, deoxy-BIGCHAP, MEGA-8, MEGA-9, MEGA-10, hexadecylpyridinium salt, octadecyltrimethylammonium salt, decyltrimethylammonium salt, nonyltrimethylammonium salt, octyltrimethylammonium salt, hexyltrimethylammonium salt, or sodium dodecyl sulfate), reducing agents (e.g., dithiothreitol, mercaptoethanol, or L-cysteine), bovine serum albumin, or saccharides (e.g., glycerine, lactose, or sucrose), may be adequately added, according to need.

The surfactant used in the present invention is not particularly limited, provided that the method of measuring HbA1c of the present invention can be carried out in the presence of the surfactant, and examples of surfactants include a nonionic surfactant and an ionic surfactant, such as a cationic surfactant, an anionic surfactant, and an amphoteric surfactant. The term "surfactant" used herein refers to 1 or more surfactants, unless specified otherwise.

Examples of the nonionic surfactant include polyoxyethylene alkyl ether, sorbitan fatty acid ester, alkyl polyglucoside, fatty acid diethanol amide, and alkyl monoglyceryl ether.

Examples of the cationic surfactant include alkyltrimethylammonium salt, dialkyldimethylammonium salt, alkylbenzyldimethylammonium salt, pyridinium salt, such as alkylpyridinium salt, phosphonium salt, such as alkylphosphonium salt, imidazolium salt, such as alkylimidazolium salt, and isoquinolinium salt, such as alkylisoquinolinium salt.

Examples of the cationic surfactant of the present invention include quaternary ammonium salt (I), pyridinium salt (II), and phosphonium salt (III) represented by the following general formulae:

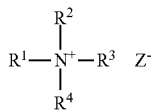

wherein $R^1$ to $R^4$, which may be the same or different, each represent a substituted or unsubstituted $C_1$ to $C_{20}$ alkyl, alkenyl, aryl, or benzyl; and $Z^-$ represents a monovalent anion;

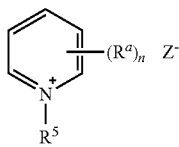

wherein $R^5$ represents substituted or unsubstituted $C_1$ to $C_{20}$ alkyl; each $R^a$, which may be the same or different, represents a hydrogen atom or a substituted or unsubstituted $C_1$ to $C_{20}$ alkyl, alkenyl, aryl or benzyl; n represents an integer of 1 to 5; and $Z^-$ represents a monovalent anion; and

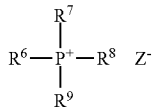

wherein, $R^6$ to $R^9$, which may be the same or different, each represent substituted or unsubstituted $C_1$ to $C_{20}$ alkyl, alkenyl, aryl or benzyl; and $Z^-$ represents a monovalent anion.

Examples of the quaternary ammonium salt include octyltrimethylammonium chloride (OTAC), octyltrimethylammonium bromide (OTAB), decyltrimethylammonium chloride, decyltrimethylammonium bromide (DTAB), dodecyltrimethylammonium chloride, dodecyltrimethylammonium bromide, tetradecyltrimethylammonium chloride (TTAC), tetradecyltrimethylammonium bromide (TTAB), hexadecyltrimethylammonium chloride (CTAC), hexadecyltrimethylammonium bromide, octadecyltrimethylammonium chloride, octadecyltrimethylammonium bromide (STAB), eicosyltrimethylammonium chloride, eicosyltrimethylammonium bromide, benzyldodecyldimethylammonium chloride, benzyldodecyldimethylammonium bromide (BDDAB), benzyltetradecyldimethylammonium chloride (BDTAC), benzyltetradecyldimethylammonium bromide, benzylcetyldimethylammonium chloride (BCDAC), benzyl cetyl dim ethyl ammonium bromide, dioctyldimethyl ammonium chloride, and dioctyldimethylammonium bromide.

Examples of the pyridinium salt include 1-decylpyridinium chloride, 1-decylpyridinium bromide, 1-dodecylpyridinium chloride (1-DPC), 1-dodecylpyridinium bromide, 1-tetradecylpyridinium chloride, 1-tetradecylpyridinium bromide, 1-hexadecylpyridinium chloride (1-CPC), 1-hexadecylpyridinium bromide (1-CPB), N-cetyl-2-methylpyridinium chloride, N-cetyl-2-methylpyridinium bromide, N-cetyl-3-methylpyridinium chloride, N-cetyl-3-methylpyridinium bromide, N-cetyl-4-methylpyridinium chloride (4Me-1-CPC), N-cetyl-4-methylpyridinium bromide, 1-octadecylpyridinium chloride, 1-octadecylpyridinium bromide, 1-eicosylpyridinium chloride, and 1-eicosylpyridinium bromide.

Examples of the phosphonium salt include tetraethylphosphonium chloride, tetraethylphosphonium bromide, tributylmethylphosphonium chloride, tributylmethylphosphonium bromide, tributylmethylphosphonium iodide, tetrabutylphosphonium chloride, tetrabutylphosphonium bromide, tetra-n-octylphosphonium chloride, tetra-n-octylphosphonium bromide, tributyldodecylphosphonium chloride, tributyldodecylphosphonium bromide, tributylhexadecylphosphonium chloride, tributylhexadecylphosphonium bromide (TBCPB), methyltriphenylphosphonium chloride, methyltriphenylphosphonium bromide, methyltriphenylphosphonium iodide, tetraphenylphosphonium chloride, and tetraphenylphosphonium bromide.

Anion $Z^-$ to be paired with a cationic surfactant can be, for example, $Cl^-$, $Br^-$, or $I^-$.

Examples of the anionic surfactant include linear alkylbenzene sulfonate, alkyl sulfate, alpha-olefin sulfonate, polyoxyethylene alkyl ether sulfate, α-sulfo fatty acid ester salt, and alkali metal salt of natural fatty acid. An example of such surfactant is sodium dodecyl sulfate (SDS).

Examples of the amphoteric surfactant include alkyl dimethyl amine oxide and alkylcarboxybetaine.

The present invention provides a method for measurement of HbA1c by measuring the amount of substances produced or consumed by the reaction of an amadoriase. An example of a product that can be easily measured and is preferable as a target of measurement is hydrogen peroxide. Hydrogen peroxide generated by the action of the amadoriase may be detected with the use of a color substrate or the like. Examples of color substrates used in the present invention include, in addition to 4-aminoantipyrine, ADOS (N-ethyl-N-(2-hydroxy-3-sulfopropyl)-m-anisidine), ALOS (N-ethyl-N-(2-hydroxy-3-sulfopropyl)aniline), TOOS (N-ethyl-N-(2- hydroxy-3-sulfopropyl)-m-toluidine sodium), DA-67 (10-(carboxymethylaminocarbonyl)-3,7-bis(dimethyl amino)-phenothiazine), and DA-64 (N-(carboxymethylaminocarbonyl)-4,4'-bis(dimethylamino)-diphenylamine). ADO S, ALOS, and TOOS develop color when condensed with 4-aminoantipyrine. DA-64 and DA-67 are each able to develop color alone without 4-aminoantipyrine. In either case, color development is catalyzed by peroxidase. In general, it is preferable that measurement of hydrogen peroxide be carried out simultaneously with the step of generating hydrogen peroxide, and it is preferable that measurement be allowed to proceed simultaneously with the reaction with an amadoriase. An example of the substance consumed by the reaction to be measured is dissolved oxygen, and the amount of dissolved oxygen in the reaction solution can be measured with the use of a dissolved oxygen meter or the like.

The present invention provides a reagent for measurement of HbA1c comprising the amadoriase described above and a reagent for measurement of hydrogen peroxide to which a buffer or the like is added according to need. Such reagent can be adequately supplemented with various known components, such as a surfactant, a salt, a buffer, a pH adjuster, or a preservative. The reagent for measurement of HbA1c according to the present invention may be prepared to separately contain various reagents in different containers. For example, it can be provided in the form of a liquid product, a frozen product of a liquid product, or a freeze-dried product. Such reagent for measurement may be used in a dried or dissolved state. Alternatively, such reagents for measurement may be used in a dried or dissolved state, or a carrier on a thin film, such as a sheet or paper that can be impregnated, may be impregnated with such reagent and used. Enzymes used for the reagent for measurement can be fixed (solidified) and used repeatedly in accordance with conventional techniques. In one embodiment, the reagent for measurement of HbA1c of the present invention does not contain a protease or the like for cleaving α-fructosyl peptide from glycated protein. According to an embodiment, the reagent for measurement of HbA1c of the present invention may contain any conventional protease, such as a protease for cleaving αF8P from glycated protein. Examples of proteases include, but are not limited to, endoproteinase Lys-C, trypsin, trypsin-like protease, *Achromobacter* proteinase I, and Lysobacter enzymogenes-derived Lys-C protease. Two or more types of appropriate proteases may be used in combination.

The optimal specification or conditions for the use of the reagent for measurement of HbA1c according to the present invention may be selected in accordance with the components thereof or other properties. For example, the reagent can be prepared to be used for measurement conducted at 20° C. to 45° C. The time necessary for measurement can be adequately determined in accordance with various measurement conditions. For example, it is 0.5 to 60 minutes, preferably 0.5 to 30 minutes, and further preferably 1 to 10 minutes. For example, an extent of the reagent colored (i.e., a change in the absorbance) may be measured using a spectrophotometer, and the measured absorbance may be compared with the reference absorbance. Thus, the glycated peptide or glycated protein contained in the sample can be measured. Measurement can be carried out with the use of a common automated analyzer.

(Quantification of HbA1c)

The method for measurement of HbA1c according to the present invention may be a qualitative or quantitative method. According to the quantitative method for measurement of HbA1c of the present invention, concentration of HbA1c in the sample is determined. Specifically, an aspect of the present invention provides a method for quantification of HbA1c in a sample involving the use of an amadoriase. This quantitative method comprises a step of bringing a HbA1c-containing sample into contact with the amadoriase of the present invention and a step of measuring the amount of substances produced or consumed by the reaction of the amadoriase with HbA1c. Here, HbA1c may be in a naturally occurring or denatured state. The "contact" that is carried out in accordance with the method of quantification can be any form of physical contact between the amadoriase of the present invention and a sample, so that the amadoriase can catalyze the oxidation reaction of HbA1c. In addition to the case in which a free enzyme is mixed with HbA1c in a solution, for example, a liquid sample containing HbA1c can be added or added dropwise to the amadoriase of the present invention immobilized to a solid support.

A sample used for the method for measurement of HbA1c of the present invention can be any type of biological sample that can contain glycated hemoglobin, such as a sample derived from blood, body fluid, or lymph. A sample can adequately be a processed sample.

Denatured HbA1c may be subjected to the reaction with an amadoriase, in order to improve the reaction efficiency between the amadoriase and HbA1c. Denatured HbA1c can be obtained by mixing HbA1c with an adequate surfactant, via heat treatment, with the addition of a surfactant in combination with heat treatment, or via denaturing treatment with the aid of an acid or alkali. When both the addition of a surfactant and heat treatment are carried out as the denaturation treatment, the order of treatment is arbitrary. Heat treatment may be carried out at a temperature and for a period of time sufficient to denature all HbA1c or a portion of the same. Treatment can be carried out at, for example, 60° C. or higher, 70° C. or higher, 80° C. or higher, or 90° C. or higher, such as at 98° C. While the duration of treatment varies depending on temperature, it can be, for example, 10 seconds or longer, 20 seconds or longer, 30 seconds or longer, 1 minute or longer, or 2 minutes or longer. Any of the surfactants mentioned above can be added at adequate concentrations.

When the amount of the amadoriase variant used and the duration of the reaction are maintained at constant levels and the amount of HbA1c being added is altered, the range of HbA1c concentration in which the absorbance of the detected luminescent substrate proportionally decreases as the amount of added HbA1c decreases can be investigated in order to determine the lowest HbA1c concentration that can be detected with the use of the amadoriase. Such concentration is also referred to as the "detection limit concentration" herein. With regard to the method for quantification of HbA1c of the present invention, it is preferable to configure the amount of the enzyme and the duration of the reaction so as to adjust the detection limit of HbA1c to a level lower than the HbA1c concentration in the sample or the glycated hemoglobin level in the blood.

According to the quantitative method of measurement of the present invention, a calibration curve can be prepared in advance by performing regression analysis such as the method of least squares based on the measured absorbance of the control sample containing HbA1c at a known concentration. The measured value of the sample containing HbA1c at an unknown concentration may be plotted on the calibration curve prepared as such, to quantify the HbA1c concentration in the sample.

The present inventors demonstrated that a modified amadoriase derived from *Coniochaeta* comprising glycine at position 64 (i.e., CFP-T7-H38) exhibits improved specific activity on αF8P, compared with CFP-T7-H37 before substitution. Further, the present inventors demonstrated that CFP-DH3 comprising glycine at position 64 exhibits improved specific activity on αF8P, compared with CFP-DH2 before substitution. These are surprising findings. Based on such findings, a person skilled in the art will appreciate that reactivity of CFP-T7-H38 and CFP-DH3 with HbA1c would also have improved. In addition, it will be appreciated that other amadoriases comprising a glycine residue at the position corresponding to position 64 of the amino acid sequence as shown in SEQ ID NO: 1 and exhibiting satisfactory activity on αF8P will also react directly with HbA1c and may be used for quantification of HbA1c. A person skilled in the art can appropriately determine the conditions for such quantification, such as the amount (concentration) of enzyme and duration of the reaction.

(Screening Method)

According to an embodiment, whether or not an amadoriase of interest reacts with αF8P or whether or not specific activity of such amadoriase on αF8P is improved can be determined by the method described above (i.e., the method for measurement of activity of amadoriase). Examples of candidate amadoriases include various naturally occurring amadoriases and amadoriases modified therefrom by substitution of the amino acid at the position corresponding to position 64 of the amino acid sequence as shown in SEQ ID NO: 1 with glycine, serine, methionine, leucine, threonine, valine, or isoleucine. In comparison with an amadoriase comprising a sequence in which the amino acid at the position corresponding to position 64 of the amino acid sequence as shown in SEQ ID NO: 1 is not glycine, or is not serine, methionine, leucine, threonine, valine, or isoleucine, whether or not specific activity of a candidate amadoriase on αF8P is increased can be determined. Such variant may be prepared via, for example, (a) substitution of the amino acid at the position corresponding to position 62 with alanine, asparagine, aspartic acid, glutamine, glutamic acid, glycine, valine, leucine, isoleucine, cysteine, serine, methionine, threonine, or proline, (b) substitution of the amino acid at the position corresponding to position 63 with histidine, alanine, or glycine (c) substitution of the amino acid at the position corresponding to position 102 with lysine, (d) substitution of the amino acid at the position corresponding to position 106 with alanine, lysine, or arginine, (e) substitution of the amino acid at the position corresponding to position 110 with leucine, tyrosine, phenylalanine, or histidine, (f) substitution of the amino acid at the position corresponding to position 113 with lysine or arginine, (g) substitution of the amino acid at the position corresponding to position 355 with serine, (h) substitution of the amino acid at the position corresponding to position 419 with lysine, (i) substitution of the amino acid at the position corresponding to position 68 with asparagine, (j) substitution of the amino acid at the position corresponding to position 356 with threonine, and/or (k) substitution of the amino acid at the position corresponding to position 99 with serine, according to need, substitution of the amino acid at the position corresponding to position 67 with histidine, substitution of the amino acid at the position corresponding to position 72 with serine, substitution of the amino acid at the position corresponding to position 76 with alanine or phenylalanine, substitution of the amino acid at the position corresponding to position 96 with glutamic acid, substitution of the amino acid at the position corresponding to position 109 with arginine or lysine, or substitution of the amino acid at the position corresponding to position 116 with arginine in the amino acid sequence as shown in SEQ ID NO: 1.

The mutation that improves surfactant resistance described above may be introduced into an amadoriase to be used and/or the deletion that improves heat stability may be performed. So long as activity on HbA1c is retained, mutation(s) that alters other properties of the enzyme can also be introduced.

In addition to the reagents for measurement of HbA1c described above, the kit for measurement of HbA1c of the present invention may include other known stabilizer(s), a system that deletes contaminants, and the like, according to need. Techniques that are employed for various conventional reagents or kits for the purpose of measuring HbA1c by enzymatic methods using a protease or the like reacting with HbA1c may be adequately modified, and such modified technique(s) can be employed for the kit for measurement of HbA1c comprising the amadoriase of the present invention. However, the kit for measurement of HbA1c of the present invention does not require such protease or the like. According to an embodiment, specifically, the kit for measurement of HbA1c of the present invention does not comprise a protease or the like for cleaving α-fructosyl peptide from HbA1c. According to an embodiment, the kit for measurement of HbA1c of the present invention can comprise Lys-C protease or the like for cleaving αF8P from HbA1c.

EXAMPLES

Hereafter, the present invention is described in greater detail with reference to the examples, although the technical scope of the present invention is not limited to these examples.

[Example 1] Preparation of Recombinant Plasmid Encoding Amadoriase

A strain of *E. coli* JM109 (pKK223-3-CFP-T7-H35) having the recombinant plasmid of an amadoriase gene derived from the genus *Coniochaeta* (SEQ ID NO: 142) (WO 2013/162035) was inoculated into 3 ml of LB-amp media (1% (w/v) bactotrypton, 0.5% (w/v) peptone, 0.5% (w/v) NaCl, and 50 µg/ml ampicillin) and shake culture was conducted at 37° C. for 16 hours to obtain a culture product.

The culture product was centrifuged at 10,000×g for 1 minute to collect strains. A recombinant plasmid pKK223-3-CFP-T7-H35 was extracted and purified therefrom using the GenElute Plasmid Mini-Prep Kit (manufactured by Sigma-Aldrich Corporation), and 2.5 µl of the recombinant plasmid pKK223-3-CFP-T7-H35 was obtained.

[Example 2] Site-Directed Modification Operation of Recombinant Plasmid Encoding Amadoriase PCR was carried out under the conditions described below using the recombinant plasmid pKK223-3-CFP-T7-H35 as the template, synthetic oligonucleotides of SEQ ID NOs: 193 and 194, and KOD-Plus-(Toyobo Co., Ltd.).

Specifically, 5 µl of 10×KOD-Plus-buffer, 5 µl of a dNTPs mixture in which each dNTP was adjusted at 2 mM, 2 µl of a 25 mM $MgSO_4$ solution, 50 ng of pKK223-3-CFP-T7-H35 as the template, 15 pmol each of the synthetic oligonucleotides, and 1 unit of KOD-Plus were mixed, and sterilized water was added thereto in order to bring the total amount of the solution to 50 µl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was electrophoresed on 1.0% agarose gel, and specific amplification of about 6,000 bp DNA was confirmed. The DNAs obtained in such a manner were treated with a restriction enzyme DpnI (manufactured by New England Biolabs), the remaining template DNAs were cleaved, strains of E. coli JM109 were transformed, and the transformants were then spread on LB-amp agar media. The grown colonies were inoculated into LB-amp media and shake-cultured therein, and plasmid DNAs were isolated in the same manner as in (1) above. The nucleotide sequences of DNAs encoding amadoriases in the plasmids were determined using a multi-capillary DNA analysis system (Applied Biosystems 3130xl Genetic Analyzer; manufactured by Life Technologies). Thus, the recombinant plasmid encoding the modified amadoriase resulting from substitution of aspartic acid at position 68 with asparagine in the amino acid sequence as shown in SEQ ID NO: 141 was obtained (pKK223-3-CFP-T7-H36).

Subsequently, in the same manner as described above, PCR was carried out using the recombinant plasmid pKK223-3-CFP-T7-H36 as the template, oligonucleotides of SEQ ID NOs: 196 and 196, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine and alanine at position 356 with threonine were obtained (pKK223-3-CFP-T7-H37).

Subsequently, in the same manner as described above, PCR was carried out using the recombinant plasmid pKK223-3-CFP-T7-H37 as the template, oligonucleotides of SEQ ID NOs: 205 and 206, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, and arginine at position 64 with glycine were obtained (pKK223-3-CFP-T7-H38-G).

Subsequently, in the same manner as described above, PCR was carried out using the recombinant plasmid pKK223-3-CFP-T7-H37 as the template, oligonucleotides of SEQ ID NOs: 205 and 206, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine alanine at position 356 with threonine, and arginine at position 64 with alanine were obtained (pKK223-3-CFP-T7-H38-A).

Subsequently, in the same manner as described above, PCR was carried out using the recombinant plasmid pKK223-3-CFP-T7-H37 as the template, oligonucleotides of SEQ ID NOs: 205 and 216, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, and arginine at position 64 with valine were obtained (pKK223-3-CFP-T7-H38-V).

Subsequently, in the same manner as described above, PCR was carried out using the recombinant plasmid pKK223-3-CFP-T7-H37 as the template, oligonucleotides of SEQ ID NOs: 205 and 217, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, and arginine at position 64 with isoleucine were obtained (pKK223-3-CFP-T7-H384).

Subsequently, in the same manner as described above, PCR was carried out using the recombinant plasmid pKK223-3-CFP-T7-H37 as the template, oligonucleotides of SEQ ID NOs: 205 and 218, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, and arginine at position 64 with leucine were obtained (pKK223-3-CFP-T7-H38-L).

Subsequently, in the same manner as described above, PCR was carried out using the recombinant plasmid pKK223-3-CFP-T7-H37 as the template, oligonucleotides of SEQ ID NOs: 205 and 219, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, and arginine at position 64 with methionine were obtained (pKK223-3-CFP-T7-H38-M).

Subsequently, in the same manner as described above, PCR was carried out using the recombinant plasmid pKK223-3-CFP-T7-H37 as the template, oligonucleotides of SEQ ID NOs: 205 and 220, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, and arginine at position 64 with serine were obtained (pKK223-3-CFP-T7-H38-S).

Subsequently, in the same manner as described above, PCR was carried out using the recombinant plasmid pKK223-3-CFP-T7-H37 as the template, oligonucleotides of SEQ ID NOs: 205 and 221, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, and arginine at position 64 with threonine were obtained (pKK223-3-CFP-T7-H38-T).

Subsequently, in the same manner as described above, PCR was carried out using the recombinant plasmid pKK223-3-CFP-T7-H38-G as the template, oligonucleotides of SEQ ID NOs: 222 and 223, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, arginine at position 64 with glycine, and leucine at position 110 with tyrosine were obtained (pKK223-3-CFP-T7-H38-GY).

Subsequently, in the same manner as described above, PCR was carried out using the recombinant plasmid pKK223-3-CFP-T7-H38-G as the template, oligonucleotides of SEQ ID NOs: 222 and 224, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, arginine at position 64 with glycine, and leucine at position 110 with phenylalanine were obtained (pKK223-3-CFP-T7-H38-GF).

Subsequently, in the same manner as described above, PCR was carried out using the recombinant plasmid pKK223-3-CFP-T7-H38-G as the template, oligonucleotides of SEQ ID NOs: 222 and 225, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, arginine at position 64 with glycine, and leucine at position 110 with histidine were obtained (pKK223-3-CFP-T7-H38-GH).

Subsequently, in the same manner as described above, PCR was carried out using the recombinant plasmid pKK223-3-CFP-T7-H38-GY as the template, oligonucleotides of SEQ ID NOs: 226 and 227, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 141 by substitution of aspartic acid at position 68 with asparagine, alanine at position 356 with threonine, arginine at position 64 with glycine, leucine at position 110 with tyrosine, and histidine at position 99 with serine were obtained (pKK223-3-CFP-T7-H38-GYS).

In order to obtain mutants with improved CFP-T7-H36 stability, modified CFP-T7-H36 comprising a sequence of 434 amino acids as shown in SEQ ID NO: 199 comprising 7 mutations exerting effects of stability improvement introduced thereinto and 3 amino acids removed from the C terminus thereof (hereafter, it is referred to as "CFP-DH1") was expressed in E. coli. The present inventors have confirmed that the mutations introduced into CFP-DH1 (i.e., E44P, E133A, E253K, V257C, N262H, Q337K, and E340P) improve surfactant tolerance of the amadoriase. More specifically, the present inventors have confirmed that while residual activity of the enzyme from CFP without mutations was 29.2% even when 0.04% tetradecyltrimethylammonium chloride (TTAC) is applied to said amadoriase in a 20 mM potassium phosphate buffer (pH 7.0), residual activity of CFP-DH1, into which mutations (E44P, E133A, E253K, V257C, N262H, Q337K, and E340P) were introduced, was 100%. The effects of such mutations are described in WO 2015/020200, the contents of which are incorporated herein by reference in their entirety. In addition, the present inventors have previously reported that deletion of amino acids from the carboxyl terminus of CFP-DH1 would improve heat stability of amadoriases. The effects of such deletion are described in WO 2013/100006.

A 1,305-bp gene sequence as shown in SEQ ID NO: 200 encoding the amino acid sequence as shown in SEQ ID NO: 199 and having an optimized codon for expression in E. coli (including the termination codon TAA) was obtained in accordance with a conventional technique; i.e., total synthesis of a gene fragment via PCR. Through this procedure, the EcoRI site and the HindIII site were added to the 5' terminus and the 3' terminus of the sequence as shown in SEQ ID NO: 200, respectively. Subsequently, the procedure described below was implemented so as to subclone the obtained CFP-DH1 gene into a plasmid for expression in E. coli. First, the gene obtained via total synthesis above and the pKK223-3 vector (Novagen) were treated with two types of restriction enzymes (EcoRI and HindIII, TakaraBio. Co., Ltd.), the gene and the vector were ligated to each other, and the recombinant plasmid pKK223-3-CFP-DH1 resulting from insertion of the CFP-DH1 gene into the multicloning site of the pKK223-3 vector was obtained. Strains of E. coli JM109 were transformed with the resulting recombinant plasmid, and the transformants were then spread on LB-amp agar medium. The grown colonies were inoculated into LB-amp media and shake-cultured therein, and plasmid DNAs were isolated in the same manner as in Example 1. Nucleotide sequences of DNAs encoding amadoriases in the plasmids were determined using a multi-capillary DNA analysis system (Applied Biosystems 3130xl Genetic Analyzer; manufactured by Life Technologies). It was thus confirmed that the recombinant plasmid pKK223-3-CFP-DH1 comprising the CFP-DH1 gene inserted into the multicloning site of the pKK223-3 vector was actually obtained.

Subsequently, in the same manner as described above, PCR was carried out with the use of the recombinant plasmid pKK223-3-CFP-DH1 as the template, oligonucleotides of SEQ ID NOs: 201 and 202, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 199 by substitution of alanine at position 356 with threonine were obtained (pKK223-3-CFP-DH2).

Subsequently, in the same manner as described above, PCR was carried out with the use of the recombinant plasmid pKK223-3-CFP-DH2 as the template, oligonucleotides of SEQ ID NOs: 207 and 208, and KOD-Plus-, strains of E. coli JM109 were transformed, and the nucleotide sequences of DNAs encoding the amadoriases in plasmid DNAs carried on the grown colonies were determined. As a result, recombinant plasmids encoding modified amadoriases each comprising an amino acid sequence derived from the amino acid sequence as shown in SEQ ID NO: 199 by substitution of alanine at position 356 with threonine and arginine at position 64 with glycine were obtained (pKK223-3-CFP-DH3).

[Example 3] Production, Purification, and Specific Activity Measurement of Various Types of Amadoriases E. coli JM109 (pKK223-3-CFP-T7-H37), E. coli JM109 (pKK223-3-CFP-T7-H38-G), E. coli JM109 (pKK223-3-CFP-T7-H38-A), E. coli JM109 (pKK223-3-CFP-T7-H38-V), E. coli JM109 (pKK223-3-CFP-T7-H38-I), E. coli JM109 (pKK223-3-CFP-T7-H38-L), E. coli JM109 (pKK223-3-CFP-T7-H38-M), E. coli JM109 (pKK223-3-CFP-T7-H38-S), E. coli JM109 (pKK223-3-CFP-T7-H38-T), E. coli JM109 (pKK223-3-CFP-T7-H38-GY), E. coli JM109 (pKK223-3-CFP-T7-H38-GF), E. coli JM109 (pKK223-3-CFP-T7-H38-GH), E. coli JM109 (pKK223-3-CFP-T7-H38-GYS), E. coli JM109 (pKK223-3-CFP-DH2), and E. coli JM109 (pKK223-3-CFP-DH3) producing the modified amadoriases obtained in the manner described above were inoculated into 200 ml of LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare 40 ml of a crude enzyme solution. The cultured strains of E. coli JM109 (pKK223-3-CFP-DH2) and E. coli JM109 (pKK223-3-CFP-DH3) were selectively washed with a 2 mM potassium phosphate buffer (pH 8.0), the washed strains were suspended in the same buffer, the resulting suspension was ultrasonically disintegrated, and the resultant was centrifuged at 20,000×g for 10 minutes to prepare 40 ml of a crude enzyme solution.

The column loaded with Q-Sepharose FF (GE Healthcare) was equilibrated with a 10 mM potassium phosphate buffer (pH 7.5), and the crude enzyme solutions each containing CFP-T7-H37, CFP-T7-H38-G, CFP-T7-H38-A, CFP-T7-H38-V, CFP-T7-H38-I, CFP-T7-H38-L, CFP-T7-H38-M, CFP-T7-H38-S, CFP-T7-H38-T, CFP-T7-H38-GY, CFP-T7-H38-GF, CFP-T7-H38-GH, and CFP-T7-H38-GYS were applied, so as to allow amadoriases to bind to anion-exchange resin. Thereafter, a 10 mM potassium phosphate buffer (pH 7.5) containing 30 mM NaCl was applied in an amount equivalent to 20 column volumes, so as to elute contaminating proteins, the proteins bound to the resin were eluted with the aid of a 10 mM potassium phosphate buffer (pH 7.5) containing 80 mM NaCl, and fractions exhibiting amadoriase activity were then collected.

After the column loaded with Q-sepharose FF (GE Healthcare) was equilibrated with a 2 mM potassium phosphate buffer (pH 8.0), the crude enzyme solution containing CFP-DH2 or CFP-DH3 was applied, so as to allow amadoriases to bind to the anion-exchange resin. Thereafter, a 4 mM potassium phosphate buffer (pH 8.0) was applied in an amount equivalent to 20 column volumes, so as to elute contaminating proteins, the proteins bound to the resin were eluted with the aid of a 4 mM potassium phosphate buffer (pH 8.0) containing 30 mM NaCl, and fractions exhibiting amadoriase activity were then collected.

Each of the obtained fractions exhibiting amadoriase activity were concentrated using Amicon Ultra Ultracel-30K (Millipore) and purified using HiLoad 26/60 Superdex 200. Resin equilibration and elution were carried out using a 10 mM potassium phosphate buffer (pH 6.5) containing 150 mM NaCl. Purity of the eluted fractions was evaluated via SDS-PAGE, and fractions containing no contaminating proteins were collected, and the collected fractions were designated to be purified samples of the CFP-T7-H37, CFP-T7-H38-G, CFP-T7-H38-A, CFP-T7-H38-V, CFP-T7-H38-I, CFP-T7-H38-L, CFP-T7-H38-M, CFP-T7-H38-S, CFP-T7-H38-T, CFP-T7-H38-GY, CFP-T7-H38-GF, CFP-T7-H38-GH, CFP-T7-H38-GYS, CFP-DH2, and CFP-DH3.

By using the purified samples of CFP-T7-H37, CFP-T7-H38-G, CFP-T7-H38-A, CFP-DH2, and CFP-DH3, specific activities thereof relative to αF8P as a substrate were measured. Results are shown in Tables 1 and 2. The concentration of the protein used for calculating specific activity was determined by the ultraviolet absorption method that makes use of the absorbance at 280 nm (see Protein Sci., 4, 2411-23, 1995). The purified sample of CFP-T7-H35 was prepared in accordance with the method described in WO 2013/162035.

TABLE 1

| Amadoriase | CFP-T7-H35-based amino acid substitution | Specific activity (U/mg) 1 mM αF8P |
| --- | --- | --- |
| CFP-T7-H37 (Comp. Ex. 1) | D68N, A356T | 4.18 |
| CFP-T7-H38-G (Invention 1) | D68N, A356T, R64G | 6.33 |
| CFP-T7-H38-A (Comp. Ex. 3) | D68N, A356T, R64A | 3.26 |

TABLE 2

| Amadoriase | CFP-DH1-based amino acid substitution | Specific activity (U/mg) 1 mM αF8P |
| --- | --- | --- |
| CFP-DH2 (Comp. Ex. 2) | A356T | 2.80 |
| CFP-DH3 (Invention 2) | A356T, R64G | 4.90 |

Based on the results demonstrated in Tables 1 and 2, the mutation R64G was found to improve the specific activities of two types of amadoriases (i.e., CFP-T7-H37 and CFP-DH2) on αF8P by 1.51 to 1.75 times.

Incidentally, according to WO 2015/005258, the amadoriase derived from Emericella nidulans (FPDX-16) has acquired improved activity on αF6P as a result of substitution R63G, or R63P, or R63A. Position 63 of the amadoriase derived from Emericella nidulans corresponds to position 64 of the amadoriase derived from Coniochaeta sp. (e.g., CFP-T7-H37). On the other hand, WO 2013/162035 reports that the introduction of the mutations R64A, R64E, and R64H into CFP-T7-H6 (SEQ ID NO: 163) has effects of lowering activity of a cell extract of a modified CFP-T7-H6-producing strain on αF6P. In addition, the present specification demonstrates that R64A has effects of lowering specific activity of a modified CFP-T7-H37-producing strain on αF8P. As such, the finding of the present invention concerning the effects of mutation R64G, focused in the present invention, for improving specific activity on αF8P was unexpected and particularly surprising.

With the use of the purified samples of CFP-T7-H37, CFP-T7-H38-G, CFP-T7-H38-V, CFP-T7-H38-I, CFP-T7-H38-L, CFP-T7-H38-M, CFP-T7-H38-S, CFP-T7-H38-T, CFP-T7-H38-GY, and CFP-T7-H38-GYS, subsequently, specific activities thereof when 10 μM of αF8P is used as the substrate were measured. The results are shown in Table 3. The concentration of the protein used for calculating specific activity was determined by using the ultraviolet absorption method which utilizes absorbance at 280 nm (see Protein Sci., 4, 2411-23, 1995).

TABLE 3

| Amadoriase | CFP-T7-H35-based amino acid substitution | Specific activity (mU/mg) 10 μM αF8P |
|---|---|---|
| CFP-T7-H37 (Comp. Ex. 1) | D68N, A356T | 44.4 |
| CFP-T7-H38-G (Present Invention 1) | D68N, A356T, R64G | 95.9 |
| CFP-T7-H38-V (Present Invention 3) | D68N, A356T, R64V | 86.0 |
| CFP-T7-H38-I (Present Invention 4) | D68N, A356T, R64I | 78.7 |
| CFP-T7-H38-L (Present Invention 5) | D68N, A356T, R64L | 84.3 |
| CFP-T7-H38-M (Present Invention 6) | D68N, A356T, R64M | 84.4 |
| CFP-T7-H38-S (Present Invention 7) | D68N, A356T, R64S | 89.7 |
| CFP-T7-H38-T (Present Invention 8) | D68N, A356T, R64T | 78.7 |
| CFP-T7-H38-GY (Present Invention 9) | D68N, A356T, R64G, L110Y | 174 |
| CFP-T7-H38-GF (Present Invention 10) | D68N, A356T, R64G, L110F | 145 |
| CFP-T7-H38-GH (Present Invention 11) | D68N, A356T, R64G, L110H | 143 |
| CFP-T7-H38-GYS (Present Invention 12) | D68N, A356T, R64G, L110Y, H99S | 196 |

As shown in Table 3, mutations of the amino acid at position 64 to V, I, L, M, S, or T were found to improve the specific activities of amadoriases on αF8P by 1.57 to 1.92 times. Such results are also unexpectedly surprising. Also, specific activities of amadoriases on αF8P were unexpectedly improved as a result of a mutation at position 64 in combination with a mutation at position 110 or a mutation at position 99.

[Example 4] Introduction of Point Mutations into Various Amadoriases

The findings (discovery) of the present invention was first confirmed using an amadoriase derived from the genus Coniochaeta. However, by introducing similar mutations into corresponding positions in the amino acid sequence of an amadoriase derived from other organism species with reference to information attained by a known sequence alignment processing based on sequence identity, similar effects can be expected. Accordingly, the findings of the present invention were actually applied to a plurality of amadoriases other than the amadoriase derived from the genus Coniochaeta, and the effects thereof were then verified.

Introduction of Point Mutation into Gene of Fructosyl Peptide Oxidase Derived from Phaeosphaeria nodorum SEQ ID NO: 187 shows the amino acid sequence of a modified fructosyl peptide oxidase derived from Phaeosphaeria nodorum (hereafter referred to as "PnFX") reacting with fructosyl hexapeptide, which can be produced by E. coli BL 21 (DE3) carrying a recombinant plasmid pET22b-PnFX-62D/63H/106K/110L/113K/351S comprising a gene encoding the amino acid sequence as shown in SEQ ID NO: 188 inserted therein (see WO 2013/162035).

PCR was carried out under the conditions described below using the recombinant plasmid pET22b-PnFX as the template, synthetic oligonucleotides of SEQ ID NOs: 228 and 229, KOD-Plus-(Toyobo Co., Ltd.), Ligation high (Toyobo Co., Ltd.), and T4 polynucleotide kinase (Toyobo Co., Ltd.).

Specifically, 5 μl of 10×KOD-Plus-buffer, 5 μl of a dNTPs mixture in which each dNTP was adjusted at 2 mM, 2 μl of a 25 mM MgSO$_4$ solution, 50 ng of pET22b-PnFX as the template, 15 pmol each of the synthetic oligonucleotides, and 1 unit of KOD-Plus were mixed, and sterilized water was added thereto in order to bring the total amount of the solution to 50 μl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 6 times.

The DNAs obtained in such a manner were treated with a restriction enzyme DpnI (manufactured by New England Biolabs), the remaining template DNAs were cleaved, 2 μl of the reaction solution was fractionated, 5 μl of Ligation high, 1 μl of T4 polynucleotide kinase, and 7 μl of sterile water were added thereto, and the reaction was allowed to proceed at 16° C. for 1 hour. Strains of E. coli JM109 were transformed with the use of the reaction solution, and the transformants were then spread on LB-amp agar media. The grown colonies were inoculated into LB-amp media and shake-cultured therein, and plasmid DNAs were isolated in the same manner as in (1) above. The nucleotide sequences of the DNAs encoding the amadoriases in the plasmids were determined using a multi-capillary DNA analysis system (Applied Biosystems 3130xl Genetic Analyzer; manufactured by Life Technologies). Thus, the recombinant plasmids encoding the PnFX gene resulting from substitution of arginine at position 64 with serine in the amino acid sequence as shown in SEQ ID NO: 187 were obtained (pET22b-PnFX-62D/63H/106K/110L/113K/351S-64S).

Then, E. coli BL21 (DE3) strains were transformed using pET22b-PnFX-62D/63H/106K/110L/113K/351S and pET22b-PnFX-62D/63H/106K/110L/113K/351S-64S, and strains of E. coli BL21 (DE3) (pET22b-PnFX-62D/63H/106K/110L/113K/351S) and E. coli BL21 (DE3) (pET22b-PnFX-62D/63H/106K/110L/113K/351S-64S) were obtained. Introduction of point mutation into gene of ketoamine oxidase derived from Neocosmospora vasinfecta SEQ ID NO: 137 shows the amino acid sequence of a modified ketoamine oxidase derived from Neocosmospora vasinfecta (hereafter referred to as "NvFX") that reacts with fructosyl hexapeptide. It can be prepared by strains of E. coli BL21 (DE3) carrying the recombinant plasmid pET22b-NvFX-62D/106K/110L into which the gene encoding the amino acid sequence as shown in SEQ ID NO: 138 has been inserted (see WO 2013/162035).

In order to introduce a mutation aimed at improvement of substrate specificity into NvFX, in the same manner as in Example 4, PCR was carried out with the use of the recombinant plasmid pET22b-NvFX-62D/106K/110L as the template, synthetic oligonucleotides of SEQ ID NOs: 230 and 231, KOD-Plus-, Ligation high, and T4 polynucleotide kinase (manufactured by TOYOBO CO., LTD.), strains of E. coli JM109 were transformed, and nucleotide sequences of DNAs encoding NvFX variants in plasmid DNAs carried by the grown colonies were determined. As a result, a recombinant plasmid encoding the NvFX gene resulting from substitution of leucine at position 63 in the amino acid sequence as shown in SEQ ID NO: 137 with histidine was obtained (pET22b-NvFX-62D/63H/106K/110L).

Subsequently, a gene encoding NvFX-62D/63H/106K/110L was ligated to the pKK223-3 plasmid using the In-Fusion HD Cloning Kit (Clontech Laboratories, Inc.) in accordance with the instructions attached to the kit, and a recombinant plasmid encoding the NvFX gene was obtained (pKK223-3-NvFX-62D/63H/106K/110L). Specifically, a DNA fragment obtained via PCR using the synthetic oligonucleotides of SEQ ID NOs: 232 and 233 and the pKK223-3 plasmid was ligated to a DNA fragment obtained via PCR using the synthetic oligonucleotides of SEQ ID NOs: 234 and 235 and pET22b-NvFX-62D/63H/106K/110L via the in-fusion reaction, so as to obtain pKK223-3-NvFX-62D/63H/106K/110L.

Further, in the same manner as described above (Example 4), using pKK223-3-NvFX-62D/63H/106K/110L as the template and the synthetic oligonucleotides of SEQ ID NOs: 236 and 237, SEQ ID NOs: 236 and 238, and SEQ ID NOs: 236 and 239, respectively, recombinant plasmids each encoding the NvFX gene resulting from substitution of arginine at position 64 with methionine, serine, and threonine in the amino acid sequence as shown in SEQ ID NO: 137 were obtained (i.e., pKK223-3-NvFX-62D/63H/106K/110L-64M, pKK223-3-NvFX-62D/63H/106K/110L-64S, and pKK223-3-NvFX-62D/63H/106K/110L-64T). The strains of E. coli JM109 carrying such plasmids were used as modified NvFX-producing strains.

Introduction of Point Mutation into Gene of Fructosyl Peptide Oxidase Derived from *Curvularia clavata*

SEQ ID NO: 117 shows the amino acid sequence of a ketoamine oxidase derived from *Curvularia clavata* (hereafter referred to as "CcFX"), which can be produced by *E. coli* JM109 carrying a recombinant plasmid pKK223-3-CcFX comprising a gene encoding the amino acid sequence as shown in SEQ ID NO: 240 inserted therein (see WO 2013/162035).

In order to introduce a mutation aimed at improvement of substrate specificity into CcFX, in the same manner as described above (Example 4), PCR was carried out with the use of the recombinant plasmid pKK223-3-CcFX as the template, synthetic oligonucleotides of SEQ ID NOs: 241 and 242, KOD-Plus-, Ligation high, and T4 polynucleotide kinase (manufactured by TOYOBO CO., LTD.), strains of *E. coli* JM109 were transformed, and nucleotide sequences of DNAs encoding CcFX variants in plasmid DNAs carried by the grown colonies were determined. As a result, a recombinant plasmid encoding the CcFX gene resulting from substitution of arginine at position 62 with aspartic acid in the amino acid sequence as shown in SEQ ID NO: 117 was obtained (pKK223-3-CcFX-62D).

Further, in the same manner as described above (Example 4), using pKK223-3-CcFX-62D as the template and the synthetic oligonucleotides of SEQ ID NOs: 241 and 243, a recombinant plasmid encoding the CcFX gene resulting from substitution of arginine at position 62 with aspartic acid and leucine at position 63 with histidine in the amino acid sequence as shown in SEQ ID NO: 117 was obtained (pKK223-3-CcFX-62D/63H).

Further, in the same manner as described above (Example 4), using pKK223-3-CcFX-62D/63H as the template and synthetic oligonucleotides of SEQ ID NOs: 244 and 245, a recombinant plasmid encoding the CcFX gene resulting from substitution of arginine at position 62 with aspartic acid, leucine at position 63 with histidine, glutamic acid at position 102 with lysine, and aspartic acid at position 106 with lysine in the amino acid sequence as shown in SEQ ID NO: 117 was obtained (pKK223-3-CcFX-62D/63H/102K/106K).

Further, in the same manner as described above (Example 4), using pKK223-3-CcFX-62D/63H/102K/106K as the template and synthetic oligonucleotides of SEQ ID NOs: 246 and 247 or SEQ ID NOs: 246 and 248, recombinant plasmids encoding the CcFX gene resulting from substitution of arginine at position 62 with aspartic acid, leucine at position 63 with histidine, glutamic acid at position 102 with lysine, aspartic acid at position 106 with lysine, and arginine at position 64 with leucine or threonine in the amino acid sequence as shown in SEQ ID NO: 117 were obtained (pKK223-3-CcFX-62D/63H/102K/106K-64L and pKK223-3-CcFX-62D/63H/102K/106K-64T). The strains of *E. coli* JM109 carrying such plasmids were used as modified CcFX-producing strains.

[Example 5] Production and Purification of Various Types of Amadoriases (Production and Purification of Fructosyl Peptide Oxidase Derived from *Phaeosphaeria nodorum*)

Strains of *E. coli* BL21 (DE3) (pET22b-PnFX-62D/63H/106K/110L/113K/351S) and *E. coli* BL21 (DE3) (pET22b-PnFX-62D/63H/106K/110L/113K/351S-64S) capable of PnFX production obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution containing PnFX was purified in accordance with the method described in the non-patent document (Biotechnology and Bioengineering, 106, 358-366, 2010). Specifically, the crude enzyme solution was fractionated with ammonium sulfate, dialyzed against a 10 mM potassium phosphate buffer (pH 8.0), purified via anion-exchange chromatography (Q Sepharose Fast Flow was used in Example 5), and then purified via gel filtration chromatography (HiLoad 26/600 Superdex 200 was used in Example 5). The obtained fraction was analyzed via SDS-PAGE to confirm that the fraction was sufficiently purified, so that no other contaminating proteins were present therein, and the fraction was designated to be a purified sample of PnFX.

(Production and Purification of Ketoamine Oxidase Derived from *Neocosmospora vasinfecta*)

Strains of *E. coli* JM109 (pKK223-3-NvFX-62D/63H/106K/110L), *E. coli* JM109 (pKK223-3-NvFX-62D/63H/106K/110L-64M), *E. coli* JM109 (pKK223-3-NvFX-62D/63H/106K/110L-64S), and *E. coli* JM109 (pKK223-3-NvFX-62D/63H/106K/110L-64T) were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to Q Sepharose Fast Flow resin (manufactured by GE Healthcare) equilibrated with a 10 mM potassium phosphate buffer (pH 8.0), the resin was washed with a 10 mM potassium phosphate buffer (pH 8.0) containing 20 mM NaCl, and modified NvFX adsorbed to the resin was then eluted and collected with the aid of a 10 mM potassium phosphate buffer (pH 8.0) containing 300 mM NaCl.

The resulting crude enzyme solution containing modified NvFX was applied to the HiLoad 26/600 Superdex 200 column equilibrated with a 20 mM MES-NaOH buffer (pH 7.0) containing 150 mM NaCl so as to elute wild-type or modified NvFX with the aid of the buffer mentioned above, and a fraction exhibiting fructosyl amino acid oxidase activity (amadoriase activity) was collected. The obtained fraction was analyzed via SDS-PAGE to confirm that the fraction was sufficiently purified, so that no other contaminating proteins were present therein, and the fraction was designated to be a purified sample of wild-type or modified NvFX.

(Production and Purification of Ketoamine Oxidase Derived from *Curvularia clavata*)

Strains of *E. coli* JM109 (pKK223-3-CcFX-62D/63H/102K/106K), *E. coli* JM109 (pKK223-3-CcFX-62D/63H/102K/106K-64L), and *E. coli* JM109 (pKK223-3-CcFX-62D/63H/102K/106K-64T) were inoculated in LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The crude enzyme solution was allowed to adsorb to HiScreen Capto Q resin (manufactured by GE Healthcare) equilibrated with a 10 mM potassium phosphate buffer (pH 8.0). Subsequently, the resin was washed with a 10 mM potassium phosphate buffer (pH 8.0) containing 0 mM NaCl, the NaCl concentration was linearly increased to 300 mM to elute and collect the modified CcFX adsorbed to the resin.

The resulting crude enzyme solution containing modified NvFX was applied to the HiLoad 26/600 Superdex 200 column equilibrated with a 20 mM MES-NaOH buffer (pH 7.0) containing 150 mM NaCl so as to elute modified CcFX with the aid of the buffer mentioned above, and a fraction exhibiting fructosyl amino acid oxidase activity (amadoriase activity) was collected. The obtained fraction was analyzed via SDS-PAGE to confirm that the fraction was sufficiently purified, so that no other contaminating proteins were present therein, and the fraction was designated to be a purified sample of wild-type or modified CcFX.

(Measurement of Protein Concentration of Fructosyl Peptide Oxidase Derived from *Phaeosphaeria nodorum*, Ketoamine Oxidase Derived from *Neocosmospora vasinfecta*, and Ketoamine Oxidase Derived from *Curvularia clavata*)

Protein concentration of the purified and modified fructosyl peptide oxidase derived from *Phaeosphaeria nodorum*, the modified ketoamine oxidase derived from *Neocosmospora vasinfecta*, and the modified ketoamine oxidase derived from *Curvularia clavata* were measured in the manner described below based on FAD of each protein.

First, solutions containing fructosyl peptide oxidase derived from *Coniochaeta* sp. (CFP-T7) at 0.3, 1.0, and 3.0 mg/ml were prepared. The absorbance of the CFP-T7 solution at each concentration was measured at 450 nm using a spectrophotometer (U-3010A, manufactured by Hitachi High-Technologies), and the calibration curve indicating the correlation between the CFP-T7 concentration and the absorbance was prepared. For reference, subsequently, the absorbance of the enzyme solutions was measured at 450 nm by the same method with the use of the modified fructosyl peptide oxidase derived from *Phaeosphaeria nodorum*, the modified ketoamine oxidase derived from *Neocosmospora vasinfecta*, and the modified ketoamine oxidase derived from *Curvularia clavata*, instead of CFP-T7. The absorbance was analyzed with reference to the calibration curve so as to quantify the protein concentration of each of the various enzyme solutions.

Next, with the use of the purified samples of PnFX-62D/63H/106K/110L/113K/351S and PnFX-62D/63H/106K/110L/113K/351S-64S, specific activity when 10 µM αF8P was used as the substrate was measured. The results are shown in Table 4.

TABLE 4

| Amadoriase | Comp. Ex. 4-based amino acid substitution | Specific activity (mU/mg) 10 µM αF8P |
|---|---|---|
| PnFX-62D/63H/106K/110L/113K/351S (Comp. Ex. 4) | None | 2.0 |
| PnFX-62D/63H/106K/110L/113K/351S-64S (Present Invention 13) | R64S | 2.2 |

As shown in Table 4, mutation of position 64 with S was found to improve the specific activity of the PnFX-derived amadoriase on αF8P as well.

Next, with the use of the purified samples of CcFX-62D/63H/102K/106K, CcFX-62D/63H/102K/106K-64L, and CcFX-62D/63H/102K/106K-64T, specific activity when 10 µM αF8P was used as the substrate was measured. The results are shown in Table 5.

TABLE 5

| Amadoriase | Comp. Ex. 5-based amino acid substitution | Specific activity (mU/mg) 10 µM αF8P |
|---|---|---|
| CcFX-62D/63H/102K/106K (Comp. Ex. 5) | None | 1.3 |
| CcFX-62D/63H/102K/106K-64L (Present Invention 14) | R64L | 2.0 |
| CcFX-62D/63H/102K/106K-64T (Present Invention 15) | R64T | 1.5 |

As shown in Table 5, mutations of position 64 with L or T were found to improve the specific activity of the CcFX-derived amadoriase on αF8P as well.

Next, using the purified samples of NvFX-62D/63H/106K/110L, NvFX-62D/63H/106K/110L-64M, NvFX-62D/63H/106K/110L-64S, and NvFX-62D/63H/106K/110L-64T, specific activity when 10 µM αF8P was used as the substrate was measured. The results are shown in Table 6.

TABLE 6

| Amadoriase | Comp. Ex. 6-based amino acid substitution | Specific activity (mU/mg) 10 µM αF8P |
|---|---|---|
| NvFX-62D/63H/106K/110L (Comp. Ex. 6) | None | 0.30 |

TABLE 6-continued

| Amadoriase | Comp. Ex. 6-based amino acid substitution | Specific activity (mU/mg) 10 μM αF8P |
|---|---|---|
| NvFX-62D/63H/106K/110L-64M (Present Invention 16) | R64M | 0.42 |
| NvFX-62D/63H/106K/110L-64S (Present Invention 17) | R64S | 0.37 |
| NvFX-62D/63H/106K/110L-64T (Present Invention 18) | R64T | 0.38 |

As shown in Table 6, mutations of position 64 with M, S, or T were found to improve the specific activity of the NvFX-derived amadoriase on αF8P as well.

As described above, amadoriases into which mutations that would improve specific activity on αF8P had been introduced, which were discovered in the present invention, are deduced to have improved specific activity on HbA1c. Accordingly, such amadoriases are expected to improve the sensitivity of the method of direct measurement of HbA1c without the use of protease, such amadoriases are expected to reduce the amount of amadoriases to be formulated, and such amadoriases are expected to have potentials at the industrial level.

A glycated peptide where a basic amino acid (lysine) first appears from the N-terminus of HbA1c is αF8P (i.e., α-fructosyl-valyl-histidyl-leucyl-threonyl-prolyl-glutamyl-glutamyl-lysine). Thus, the amadoriase of the present invention can be used for measurement of αF8P generated upon digestion of HbA1c with the use of Lys-C protease or the like that cleaves a protein on the C terminal side of the lysine residue.

BRIEF DESCRIPTION OF SEQUENCE LISTING

SEQ ID NO: 1: the amino acid sequence of the amadoriase derived from the *Coniochaeta* sp. NISL 9330 strain (CFP-T7);
SEQ ID NO: 2: the nucleotide sequence encoding the amino acid sequence as shown in SEQ ID NO: 1;
SEQ ID NOs: 3-33: PCR primers;
SEQ ID NO: 34: PCR primer;
SEQ ID NO: 35: PCR primer;
SEQ ID NO: 36: the amino acid sequence of the amadoriase derived from *Aspergillus oryzae* RIB40 (FAOAo2);
SEQ ID NO: 37: the nucleotide sequence encoding the amino acid sequence as shown in SEQ ID NO: 36;
SEQ ID NO: 38: the amino acid sequence of the amadoriase derived from *Phaeosphaeria nodorum* (PnFX);
SEQ ID NO: 39: the nucleotide sequence encoding the amino acid sequence as shown in SEQ ID NO: 38;
SEQ ID NO: 40: the amino acid sequence of the amadoriase derived from *Eupenicillium terrenum* (EFP-T5);
SEQ ID NO: 41: the nucleotide sequence encoding the amino acid sequence as shown in SEQ ID NO: 40;
SEQ ID NOs: 42-53: PCR primers;
SEQ ID NO: 54: the amino acid sequence of the amadoriase derived from *Neocosmospora vasinfecta* (NvFX);
SEQ ID NO: 55: the nucleotide sequence encoding the amino acid sequence as shown in SEQ ID NO: 54;
SEQ ID NOs: 56-61: PCR primers;
SEQ ID NO: 62: the amino acid sequence of the amadoriase derived from *Aspergillus nidulans* (AnFX) comprising amino acid substitution S59G introduced thereinto;
SEQ ID NO: 63: the nucleotide sequence encoding the amino acid sequence as shown in SEQ ID NO: 62;
SEQ ID NOs: 64-88: PCR primers;
SEQ ID NO: 89: the amino acid sequence of the amadoriase derived from *Cryptococcus neoformans* (CnFX);
SEQ ID NO: 90: the nucleotide sequence encoding the amino acid sequence as shown in SEQ ID NO: 89;
SEQ ID NOs: 91-98: PCR primers;
SEQ ID NO: 99: the amino acid sequence of the amadoriase (Cc95FX) exhibiting 95% sequence identity with the ketoamine oxidase derived from *Curvularia clavata*;
SEQ ID NO: 100: the nucleotide sequence encoding the amino acid sequence as shown in SEQ ID NO: 99;
SEQ ID NOs: 101-112: PCR primers;
SEQ ID NO: 113: the amino acid sequence of the amadoriase derived from *Pyrenochaeta* sp. (Py);
SEQ ID NO: 114: the nucleotide sequence encoding the amino acid sequence as shown in SEQ ID NO: 113;
SEQ ID NO: 115: the amino acid sequence of the amadoriase derived from *Arthrinium* sp. (Ar);
SEQ ID NO: 116: the nucleotide sequence encoding the amino acid sequence as shown in SEQ ID NO: 115;
SEQ ID NO: 117: the amino acid sequence of the amadoriase derived from *Curvularia clavata* (Cc);
SEQ ID NO: 118: the nucleotide sequence encoding the amino acid sequence as shown in SEQ ID NO: 117;
SEQ ID NO: 119: the amino acid sequence of the amadoriase derived from *Emericella nidulans* (En);
SEQ ID NO: 120: the nucleotide sequence encoding the amino acid sequence as shown in SEQ ID NO: 119;
SEQ ID NO: 121: the amino acid sequence of the amadoriase derived from *Ulocladium* sp. (Ul);
SEQ ID NO: 122: the nucleotide sequence encoding the amino acid sequence as shown in SEQ ID NO: 121;
SEQ ID NO: 123: the amino acid sequence of the amadoriase derived from *Penicillium janthinellum* (Pj);
SEQ ID NO: 124: the nucleotide sequence encoding the amino acid sequence as shown in SEQ ID NO: 123;
SEQ ID NO: 125: the amino acid sequence of the amadoriase derived from *Aspergillus fumigatus* (Amadoriase I);
SEQ ID NO: 126: the nucleotide sequence encoding the amino acid sequence as shown in SEQ ID NO: 125;
SEQ ID NO: 127: the amino acid sequence of the amadoriase derived from *Aspergillus oryzae* (FAOAo1);
SEQ ID NO: 128: the nucleotide sequence encoding the amino acid sequence as shown in SEQ ID NO: 127;
SEQ ID NO: 129: the amino acid sequence of the amadoriase derived from *Aspergillus fumigatus* (Amadoriase II);
SEQ ID NO: 130: the nucleotide sequence encoding the amino acid sequence as shown in SEQ ID NO: 129;
SEQ ID NO: 131: the amino acid sequence of the amadoriase derived from *Aspergillus terreus* (FAOD-A);
SEQ ID NO: 132: the nucleotide sequence encoding the amino acid sequence as shown in SEQ ID NO: 131;
SEQ ID NO: 133: the amino acid sequence of CFP-T7-H20;
SEQ ID NO: 134: the nucleotide sequence encoding the amino acid sequence as shown in SEQ ID NO: 133;
SEQ ID NO: 135: the amino acid sequence of PnFPOX comprising amino acid substitutions S62D, D106K, G110L, and A113K introduced thereinto;
SEQ ID NO: 136: the nucleotide sequence encoding the amino acid sequence as shown in SEQ ID NO: 135;
SEQ ID NO: 137: the amino acid sequence of NvFX comprising amino acid substitutions R62D, G106K, and E110L introduced thereinto (NvFX-62D/106K/110L);
SEQ ID NO: 138: the nucleotide sequence encoding the amino acid sequence as shown in SEQ ID NO: 137;

SEQ ID NO: 139: the amino acid sequence of AnFX comprising amino acid substitutions R61D, G105K, and K1091L introduced thereinto (AnFX-61D/105K/109L);

SEQ ID NO: 140: the nucleotide sequence encoding the amino acid sequence as shown in SEQ ID NO: 139;

SEQ ID NO: 141: the amino acid sequence of CFP-T7 comprising amino acid substitutions R62D, L63H, E102K, D106K, Q110L, A113K, and A355S introduced thereinto (CFP-T7-H35);

SEQ ID NO: 142: the nucleotide sequence encoding the amino acid sequence as shown in SEQ ID NO: 141;

SEQ ID NO: 143: the amino acid sequence of EFP-T5 comprising amino acid substitutions R62D, L63H, D106K, K110L, T113K, and A355S introduced thereinto (EFP-T5-62D/63H/106K/110L/113K/355S);

SEQ ID NO: 144: the nucleotide sequence encoding the amino acid sequence as shown in SEQ ID NO: 143;

SEQ ID NO: 145: the amino acid sequence of the wild-type amadoriase derived from *Eupenicillium terrenum*;

SEQ ID NO: 146: the nucleotide sequence encoding the amino acid sequence as shown in SEQ ID NO: 145;

SEQ ID NO: 147: the amino acid sequence of the wild-type amadoriase derived from *Aspergillus nidulans*;

SEQ ID NO: 148: the nucleotide sequence encoding the amino acid sequence as shown in SEQ ID NO: 147;

SEQ ID NO: 149: the amino acid sequence of the wild-type amadoriase derived from *Cryptococcus neoformans*;

SEQ ID NO: 150: the nucleotide sequence encoding the amino acid sequence as shown in SEQ ID NO: 149;

SEQ ID NO: 151: the amino acid sequence of CFP-T7 comprising amino acid substitution R62A introduced thereinto (CFP-T7-H1);

SEQ ID NO: 152: the nucleotide sequence encoding the amino acid sequence as shown in SEQ ID NO: 151;

SEQ ID NO: 153: the amino acid sequence of CFP-T7 comprising amino acid substitution R62D introduced thereinto (CFP-T7-62D);

SEQ ID NO: 154: the nucleotide sequence encoding the amino acid sequence as shown in SEQ ID NO: 153;

SEQ ID NO: 155: the amino acid sequence of EFP-T5 comprising amino acid substitution R62D introduced thereinto (EFP-T5-R62D);

SEQ ID NO: 156: the nucleotide sequence encoding the amino acid sequence as shown in SEQ ID NO: 155;

SEQ ID NO: 157: the amino acid sequence of CFP-T7 comprising amino acid substitutions R62A and Q110L introduced thereinto (CFP-T7-H2);

SEQ ID NO: 158: the nucleotide sequence encoding the amino acid sequence as shown in SEQ ID NO: 157;

SEQ ID NO: 159: the amino acid sequence of CFP-T7 comprising amino acid substitutions R62A and Q110Y introduced thereinto (CFP-T7-H4);

SEQ ID NO: 160: the nucleotide sequence encoding the amino acid sequence as shown in SEQ ID NO: 159;

SEQ ID NO: 161: the amino acid sequence of CFP-T7 comprising amino acid substitutions R62N and Q110L introduced thereinto (CFP-T7-H2-62N);

SEQ ID NO: 162: the nucleotide sequence encoding the amino acid sequence as shown in SEQ ID NO: 161;

SEQ ID NO: 163: the amino acid sequence of CFP-T7 comprising amino acid substitutions R62D and Q110L introduced thereinto (CFP-T7-H6);

SEQ ID NO: 164: the nucleotide sequence encoding the amino acid sequence as shown in SEQ ID NO: 163;

SEQ ID NO: 165: the amino acid sequence of CFP-T7 comprising amino acid substitutions R62D, D106A, and Q110L introduced thereinto (CFP-T7-H10);

SEQ ID NO: 166: the nucleotide sequence encoding the amino acid sequence as shown in SEQ ID NO: 165;

SEQ ID NO: 167: the amino acid sequence of CFP-T7 comprising amino acid substitutions R62D, D106K, and Q110L introduced thereinto (CFP-T7-H11);

SEQ ID NO: 168: the nucleotide sequence encoding the amino acid sequence as shown in SEQ ID NO: 167;

SEQ ID NO: 169: the amino acid sequence of CFP-T7 comprising amino acid substitutions R62D, D106R, and Q110L introduced thereinto (CFP-T7-H12);

SEQ ID NO: 170: the nucleotide sequence encoding the amino acid sequence as shown in SEQ ID NO: 169;

SEQ ID NO: 171: the amino acid sequence of CFP-T7 comprising amino acid substitutions R62D, Q110L, and A113K introduced thereinto (CFP-T7-H13);

SEQ ID NO: 172: the nucleotide sequence encoding the amino acid sequence as shown in SEQ ID NO: 171;

SEQ ID NO: 173: the amino acid sequence of CFP-T7 comprising amino acid substitutions R62D, Q110L, and A113R introduced thereinto (CFP-T7-H14);

SEQ ID NO: 174: the nucleotide sequence encoding the amino acid sequence as shown in SEQ ID NO: 173;

SEQ ID NO: 175: the amino acid sequence of CFP-T7 comprising amino acid substitutions R62D, D106K, Q110L, and A113R introduced thereinto (CFP-T7-H21);

SEQ ID NO: 176: the nucleotide sequence encoding the amino acid sequence as shown in SEQ ID NO: 175;

SEQ ID NO: 177: the amino acid sequence of CFP-T7 comprising amino acid substitutions R62D, L63A, D106K, Q110L, and A113K introduced thereinto (CFP-T7-H24);

SEQ ID NO: 178: the nucleotide sequence encoding the amino acid sequence as shown in SEQ ID NO: 177;

SEQ ID NO: 179: the amino acid sequence of CFP-T7 comprising amino acid substitutions R62D, L63H, D106K, Q110L, and A113K introduced thereinto (CFP-T7-H26);

SEQ ID NO: 180: the nucleotide sequence encoding the amino acid sequence as shown in SEQ ID NO: 179;

SEQ ID NO: 181: the amino acid sequence of CFP-T7 comprising amino acid substitutions R62D, L63H, E102K, D106K, Q110L, and A113K introduced thereinto (CFP-T7-H28);

SEQ ID NO: 182: the nucleotide sequence encoding the amino acid sequence as shown in SEQ ID NO: 181;

SEQ ID NO: 183: the amino acid sequence of CFP-T7 comprising amino acid substitutions R62D, L63H, D106K, Q110L, A113K, and A419K introduced thereinto (CFP-T7-H29);

SEQ ID NO: 184: the nucleotide sequence encoding the amino acid sequence as shown in SEQ ID NO: 183;

SEQ ID NO: 185: the amino acid sequence of AnFX comprising amino acid substitutions R61D, L62H, E101K, G105K, K109L, S112K, and A355S introduced thereinto (AnFX-61D/62H/101K/105K/109L/112K/355S);

SEQ ID NO: 186: the nucleotide sequence encoding the amino acid sequence as shown in SEQ ID NO: 185;

SEQ ID NO: 187: the amino acid sequence of PnFX comprising amino acid substitutions S62D, L63H, D106K, G110L, A113K, and A351S introduced thereinto (PnFX-62D/63H/106K/110L/113K/351S);

SEQ ID NO: 188: the nucleotide sequence encoding the amino acid sequence as shown in SEQ ID NO: 187;

SEQ ID NO: 189: the amino acid sequence of CnFX comprising amino acid substitutions R62D, S106K, S110L, and A113K introduced thereinto (CnFX-62D/106K/110L/113K);

SEQ ID NO: 190: the nucleotide sequence encoding the amino acid sequence as shown in SEQ ID NO: 189;

SEQ ID NO: 191: the amino acid sequence of Cc95Fx comprising amino acid substitutions R62D, L63H, D106K, A110L, A113K, and A353S introduced thereinto (Cc95FX-62D/63H/106K/110L/113K/353S);
SEQ ID NO: 192: the nucleotide sequence encoding the amino acid sequence as shown in SEQ ID NO: 191;
SEQ ID NOs: 193-198: PCR primers;
SEQ ID NO: 199: the amino acid sequence of CFP-T7-H35 comprising amino acid substitutions E44P, D68N, E133A, E253K, V257C, N262H, Q337K, and E340P introduced thereinto and P435, K436, and L437 deleted therefrom (CFP-DH1);
SEQ ID NO: 200: the nucleotide sequence encoding the amino acid sequence as shown in SEQ ID NO: 199;
SEQ ID NOs: 201-202: PCR primers;
SEQ ID NO: 203: the amino acid sequence of CFP-DH1 comprising amino acid substitution A356T introduced thereinto (CFP-DH2);
SEQ ID NO: 204: the nucleotide sequence encoding the amino acid sequence as shown in SEQ ID NO: 203;
SEQ ID NOs: 205-208: PCR primers;
SEQ ID NO: 209: the amino acid sequence of CFP-T7-H35 comprising amino acid substitutions D68N and A356T introduced thereinto (CFP-T7-H37);
SEQ ID NO: 210: the nucleotide sequence encoding the amino acid sequence as shown in SEQ ID NO: 209;
SEQ ID NO: 211: the amino acid sequence of CFP-T7-H35 comprising amino acid substitutions R64G, D68N, and A356T introduced thereinto (CFP-T7-H38);
SEQ ID NO: 212: the nucleotide sequence encoding the amino acid sequence as shown in SEQ ID NO: 211;
SEQ ID NO: 213: the amino acid sequence of CFP-DH1 comprising amino acid substitutions R64G and A356T introduced thereinto (CFP-DH3);
SEQ ID NO: 214: the nucleotide sequence encoding the amino acid sequence as shown in SEQ ID NO: 213;
SEQ ID NOs: 215-239: PCR primers;
SEQ ID NO: 240: the nucleotide sequence encoding the amino acid sequence as shown in SEQ ID NO: 117; and
SEQ ID NOs: 241-248: PCR primers.

All publications, patents, and patent applications cited herein are incorporated herein by reference in their entirety.

---

The invention claimed is:

1. An amadoriase selected from the group consisting of the following (i) to
   (i) an amadoriase comprising an amino acid sequence having 90% or higher sequence identity with the amino acid sequence as shown in SEQ ID NO: 1 over the full length, wherein the amino acid at the position corresponding to position 64 of the amino acid sequence as shown in SEQ ID NO: 1 is an amino acid selected from the group consisting of glycine, methionine, leucine, threonine, valine, and isoleucine and having amadoriase activity on a glycated peptide; and
   (ii) an amadoriase comprising an amino acid sequence having 90% or higher sequence identity with the amino acid sequence as shown in SEQ ID NO: 1 over the full length, wherein the amino acid at the position corresponding to position 64 of the amino acid sequence as shown in SEQ ID NO: 1 is an amino acid selected from the group consisting of glycine, methionine, leucine, threonine, valine, and isoleucine and having amadoriase activity on α-fructosyl-valyl-histidyl-leucyl-threonyl-prolyl-glutamyl-glutamyl-lysine (αF8P).

2. The amadoriase according to claim 1, comprising a substitution of 1 or more amino acid residues at a position corresponding to a position selected from the group consisting of (a) to (i) below:
   (a) position 99 in SEQ ID NO: 1;
   (b) position 62 in SEQ ID NO: 1;
   (c) position 63 in SEQ ID NO: 1;
   (d) position 102 in SEQ ID NO: 1;
   (e) position 106 in SEQ ID NO: 1;
   (f) position 110 in SEQ ID NO: 1;
   (g) position 113 in SEQ ID NO: 1;
   (h) position 355 in SEQ ID NO: 1; and
   (i) position 419 in SEQ ID NO: 1.

3. The amadoriase according to claim 2, wherein
   (a) the amino acid at a position corresponding to position 99 in SEQ ID NO: 1 is serine;
   (b) the amino acid at a position corresponding to position 62 in SEQ ID NO: 1 is alanine, aspartic acid, asparagine, glutamine, glutamic acid, glycine, valine, leucine, isoleucine, cysteine, serine, methionine, threonine, or proline;
   (c) the amino acid at a position corresponding to position 63 in SEQ ID NO: 1 is alanine, histidine, or glycine;
   (d) the amino acid at a position corresponding to position 102 in SEQ ID NO: 1 is lysine;
   (e) the amino acid at a position corresponding to position 106 in SEQ ID NO: 1 is alanine, lysine, or arginine;
   (f) the amino acid at a position corresponding to position 110 in SEQ ID NO: 1 is phenylalanine, histidine, leucine, or tyrosine;
   (g) the amino acid at a position corresponding to position 113 in SEQ ID NO: 1 is lysine or arginine;
   (h) the amino acid at a position corresponding to position 355 in SEQ ID NO: 1 is serine; and/or
   (i) the amino acid at a position corresponding to position 419 in SEQ ID NO: 1 is lysine.

4. The amadoriase according to claim 1, comprising a substitution of 1 or 2 amino acid residue(s) at a position corresponding to the position (j) or (k) below:

(j) position 68 in SEQ ID NO: 1; or
(k) position 356 in SEQ ID NO: 1.

5. The amadoriase according to claim 4, wherein
(j) the amino acid at a position corresponding to position 68 in SEQ ID NO: 1 is asparagine; and/or
(k) the amino acid at a position corresponding to position 356 in SEQ ID NO: 1 is threonine.

6. The amadoriase according to claim 1, comprising a substitution of 1 or more amino acid residues at a position corresponding to a position selected from the group consisting of (i) to (xiv) below:
(i) position 262;
(ii) position 257;
(iii) position 249;
(iv) position 253;
(v) position 337;
(vi) position 340;
(vii) position 232;
(viii) position 129;
(ix) position 132;
(x) position 133;
(xi) position 44;
(xii) position 256;
(xiii) position 231; and
(xiv) position 81.

7. The amadoriase according to claim 1, which has specific activity on αF8P of 0.1 U/mg or greater.

8. The amadoriase according to claim 1, which has specific activity on αF8P of 1 U/mg or greater.

9. The amadoriase according to claim 1, which has specific activity on αF8P of 4 U/mg or greater.

10. The amadoriase according to claim 1, which is derived from the genus *Coniochaeta*.

11. An amadoriase comprising the amino acid sequence as shown in SEQ ID NO: 211 or 213.

12. The amadoriase according to claim 1, comprising a substitution of or more amino acid residue(s) at a position corresponding to a position selected from the group consisting of (l) to (q) below: 1:
(l) position 67 in SEQ ID NO: 1;
(m) position 72 in SEQ ID NO: 1;
(n) position 76 in SEQ ID NO: 1;
(o) position 96 in SEQ ID NO: 1;
(p) position 109 in SEQ ID NO: 1; and
(q) position 116 in SEQ ID NO: 1.

13. The amadoriase according to claim 12, wherein
(l) the amino acid at a position corresponding to position 67 in SEQ ID NO: 1 is histidine;
(m) the amino acid at a position corresponding to position 72 in SEQ ID NO: 1 is serine;
(n) the amino acid at a position corresponding to position 76 in SEQ ID NO: 1 is alanine or phenylalanine;
(o) the amino acid at a position corresponding to position 96 in SEQ ID NO: 1 is glutamic acid;
(p) the amino acid at a position corresponding to position 109 in SEQ ID NO: 1 is arginine or lysine; and/or
(q) the amino acid at a position corresponding to position 116 in SEQ ID NO: 1 is arginine.

14. A reagent kit for measurement of hemoglobin A1c comprising the amadoriase according to claim 1.

* * * * *

SEQUENCE LISTING

```
<160> NUMBER OF SEQ ID NOS: 248

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Arg Leu Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220
```

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
            245                 250                 255

Val Pro Val Val Tyr Asn Gly Glu Phe Gly Phe Phe Glu Pro Asp
        260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 2
<211> LENGTH: 1314
<212> TYPE: DNA
<213> ORGANISM: Coniochaeta sp.

<400> SEQUENCE: 2
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atacgactgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagcag taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc      540 ggattcggcg cgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900

-continued

```
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
tcatgggaat agcactgcgc aacaaggtgg                                      30

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
tattcccatg atcttgttga gatcatggc                                       29

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
acctgaaaaa gctgtaccag gcactgcac                                       29

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
acctgaaaaa gttctaccag gcactgcac                                       29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
acctgaaaaa gtattaccag gcactgcac                                       29

<210> SEQ ID NO 8
<211> LENGTH: 28
<212> TYPE: DNA
```

```
<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8 cttttcagg tcctcgatac cctcaggc                                        28

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
tcatgggaat aaacctgcgc aacaaggtgg                                     30

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
tcatgggaat agatctgcgc aacaaggtgg                                     30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
tcatgggaat acaactgcgc aacaaggtgg                                     30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
tcatgggaat agaactgcgc aacaaggtgg                                     30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
tgggaataga tctggccaac aaggtggacc                                     30

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
tgggaataga tctggaaaac aaggtggacc                                     30
```

```
<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
tgggaataga tctgcacaac aaggtggacc                                    30

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
cagatctatt cccatgatct tgttgag                                       27

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
tgagggtatc gaggccctga aaaagctg                                      28

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18
tgagggtatc gagaaactga aaaagctg                                      28

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
tgagggtatc gagcgcctga aaaagctg                                      28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
ctcgataccc tcaggcgtgt gttcgcag                                      28

<210> SEQ ID NO 21
<211> LENGTH: 30
<212> TYPE: DNA
<213> ORGANISM: Artificial
<220> FEATURE:
```

<223> OTHER INFORMATION: primer

<400> SEQUENCE: 21
aaaaagctgt accagaaact gcacgatgcc                30

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
gcatcgtgca gtttctggta cagcttttc                30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
aaaaagctgt accagcgtct gcacgatgcc                30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
gcatcgtgca gacgctggta cagcttttc                30

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
tcatgggaat agatgcgcgc aacaaggtgg                30

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
tcatgggaat agatgaccgc aacaaggtgg                30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
tcatgggaat agatcatcgc aacaaggtgg                30

```
<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
tcatgggaat agataagcgc aacaaggtgg                                      30

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
atctattccc atgatcttgt tgagatcat                                       29

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
aggcgtgtgt tcgcagtcca ttctg                                           25

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
gcgaacacac gcctaagggt atcgagaaac                                      30

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
acgtctagac ttgagtgcat cgcctcctg                                       29

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
tcaagtctag acgtaaggca ccgccaaaag                                      30

<210> SEQ ID NO 34
<211> LENGTH: 30
<212> TYPE: DNA
<213> ORGANISM: Artificial
<220> FEATURE:
<223> OTHER INFORMATION: primer
```

<400> SEQUENCE: 34
acagacactg cggactctgc tctcttgatg                                30

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
gtccgcagtg tctgtacacc agcacaag                                  28

<210> SEQ ID NO 36
<211> LENGTH: 436
<212> TYPE: PRT
<213> ORGANISM: Aspergillus oryzae

<400> SEQUENCE: 36

```
Met Thr Val Thr Lys Ser Ser Ile Leu Ile Ile Gly Ala Gly Thr
 1               5                  10                  15

Trp Gly Ala Ser Thr Ala Leu His Leu Gly Arg Arg Gly Tyr Thr Asn
            20                  25                  30

Val Thr Val Leu Asp Pro Tyr Thr Val Pro Ser Ala Ile Ser Ala Gly
        35                  40                  45

Asn Asp Val Asn Lys Ile Ile Ser Ser Gly Gln Tyr Ser Asn Lys Lys
    50                  55                  60

Asp Glu Ile Glu Val Asn Glu Ile Leu Ala Glu Glu Ala Phe Lys Gly
65                  70                  75                  80

Trp Thr Thr Asp Pro Leu Phe Lys Pro Tyr Tyr His Asp Thr Gly Val
                85                  90                  95

Val Met Ser Ala Cys Ser Ser Ala Gly Leu Asp Arg Leu Gly Ile Arg
            100                 105                 110

Val Arg Pro Glu Glu Glu Pro Asp Val Ser Glu Val Thr Lys Pro Glu
        115                 120                 125

His Phe Arg Gln Leu Ala Pro Ala Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Ile Arg Glu Ala Glu Lys Leu Gly Val Lys
                165                 170                 175

Phe Val Thr Gly Thr Gln Gly Arg Val Ile Thr Leu Ile Phe Glu Asn
            180                 185                 190

Asn Asp Val Lys Gly Ala Val Thr Ala Asp Gly Lys Ile Trp Arg Ala
        195                 200                 205

Glu Gln Thr Val Leu Cys Ala Gly Ala Asn Ala Ala Gln Phe Leu Asp
    210                 215                 220

Phe Lys Asp Gln Leu Arg Pro Thr Ala Trp Thr Leu Ala His Ile Arg
225                 230                 235                 240

Leu Lys Pro Glu Glu Arg Ala Leu Tyr Lys Asn Leu Pro Val Ile Phe
                245                 250                 255

Asn Ile Glu Lys Gly Phe Phe Phe Glu Pro Asp Glu Glu Arg Gly Glu
            260                 265                 270

Ile Lys Ile Cys Asp Glu His Pro Gly Tyr Thr Asn Met Val Lys Ser
        275                 280                 285

Ala Asp Gly His Leu Thr Ser Leu Pro Phe Glu Lys Thr Gln Ile Pro
```

```
                290                 295                 300
Lys Glu Ser Glu Ala Arg Val Arg Ala Leu Leu Ser Glu Thr Met Pro
305                 310                 315                 320

Gln Leu Ala Asp Arg Pro Phe Ser Phe Ala Arg Val Cys Trp Cys Ala
                325                 330                 335

Asp Thr Ala Asn Arg Glu Phe Ile Ile Asp Arg His Pro Glu His Pro
                340                 345                 350

Ser Leu Val Leu Gly Cys Gly Ala Ser Gly Arg Gly Phe Lys Tyr Leu
            355                 360                 365

Pro Ser Ile Gly Asn Leu Ile Val Asp Ala Ile Glu Asp Lys Val Pro
        370                 375                 380

Glu Lys Val His Lys Leu Thr Arg Trp Ser Pro Asp Ile Ala Val Asp
385                 390                 395                 400

Arg Lys Trp Arg Asp Thr Leu Gly Arg Phe Gly Gly Pro Asn Arg Val
                405                 410                 415

Met Asp Phe His Asp Val Lys Glu Trp Thr Asn Val Gln Asn Lys Asp
                420                 425                 430

Thr Ala Lys Leu
        435

<210> SEQ ID NO 37
<211> LENGTH: 1311
<212> TYPE: DNA
<213> ORGANISM: Aspergillus oryzae

<400> SEQUENCE: 37
atgactgtca ccaaatcttc ctcaatcctg atcatcggcg caggcacttg gggcgcttca      60
actgcccttc accttggtcg cagaggatac accaatgtca ccgtcctaga cccttacaca     120
gtgccctcag caatttcagc tggaaatgac gtgaacaaga tcatctcctc ggggcaatac     180
agcaacaaaa aggatgagat tgaagttaac gaaattctcg ccgaggaggc attcaaaggc     240
tggacaaccg acccttttgtt caagccatac taccacgaca ctggcgttgt aatgtctgct     300
tgcagcagcg ccggtctgga tcgcctcgga atccgagtaa ggccggaaga ggaacctgat     360
gtttccgaag tcacgaagcc ggagcacttc cgccaactgg ccccgctgt gctgaaagga      420 aacttcccgg ggtggagagg ctaccacatt cgttcgaacg ctggctgggc gcacgcccga     480
aatgccctcg tggccgctat acgcgaagca gagaaacttg tgttaaatt cgtaacaggc      540 acccaaggaa gagtcatcac ccttatcttc gagaacaacg acgtcaaggg cgcagtcacc     600
gccgacggaa agatctggcg cgcggagcaa acagttctct cgctggcgc aaatgctgcg      660 cagttcttgg atttttaagga ccagctccgc ccaacggcat ggacactcgc ccatatccgg    720
ctcaaacctg aggaacgcgc gctctacaaa aacttgccgg tgattttcaa cattgagaaa    780 ggattttttct tcgagcctga tgaggagcgc ggggagatca agatctgcga cgaacatccg    840
ggatacacta acatggttaa atctgcggat ggccacttga cgagtttgcc ctttgagaag    900
acccagatcc ccaaggagtc tgaagctaga gtcagagctt actatcggga gaccatgcct     960
caattagccg atcgcccatt tagcttcgcc cgcgtttgct ggtgtgcgga caccgcaaac   1020
cgtgaattca tcattgaccg ccaccctgaa cacccgtctc ttgttttggg atgcggtgct   1080
tccggaaggg gtttcaaata tctcccctca atcggcaacc tcattgttga cgccattgaa   1140
gacaaagtcc cagagaaagt tcacaagctt acgaggtgga gtccagacat tgctgttgac   1200
agaaagtgga gggacactct ggggcgcttt ggagggccta accgtgtcat ggacttccat   1260
```
gatgtcaagg aatggactaa cgtgcagaac aaggatactg cgaagctgta g    1311

<210> SEQ ID NO 38
<211> LENGTH: 437
<212> TYPE: PRT
<213> ORGANISM: Phaeosphaeria nodorum

<400> SEQUENCE: 38

```
Met Ala Pro Ser Arg Ala Asn Thr Ser Val Ile Val Val Gly Gly Gly
 1               5                  10                  15

Gly Thr Ile Gly Ser Ser Thr Ala Leu His Leu Val Arg Ser Gly Tyr
             20                  25                  30

Thr Pro Ser Asn Val Thr Val Leu Asp Ala Tyr Pro Ile Pro Ser Ser
         35                  40                  45

Gln Ser Ala Gly Asn Asp Leu Asn Lys Ile Met Gly Val Ser Leu Arg
     50                  55                  60

Asn Pro Val Asp Leu Gln Leu Ala Leu Glu Ala Arg Gln Met Trp Asn
 65                  70                  75                  80

Glu Asp Glu Leu Phe Lys Lys Phe Phe His Asn Thr Gly Arg Leu Asp
                 85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365
```

```
Gly Asp Ser Gly His Ser Phe Lys Leu Leu Pro Asn Ile Gly Lys His
        370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 39
<211> LENGTH: 1314
<212> TYPE: DNA
<213> ORGANISM: Phaeosphaeria nodorum

<400> SEQUENCE: 39
atggccccgt cgcgtgctaa tacgtcggtc attgtggttg gtggtggtgg tacgattggc      60
tcatctacgg ctctgcatct ggtccgctca ggctataccc cgtcgaacgt gacggttctg     120
gatgcatacc cgattccgag ctctcagagc gctggcaacg acctgaataa atcatgggt      180
gtctctctgc gtaatccggt ggatctgcag ctggctctgg aagcgcgcca aatgtggaac     240
gaagacgaac tgttcaagaa gttttttccat aacaccggcc gtctggattg cgcgcacggt    300
gaaaaagata ttgccgacct gaagagcggc tatcaggctc tggtggatgc gggtctggac    360
gccacgaacg aatggctgga tagtgaagac gaaatcctga acgtatgcc gctgctgtcc      420
cgcgatcaaa ttaaaggctg gaaggcgatc ttttcaaaag acggtggttg gctggcagca     480
gcaaaggcaa ttaatgcagt tggtgaatat ctgcgtgatc agggcgtccg cttcggtttt    540
tacggcgccg gttctttcaa agcaccgctg ctggctgaag gcgtctgcat cggtgtcgaa    600
accgtggatg gcacgcgcta ttacgcagac aaagtggttc tggctgcagg tgcatggtcg     660
ccgaccctgg ttgaactgca tgaacagtgt gtgagcaaag cgtgggttta cggccacatt    720
caactgacgc cggaagaagc cgcacgttat aagaacagcc cggtcgtgta caatggcgat    780
gtgggcttt tctttgaacc gaacgaacat ggcgttatca aagtctgcga tgaatttccg     840
ggttttaccc gcttcaagat gcaccagccg tttggtgcca aagcaccgaa gcgtattagt     900
gtgccgcgct cccatgccaa acacccgacc gatacgatcc cggatgcaag tgacgtttcc    960
attcgtcgcg ctatcgcgac ctttatgccg cagttcaaga acaaaaagat gttcaaccaa   1020
gcgatgtgct ggtgtaccga tacggccgac gctgcgctgc tgatttgtga acatccggaa   1080
tggaaaaact tgttctggc gaccggcgat tcaggtcatt cgttcaaact gctgccgaat    1140
atcggcaagc acgttgtcga actgctggag ggtacgctgg cagatgacct ggcacacgca   1200
tggcgttggc gtccgggtag tggtgatgca ctgaaaagcc gtcgctctgc tccggcgaaa   1260
gacctggctg atatgccggg ctggaaccat gacaaaccgc gtgctaatct gtaa         1314

<210> SEQ ID NO 40
<211> LENGTH: 437
<212> TYPE: PRT
<213> ORGANISM: Eupenicillium terrenum

<400> SEQUENCE: 40

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
```

-continued

```
                20                  25                  30
Thr Pro Ser Asn Ile Thr Val Leu Asp Val Tyr Lys Thr Pro Ser Leu
            35                  40                  45

Gln Ser Ala Gly His Asp Leu Asn Lys Ile Met Gly Ile Arg Leu Arg
        50                  55                  60

Asn Gly Pro Asp Leu Gln Leu Ser Leu Glu Ser Leu Asp Met Trp Gln
 65                  70                  75                  80

Asn Asp Glu Leu Phe Lys Pro Phe His Gln Val Gly Met Ile Asp
                85                  90                  95

Cys Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
        130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
            165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
            245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
        290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
            325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
            405                 410                 415

Arg Arg Gly Ala Pro Ala Lys Asp Leu Ala Glu Met Pro Gly Trp Lys
        420                 425                 430

His Asp Ala His Leu
        435
```

<210> SEQ ID NO 41
<211> LENGTH: 1314
<212> TYPE: DNA
<213> ORGANISM: Eupenicillium terrenum

<400> SEQUENCE: 41

| | |
|---|---|
| atggctcatt cgcgtgcaag caccaaagtc gtcgtggttg ggggaggtgg tacgatcggg | 60 |
| tcttcgacgg ctctgcactt aatccgctct ggatataccc cctcaaatat caccgtgctt | 120 |
| gacgtataca agaccccttc attgcaatct gcaggacatg atttgaacaa gatcatgggc | 180 |
| attcgattgc gcaacgggcc tgacttgcag ctttcgctgg aatcactcga catgtggcaa | 240 |
| aacgatgagt tgttcaagcc attctttcac caagtgggca tgattgattg ttcgtcatcc | 300 |
| aaagagggta ttgaaaatct tcgacgaaaa taccagaccc tcctcgatgc gggcattggg | 360 |
| ctggagaaga cgaacgtttg gctggaatct gaagatgaga tcctcgccaa agcgccgaat | 420 |
| ttcacgcgtg aacaagtcaa ggggtggaaa ggcttatttt gcactgatgg aggctggctt | 480 |
| gctgcagcca aggctatcaa tgcgatcgga attttcctcc aggacaaagg tgtcaagttt | 540 |
| ggctttggag atgctggtac ctttcagcaa cctctgttcg ccgctgatgg aaaaacttgc | 600 |
| atcggacttg aaactacaga cggaaccaag tactttgctg acaaggttgt cttggctgct | 660 |
| ggtgcgtgga gtcccacctt ggtggatcta aagatcagt gtgtttcaaa ggcctgggtt | 720 |
| ttcgctcata ttcaactcac acccaaagaa gcggacgcgt acaagaatgt gcctgtggtc | 780 |
| tatgatggtg aatatgggtt cttttttcgaa cccgacgagt atggggtgat caaagtctgt | 840 |
| gacgagttcc ctggtttctc tcgcttcaaa ctgcatcaac cgtacggggc tgcatctccc | 900 |
| aagatgatat ccgtaccgcg atcacacgcc aagcatccca cagataccta ccctgatgcc | 960 |
| tccgaagtca ccatacgcaa agcgatcgca aggttcctgc agaatttaa agacaaggag | 1020 |
| ctcttcaacc gtaccatgtg ctggtgtaca gatacggccg atgctaactt attgatttgc | 1080 |
| gaacacccga agtggaagaa tttcattctg gccactggag atagcggaca ttccttcaag | 1140 |
| ctgttgccaa acatcgggaa atacgtagtt gagcttttag agggatctct atcgcaggaa | 1200 |
| atggctggtg cctggagatg gagacccgga ggtgatgctc ttagatctag acgcggtgct | 1260 |
| ccggcaaagg atcttgctga gatgccggga tggaagcatg atgcacattt gtga | 1314 |

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
aagatcatgg gcattgattt gcgcaacggg                                      30

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
aatgcccatg atcttgttca aatcatgtcc                                      30

<210> SEQ ID NO 44

```
<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
gagggtattg aaaaacttcg acgaaaatac                                    30

<210> SEQ ID NO 45
<211> LENGTH: 26
<212> TYPE: DNA
<213> ORGANISM: Artificial
<220> FEATURE:
<223> OTHER INFORMATION: primer

<400> SEQUENCE: 45
ttcaataccc tctttggatg acgaac                                        26

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
aaaaacttcg acgattatac cagaccctcc                                    30

<210> SEQ ID NO 47
<211> LENGTH: 29
<212> TYPE: DNA
<213> ORGANISM: Artificial
<220> FEATURE:
<223> OTHER INFORMATION: primer

<400> SEQUENCE: 47
tcgtcgaagt ttttcaatac cctctttgg                                     29

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
cgacgattat accagaaaact cctcgatgcg                                   30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
ctggtataat cgtcgaagtt tttcaatacc                                    30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
```

```
agatacggcc gattctaact tattgatttg                                    30
```

<210> SEQ ID NO 51
<211> LENGTH: 29
<212> TYPE: DNA
<213> ORGANISM: Artificial
<220> FEATURE:
<223> OTHER INFORMATION: primer

<400> SEQUENCE: 51

```
atcggccgta tctgtacacc agcacatgg                                     29
```

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52

```
tcatgggcat tgatcatcgc aacgggcctg                                    30
```

<210> SEQ ID NO 53
<211> LENGTH: 29
<212> TYPE: DNA
<213> ORGANISM: Artificial
<220> FEATURE:
<223> OTHER INFORMATION: primer

<400> SEQUENCE: 53

```
atcaatgccc atgatcttgt tcaaatcat                                     29
```

<210> SEQ ID NO 54
<211> LENGTH: 441
<212> TYPE: PRT
<213> ORGANISM: Neocosmospora vasinfecta

<400> SEQUENCE: 54

```
Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175
```

Gly Val Arg Phe Gly Phe Gly Ala Gly Ser Phe Lys Arg Pro Leu
            180                 185                 190

Phe Ala Asp Asp Gly Thr Thr Cys Ile Gly Val Glu Thr Val Asp Gly
            195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Val Tyr Lys Gly
                245                 250                 255

Cys Pro Val Val Tyr His Gly Asp Val Gly Phe Phe Glu Pro Asn
                260                 265                 270

Glu Asn Gly Val Ile Lys Val Cys Asp Glu Phe Pro Gly Phe Thr Arg
            275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
                340                 345                 350

Ala Asp Ser Ala Leu Leu Ile Cys Glu His Pro Arg Trp Lys Asn Phe
            355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
    435                 440

<210> SEQ ID NO 55
<211> LENGTH: 1326
<212> TYPE: DNA
<213> ORGANISM: Neocosmospora vasinfecta

<400> SEQUENCE: 55
atgacgaccc cgcgtaaaga aacgacggtc ctgattattg gtggtggtgg cacgattggt        60
agctcgacgg ctctgcatct gctgcgtgcc ggctataccc cgtctaacat taccgtgctg       120
gatacgtacc cgatcccgag tgcccagtcc gcaggcaacg acctgaataa aattatgggt       180
atccgtctgc gcaataaagt tgatctgcaa ctgagcctgg aagcccgtga tatgtggcgc       240
aacgacgcac tgtttcgtcc gttttttccat aataccggcc gcctggactg cgaaagctct      300
gctgaaggcg tggaaggtct cgtcgcgaa tatcagaaac tggtggaagc aggcgttggt        360
ctggaagaaa cgcacgaatg gctggatagc gaagaagcta ttctggaaaa agcgccgctg       420
ctgcaacgtg aagaaattga aggttggaaa gccatctggt ctgaagaagg cggttggctg       480
gcggccgcaa aagctattaa cgcgatcggt gaagaactgc agcgtcaagg cgttcgcttc       540
ggttttggcg gtgccggtag ttttaaacgc ccgctgttcg cagatgacgg caccacgtgt       600

| | | | | |
|---|---|---|---|---|
| atcggtgtcg | aaaccgtgga | tggcacgcag | tatcatgcgg | acaaagtggt tctggctgca | 660 |
| ggtgcttggt | caccggcgct | ggtcgatctg | gaagaacagt | gctgttcgaa agcctgggtg | 720 |
| tacgcacaca | tgcaactgac | cccggaagaa | gccgcagttt | ataaaggctg cccggtcgtg | 780 |
| taccacggcg | atgtcggctt | tttctttgaa | ccgaacgaaa | atggcgttat taaagtctgt | 840 |
| gacgaattcc | cgggttttac | gcgtttcaaa | cagcatcaac | cgtatggtgc cccggcaccg | 900 |
| aaacctgtga | gtgttccgcg | ctcccatgcg | aaacacccga | ccgatacgta cccggacgct | 960 |
| tcagaagaat | cgatcaaacg | tgccgtgagt | acctttctgc | cgcgcttcaa agataaaccg | 1020 |
| ctgtttaacc | gtgcactgtg | ctggtgtacc | gatacggccg | actccgcact gctgatttgc | 1080 |
| gaacacccgc | gctggaaaaa | ttttatcctg | gcgaccggcg | atagcggtca ttctttcaaa | 1140 |
| ctgctgccga | ttatcggcaa | acacgttgtc | gaactggttg | aaggtcgtct ggcggatgac | 1200 |
| ctggctgaag | cgtggcgttg | gcgtccgggt | cagggtgatg | cacgtaaaag cattcgcgct | 1260 |
| gcgccggcga | agacctggcc | ggatatgccg | ggctggaaac | acgaccaaga ctcggaatca | 1320 |
| cgctga | | | | | 1326 |

<210> SEQ ID NO 56
<211> LENGTH: 29
<212> TYPE: DNA
<213> ORGANISM: Artificial
<220> FEATURE:
<223> OTHER INFORMATION: primer

<400> SEQUENCE: 56
ttatgggtat cgatctgcgc aataaagtt                                    29

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57
gctcagttgc agatcaactt tattgcgcag                                   30

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
gaaggcgtgg aaaaactgcg tcgcgaatat                                   30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
ttccaccagt ttctgatatt cgcgacgcag                                   30

<210> SEQ ID NO 60
<211> LENGTH: 27
<212> TYPE: DNA

<213> ORGANISM: Artificial
<220> FEATURE:
<223> OTHER INFORMATION: primer

<400> SEQUENCE: 60
ctgcgtcgcc tgtatcagaa actggtg                                27

<210> SEQ ID NO 61
<211> LENGTH: 30
<212> TYPE: DNA
<213> ORGANISM: Artificial
<220> FEATURE:
<223> OTHER INFORMATION: primer

<400> SEQUENCE: 61
accaacgcct gcttccacca gtttctgata                             30

<210> SEQ ID NO 62
<211> LENGTH: 438
<212> TYPE: PRT
<213> ORGANISM: Aspergillus nidulans

<400> SEQUENCE: 62

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Arg Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Phe Glu Pro Asn
            260                 265                 270

```
Glu Asn Gly Ile Ile Lys Val Cys Asp Glu Phe Pro Gly Phe Thr His
            275                 280                 285
Phe Lys Met His Gln Pro Tyr Gly Ser Pro Ala Pro Lys Pro Ile Ser
        290                 295                 300
Val Pro Arg Ser His Ala Lys His Pro Thr Asp Thr Tyr Pro His Ala
305                 310                 315                 320
Ser Glu Val Thr Ile Lys Lys Ala Ile Asn Arg Phe Leu Pro Arg Phe
                325                 330                 335
Asn Asp Lys Glu Leu Phe Asn Arg Ala Met Cys Trp Cys Thr Asp Thr
            340                 345                 350
Ala Asp Ala Asn Leu Leu Val Cys Glu His Pro Arg Trp Lys Gly Phe
        355                 360                 365
Tyr Leu Ala Thr Gly Asp Ser Gly His Ser Phe Lys Leu Leu Pro Asn
370                 375                 380
Ile Gly Lys His Val Val Glu Leu Leu Glu Glu Arg Leu Glu Ser Val
385                 390                 395                 400
Phe Lys Asp Ala Trp Arg Trp Arg Pro Gly Ser Gly Asp Ala Leu Lys
                405                 410                 415
Ser Arg Arg Ala Ala Pro Ala Lys Asp Leu Ala Asp Met Pro Gly Trp
            420                 425                 430
Arg Asn Glu Ala Lys Met
        435
```

<210> SEQ ID NO 63
<211> LENGTH: 1317
<212> TYPE: DNA
<213> ORGANISM: Aspergillus nidulans

<400> SEQUENCE: 63

```
atgacgcccc gagccaacac caaaatcatt gtcgtcggcg gcggcggcac aatgggctcg      60
tcgacagccc tacacctcct gcgcgccggc tacgccgt  ccaacattac agtgctcgac     120
acgtgcccta tccctccgc  acagtctgca ggctacgacc tgaacaaaat catggggatc     180
cgtctgcgca acaagcctga tttacagctc tctcttgagg cgctggacat gtggaaaaat     240
gatcctctct tcaagccgtt tttccacaat gttggaatga tcgacgtctc ttcaacagag     300
gaaggcatcg agggtcttcg gaagaaatac cagtctcttc tcgacgcagg cattgggctc     360
gagaagacga tttcatgct  ggaaagtgaa acgagatcc  tggctaaagc gccgcatttc     420
acgcaggagc agattaaagg ctggaaaggc ctgttctgtg cgacggcgg  ctggctcgct     480
gcagccaaag ccatcaatgc cattgggcag ttcctcaagg aacagggcgt caagtttgga     540
ttcggcggcg ccggcacgtt caaaaagcca ctcttcgccg atgcccacga agacgtgc      600
atcggcgtcg agactgtaga cggcacaaag tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt ataagaacac tcctgttata     780
tacgacggtg actatgggtt tttctttgag ccgaatgaaa acggcatcat aaaagtctgt     840
gacgaattcc ctggcttcac gcatttcaaa atgcaccagc cgtacggctc gccggcgccc     900
aaacccatct ctgtgcctcg ttcccatgcg aagcacccca cagatacata cccgcacgcg     960
tcggaggtca cgatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagtgggca ttcgttcaag    1140
```

```
ttgctgccga atattggaaa gcatgttgtc gagttattgg aggagaggct ggaaagtgtg   1200
tttaaggatg cttggaggtg gaggcctggc agtggggatg cattaaaaag tagacgggct   1260
gcgcctgcga aggacctggc ggatatgccg gggtggagga atgaggcaaa gatgtag      1317
```

```
<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
atcatgggca tcgatctgcg caacaagcct                                       30

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
agagagctgt aaatcaggct tgttgcgcag                                       30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
gaaggcatcg agaaacttcg gaagaaatac                                       30

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
gtcgagaaga gactggtatt tcttccgaag                                       30

<210> SEQ ID NO 68
<211> LENGTH: 27
<212> TYPE: DNA
<213> ORGANISM: Artificial
<220> FEATURE:
<223> OTHER INFORMATION: primer

<400> SEQUENCE: 68
cttcggaagc tgtaccagtc tcttctc                                          27

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
cccaatgcct gcgtcgagaa gagactggta                                       30
```

<210> SEQ ID NO 70
<211> LENGTH: 30
<212> TYPE: DNA
<213> ORGANISM: Artificial
<220> FEATURE:
<223> OTHER INFORMATION: primer

<400> SEQUENCE: 70
cttctcgagc ccaatgcctg cgtcgagaag                              30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
gataccgcgg atagcaatct gcttgtttgt                              30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
ccagcgtgga tgctcacaaa caagcagatt                              30

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
atcatgggca tcgatcatcg caacaagcct                              30

<210> SEQ ID NO 74
<211> LENGTH: 27
<212> TYPE: DNA
<213> ORGANISM: Artificial
<220> FEATURE:
<223> OTHER INFORMATION: primer

<400> SEQUENCE: 74
agagagctgt aaatcaggct tgttgcg                                 27

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
tcttcaacag agaaaggcat cgagaaactt                              30

<210> SEQ ID NO 76
<211> LENGTH: 27
<212> TYPE: DNA
<213> ORGANISM: Artificial
<220> FEATURE:
<223> OTHER INFORMATION: primer

<400> SEQUENCE: 76
gtacagcttc cgaagtttct cgatgcc                                       27

<210> SEQ ID NO 77
<211> LENGTH: 29
<212> TYPE: DNA
<213> ORGANISM: Artificial
<220> FEATURE:
<223> OTHER INFORMATION: primer

<400> SEQUENCE: 77
atcatgggtg tcgatctgcg taatccggt                                     29

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
agccagctgc agatccaccg gattacgcag                                    30

<210> SEQ ID NO 79
<211> LENGTH: 30
<212> TYPE: DNA
<213> ORGANISM: Artificial
<220> FEATURE:
<223> OTHER INFORMATION: primer

<400> SEQUENCE: 79
aaagatattg ccaaactgaa gagcggctat                                    30

<210> SEQ ID NO 80
<211> LENGTH: 30
<212> TYPE: DNA
<213> ORGANISM: Artificial
<220> FEATURE:
<223> OTHER INFORMATION: primer

<400> SEQUENCE: 80
atccaccaga gcctgatagc cgctcttcag                                    30

<210> SEQ ID NO 81
<211> LENGTH: 27
<212> TYPE: DNA
<213> ORGANISM: Artificial
<220> FEATURE:
<223> OTHER INFORMATION: primer

<400> SEQUENCE: 81
ctgaagagcc tgtatcaggc tctggtg                                       27

<210> SEQ ID NO 82
<211> LENGTH: 30
<212> TYPE: DNA
<213> ORGANISM: Artificial
<220> FEATURE:
<223> OTHER INFORMATION: primer

<400> SEQUENCE: 82
gtccagaccc gcatccacca gagcctgata                                    30

<210> SEQ ID NO 83
<211> LENGTH: 30

<212> TYPE: DNA
<213> ORGANISM: Artificial
<220> FEATURE:
<223> OTHER INFORMATION: primer

<400> SEQUENCE: 83
agcctgtatc agaaactggt ggatgcgggt                                    30

<210> SEQ ID NO 84
<211> LENGTH: 30
<212> TYPE: DNA
<213> ORGANISM: Artificial
<220> FEATURE:
<223> OTHER INFORMATION: primer

<400> SEQUENCE: 84
gttcgtggcg tccagacccg catccaccag                                    30

<210> SEQ ID NO 85
<211> LENGTH: 30
<212> TYPE: DNA
<213> ORGANISM: Artificial
<220> FEATURE:
<223> OTHER INFORMATION: primer

<400> SEQUENCE: 85
gatacggccg acagcgcgct gctgatttgt                                    30

<210> SEQ ID NO 86
<211> LENGTH: 30
<212> TYPE: DNA
<213> ORGANISM: Artificial
<220> FEATURE:
<223> OTHER INFORMATION: primer

<400> SEQUENCE: 86
ccattccgga tgttcacaaa tcagcagcgc                                    30

<210> SEQ ID NO 87
<211> LENGTH: 29
<212> TYPE: DNA
<213> ORGANISM: Artificial
<220> FEATURE:
<223> OTHER INFORMATION: primer

<400> SEQUENCE: 87
atgggtgtcg atcatcgtaa tccggtgga                                     29

<210> SEQ ID NO 88
<211> LENGTH: 30
<212> TYPE: DNA
<213> ORGANISM: Artificial
<220> FEATURE:
<223> OTHER INFORMATION: primer

<400> SEQUENCE: 88
cagagccagc tgcagatcca ccggattacg                                    30

<210> SEQ ID NO 89
<211> LENGTH: 443
<212> TYPE: PRT
<213> ORGANISM: Cryptococcus neoformans

<400> SEQUENCE: 89

Met Pro Pro Ser Arg Ala Ser Thr Lys Val Ile Val Ile Gly Gly Gly
1               5                   10                  15

-continued

Gly Thr Leu Gly Ser Ser Thr Ala Leu His Leu Leu Arg Ala Gly Tyr
        20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
                100                 105                 110

Ala Ile Leu Lys Ala Gly Ser Gly Leu Glu Lys Thr His His Trp Leu
            115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
                180                 185                 190

Phe Asp Glu Asp Gly Thr Lys Ala Ile Gly Ile Glu Thr Val Asp Gly
            195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Glu Pro Asn
                260                 265                 270

Glu Lys Gly Val Ile Lys Val Cys Asp Glu Phe Pro Gly Phe Thr Arg
            275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
    355                 360                 365

Ile Leu Ala Thr Gly Asp Ser Gly His Ser Phe Lys Ile Leu Pro Asn
        370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Asp Met Asp
      435                 440

<210> SEQ ID NO 90
<211> LENGTH: 1332
<212> TYPE: DNA
<213> ORGANISM: Cryptococcus neoformans

<400> SEQUENCE: 90

| | |
|---|---:|
| atgccgccgt cccgtgcttc aacgaaagtg attgtcattg gtggtggtgg tacgctgggc | 60 |
| tcctcaaccg ccctgcatct gctgcgcgcg ggctataccc cgagtaacat taccgtgctg | 120 |
| gatacgtacc tgatcccgag tgcccagtcc gcaggcaacg acctgaataa aattatgggt | 180 |
| attcgtatcc gcaatccggt ggataaacaa ctgagcctgg aagcccgtga tatgtggcgc | 240 |
| aacgacgaag ttttcaaacc gtacttccat aacaccggtc gtctggactg cgctcacacg | 300 |
| ccggaatcaa ttgcgtcgct gcgtaaaagc tacgaagcca tcctgaaagc aggctcaggt | 360 |
| ctggaaaaaa cccatcactg gctgtcgacg gaagatgaaa tcctggcacg tgcaccgctg | 420 |
| ctggaccgta aacagattaa aggttggaaa gcaatctata gtgaagatgg cggttggctg | 480 |
| gcggccgcaa aagctattaa ctccatcggc caagtcctga agaaaaaggt gtgaccttc | 540 |
| ggctttggta gcgcaggctc ttttaaaaaa ccgctgttcg atgaagacgg cacgaaagcc | 600 |
| attggtatcg aaaccgttga tggtacgcag tattttgccg acaaagtggt tctggctgca | 660 |
| ggtgcatgga gcccgaccct ggttgatctg gaaggccagt gctgttctaa agcttgggtc | 720 |
| tacgcgcaca tgcaactgac gccggaagaa gccgcagaat ataaagaatg cccggtcgtg | 780 |
| tacaacagcg aactgggctt tttctttgaa ccgaacgaaa aggtgtgat caaagtttgt | 840 |
| gatgaattcc cgggctttac ccgtttcaaa cagcatcaac cgtacggtgc tagctctacg | 900 |
| aaacacatta gctttccgcg ctctcatgcg aaacacccga ccgatacgat cccggatgaa | 960 |
| agtgacgcct ccattcgtcg cgctatctct gcgtttctgc gcgtttcaa agaaaaagaa | 1020 |
| ctgtttaacc gcgcgctgtg ctggtgtacc gatacggctg acgcgaacct gctgatttgt | 1080 |
| gaacacccga atggaaaaa ttttatcctg ccaccggcg attcaggtca ttcgttcaaa | 1140 |
| attctgccga atatcggcaa acacgttgtc gaactgattg aaggtaccct ggccgaagat | 1200 |
| ctggcagaaa gctggcgttg gcgtccgggc agtggtgacc cgctgatctc ccgtcgcgct | 1260 |
| gcgccggcgc gcgacctggc ggacctgccg ggctggaacc acgacgaacc gagcgacgat | 1320 |
| gacatggact ga | 1332 |

<210> SEQ ID NO 91
<211> LENGTH: 30
<212> TYPE: DNA
<213> ORGANISM: Artificial
<220> FEATURE:
<223> OTHER INFORMATION: primer

<400> SEQUENCE: 91

| | |
|---|---:|
| attatgggta ttgatatccg caatccggtg | 30 |

<210> SEQ ID NO 92
<211> LENGTH: 30
<212> TYPE: DNA
<213> ORGANISM: Artificial
<220> FEATURE:
<223> OTHER INFORMATION: primer

<400> SEQUENCE: 92
gctcagttgt ttatccaccg gattgcggat                               30

<210> SEQ ID NO 93
<211> LENGTH: 30
<212> TYPE: DNA
<213> ORGANISM: Artificial
<220> FEATURE:
<223> OTHER INFORMATION: primer

<400> SEQUENCE: 93
gaatcaattg cgaaactgcg taaaagctac                               30

<210> SEQ ID NO 94
<211> LENGTH: 30
<212> TYPE: DNA
<213> ORGANISM: Artificial
<220> FEATURE:
<223> OTHER INFORMATION: primer

<400> SEQUENCE: 94
tttcaggatg gcttcgtagc ttttacgcag                               30

<210> SEQ ID NO 95
<211> LENGTH: 30
<212> TYPE: DNA
<213> ORGANISM: Artificial
<220> FEATURE:
<223> OTHER INFORMATION: primer

<400> SEQUENCE: 95 ctgcgtaaaac tgtacgaagc catcctgaaa                              30

<210> SEQ ID NO 96
<211> LENGTH: 30
<212> TYPE: DNA
<213> ORGANISM: Artificial
<220> FEATURE:
<223> OTHER INFORMATION: primer

<400> SEQUENCE: 96
acctgagcct gctttcagga tggcttcgta                               30

<210> SEQ ID NO 97
<211> LENGTH: 30
<212> TYPE: DNA
<213> ORGANISM: Artificial
<220> FEATURE:
<223> OTHER INFORMATION: primer

<400> SEQUENCE: 97
aaactgtacg aaaaaatcct gaaagcaggc                               30

<210> SEQ ID NO 98
<211> LENGTH: 30
<212> TYPE: DNA
<213> ORGANISM: Artificial
<220> FEATURE:
<223> OTHER INFORMATION: primer

<400> SEQUENCE: 98
tttttccaga cctgagcctg ctttcaggat                               30

<210> SEQ ID NO 99
<211> LENGTH: 440
<212> TYPE: PRT
<213> ORGANISM: Curvularia clavata

<400> SEQUENCE: 99

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Ala Tyr Pro Ile Pro Ser Ser
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
            115                 120                 125

Asp Ser Glu Asp Glu Ile Leu Lys Lys Met Pro Leu Leu Ser Arg Asp
        130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Thr
210                 215                 220

Leu Val Glu Leu His Glu Gln Cys Val Ser Lys Ala Trp Val Tyr Gly
225                 230                 235                 240

His Ile Gln Leu Thr Pro Glu Glu Ala Ala Glu Tyr Lys Asn Ser Pro
                245                 250                 255

Val Val Tyr Asn Gly Asp Val Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Met His Gln Pro Phe Gly Ala Lys Ala Pro Lys Arg Ile Ser Val Pro
    290                 295                 300

Arg Ser His Ala Lys His Pro Thr Asp Thr Ile Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Ile Cys Glu His Pro Glu Trp Lys Asn Phe Val Leu
        355                 360                 365

Ala Thr Gly Asp Ser Gly His Ser Phe Lys Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Ser Gly Asp Ala Leu Lys Ser Arg

```
                   405                 410                 415
Arg Ser Ala Pro Ala Lys Asp Leu Ala Asp Met Pro Gly Trp Lys His
            420                 425                 430

Asp Asp Val Val Lys Ser Lys Leu
            435                 440

<210> SEQ ID NO 100
<211> LENGTH: 1323
<212> TYPE: DNA
<213> ORGANISM: Curvularia clavata

<400> SEQUENCE: 100
atggccccgt cgcgtgctaa tacgtcggtc attgtggttg gtggtggtgg tacgattggc      60
tcatctacgg ctctgcatct ggtccgctca ggctataccc cgtcgaacat tacggttctg     120
gatgcatacc cgattccgag ctctcagagc gctggcaacg acctgaataa aatcatgggt     180
atccgtctgc gtaataaggt ggatctgcag ctgtctctgg aagcgcgcca aatgtggcgc     240
gaagacgatc tgttcaagga gtatttccat aacaccggcc gtctggattg cgcgcacggt     300
gaagaaggtc ttgccgacct gcgtcaagcc tatcaggctc tgctggatgc gaatgcgggt     360
ctggaagaga cgaccgaatg gctggatagt gaagacgaaa tcctgaaaaa aatgccgctg     420
ctgtcccgcg atcaaattaa aggctggaag gcggtgtatt cacaggacgg tggttggctg     480
gcagcagcaa aggcaattaa tgcaattggt gaatatctgc gtgctcaggg cgtcaaattc     540
ggttttggcg cgccggttc tttcaaacaa ccgctgctgg ctgaaggcgt ctgcatcggt     600
gtcgaaaccg tggatggcac gcgctattac gcagacaaag tggttctggc tgcaggtgca     660
tggtcgccga ccctggttga actgcatgaa cagtgtgtga gcaaagcgtg ggtttacggc     720
cacattcaac tgacgccgga agaagccgca gaatataaga cagcccggt cgtgtacaat     780 ggcgatgtgg gcttttttctt tgaaccgaac gaacatggcg ttatcaaagt ctgcgatgaa     840
tttccgggtt ttacccgctt caagatgcac cagccgtttg gtgccaaagc accgaagcgt     900
attagtgtgc gcgctcca tgccaaacac ccgaccgata cgatcccgga tgcaagtgaa     960
aaatccattc gtaaagctat cgcgacccttt ctgccgaagt tcacggagaa agagctgttc    1020
aaccgtcatc tgtgctggtg taccgatacg gccgacgctg cgctgctgat tgtgaacat    1080 ccggaatgga aaaactttgt tctggcgacc ggcgattcag gtcattcgtt caaactgctg    1140
ccgaatatcg gcaagcacgt tgtcgaactg ctggagggta cgctggcaga tgacctggca    1200
cacgcatggc gttggcgtcc gggtagtggt gatgcactga aaagccgtcg ctctgctccg    1260
gcgaaagacc tggctgatat gccgggctgg aaacatgacg atgtggtgaa aagcaaactg    1320
taa                                                                  1323

<210> SEQ ID NO 101
<211> LENGTH: 30
<212> TYPE: DNA
<213> ORGANISM: Artificial
<220> FEATURE:
<223> OTHER INFORMATION: primer

<400> SEQUENCE: 101
atcatgggta tcgatctgcg taataaggtg                                       30

<210> SEQ ID NO 102
<211> LENGTH: 30
<212> TYPE: DNA
<213> ORGANISM: Artificial
```

<220> FEATURE:
<223> OTHER INFORMATION: primer

<400> SEQUENCE: 102
cagagacagc tgcagatcca ccttattacg           30

<210> SEQ ID NO 103
<211> LENGTH: 30
<212> TYPE: DNA
<213> ORGANISM: Artificial
<220> FEATURE:
<223> OTHER INFORMATION: primer

<400> SEQUENCE: 103
gaaggtcttg ccaaactgcg tcaagcctat           30

<210> SEQ ID NO 104
<211> LENGTH: 30
<212> TYPE: DNA
<213> ORGANISM: Artificial
<220> FEATURE:
<223> OTHER INFORMATION: primer

<400> SEQUENCE: 104
atccagcaga gcctgatagg cttgacgcag           30

<210> SEQ ID NO 105
<211> LENGTH: 30
<212> TYPE: DNA
<213> ORGANISM: Artificial
<220> FEATURE:
<223> OTHER INFORMATION: primer

<400> SEQUENCE: 105
cttgccaaac tgcgtcaact gtatcaggct           30

<210> SEQ ID NO 106
<211> LENGTH: 30
<212> TYPE: DNA
<213> ORGANISM: Artificial
<220> FEATURE:
<223> OTHER INFORMATION: primer

<400> SEQUENCE: 106
acccgcattc gcatccagca gagcctgata           30

<210> SEQ ID NO 107
<211> LENGTH: 30
<212> TYPE: DNA
<213> ORGANISM: Artificial
<220> FEATURE:
<223> OTHER INFORMATION: primer

<400> SEQUENCE: 107
cgtcaactgt atcagaaact gctggatgcg           30

<210> SEQ ID NO 108
<211> LENGTH: 30
<212> TYPE: DNA
<213> ORGANISM: Artificial
<220> FEATURE:
<223> OTHER INFORMATION: primer

<400> SEQUENCE: 108
ctcttccaga cccgcattcg catccagcag           30

<210> SEQ ID NO 109
<211> LENGTH: 30
<212> TYPE: DNA
<213> ORGANISM: Artificial
<220> FEATURE:
<223> OTHER INFORMATION: primer

<400> SEQUENCE: 109
gatacggccg acagcgcgct gctgatttgt                    30

<210> SEQ ID NO 110
<211> LENGTH: 30
<212> TYPE: DNA
<213> ORGANISM: Artificial
<220> FEATURE:
<223> OTHER INFORMATION: primer

<400> SEQUENCE: 110
ccattccgga tgttcacaaa tcagcagcgc                    30

<210> SEQ ID NO 111
<211> LENGTH: 30
<212> TYPE: DNA
<213> ORGANISM: Artificial
<220> FEATURE:
<223> OTHER INFORMATION: primer

<400> SEQUENCE: 111
atcatgggta tcgatcatcg taataaggtg                    30

<210> SEQ ID NO 112
<211> LENGTH: 30
<212> TYPE: DNA
<213> ORGANISM: Artificial
<220> FEATURE:
<223> OTHER INFORMATION: primer

<400> SEQUENCE: 112
aagctgtacc agaaacttct cgacgcaggc                    30

<210> SEQ ID NO 113
<211> LENGTH: 440
<212> TYPE: PRT
<213> ORGANISM: Pyrenochaeta sp.

<400> SEQUENCE: 113

Met Ala Ala Ser Arg Ala Lys Thr Thr Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
            130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
            195                 200                 205

Tyr Tyr Ala Asp Lys Val Val Leu Ala Ala Gly Ala Trp Ser Pro Ala
210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Glu Pro Asn Glu His
            260                 265                 270

Gly Val Ile Lys Val Cys Asp Glu Phe Pro Gly Phe Thr Arg Phe Lys
            275                 280                 285

Lys His Gln Pro Phe Gly Ala Arg Ala Pro Lys Arg Ile Ser Val Pro
290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
            355                 360                 365

Ala Thr Gly Asp Ser Gly His Ser Phe Lys Leu Leu Pro Asn Ile Gly
            370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
            420                 425                 430

Asp Glu Ser Pro Arg Ala Lys Leu
            435                 440

<210> SEQ ID NO 114
<211> LENGTH: 1323
<212> TYPE: DNA
<213> ORGANISM: Pyrenochaeta sp.

<400> SEQUENCE: 114
atggccgctt cacgagcaaa gacgacagtg atcgtcgtgg gtggcggcgg taccattggg      60
tcatcaacag cgctccacct tctacgttca ggttatactc catcgaatat cacagttttg     120
gacacatatc caattccttc attacagtcc gcgggcaatg atttaaacaa gattatgggc     180
attcgcttgc gaaacaaagt cgacctccaa ttgagtttag aggctaggga gatgtggaga     240
gaagatgaac tttttagaga ttttttttcac aatactgggc gactggattg tgcccatggc     300

```
gaaaaaggaa tcaatgatct taggcaggca tatcaaacac tactcgacgc caatgccggt    360
ttggaagaga cgaacgagtg gctggactct gaggacgaaa ttctggcaag aatgccgctc    420
ttgagtcgag agcagatcaa gggctggaaa gcggtcttca gccgagacgg cggttggctc    480
gccgcaggta aggccatcaa tgcaattggc gagtatctgc gcaaggaagg agtcaagttt    540
ggctttggcg gcgcgggatc gttccagcag ccgcttcttg cagagggtat ttgcattggc    600
gtggaaacaa cggatggaac tagatactac gccgacaaag ttgtcctggc agctggtgca    660
tggagtcctg cattggtgga cttggaagac cagtgtgttt caaaagcatg ggtctatgct    720
cacatgcagc tcaccccgaa ggaggctgcg catacaaag acacaccagt agtctacaat     780
ggcgatctgg gatttttctt tgaaccaaac gagcatggcg tgatcaaagt ctgcgacgag    840
ttcccaggct tcacacgttt taagaagcat caaccatttg gtgcaagggc accaaaacgg    900
atatcggttc ccagatctca tgccaaacac cctactgata cttatcctca cgcatccgaa    960
gccagtatca agaaagctat tgcggcattc ttaccacagt tcaaggacaa ggagctgttc   1020
aaccgcgcaa tgtgctggtg cacagataca gctgatgcag ccttgttgat ctgcgaacac   1080
ccgcaatgga agaatttcat gcttgctact ggagacagcg ggcactcatt taagctctta   1140
ccaaatatcg gcaagcatgt agttgaactg attgaaggca ctctggcggc agatcttgcc   1200
catgcttgga ggtggcgacc tgggattggt gacgctttgc agtcaaggcg agcggcacct   1260
gcgaaggatc tggcggacat gccaggatgg aatcatgatg aatctcctag ggcgaaattg   1320
taa                                                                 1323
```

<210> SEQ ID NO 115
<211> LENGTH: 452
<212> TYPE: PRT
<213> ORGANISM: Arthrinium sp.

<400> SEQUENCE: 115

```
Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
    130                 135                 140

Gln Ile Lys Gly Trp Lys Ala Ile Phe Ser Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
            180                 185                 190
```

Phe Ala Pro Asp Gly Ser Thr Cys Ile Gly Val Glu Thr Val Asp Gly
            195                 200                 205

Thr Lys Tyr Tyr Gly Asp Lys Val Val Leu Ala Ala Gly Ala Trp Ser
        210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
        355                 360                 365

Phe Ile Leu Ala Thr Gly Asp Ser Gly His Ser Phe Lys Leu Leu Pro
370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
        435                 440                 445

Glu His Lys Leu
    450

<210> SEQ ID NO 116
<211> LENGTH: 1359
<212> TYPE: DNA
<213> ORGANISM: Arthrinium sp.

<400> SEQUENCE: 116
atggcggcgt cacgaaagac caccaaagtg attgtcgtgg gcggcggagg caccatcggc      60
tcatccacgg ctctacatct tctccggtcg gggtatacgg ccaccaacat taccgtcctg     120
gacacctacc ccatcccctc ggcgcagtcg gccggcaacg acctgaacaa gattatgggg     180
atccgcctgc ggaacccggt cgacaagcag ctcagccttg aagcccagga catgtggtgc     240
catgacgagc tcttcaagcc ctacttccac aacaccggca ggatggactg cgagggcacc     300
gagaagggca tcgcggcgct caagcagcag taccagacct tgcttgacgc cgacgtgggc     360
ctcgagaaga cgacggagtg gctcgacagt gaggatgcca tcctggcaaa gatgccactc     420
ctggagcgcg accaaatcaa aggatggaaa gcgatattta gccaggacgg cggttggctg     480
gccgcagcta aagccatcaa cgcgataggc gaggaactga gaggcaggg cgtcaacttc     540 gggttcggcg gggcgggcgc cttcaagaag ccccttttcg ccccggacgg atccacctgc     600

```
atcggcgtcg agacggtgga tggaaccaag tactacggcg acaaggtcgt cctggccgcg    660
ggcgcgtgga gccctgcgct ggtcgacctg gaagagcagt gctgctccaa ggcctgggtg    720
tacgcccaca tgcagctgac gccgcacgag gcagccgagt accagggctg tccggtcgtg    780
taccacggcg acctcggctt cttcttcgag cccaacgagc acggcgtcat caaggtgtgc    840
gacgagttcc ccggcttcac gcggttcctc gagcagcacc agtcgtacgg cgcgccggcg    900
ccgacgcgcg tctcggtgcc ccggtcgcac gcgaagcacc ccaccgacac atacccggac    960
gcgtcggagc agtcgatccg gcgggccgtg ccgcgttcc tgccgcgatt ccaaagcaaa     1020
gagcttttca accgcgccat gtgctggtgc accgacacgg ccgacgccgc gctgctgatc    1080
tgcgagcacc cccgctggcg caatttttatt ctggctacgg gcgacagcgg acactcgttc   1140
aagctcctgc ccaacatcgg caagcacgtg gtcgagctgc tggaaggccg gctagcggat    1200
gacctggcgc aggcgtggag gtggcgcccc ggtcaggggg atgcgttgaa gtctagacgg    1260
gcggctccgg ctaaggatct ggcggatatg ccagggtgga atcatgacgg ggattcaggg    1320
aatgctacgt ctggaacaag ctcggagcac aaattgtag                           1359
```

<210> SEQ ID NO 117
<211> LENGTH: 440
<212> TYPE: PRT
<213> ORGANISM: Curvularia clavata

<400> SEQUENCE: 117

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Asp Arg Glu
130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240
```

```
His Ile Gln Leu Thr Pro Glu Glu Ala Ala Glu Tyr Lys Asn Val Pro
                245                 250                 255

Val Val Tyr Asn Gly Asp Val Gly Phe Phe Glu Pro Asp Glu His
            260                 265                 270

Gly Val Ile Lys Val Cys Asp Glu Phe Pro Gly Phe Thr Arg Phe Lys
        275                 280                 285

Gln His Gln Pro Tyr Gly Ala Lys Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
                340                 345                 350

Ala Ala Leu Leu Met Cys Glu His Pro Glu Trp Lys Asn Phe Val Leu
                355                 360                 365

Ala Thr Gly Asp Ser Gly His Thr Phe Lys Leu Leu Pro Asn Ile Gly
            370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
                420                 425                 430

Asp Asp Val Val Lys Ser Lys Leu
            435                 440
```

<210> SEQ ID NO 118
<211> LENGTH: 1323
<212> TYPE: DNA
<213> ORGANISM: Curvularia clavata

<400> SEQUENCE: 118

```
atggcgccct caagagcaaa cacttctgtt atcgttgtcg gtggcggtgg cactattggc        60
tcttcaaccg ctcttcatct agtccgctcg ggctacacac catctaacat caccgttctt       120
gacacatacc ctatcccatc agcgcagtca gctggaaatg acctgaataa gatcatgggt       180
atccgcttgc ggaacaaggt cgatctccaa ttgagtctag aagccaggca gatgtggaga       240
gaggatgacc tattcaaaga gtatttccac aacactggaa gactcgactg tgcacatggg       300
gaagagggac ttgcagattt gagacaggca taccaggctc tgctcgacgc taacgcgggt       360
ctcgaagaaa caacagaatg gcttgactcc gaagacgaaa ttctaaagaa atgccgcttt       420
ctggaccgcg agcaaatcaa gggctggaaa gcggtttaca gccaagacgg cggctggctg       480
gctgcagcaa aagccatcaa tgctataggc gagtacttgc gagcccaagg agttaagttt       540
ggttttggtg gtgctggatc gttcaagcag cctcttttgg ccgagggagt gtgcattggc       600
gtagagacag tcgacgggac gaggtactac gccgataaag ttgtgcttgc agctggtgct       660
tggagtccgg tattggtcga cctggaagat caatgcgttt caaaagcttg ggtatatgct       720
cacatacagc ttacgcctga ggaagcagca gagtacaaaa acgtgcctgt ggtatacaac       780
ggcgacgtcg gcttcttctt cgagcctgac gagcacggcg ttatcaaggt ttgtgacgaa       840
tttccaggtt ttacacgctt caagcaacat cagccatatg gcgccaaagc accgaaacgt       900
atctccgtgc ccagatcggc agcgaagcac ccgacggata cttaccccga tgcgtcggag       960
```

```
aagagcatcc gcaaggccat tgcaactttc ctgcccaagt tcacagagaa ggagctattc    1020
aaccggcatc tatgttggtg tacggatacg gctgacgctg cgctattgat gtgtgagcat    1080
cccgagtgga agaactttgt gctggcgaca ggggacagcg ggcacacatt caaacttttg    1140
ccaaatatcg gcaagcatgt ggttgagctt ctcgagggta cactcgcgga ggatctggca    1200
catgcatgga gatggcggcc tggtactggc gatgcgctga aatcaagaag agcggcaccg    1260
gcgaaggatt tagcagatat gcctggctgg aagcatgacg atgttgtcaa gtccaagtta    1320
tag                                                                  1323
```

<210> SEQ ID NO 119
<211> LENGTH: 438
<212> TYPE: PRT
<213> ORGANISM: Emericella nidulans

<400> SEQUENCE: 119

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300
```

```
Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435
```

<210> SEQ ID NO 120
<211> LENGTH: 1317
<212> TYPE: DNA
<213> ORGANISM: Emericella nidulans

<400> SEQUENCE: 120

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaaaat cttcggcatc     180
aggctgcgca acaagcctga cttacaactc tatcttgagg cgctggacat gtggaaaaat     240
gatcctctat tcaagccgtt tttccacaat gttggacaga tggacgtctc ttcaacagaa     300
gaaggcatca aaaagcttcg catgagatac cagtctcttc tcgacgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga agacgtgcc     600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgaggcaaa gatgtag       1317
```

<210> SEQ ID NO 121
<211> LENGTH: 441
<212> TYPE: PRT
<213> ORGANISM: Ulocladium sp.

<400> SEQUENCE: 121

| Met | Ala | Pro | Asn | Arg | Ala | Asn | Ile | Ser | Val | Ile | Val | Gly | Gly | Gly |
|---|---|---|---|---|---|---|---|---|---|---|---|---|---|---|
| 1 | | | | 5 | | | | | 10 | | | | | 15 |

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Gly Ala Gly Ser Phe Lys Gln Pro Leu
            180                 185                 190

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr
            260                 265                 270

Gly Val Ile Lys Val Cys Asp Glu Phe Pro Gly Phe Thr Arg Phe Lys
        275                 280                 285

Gln His Gln Pro Phe Gly Ala Ser Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
            405                 410                 415

Arg Ala Ala Arg Ala Lys Asp Leu Ala Asp Met Pro Gly Trp Asn His
            420                 425                 430

Asp Gly Glu Ala Pro Arg Ala Lys Leu
        435                 440

<210> SEQ ID NO 122
<211> LENGTH: 1326
<212> TYPE: DNA
<213> ORGANISM: Ulocladium sp.

<400> SEQUENCE: 122

| | |
|---|---|
| atggcaccta acagagctaa tatttctgtc atcgtcgtgg gtggtggcgg caccattggg | 60 |
| tcttcaacgg ccccttcatct cgtacgctcg ggatacacac cgtcgaatat cacggttctg | 120 |
| gacacttatc caattccatc agcgcaatca gctggcaatg acttgaacaa gatcatgggt | 180 |
| atccgtttgc ggaacaaggt ggatttgcag ttgagcttag aggcgagaca aatgtggaca | 240 |
| gaagacgatc tgttcaagga gtactttcat aaaaccgggc ggctcgactg cgcacatggc | 300 |
| gagaaaggcc ttgcagatct caaacaagcc taccaagccc ttcttgatgc gaacgctggc | 360 |
| ctggaggcga cgacagaatg gttagattcc gaggacaaga ttcttgagaa gatgccgctt | 420 |
| ctcaatcgcg atcagatcaa aggatggaaa gccgtcttca gcgaagacgg cggatggctc | 480 |
| gctgcggcaa agccatcaa cgctatcggt agatttctgc gcgatcaagg cgtcaagttt | 540 |
| ggctttggcg agcaggatc attcaaacaa cctcttcttg ccgagggtgt ttgtgttggt | 600 |
| gttgaaacag ttgacgggac gagatattat gctgacaagg ttgtgttggc ggctggtgcg | 660 |
| tggagtcctg cattggtcga tctacaagac caatgtgtgt cgaaagcatg gtatacgct | 720 |
| cacatccaac tgtccccgag cgaggcggcg aatacaaaa atgttcctgt agtctataat | 780 |
| ggcgacgtgg gcttcttctt cgagcctgac gaatacggcg tcatcaaagt ctgtgacgag | 840 |
| tttccaggtt ttacgcgctt caagcagcat caaccttcg gcgcatcggc tccaaagcgc | 900 |
| atttctgtgc ctcgatctgc cgcaaaaaca cccacagata cctatccgga cgcctcggaa | 960 |
| gtcagtatcc gcaaggccat cgcgacgttc ctgcccaagt tcacagaaaa ggaagtgttc | 1020 |
| aacaggcatc tgtgttggtg tactgatacg gctgatgcgg cgcttttgat gtgcgaacat | 1080 |
| cctgagtgga agaactttgt tttggccacg ggtgacagtg gtcacacctt caagcttcta | 1140 |
| cctaacatcg gtaagcatgt ggtcgagcta ctagaggta cattagcaga cgacctagcg | 1200 |
| catgcgtgga gatggcgtcc cggtaccggc gatgcgctga agtcgcgaag gcggcgcgt | 1260 |
| gcgaaagacc ttgcagatat gccaggatgg aatcatgacg gggaagcccc cagagcgaag | 1320 |
| ctgtga | 1326 |

<210> SEQ ID NO 123
<211> LENGTH: 437
<212> TYPE: PRT
<213> ORGANISM: Penicillium janthinellum

<400> SEQUENCE: 123

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125

Glu Ser Glu Asp Asp Ile Leu Ala Lys Ala Pro His Phe Thr Arg Glu
    130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Phe Glu Pro Asn
            260                 265                 270

Glu His Gly Val Ile Lys Val Cys Asp Glu Phe Pro Gly Phe Ser Arg
        275                 280                 285

Phe Lys Leu His Gln Pro Tyr Gly Ala Thr Ser Pro Lys Leu Ile Ser
    290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Val Leu Pro Asn
    370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu

-continued

435

<210> SEQ ID NO 124
<211> LENGTH: 1314
<212> TYPE: DNA
<213> ORGANISM: Penicillium janthinellum

<400> SEQUENCE: 124

| | | | | |
|---|---|---|---|---|
| atggctcatt cgcgagaaag cacaaagatt gtcattgtcg ggggaggtgg cacaatggga | 60 |
| tcttcaaccg cgctacacct gatacgctct ggatacaccc cgtcaaacat caccgtcctt | 120 |
| gatgtatacc caattccatc cttgcaatcc gcaggatatg atcttaacaa gatcatgagc | 180 |
| atccgattac gcaacgggcc tgacttgcaa cttttccctgg aggctctcga tatgtggaaa | 240 |
| aacgatccgt tgttcaagcc tttctttcac aacgttggca tgctagactg ttcatcgtca | 300 |
| caagagggta ttgcaagcct tcgacggaag caccaagacc tcatagacgc gaatatcgga | 360 |
| ctagagaaga cgaatatctg gttagagagt gaagatgata ttctggcaaa agccccgcac | 420 |
| ttcacgcggg aacagatcaa ggggtggaag ggcttgtttt gcggcgatgg aggatggctt | 480 |
| gctgcagcca aggccatcaa tgcgatcgga acctttctaa aaagtcaagg cgtcaagttc | 540 |
| ggatttggaa gtgccgggac tttcaagcga cctttgtttg ctccagatgg ggcgacatgc | 600 |
| agcggtgttg agacagtaga tggaacaaaa tacttcgccg acaaggtggt tttggccgct | 660 |
| ggtgcttgga gttcgacgtt agtagatttg gaggaccaat gtgtttcgaa ggcctgggtc | 720 |
| ttcgctcata tccaactcac gccccaagaa tcggcccagt acaaggacgt gcccgtagta | 780 |
| tacgacggtg attatggctt tttcttcgag cccaacgaac acgagtaat caaagtctgc | 840 |
| gatgagttcc ccgggttctc ccgcttcaag ctgcatcaac cttacggtgc cacctctcct | 900 |
| aagcttatat ccgttcctcg atcacacgcc aagcatccca ccgataccta cccagattct | 960 |
| tctgaagaga ccattcgaaa agcgattgcg aggtttatgc cacgcttcaa ggataaggag | 1020 |
| cttttaata ggagcatgtg ctggtgcacc gatactgctg atgccaactt gttgatctgc | 1080 |
| gagcacccca gtggaagaa ctttatcttg gccacaggag acagcggcca tagtttcaag | 1140 |
| gttttgccca atataggaaa acatgtcgtt gagttgatag aaggacgcct accacaagac | 1200 |
| ctggctggtg cgtggagatg gagaccaggg ggagatgccc ttaagtccaa acgcagtgct | 1260 |
| ccggcaaagg accttgctga aatgccgggc tggaagcatg atgcgaagct ctga | 1314 |

<210> SEQ ID NO 125
<211> LENGTH: 445
<212> TYPE: PRT
<213> ORGANISM: Aspergillus fumigatus

<400> SEQUENCE: 125

Met Ala Pro Ser Ile Leu Ser Thr Glu Ser Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

Ala Ala Gly Asn Asp Ile Asn Lys Ile Met Glu His Ser Glu Leu Lys
    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Glu Thr Asn Phe Val Lys
            115                 120                 125

Leu Glu Thr Ala Glu Asp Phe Arg Arg Thr Met Pro Pro Gly Val Leu
            130                 135             140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
                180                 185                 190

Val Ser Leu Val Tyr Glu Asp Gly Asp Val Val Gly Ala Arg Thr Ala
            195                 200                 205

Asp Gly Arg Val His Lys Ala His Arg Thr Ile Leu Ser Ala Gly Ala
210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
                260                 265                 270

Pro Asp Glu Asp Lys His Glu Leu Lys Ile Cys Asp Glu His Pro Gly
            275                 280                 285

Tyr Cys Asn Phe Leu Pro Asp Pro Asn Arg Pro Gly Gln Glu Lys Ser
            290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Asp Arg Ala Phe
                340                 345                 350

Leu Ile Asp Arg His Pro Glu His Pro Ser Leu Leu Val Ala Val Gly
            355                 360                 365

Gly Ser Gly Asn Gly Ala Met Gln Met Pro Thr Ile Gly Gly Phe Ile
370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
            435                 440                 445

<210> SEQ ID NO 126
<211> LENGTH: 1338
<212> TYPE: DNA
<213> ORGANISM: Aspergillus fumigatus

<400> SEQUENCE: 126
atggcgcctt caattttgag cactgaatct tccattatcg ttatcggagc aggcacatgg    60
ggctgctcaa ctgctctgca cctcgctcgt cgaggctaca agatgtcac tgttctcgac   120

```
cctcatccag ttccttcgcc cattgcagca ggcaatgaca tcaacaagat tatggagcac    180
agcgagctga agatggctc atccgaccct cgaagcgcag ccttctcgac atttacgcga     240
gctgctctta aggcgtggaa aactgacccg ttttccagc cttactttca cgaaactggc     300
tttatcatat cggggcacac acctgctctg attgaccaca tacgaaaaga cgaggtagaa    360
ccgtcagaaa caaacttcgt caagctggag acagccgagg acttccgccg gaccatgccg    420
ccaggtgtac tgacaggcga cttccctggc tggaaaggct ggttgcacaa gtctggtgct    480
gggtggattc atgccaaaaa ggctatgatc tctgctttca atgaagctaa gcgcttggga    540
gtcagatttg tcactggctc tccggaaggg aatgttgtat cgttggtata cgaggacgga    600
gacgtcgttg gagccagaac tgccgatggt cgcgtgcaca aagcccatcg cactattctt    660
tcggcaggtg ctggcagtga cagtctccta gacttcaaga agcagcttcg gcctaccgcg    720
tggactctct gtcatattca gatgggccct gaagaggtca agcaatatcg gaaccttcct    780
gtgttgttca acatcgccaa agggttcttc atggagcctg atgaggataa acacgagctc    840
aagatttgtg acgagcatcc agggtactgc aactttctcc ctgacccaaa cagaccgggc    900
caggagaaga gtgtcccctt cgcaaagcat cagatcccgc tcgaggccga agcccgcgca    960
cgagactttc tccatgatac aatgccgcat ctggctgacc ggccactgtc tttcgcgcgt   1020
atttgctggg atgctgatac cccagaccgt gctttcttga tcgatagaca tcctgaacac   1080
ccctcactgc tagtcgctgt tggaggttcc ggcaatggcg ccatgcaaat gcctacaatt   1140
ggcggtttta tcgcagatgc tctagagagt aaactacaga aggaggtgaa ggacatcgtt   1200
cgatggaggc cagagacggc tgtcgatcga gattggagag cgactcagaa tcgctttggc   1260
gggcctgaca ggatcatgga ttttcagcag gtcggagagg atcagtggac caagattgga   1320
gagagcagag gtccgtaa                                                  1338
```

<210> SEQ ID NO 127
<211> LENGTH: 445
<212> TYPE: PRT
<213> ORGANISM: Aspergillus oryzae

<400> SEQUENCE: 127

```
Met Thr Ser Ser Lys Leu Thr Pro Thr Ser Ile Leu Ile Val Gly
1               5                   10                  15

Ala Gly Thr Trp Gly Cys Ser Thr Ala Leu His Leu Ala Arg Arg Gly
            20                  25                  30

Tyr Lys Asn Val Thr Val Leu Asp Pro His Pro Val Pro Ser Pro Ile
        35                  40                  45

Ala Ala Gly Asn Asp Ile Asn Lys Ile Met Glu His Arg Glu Val Lys
    50                  55                  60

Ala Ser Glu Thr Asp Pro Trp Ser Ile Ala Phe Ser Thr Cys Thr Arg
65                  70                  75                  80

Ala Ala Leu Lys Gly Trp Lys Asn Asp Pro Val Phe Gln Pro Tyr Phe
                85                  90                  95

His Glu Thr Gly Ala Ile Val Ser Gly His Thr Ala Ser Leu Ile Lys
            100                 105                 110

His Ile Gln Glu His Glu Ile Asp Ser Ser Asp Ala Glu Phe Ile Lys
        115                 120                 125

Leu Asn Thr Ala Glu Asp Phe Arg Lys Thr Met Pro Pro Gly Ile Leu
    130                 135                 140

Thr Gly Asn Phe Pro Gly Trp Lys Gly Trp Leu Asn Lys Thr Gly Ala
145                 150                 155                 160
```

Gly Trp Ile His Ala Lys Lys Ala Met Phe Ser Ala Tyr Thr Glu Ala
            165                 170                 175
Lys Arg Leu Gly Val Thr Phe Ile Thr Gly Ser Pro Glu Gly Asp Val
        180                 185                 190
Val Ser Leu Ile Tyr Glu Asn Gly Asp Val Val Gly Ala Arg Thr Ala
    195                 200                 205
Asp Gly Thr Val His Arg Ala Asp His Thr Ile Leu Ser Ala Gly Ala
210                 215                 220
Gly Ser Asp Arg Leu Leu Asp Phe Lys Lys Gln Leu Arg Pro Thr Ala
225                 230                 235                 240
Trp Thr Leu Cys His Ile Arg Met Thr Pro Asp Glu Ala Lys Lys Tyr
            245                 250                 255
Arg Asn Leu Pro Val Leu Phe Asn Val Ala Lys Gly Phe Phe Met Glu
        260                 265                 270
Pro Asp Glu Asp Asn His Glu Leu Lys Ile Cys Asp Glu His Pro Gly
    275                 280                 285
Tyr Cys Asn Phe Val Pro Asp Pro Lys His Gly Gly Glu Val Arg Ser
290                 295                 300
Ile Pro Phe Ala Lys His Gln Ile Pro Leu Glu Ala Glu Ala Arg Ala
305                 310                 315                 320
Arg Asp Phe Leu Arg Asp Thr Met Pro His Leu Ala Asp Arg Pro Leu
            325                 330                 335
Ser Phe Ala Arg Ile Cys Trp Asp Ala Asp Thr Val Asp Arg Ala Phe
        340                 345                 350
Leu Ile Asp Arg His Pro Glu Tyr Arg Ser Leu Leu Leu Ala Val Gly
    355                 360                 365
Gly Ser Gly Asn Gly Ala Met Gln Met Pro Thr Ile Gly Gly Phe Ile
370                 375                 380
Ala Asp Ala Leu Glu Gly Asn Leu Gln Lys Glu Leu Lys His Ala Leu
385                 390                 395                 400
Arg Trp Arg Pro Glu Ile Ala Ala Gln Arg Asp Trp Lys Asp Thr Gln
            405                 410                 415
Asn Arg Phe Gly Gly Pro Asn Lys Val Met Asp Phe Gln Lys Val Gly
        420                 425                 430
Glu Asn Glu Trp Thr Lys Ile Gly Asp Lys Ser Arg Leu
    435                 440                 445

<210> SEQ ID NO 128
<211> LENGTH: 1338
<212> TYPE: DNA
<213> ORGANISM: Aspergillus oryzae

<400> SEQUENCE: 128
atgacatcct ccaagttgac tcccacatca tctatcttaa ttgtcggtgc agggacctgg     60
ggttgttcta ctgctttaca tcttgcccgt cgaggataca aaaatgtcac ggtcctagat    120
ccgcacccgg tcccttctcc cattgcagct ggcaatgaca ttaacaagat tatggagcac    180
agggaggtaa aagcctctga aaccgatcct tggagtatcg ccttctcaac atgcacacga    240
gctgcactga aaggttggaa aaacgaccca gtattccagc atacttcca tgaaacgggg     300 gcaatagttt ctggccacac cgcctctttg attaaacata caagaaca cgaaatcgac      360 tcgtcagacg ccgagttcat aaaattgaac accgcagagg atttccgcaa aactatgccc    420
ccgggaatcc tcactggcaa cttccccggc tggaagggct ggctgaacaa gaccggcgcc    480

```
ggatggatcc acgccaagaa ggccatgttc tccgcataca ccgaagcaaa gcgcctagga     540
gtcactttca tcaccggctc ccctgaagga gacgttgtat ctctaattta cgagaatgga     600
gacgtagtcg gagccagaac ggccgacggc accgtccacc gagcagacca taccattctt     660
tccgcagggg ctggcagtga tcgtctcctg gactttaaga acagctccg tcctaccgcc      720
tggacgctct gccacatcag aatgacgccc gacgaggcca agaagtaccg gaatcttcct    780
gtgctgttca acgtcgctaa ggggttcttc atggaacctg atgaggataa tcatgagctt    840
aagatctgcg acgagcatcc tggatattgc aacttcgtcc cggacccgaa gcacggcggt   900
gaggtgcgca gtatcccatt tgcaaagcat cagattcctc ttgaagccga ggcccgtgca   960
agggacttcc tccgtgatac gatgcctcat cttgctgatc gaccactgtc ttttgctcgt  1020
atatgctggg atgctgatac agtggatcgc gccttcttga tcgataggca tcctgagtat  1080
cgctctttac tgcttgctgt cggtggatct ggtaatggag ccatgcaaat gcctaccatt  1140
ggtgggttca tagcggatgc tctggaggga aacctgcaaa aggaactgaa gcatgcacta  1200
cggtggaggc ctgagattgc cgcccaacga gactggaagg atacgcaaaa tagattcgga  1260
ggtccgaata agtaatgga tttccaaaag gttggagaga atgagtggac caagattggc    1320
gataagagtc ggctttaa                                                 1338
```

<210> SEQ ID NO 129
<211> LENGTH: 438
<212> TYPE: PRT
<213> ORGANISM: Aspergillus fumigatus

<400> SEQUENCE: 129

```
Met Ala Val Thr Lys Ser Ser Leu Leu Ile Val Gly Ala Gly Thr
1               5                   10                  15

Trp Gly Thr Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
            35                  40                  45

Asn Asp Val Asn Lys Val Ile Ser Ser Gly Gln Tyr Ser Asn Asn Lys
        50                  55                  60

Asp Glu Ile Glu Val Asn Glu Ile Leu Ala Glu Gly Ala Phe Asn Gly
65                  70                  75                  80

Trp Lys Asn Asp Pro Leu Phe Lys Pro Tyr Tyr His Asp Thr Gly Leu
                85                  90                  95

Leu Met Ser Ala Cys Ser Gln Glu Gly Leu Asp Arg Leu Gly Val Arg
            100                 105                 110

Val Arg Pro Gly Glu Asp Pro Asn Leu Val Glu Leu Thr Arg Pro Glu
        115                 120                 125

Gln Phe Arg Lys Leu Ala Pro Glu Gly Val Leu Gln Gly Asp Phe Pro
    130                 135                 140

Gly Trp Lys Gly Tyr Phe Ala Arg Ser Gly Ala Gly Trp Ala His Ala
145                 150                 155                 160

Arg Asn Ala Leu Val Ala Ala Arg Glu Ala Gln Arg Met Gly Val
                165                 170                 175

Lys Phe Val Thr Gly Thr Pro Gln Gly Arg Val Thr Leu Ile Phe
            180                 185                 190

Glu Asn Asn Asp Val Lys Gly Ala Val Thr Gly Asp Gly Lys Ile Trp
        195                 200                 205

Arg Ala Glu Arg Thr Phe Leu Cys Ala Gly Ala Ser Ala Gly Gln Phe
    210                 215                 220
```

```
Leu Asp Phe Lys Asn Gln Leu Arg Pro Thr Ala Trp Thr Leu Val His
225                 230                 235                 240

Ile Ala Leu Lys Pro Glu Glu Arg Ala Leu Tyr Lys Asn Ile Pro Val
                245                 250                 255

Ile Phe Asn Ile Glu Arg Gly Phe Phe Phe Glu Pro Asp Glu Glu Arg
            260                 265                 270

Gly Glu Ile Lys Ile Cys Asp Glu His Pro Gly Tyr Thr Asn Met Val
        275                 280                 285

Gln Ser Ala Asp Gly Thr Met Met Ser Ile Pro Phe Glu Lys Thr Gln
    290                 295                 300

Ile Pro Lys Glu Ala Glu Thr Arg Val Arg Ala Leu Leu Lys Glu Thr
305                 310                 315                 320

Met Pro Gln Leu Ala Asp Arg Pro Phe Ser Phe Ala Arg Ile Cys Trp
                325                 330                 335

Cys Ala Asp Thr Ala Asn Arg Glu Phe Leu Ile Asp Arg His Pro Gln
            340                 345                 350

Tyr His Ser Leu Val Leu Gly Cys Gly Ala Ser Gly Arg Gly Phe Lys
        355                 360                 365

Tyr Leu Pro Ser Ile Gly Asn Leu Ile Val Asp Ala Met Glu Gly Lys
    370                 375                 380

Val Pro Gln Lys Ile His Glu Leu Ile Lys Trp Asn Pro Asp Ile Ala
385                 390                 395                 400

Ala Asn Arg Asn Trp Arg Asp Thr Leu Gly Arg Phe Gly Gly Pro Asn
                405                 410                 415

Arg Val Met Asp Phe His Asp Val Lys Glu Trp Thr Asn Val Gln Tyr
            420                 425                 430

Arg Asp Ile Ser Lys Leu
        435

<210> SEQ ID NO 130
<211> LENGTH: 1317
<212> TYPE: DNA
<213> ORGANISM: Aspergillus fumigatus

<400> SEQUENCE: 130
atggcggtaa ccaagtcatc ttccctttg atcgtggggg caggcacctg gggcacatcg      60
actgctctcc acctggcacg aagaggatac acaaatgtga cggttctaga tccctacccc     120
gttccctcag ccatctcggc tgggaatgat gtgaacaagg tcatctcctc cggccaatat     180
agcaacaaca aggacgaaat tgaggtcaac gagattctgg ctgaagaagc gttcaatggc     240
tggaagaacg accccttgtt caaaccatac tatcacgata ctggattgct catgtccgcc     300
tgctcccagg aaggcttgga ccgccttgga gtccgtgtca ggcccggtga ggaccccaac     360
cttgtggaac tgacacggcc ggagcaattc cgcaaattag ctcctgaggg tgttctacag     420
ggagatttcc ccggctggaa gggctacttt gcgcgttcag gagctggttg ggcccatgct     480
cgcaatgcac tcgtggctgc tgcaagggag gctcagagaa tgggcgtgaa gttcgtaact     540
ggcactcctc agggcagagt agtcactcta atatttgaga ataacgatgt caaaggtgcc     600
gttaccggag acggcaagat tggcgtgca gagcgcacat cctctgcgc cggtgccagc       660 gctggtcagt cctcgactt caagaatcag ttgcgtccaa cggcatggac gctggttcat      720
attgctctga gcctgagga gcgggctctt tacaagaata tcccagttat cttcaacatt      780
gagagggggt tcttcttcga accagatgag gagcgcggtg agattaagat ctgcgacgaa     840
```

```
catccggggt ataccaatat ggtacagtct gccgacggca cgatgatgag cattccttttt    900 gaaaagactc agattcctaa agaagccgag acgagggtta gagctctgct taaagagacg    960
atgccacagc ttgcagaccg tccattcagt ttcgccagga tttgctggtg cgccgacact   1020
gccaaccggg agttcttgat cgatcgccat cctcagtacc attcgcttgt gctgggctgc   1080
ggcgcttccg gcagaggatt caaatatcta ccttcaattg gcaatctcat cgttgatgct   1140
atggaaggca aggtccctca aaagatccac gaactgatta atggaaccc agatattgct   1200 gccaatcgca actggaggga tactttgggg agattcgggg gtcccaacag agtaatggac   1260
ttccacgacg tcaaggagtg gacaaatgta caatatagag atatttccaa gttataa      1317
```

<210> SEQ ID NO 131
<211> LENGTH: 437
<212> TYPE: PRT
<213> ORGANISM: Aspergillus terreus

<400> SEQUENCE: 131

```
Met Pro Val Thr Lys Ser Ser Ile Leu Ile Ile Gly Ala Gly Thr
1               5                   10                  15

Trp Gly Cys Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
            35                  40                  45

Asn Asp Val Asn Lys Ile Ile Ser Ser Gly Gln Tyr Ser Ser Lys Lys
        50                  55                  60

Asp Glu Val Glu Val Asn Glu Ile Ile Ala Glu Gln Ala Phe Asn Gly
65                  70                  75                  80

Trp Lys Asn Asp Pro Ile Phe Lys Pro Tyr Tyr His Asp Thr Gly Val
                85                  90                  95

Val Met Ser Ala Thr Thr Gln Glu Gly Leu Glu Arg Leu Gly Val Arg
            100                 105                 110

Val Arg Pro Glu Asp Glu Pro Asp Val Ala Glu Leu Thr Arg Pro Glu
        115                 120                 125

Gln Phe Arg Gln Leu Ala Pro Gly Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Arg Glu Ala Gln Arg Leu Gly Val Arg
                165                 170                 175

Phe Val Ala Gly Ser Pro Gln Gly Arg Val Ile Thr Leu Ile Phe Glu
            180                 185                 190

Asn Asn Asp Val Lys Gly Ala Val Thr Ala Asp Gly Lys Ile Trp Arg
        195                 200                 205

Ala Glu Gln Thr Ile Leu Cys Ala Gly Ala Ala Gly Gln Phe Leu
    210                 215                 220

Asp Phe Lys Asp Gln Leu Arg Pro Thr Ala Trp Thr Leu Val His Ile
225                 230                 235                 240

Gln Leu Lys Pro Glu Glu Arg Ala Gln Tyr Lys Asn Met Pro Val Val
                245                 250                 255

Phe Asn Ile Glu Lys Gly Phe Phe Glu Pro Asp Glu Glu Arg Gly
            260                 265                 270

Glu Ile Lys Ile Cys Asp Glu His Pro Gly Tyr Thr Asn Met Thr Thr
        275                 280                 285

Gly Ala Asp Gly Arg Val Arg Ser Ile Pro Phe Glu Lys Thr Gln Val
```

```
                    290                 295                 300
Pro Arg Glu Ala Glu Met Arg Val Arg Lys Leu Leu Ser Glu Thr Met
305                 310                 315                 320

Pro Gln Leu Ala Asp Arg Pro Phe Ser Phe Ala Arg Ile Cys Trp Cys
                    325                 330                 335

Ala Asp Thr Pro Asn Arg Glu Phe Ile Ile Asp Arg His Pro Glu Tyr
                340                 345                 350

Pro Ser Leu Val Leu Gly Cys Gly Ala Ser Gly Arg Gly Phe Lys Tyr
            355                 360                 365

Leu Pro Ser Ile Gly Ser Ile Ile Ala Asp Ala Met Glu Asp Lys Thr
        370                 375                 380

Pro Ala Lys Ile His Lys Leu Ile Arg Trp Ser Pro Glu Ile Ala Ile
385                 390                 395                 400

Asn Arg Asn Trp Gly Asp Arg Leu Gly Arg Phe Gly Gly Pro Asn Arg
                    405                 410                 415

Val Met Asp Phe Asn Glu Val Lys Glu Trp Thr Asn Val Thr Gln Arg
                420                 425                 430

Asp Ile Ser Lys Leu
            435

<210> SEQ ID NO 132
<211> LENGTH: 1314
<212> TYPE: DNA
<213> ORGANISM: Aspergillus terreus

<400> SEQUENCE: 132
atgccagtca ccaagtcttc gtcgatattg atcatcgggg cgggcacctg gggttgctca      60
actgccctgc atcttgcccg cagaggatac accaatgtca ctgtccttga cccgtacccg     120
gttccatcag ccatttcggc cggcaacgac gtcaacaaga tcatctcgtc cggccagtac     180
agcagcaaga aggacgaggt cgaagtcaat gagattatcg ccgaacaggc cttcaatggc     240
tggaaaaatg accccatctt caagccgtac taccacgaca ccggcgtcgt gatgtccgcc     300
accacacagg aaggattgga gcgtctgggg gtccgcgtgc gacctgaaga tgaacccgat     360
gtagccgaat tgactcggcc ggagcagttc cgccagctgg cccccggcgt cttgaagggt     420
aacttccccg gttggagggg gtaccacatt cgctcaaacg cgggctgggc catgcgcgc     480 aacgccctgg tcgccgcggc gcgggaggca cagcgcctgg tgtgcgcttc gtcgcggga     540 tcgccgcagg gcagagtcat cacgttgatt tttgagaaca acgatgtgaa gggtgccgtc     600
acggcggacg gcaagatctg gcgggccgag cagactatcc tctgcgctgg tgcggccgcc     660
ggccagtttc tggatttcaa ggaccaactg cgtcccactg cgtggactct ggtccacatc     720
cagttgaagc cggaagagcg tgcccagtat aaaaacatgc cggtggtctt caacatcgag     780
aaggggttct tcttcgagcc ggatgaggag cgtggtgaaa tcaagatctg cgacgaacac     840
cccgggtaca cgaatatgac cacggggggcc gacggccgcg tgaggagcat tcccttcgag     900
aagacgcagg ttcctcgaga agcggagatg cgcgtccgca agcttctgtc tgaaacgatg     960
cctcagcttg cggaccggcc gttcagtttc gcaaggatct gctggtgtgc ggataccccc    1020
aatcgcgagt ttatcattga ccgtcatccc gaataccccgt cgcttgttct tgggtgtggt    1080
gcttcaggac gaggcttcaa atatcttccc tcgatcggaa gcatcatcgc agacgccatg    1140
gaggacaaaa cccccgcaaa aatccacaag ctgatccgct ggagcccgga aatcgcgatc    1200
aaccgtaact gggggggacag attaggtcga tttggaggggc ccaaccgggt catggatttc    1260
```
aatgaagtga aggagtggac taatgtcacc caaagggaca tctcgaagtt atag 1314

<210> SEQ ID NO 133
<211> LENGTH: 437
<212> TYPE: PRT
<213> ORGANISM: Coniochaeta sp.

<400> SEQUENCE: 133

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365
```

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 134
<211> LENGTH: 1314
<212> TYPE: DNA
<213> ORGANISM: Coniochaeta sp.

<400> SEQUENCE: 134

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc     540
ggattcggcg cgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg     720
tatgctcata ttcagttgac gcctgaagag gccgctgagt ataagggtgt cccagttgtg     780
tataatggcg aatttggctt cttcttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacaccca atggaagaa tttcattcta gcgaccggcg acagcggaca ctcattcaaa    1140
atcttgccta acgtcggaaa atacgtagtc gagttgatag agggccgcct gccgaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa         1314
```

<210> SEQ ID NO 135
<211> LENGTH: 437
<212> TYPE: PRT
<213> ORGANISM: Phaeosphaeria nodorum

<400> SEQUENCE: 135

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr

```
                20                  25                  30
Thr Pro Ser Asn Val Thr Val Leu Asp Ala Tyr Pro Ile Pro Ser Ser
            35                  40                  45
Gln Ser Ala Gly Asn Asp Leu Asn Lys Ile Met Gly Val Asp Leu Arg
            50                  55                  60
Asn Pro Val Asp Leu Gln Leu Ala Leu Glu Ala Arg Gln Met Trp Asn
 65                  70                  75                  80
Glu Asp Glu Leu Phe Lys Lys Phe Phe His Asn Thr Gly Arg Leu Asp
                85                  90                  95
Cys Ala His Gly Glu Lys Asp Ile Ala Lys Leu Lys Ser Leu Tyr Gln
               100                 105                 110
Lys Leu Val Asp Ala Gly Leu Asp Ala Thr Asn Glu Trp Leu Asp Ser
           115                 120                 125
Glu Asp Glu Ile Leu Lys Arg Met Pro Leu Leu Ser Arg Asp Gln Ile
           130                 135                 140
Lys Gly Trp Lys Ala Ile Phe Ser Lys Asp Gly Gly Trp Leu Ala Ala
145                 150                 155                 160
Ala Lys Ala Ile Asn Ala Val Gly Glu Tyr Leu Arg Asp Gln Gly Val
               165                 170                 175
Arg Phe Gly Phe Tyr Gly Ala Gly Ser Phe Lys Ala Pro Leu Leu Ala
               180                 185                 190
Glu Gly Val Cys Ile Gly Val Glu Thr Val Asp Gly Thr Arg Tyr Tyr
               195                 200                 205
Ala Asp Lys Val Val Leu Ala Ala Gly Ala Trp Ser Pro Thr Leu Val
           210                 215                 220
Glu Leu His Glu Gln Cys Val Ser Lys Ala Trp Val Tyr Gly His Ile
225                 230                 235                 240
Gln Leu Thr Pro Glu Glu Ala Ala Arg Tyr Lys Asn Ser Pro Val Val
               245                 250                 255
Tyr Asn Gly Asp Val Gly Phe Phe Glu Pro Asn Glu His Gly Val
               260                 265                 270
Ile Lys Val Cys Asp Glu Phe Pro Gly Phe Thr Arg Phe Lys Met His
           275                 280                 285
Gln Pro Phe Gly Ala Lys Ala Pro Lys Arg Ile Ser Val Pro Arg Ser
           290                 295                 300
His Ala Lys His Pro Thr Asp Thr Ile Pro Asp Ala Ser Asp Val Ser
305                 310                 315                 320
Ile Arg Arg Ala Ile Ala Thr Phe Met Pro Gln Phe Lys Asn Lys Lys
               325                 330                 335
Met Phe Asn Gln Ala Met Cys Trp Cys Thr Asp Thr Ala Asp Ala Ala
               340                 345                 350
Leu Leu Ile Cys Glu His Pro Glu Trp Lys Asn Phe Val Leu Ala Thr
           355                 360                 365
Gly Asp Ser Gly His Ser Phe Lys Leu Leu Pro Asn Ile Gly Lys His
           370                 375                 380
Val Val Glu Leu Leu Glu Gly Thr Leu Ala Asp Leu Ala His Ala
385                 390                 395                 400
Trp Arg Trp Arg Pro Gly Ser Gly Asp Ala Leu Lys Ser Arg Arg Ser
               405                 410                 415
Ala Pro Ala Lys Asp Leu Ala Asp Met Pro Gly Trp Asn His Asp Lys
               420                 425                 430
Pro Arg Ala Asn Leu
           435
```

<210> SEQ ID NO 136
<211> LENGTH: 1314
<212> TYPE: DNA
<213> ORGANISM: Phaeosphaeria nodorum

<400> SEQUENCE: 136

```
atggccccgt cgcgtgctaa tacgtcggtc attgtggttg gtggtggtgg tacgattggc    60
tcatctacgg ctctgcatct ggtccgctca ggctataccc cgtcgaacgt gacggttctg   120
gatgcatacc cgattccgag ctctcagagc gctggcaacg acctgaataa aatcatgggt   180
gtcgatctgc gtaatccggt ggatctgcag ctggctctgg aagcgcgcca aatgtggaac   240
gaagacgaac tgttcaagaa gtttttccat aacaccggcc gtctggattg cgcgcacggt   300
gaaaaagata ttgccaaact gaagagcctg tatcagaaac tggtggatgc gggtctggac   360
gccacgaacg aatggctgga tagtgaagac gaaatcctga acgtatgcc gctgctgtcc   420
cgcgatcaaa ttaaaggctg gaaggcgatc ttttcaaaag acggtggttg gctggcagca   480
gcaaaggcaa ttaatgcagt tggtgaatat ctgcgtgatc agggcgtccg cttcggtttt   540
tacggcgccg gttcttttcaa agcaccgctg ctggctgaag cgtctgcat cggtgtcgaa   600
accgtggatg gcacgcgcta ttacgcagac aaagtggttc tggctgcagg tgcatggtcg   660
ccgaccctgg ttgaactgca tgaacagtgt gtgagcaaag cgtgggttta cggccacatt   720
caactgacgc cggaagaagc cgcacgttat aagaacagcc cggtcgtgta caatggcgat   780
gtgggctttt tctttgaacc gaacgaacat ggcgttatca aagtctgcga tgaatttccg   840
ggttttaccc gcttcaagat gcaccagccg tttggtgcca aagcaccgaa gcgtattagt   900
gtgccgcgct cccatgccaa acacccgacc gatacgatcc cggatgcaag tgacgtttcc   960
attcgtcgcg ctatcgcgac ctttatgccg cagttcaaga acaaaaagat gttcaaccaa  1020
gcgatgtgct ggtgtaccga tacggccgac gctgcgctgc tgatttgtga acatccggaa  1080
tggaaaaact ttgttctggc gaccggcgat tcaggtcatt cgttcaaact gctgccgaat  1140
atcggcaagc acgttgtcga actgctggag ggtacgctgg cagatgacct ggcacacgca  1200
tggcgttggc gtccgggtag tggtgatgca ctgaaaagcc gtcgctctgc tccggcgaaa  1260
gacctggctg atatgccggg ctggaaccat gacaaaccgc gtgctaatct gtaa        1314
```

<210> SEQ ID NO 137
<211> LENGTH: 441
<212> TYPE: PRT
<213> ORGANISM: Neocosmospora vasinfecta

<400> SEQUENCE: 137

```
Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Asp Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95
```

Cys Glu Ser Ser Ala Glu Gly Val Glu Lys Leu Arg Arg Leu Tyr Gln
                100                 105                 110

Lys Leu Val Glu Ala Gly Val Gly Leu Glu Glu Thr His Glu Trp Leu
            115                 120                 125

Asp Ser Glu Glu Ala Ile Leu Glu Lys Ala Pro Leu Leu Gln Arg Glu
        130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Glu Pro Asn
            260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
        435                 440

<210> SEQ ID NO 138
<211> LENGTH: 1326
<212> TYPE: DNA
<213> ORGANISM: Neocosmospora vasinfecta

<400> SEQUENCE: 138
atgacgaccc cgcgtaaaga aacgacggtc ctgattattg gtggtggtgg cacgattggt      60
agctcgacgg ctctgcatct gctgcgtgcc ggctataccc cgtctaacat taccgtgctg     120
gatacgtacc cgatcccgag tgcccagtcc gcaggca

```
atcgatctgc gcaataaagt tgatctgcaa ctgagcctgg aagcccgtga tatgtggcgc    240
aacgacgcac tgtttcgtcc gttttccat aataccggcc gcctggactg cgaaagctct    300
gctgaaggcg tggaaaaact gcgtcgcctg tatcagaaac tggtggaagc aggcgttggt    360
ctggaagaaa cgcacgaatg gctggatagc gaagaagcta ttctggaaaa agcgccgctg    420
ctgcaacgtg aagaaattga aggttggaaa gccatctggt ctgaagaagg cggttggctg    480
gcggccgcaa aagctattaa cgcgatcggc gaagaactgc agcgtcaagg cgttcgcttc    540
ggttttggcg gtgccggtag ttttaaacgc ccgctgttcg cagatgacgg caccacgtgt    600
atcggtgtcg aaaccgtgga tggcacgcag tatcatgcgg acaaagtggt tctggctgca    660
ggtgcttggt caccggcgct ggtcgatctg aagaacagt gctgttcgaa agcctgggtg    720
tacgcacaca tgcaactgac cccggaagaa gccgcagttt ataaaggctg cccggtcgtg    780
taccacggcg atgtcggctt tttctttgaa ccgaacgaaa atggcgttat taaagtctgt    840
gacgaattcc cgggttttac gcgtttcaaa cagcatcaac cgtatggtgc cccggcaccg    900
aaacctgtga gtgttccgcg ctcccatgcg aaacacccga ccgatacgta cccggacgct    960
tcagaagaat cgatcaaacg tgccgtgagt accttctgc cgcgcttcaa agataaaccg   1020
ctgtttaacc gtgcactgtg ctggtgtacc gatacggccg actccgcact gctgatttgc   1080
gaacacccgc gctggaaaaa ttttatcctg gcgaccggcg atagcggtca ttctttcaaa   1140
ctgctgccga ttatcggcaa acacgttgtc gaactggttg aaggtcgtct ggcggatgac   1200
ctggctgaag cgtggcgttg gcgtccgggt cagggtgatg cacgtaaaag cattcgcgct   1260
gcgccggcga aagacctggc ggatatgccg ggctggaaac acgaccaaga ctcggaatca   1320
cgctga                                                              1326

<210> SEQ ID NO 139
<211> LENGTH: 438
<212> TYPE: PRT
<213> ORGANISM: Aspergillus nidulans

<400> SEQUENCE: 139

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Asp Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Lys Leu Arg Lys Leu Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160
```

```
Ala Ala Lys Ala Ile Asn Ala Ile Gly Gln Phe Leu Lys Glu Gln Gly
            165                 170                 175

Val Lys Phe Gly Phe Gly Gly Ala Gly Thr Phe Lys Lys Pro Leu Phe
        180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Phe Glu Pro Asn
        260                 265                 270

Glu Asn Gly Ile Ile Lys Val Cys Asp Glu Phe Pro Gly Phe Thr His
    275                 280                 285

Phe Lys Met His Gln Pro Tyr Gly Ser Pro Ala Pro Lys Pro Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
    355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 140
<211> LENGTH: 1317
<212> TYPE: DNA
<213> ORGANISM: Aspergillus nidulans

<400> SEQUENCE: 140
atgacgcccc gagccaacac caaaatcatt gtcgtcggcg gcggcggcac aatgggctcg      60
tcgacagccc tacacctcct gcgcgccggc tacacgccgt ccaacattac agtgctcgac     120
acgtgcccta tccctccgc acagtctgca ggctacgacc tgaacaaaat catgggcatc     180
gatctgcgca caagcctga tttacagctc tctcttgagg cgctggacat gtggaaaaat     240
gatcctctct tcaagccgtt tttccacaat gttggaatga tcgacgtctc ttcaacagag     300
gaaggcatcg agaaacttcg gaagctgtac cagtctcttc tcgacgcagg cattgggctc     360
gagaagacga atttcatgct ggaaagtgaa gacgagatcc tggctaaagc gccgcatttc     420
acgcaggagc agattaaagg ctggaaaggc ctgttctgtg cgacggcgg ctggctcgct     480 gcagccaaag ccatcaatgc cattgggcag ttcctcaagg aacagggcgt caagtttgga     540
```

-continued

```
ttcggcggcg ccggcacgtt caaaaagcca ctcttcgccg atgcccacga gaagacgtgc      600
atcggcgtcg agactgtaga cggcacaaag tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt ataagaacac tcctgttata      780
tacgacggtg actatgggtt tttctttgag ccgaatgaaa acggcatcat aaaagtctgt      840
gacgaattcc ctggcttcac gcatttcaaa atgcaccagc cgtacggctc gccggcgccc      900
aaacccatct ctgtgcctcg ttcccatgcg aagcacccca cagatacata cccgcacgcg      960
tcggaggtca cgatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagtgggca ttcgttcaag     1140
ttgctgccga atattggaaa gcatgttgtc gagttattgg aggagaggct ggaaagtgtg     1200
tttaaggatg cttggaggtg gaggcctggc agtggggatg cattaaaaag tagacgggct     1260
gcgcctgcga aggacctggc ggatatgccg gggtggagga atgaggcaaa gatgtag        1317
```

<210> SEQ ID NO 141
<211> LENGTH: 437
<212> TYPE: PRT
<213> ORGANISM: Coniochaeta sp.

<400> SEQUENCE: 141

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240
```

```
Tyr Ala His Ile Gln Leu Thr Pro Glu Glu Ala Ala Glu Tyr Lys Gly
            245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
            290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ser Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
            370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
            420                 425                 430

His Asp Pro Lys Leu
            435

<210> SEQ ID NO 142
<211> LENGTH: 1314
<212> TYPE: DNA
<213> ORGANISM: Coniochaeta sp.

<400> SEQUENCE: 142
atgacgtcga atcgtgcaga tacaagggtg attgtcgtcg gtggcggagg aacgattggt        60
tcctcgacag cgctgcatct tgtgaggagt ggttatgctc ccgcaaatat cacggtcttg       120
gacacatttg agattccatc ggctcaatca gccggccatg atctcaacaa gatcatggga       180
atagatcatc gcaacaaggt ggacctgcaa atgagtctag aggctagaca gatgtggaag       240
gaggatgagt tattccagcc cttctttcac aataccggca gaatggactg cgaacacacg       300
cctaagggta tcgagaaact gaaaaagctg taccagaaac tgcacgatgc cggtgcgggt       360
ctggagaaga ctcatgcctg gttggacaac gaggatgaga tcttatccaa gatgccgttg       420
cttcaacgtg accaaataca aggatggaaa gcaatatgga gtcaagatgg cggctggtta       480
gctgcggcaa aggccatcaa tgcgatcgga cagttcttga agaacgtggt gtaaagttc        540 ggattcggcg gcgctggatc cttcaagcaa ccccttttcg acgatgaagg cacaacttgc       600
attggcgttg agacggcaga tggtaccaaa tattacgctg acaaggtggt cttagcagct       660
ggcgcatgga gcccaaccct ggtggacctg aagatcaat gttgctcgaa ggcttgggtg        720
tatgctcata ttcagttgac gcctgaagag gccgctgagt ataagggtgt cccagttgtg       780
tataatggcg aatttggctt cttctttgag cctgatgagt ttggtgtaat aaaggtgtgc       840
gacgagttcc caggattctc gcgcttcaag gaacatcaac cctatggcgc cccatctccg       900
aaacggatat cagtaccacg atcgcacgcc aagcatccca cagacactta tccagacgca       960
```

-continued

```
tccgaagtca gcatcaaaaa agcaatcgcg acgtttctcc ctcgatttca ggacaaggag    1020
ctcttcaatc gcgccttgtg ctggtgtaca gacactgcgg actctgctct cttgatgtgt    1080
gaacacccca aatggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 143
<211> LENGTH: 437
<212> TYPE: PRT
<213> ORGANISM: Eupenicillium terrenum

<400> SEQUENCE: 143

```
Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Asp His Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Lys Glu Gly Ile Glu Lys Leu Arg Arg Leu Tyr Gln
            100                 105                 110

Lys Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
```

```
                305                 310                 315                 320
Ser Glu Val Thr Ile Arg Lys Ala Ile Ala Arg Phe Leu Pro Glu Phe
                    325                 330                 335

Lys Asp Lys Glu Leu Phe Asn Arg Thr Met Cys Trp Cys Thr Asp Thr
                340                 345                 350

Ala Asp Ser Asn Leu Leu Ile Cys Glu His Pro Lys Trp Lys Asn Phe
                355                 360                 365

Ile Leu Ala Thr Gly Asp Ser Gly His Ser Phe Lys Leu Leu Pro Asn
        370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
                420                 425                 430

His Asp Ala His Leu
            435

<210> SEQ ID NO 144
<211> LENGTH: 1314
<212> TYPE: DNA
<213> ORGANISM: Eupenicillium terrenum

<400> SEQUENCE: 144
atggctcatt cgcgtgcaag caccaaagtc gtcgtggttg ggggaggtgg tacgatcggg       60
tcttcgacgg ctctgcactt aatccgctct ggatataccc cctcaaatat caccgtgctt      120
gacgtataca agaccccttc attgcaatct gcaggacatg atttgaacaa gatcatgggc      180
attgatcatc gcaacgggcc tgacttgcag ctttcgctgg aatcactcga catgtggcaa      240
aacgatgagt tgttcaagcc attctttcac caagtgggca tgattgattg ttcgtcatcc      300
aaagagggta ttgaaaaact tcgacgatta taccagaaac tcctcgatgc gggcattggg      360
ctggagaaga cgaacgtttg gctggaatct gaagatgaga tcctcgccaa agcgccgaat      420
ttcacgcgtg aacaagtcaa ggggtggaaa ggcttatttt gcactgatgg aggctggctt      480
gctgcagcca aggctatcaa tgcgatcgga atttttcctcc aggacaaagg tgtcaagttt      540
ggctttggag atgctggtac ctttcagcaa cctctgttcg ccgctgatgg aaaaacttgc      600
atcggacttg aaactacaga cggaaccaag tactttgctg acaaggttgt cttggctgct      660
ggtgcgtgga gtcccacctt ggtggatcta gaagatcagt gtgtttcaaa ggcctgggtt      720
ttcgctcata ttcaactcac acccaaagaa gcggacgcgt acaagaatgt gcctgtggtc      780
tatgatggtg aatatgggtt cttttttcgaa cccgacgagt atgggtgat caaagtctgt      840
gacgagttcc ctggtttctc tcgcttcaaa ctgcatcaac cgtacggggc tgcatctccc      900
aagatgatat ccgtaccgcg atcacacgcc aagcatccca cagatacctta ccctgatgcc      960
tccgaagtca ccatacgcaa agcgatcgca aggttcctgc cagaatttaa agacaaggag    1020
ctcttcaacc gtaccatgtg ctggtgtaca gatacggccg attctaactt attgatttgc    1080
gaacacccga gtggaagaa tttcattctg ccactggag atagcggaca ttccttcaag    1140
ctgttgccaa acatcgggaa atacgtagtt gagcttttag agggatctct atcgcaggaa    1200
atggctggtg cctggagatg gagacccgga ggtgatgctc ttagatctag acgcggtgct    1260
ccggcaaagg atcttgctga gatgccggga tggaagcatg atgcacattt gtga          1314
```

<210> SEQ ID NO 145
<211> LENGTH: 437
<212> TYPE: PRT
<213> ORGANISM: Eupenicillium terrenum

<400> SEQUENCE: 145

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
                20                  25                  30

Thr Pro Ser Asn Ile Thr Val Leu Asp Val Tyr Lys Thr Pro Ser Leu
            35                  40                  45

Gln Ser Ala Gly His Asp Leu Asn Lys Ile Met Gly Ile Arg Leu Arg
50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe His Gln Val Gly Met Ile Asp
                85                  90                  95

Cys Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
            115                 120                 125

Glu Ser Glu Asp Glu Ile Leu Ala Lys Ala Pro Asn Phe Thr Arg Glu
130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Ala Gly Thr Phe Gln Gln Pro Leu
            180                 185                 190

Phe Ala Ala Asp Gly Lys Thr Cys Ile Gly Leu Glu Thr Thr Asp Gly
            195                 200                 205

Thr Lys Tyr Phe Ala Asp Lys Val Val Leu Ala Ala Gly Ala Trp Ser
210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asn
            260                 265                 270

Glu Tyr Gly Val Ile Lys Val Cys Asp Glu Phe Pro Gly Phe Ser Arg
            275                 280                 285

Phe Lys Leu His Gln Pro Tyr Gly Ala Ala Ser Pro Lys Met Ile Ser
        290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Leu Leu Pro Asn
        370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435

<210> SEQ ID NO 146
<211> LENGTH: 1314
<212> TYPE: DNA
<213> ORGANISM: Eupenicillium terrenum

<400> SEQUENCE: 146

| | |
|---|---:|
| atggctcatt cgcgtgcaag caccaaagtc gtcgtggttg ggggaggtgg tacgatcggg | 60 |
| tcttcgacgg ctctgcactt aatccgctct ggatataccc cctcaaatat caccgtgctt | 120 |
| gacgtataca agacccctttc attgcaatct gcaggacatg atttgaacaa gatcatgggc | 180 |
| attcgattgc gcaacgggcc tgacttgcag cttttcgctgg aatcactcga catgtgtgcaa | 240 |
| aacgatgagt tgttcaagcc attctttcac caagtgggca tgattgattg ttcgtcatcc | 300 |
| aaagagggta ttgaaaatct tcgacgaaaa taccagaccc tcctcgatgc gggcattggg | 360 |
| ctggagaaga cgaacgtttg gctggaatct gaagatgaga tcctcgccaa agcgccgaat | 420 |
| ttcacgcgtg aacaagtcaa ggggtggaaa ggcttatttt gcactgatgg aggctggctt | 480 |
| gctgcagcca aggctatcaa tgcgatcgga attttcctcc aggacaaagg tgtcaagttt | 540 |
| ggctttggag gtgctggaac atttcagcaa cctctgttcg ccgctgatgg aaaaacttgc | 600 |
| atcggacttg aaactacaga cggaaccaag tactttgctg acaaggttgt cttggctgct | 660 |
| ggtgcgtgga gtcccacctt ggtggatcta aagatcagt gtgtttcaaa ggcctgggtt | 720 |
| ttcgctcata ttcaactcac acccaaagaa gcggacgcgt acaagaatgt gcctgtggtc | 780 |
| tatgatggtg aatatgggtt cttttttgag cccaacgagt atggggtgat caaagtctgt | 840 |
| gacgagttcc ctggtttctc tcgcttcaaa ctgcatcaac cgtacggggc tgcatctccc | 900 |
| aagatgatat ccgtaccgcg atcacacgcc aagcatccca cagataccta ccctgatgcc | 960 |
| tccgaagtca ccatacgcaa agcgatcgca aggttcctgc cagaatttaa agacaaggag | 1020 |
| ctcttcaacc gtaccatgtg ctggtgtaca gatacggccg atgctaactt attgatttgc | 1080 |
| gaacacccga gtggaagaa tttcattctg gccactggag atagcggaca ttccttcaag | 1140 |
| ctgttgccaa acatcgggaa acacgttgtt gagcttttag agggatctct atcgcaggaa | 1200 |
| atggctggtg cctggagatg gagacccgga ggtgatgctc ttagatctag acgcggtgct | 1260 |
| ccggcaaagg atcttgctga gatgccggga tggaagcatg atgcacattt gtga | 1314 |

<210> SEQ ID NO 147
<211> LENGTH: 438
<212> TYPE: PRT
<213> ORGANISM: Aspergillus nidulans

<400> SEQUENCE: 147

Met Thr Pro Arg Ala Asn Thr Lys Ile Ile Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Cys Pro Ile Pro Ser Ala Gln

```
            35                  40                  45
Ser Ala Gly Tyr Asp Leu Asn Lys Ile Met Ser Ile Arg Leu Arg Asn
 50                  55                  60

Lys Pro Asp Leu Gln Leu Ser Leu Glu Ala Leu Asp Met Trp Lys Asn
 65                  70                  75                  80

Asp Pro Leu Phe Lys Pro Phe Phe His Asn Val Gly Met Ile Asp Val
                     85                  90                  95

Ser Ser Thr Glu Glu Gly Ile Glu Gly Leu Arg Lys Lys Tyr Gln Ser
                    100                 105                 110

Leu Leu Asp Ala Gly Ile Gly Leu Glu Lys Thr Asn Phe Met Leu Glu
                115                 120                 125

Ser Glu Asp Glu Ile Leu Ala Lys Ala Pro His Phe Thr Gln Glu Gln
            130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                    165                 170                 175

Val Lys Phe Gly Phe Gly Gly Ala Gly Thr Phe Lys Lys Pro Leu Phe
                180                 185                 190

Ala Asp Ala His Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                    245                 250                 255

Thr Pro Val Ile Tyr Asp Gly Asp Tyr Gly Phe Phe Glu Pro Asn
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Ala Pro Lys Pro Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                    405                 410                 415

Ser Arg Arg Ala Ala Pro Ala Lys Asp Leu Ala Asp Met Pro Gly Trp
                420                 425                 430

Arg Asn Glu Ala Lys Met
                435

<210> SEQ ID NO 148
```

<211> LENGTH: 1317
<212> TYPE: DNA
<213> ORGANISM: Aspergillus nidulans

<400> SEQUENCE: 148

```
atgacgcccc gagccaacac caaaatcatt gtcgtcggcg gcggcggcac aatgggctcg      60
tcgacagccc tacacctcct gcgcgccggc tacacgccgt ccaacattac agtgctcgac     120
acgtgcccta tccctccgc acagtctgca ggctacgacc tgaacaaaat catgagcatc      180
aggctgcgca acaagcctga tttacagctc tctcttgagg cgctggacat gtggaaaaat     240
gatcctctct tcaagccgtt tttccacaat gttggaatga tcgacgtctc ttcaacagag     300
gaaggcatcg agggtcttcg aagaaatac cagtctcttc tcgacgcagg cattgggctc      360
gagaagacga atttcatgct ggaaagtgaa gacgagatcc tggctaaagc gccgcatttc     420
acgcaggagc agattaaagg ctggaaaggc ctgttctgtg gcgacggcgg ctggctcgct     480
gcagccaaag ccatcaatgc cattgggcag ttcctcaagg aacagggcgt caagtttgga     540
ttcggcggcg ccggcacgtt caaaaagcca ctcttcgccg atgcccacga aagacgtgc      600
atcggcgtcg agactgtaga cggcacaaag tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt ataagaacac tcctgttata     780
tacgacggtg actatgggtt tttctttgag ccgaatgaaa acggcatcat aaaagtctgt     840
gacgaattcc ctggcttcac gcatttcaaa atgcaccagc cgtacggctc gccggcgccc     900
aaacccatct ctgtgcctcg ttcccatgcg aagcacccca cagatacata cccgcacgcg     960
tcggaggtca cgatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagtgggca ttcgttcaag    1140
ttgctgccga atattggaaa gcatgttgtc gagttattgg aggagaggct ggaaagtgtg    1200
tttaaggatg cttggaggtg gaggcctggc agtggggatg cattaaaaag tagacgggct    1260
gcgcctgcga aggacctggc ggatatgccg gggtggagga atgaggcaaa gatgtag       1317
```

<210> SEQ ID NO 149
<211> LENGTH: 477
<212> TYPE: PRT
<213> ORGANISM: Cryptococcus neoformans

<400> SEQUENCE: 149

```
Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110
```

Ala Ile Leu Lys Ala Gly Ser Gly Leu Glu Lys Thr His His Trp Leu
115                 120                 125

Ser Thr Glu Asp Glu Ile Leu Ala Arg Ala Pro Leu Leu Asp Arg Lys
130                 135                 140

Gln Ile Lys Gly Trp Lys Ala Ile Tyr Ser Glu Asp Gly Trp Leu
145                 150                 155                 160

Ala Ala Ala Lys Ala Ile Asn Ser Ile Gly Gln Val Leu Lys Glu Lys
            165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
            195                 200                 205

Thr Gln Tyr Phe Ala Asp Lys Val Val Leu Ala Ala Gly Ala Trp Ser
210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
            245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
            275                 280                 285

Phe Lys Gln His Gln Pro Tyr Gly Ala Ser Ser Thr Lys His Ile Ser
            290                 295                 300

Phe Pro Arg Ser His Ala Lys His Pro Thr Thr Ile Pro Asp Glu
305                 310                 315                 320

Ser Asp Ala Ser Ile Arg Arg Ala Ile Ser Ala Phe Leu Pro Arg Phe
            325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
355                 360                 365

Ile Leu Ala Thr Gly Asp Ser Gly His Ser Phe Lys Ile Leu Pro Asn
370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
            405                 410                 415

Ser Arg Arg Ala Ala Pro Ala Arg Asp Leu Ala Asp Leu Pro Gly Trp
            420                 425                 430

Asn His Asp Glu Pro Ser Asp Asp Met Asp Val Lys Asp Val Ala
            435                 440                 445

Val Ser Leu Ala Ser Val Lys Ile Gly Glu Asn Ile Gly Glu Lys Val
450                 455                 460

Val Glu Asp Gly Ala Arg Val Gly Val Lys Val Leu Ala
465                 470                 475

<210> SEQ ID NO 150
<211> LENGTH: 1434
<212> TYPE: DNA
<213> ORGANISM: Cryptococcus neoformans

<400> SEQUENCE: 150
atgccacctt cgcgcgccag tactaaggtc atagttatcg ggggcggtgg tactctcggg    60

| | |
|---|---|
| tcctctactg ctcttcacct tttacgagcc ggttacactc catccaacat cactgtgctt | 120 |
| gacacgtatc taatcccatc agcacagtcg gctggcaatg acctcaataa gatcatgggt | 180 |
| attcgtatca ggaatcctgt agataaacag ttgagcctgg aagcaagaga catgtggagg | 240 |
| aatgatgaag ttttcaagcc ttatttccac aacacgggaa gacttgattg tgctcataca | 300 |
| ccggagagca ttgcatcttt gcgtaaatcg tacgaggcta tcttaaaggc cgggagcggg | 360 |
| ctcgagaaga cccaccattg gctgagtaca aagatgaaa tactggctag agccccttg | 420 |
| ttggatcgga aacagatcaa aggatggaaa gctatttaca gcgaagatgg gggctggctt | 480 |
| gcggcggcga aagctatcaa cagtatcggc caggtgttga agagaaagg tgtgacattc | 540 |
| ggattcggga gtgcgggctc attcaagaaa cccttgtttg acgaagacgg taccaaggcc | 600 |
| atcggcattg agacagttga tggtacgcaa tattttgccg acaaggtcgt tctggctgcc | 660 |
| ggagcttgga gtcctaccct cgtggatttg aagggcaat gctgttcaaa ggcttgggtt | 720 |
| tacgcccata tgcaattgac accagaagag gctgccgaat acaaggagtg tcctgtggtg | 780 |
| tacaactctg aacttgggtt cttcttcgag cccaatgaaa aggagtcat caaagtgtgc | 840 |
| gacgaattcc cagggttcac ccgtttcaag caacatcaac cttacggcgc ctcctctact | 900 |
| aaacacatct ctttcccgcg ctcccatgcc aaacacccta ccgataccat tccggacgag | 960 |
| tcggacgcat ctatccgccg tgctatctct gccttttta cgagattcaa agaaaaagaa | 1020 |
| ctgttcaaca gagcactgtg ctggtgtaca gataccgccg atgccaatct tttgatatgc | 1080 |
| gaacatccca atggaaaaa ttttatctta gctacagggg atagtggaca ttcattcaaa | 1140 |
| attcttccca atatcggtaa acatgtcgtt gaacttatag aaggtaccct tgccgaggac | 1200 |
| ttggctgaga gctggagatg gagacctgga agcggtgacc ccctgatctc tcgtcgggca | 1260 |
| gccccctgcaa gggatcttgc tgatcttcca ggatggaacc atgatgagcc ctcggatgac | 1320 |
| gatatggatg taaaggatgt cgctgtatcg cttgcttctg tgaaaattgg cgaaaacatc | 1380 |
| ggggagaagg ttgtggaaga tggagcacga gtcggagtca aagttctagc ttag | 1434 |

<210> SEQ ID NO 151
<211> LENGTH: 437
<212> TYPE: PRT
<213> ORGANISM: Coniochaeta sp.

<400> SEQUENCE: 151

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp

```
        130                 135                 140
Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
                195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 152
<211> LENGTH: 1314
<212> TYPE: DNA
<213> ORGANISM: Coniochaeta sp.

<400> SEQUENCE: 152
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagcactgc gcaacaaggt ggacctgcaa atgagtctag aggctagaca gatgtggaag     240
gaggatgagt tattccagcc cttctttcac aataccggca gaatgactg cgaacacacg      300 cctgagggta tcgaggacct gaaaaagcag taccaggcac tgcacgatgc cggtgcgggt     360
```

```
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtggt gtaaagttc     540 ggattcggcg cgctggatc cttcaagcaa ccccttttcg acgatgaagg cacaacttgc    600
attggcgttg agacggcaga tggtaccaaa tattacgctg acaaggtggt cttagcagct    660
ggcgcatgga gcccaaccct ggtggacctg gaagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgataga gggccgcct gccggaggaa    1200 atggcttatc aatggaggtg gcggccagga ggcgatgcac tcaagtctag acgtgccgca    1260
ccgccaaaag atcttgcaga catgccagga tggaaacatg atccgaaatt gtaa          1314

<210> SEQ ID NO 153
<211> LENGTH: 437
<212> TYPE: PRT
<213> ORGANISM: Coniochaeta sp.

<400> SEQUENCE: 153

Met Thr Ser Asn Arg Ala Asp Thr Arg Val Ile Val Val Gly Gly Gly
 1               5                  10                  15

Gly Thr Ile Gly Ser Ser Thr Ala Leu His Leu Val Arg Ser Gly Tyr
             20                  25                  30

Ala Pro Ala Asn Ile Thr Val Leu Asp Thr Phe Glu Ile Pro Ser Ala
         35                  40                  45

Gln Ser Ala Gly His Asp Leu Asn Lys Ile Met Gly Ile Asp Leu Arg
     50                  55                  60

Asn Lys Val Asp Leu Gln Met Ser Leu Glu Ala Arg Gln Met Trp Lys
 65                  70                  75                  80

Glu Asp Glu Leu Phe Gln Pro Phe His Asn Thr Gly Arg Met Asp
                 85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205
```

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 154
<211> LENGTH: 1314
<212> TYPE: DNA
<213> ORGANISM: Coniochaeta sp.

<400> SEQUENCE: 154
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagcag taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggg tgtaaagttc     540
ggattcggcg cgctggatcc ttcaagcaa cccctttcg acgatgaagg cacaacttgc      600
attggcgttg agacggcaga tggtaccaaa tattacgctg acaaggtggt cttagcagct     660
ggcgcatgga gcccaacccct ggtggacctg aagatcaat gttgctcgaa ggcttgggtg     720
tatgctcata ttcagttgac gcctgaagag gccgctgagt ataagggtgt cccagttgtg     780

```
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314
```

<210> SEQ ID NO 155
<211> LENGTH: 437
<212> TYPE: PRT
<213> ORGANISM: Eupenicillium terrenum

<400> SEQUENCE: 155

```
Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Asp Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285
```

```
Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435

<210> SEQ ID NO 156
<211> LENGTH: 1314
<212> TYPE: DNA
<213> ORGANISM: Eupenicillium terrenum

<400> SEQUENCE: 156
atggctcatt cgcgtgcaag caccaaagtc gtcgtggttg ggggaggtgg tacgatcggg      60
tcttcgacgg ctctgcactt aatccgctct ggatataccc cctcaaatat caccgtgctt     120
gacgtataca agaccccttc attgcaatct gcaggacatg atttgaacaa gatcatgggc     180
attgatttgc gcaacgggcc tgacttgcag cttttcgctg gaatcactcg catgtggcaa     240
aacgatgagt tgttcaagcc attctttcac caagtgggca tgattgattg ttcgtcatcc     300
aaagagggta ttgaaaatct tcgacgaaaa taccagaccc cctcgatgc gggcattggg      360 ctggagaaga cgaacgtttg gctggaatct gaagatgaga tcctcgccaa agcgccgaat     420
ttcacgcgtg aacaagtcaa ggggtggaaa ggcttatttt gcactgatgg aggctggctt     480
gctgcagcca aggctatcaa tgcgatcgga atttcctcc aggacaaagg tgtcaagttt      540
ggctttggag atgctggtac ctttcagcaa cctctgttcg ccgctgatgg aaaaacttgc     600
atcggacttg aaactacaga cggaaccaag tactttgctg acaaggttgt cttggctgct     660
ggtgcgtgga gtcccacctt ggtggatcta aagatcagt gtgtttcaaa ggcctggtt      720 ttcgctcata ttcaactcac acccaaagaa gcggacgcgt acaagaatgt gcctgtggtc     780
tatgatggtg aatatgggtt cttttttcgaa cccgacgagt atgggtgat caaagtctgt    840 gacgagttcc ctggtttctc tcgcttcaaa ctgcatcaac cgtacggggc tgcatctccc     900
aagatgatat ccgtaccgcg atcacacgcc aagcatccca cagataccta ccctgatgcc     960
tccgaagtca ccatacgcaa agcgatcgca aggttcctgc cagaatttaa agacaaggag    1020
ctcttcaacc gtaccatgtg ctggtgtaca gatacggccg atgctaactt attgatttgc    1080
gaacacccga gtggaagaa tttcattctg ccactggag atagcggaca ttccttcaag     1140
ctgttgccaa acatcgggaa atacgtagtt gagcttttag agggatctct atcgcaggaa    1200
```

```
atggctggtg cctggagatg gagacccgga ggtgatgctc ttagatctag acgcggtgct   1260
ccggcaaagg atcttgctga gatgccggga tggaagcatg atgcacattt gtga         1314
```

<210> SEQ ID NO 157
<211> LENGTH: 437
<212> TYPE: PRT
<213> ORGANISM: Coniochaeta sp.

<400> SEQUENCE: 157

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Leu Tyr Gln
                100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
```

```
                355                 360                 365
Ile Leu Ala Thr Gly Asp Ser Gly His Ser Phe Lys Ile Leu Pro Asn
            370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 158
<211> LENGTH: 1314
<212> TYPE: DNA
<213> ORGANISM: Coniochaeta sp.

<400> SEQUENCE: 158
atgacgtcga atcgtgcaga tacaagggtg attgtcgtcg gtggcggagg aacgattggt        60
tcctcgacag cgctgcatct tgtgaggagt ggttatgctc ccgcaaatat cacggtcttg       120
gacacatttg agattccatc ggctcaatca gccggccatg atctcaacaa gatcatggga       180
atagcactgc gcaacaaggt ggacctgcaa atgagtctag aggctagaca gatgtggaag       240
gaggatgagt tattccagcc cttctttcac aataccggca gaatggactg cgaacacacg       300
cctgagggta tcgaggacct gaaaaagctg taccaggcac tgcacgatgc cggtgcgggt       360
ctggagaaga ctcatgcctg gttggacaac gaggatgaga tcttatccaa gatgccgttg       420
cttcaacgtg accaaataca aggatggaaa gcaatatgga gtcaagatgg cggctggtta       480
gctgcggcaa aggccatcaa tgcgatcgga cagttcttga agaacgtggt tgtaaagttc       540
ggattcggcg cgctggatc cttcaagcaa cccctttttcg acgatgaagg cacaacttgc       600
attggcgttg agacggcaga tggtaccaaa tattacgctg acaaggtggt cttagcagct       660
ggcgcatgga gcccaaccct ggtggacctg aagatcaat gttgctcgaa ggcttgggtg       720
tatgctcata ttcagttgac gcctgaagag gccgctgagt ataagggtgt cccagttgtg       780
tataatggcg aatttggctt cttctttgag cctgatgagt ttggtgtaat aaaggtgtgc       840
gacgagttcc caggattctc gcgcttcaag gaacatcaac cctatggcgc cccatctccg       900
aaacggatat cagtaccacg atcgcacgcc aagcatccca cagacactta tccagacgca       960
tccgaagtca gcatcaaaaa agcaatcgcg acgtttctcc ctcgatttca ggacaaggag      1020
ctcttcaatc gcgccttgtg ctggtgtaca gacactgcgg acgctgctct cttgatgtgt      1080
gaacacccca atggaagaa tttcattcta gcgaccggcg acagcggaca ctcattcaaa      1140
atcttgccta acgtcggaaa atacgtagtc gagttgatag agggccgcct gccggaggaa      1200
atggcttatc aatggaggtg gcggccagga ggcgatgcac tcaagtctag acgtgcggca      1260
ccgccaaaag atcttgcaga catgccagga tggaaacatg atccgaaatt gtaa            1314

<210> SEQ ID NO 159
<211> LENGTH: 437
<212> TYPE: PRT
<213> ORGANISM: Coniochaeta sp.

<400> SEQUENCE: 159

Met Thr Ser Asn Arg Ala Asp Thr Arg Val Ile Val Val Gly Gly Gly
1               5                   10                  15
```

```
Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Tyr Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
            165                 170                 175

Gly Val Lys Phe Gly Phe Gly Ala Gly Ser Phe Lys Gln Pro Leu
        180                 185                 190

Phe Asp Asp Glu Gly Thr Thr Cys Ile Gly Val Glu Thr Ala Asp Gly
    195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
            245                 250                 255

Val Pro Val Val Tyr Asn Gly Glu Phe Gly Phe Phe Glu Pro Asp
        260                 265                 270

Glu Phe Gly Val Ile Lys Val Cys Asp Glu Phe Pro Gly Phe Ser Arg
    275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
            325                 330                 335

Gln Asp Lys Glu Leu Phe Asn Arg Ala Leu Cys Trp Cys Thr Asp Thr
        340                 345                 350

Ala Asp Ala Ala Leu Leu Met Cys Glu His Pro Lys Trp Lys Asn Phe
    355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
        420                 425                 430
```

His Asp Pro Lys Leu
        435

<210> SEQ ID NO 160
<211> LENGTH: 1314
<212> TYPE: DNA
<213> ORGANISM: Coniochaeta sp.

<400> SEQUENCE: 160

| | |
|---|---|
| atgacgtcga atcgtgcaga tacaagggtg attgtcgtcg gtggcggagg aacgattggt | 60 |
| tcctcgacag cgctgcatct tgtgaggagt ggttatgctc ccgcaaatat cacggtcttg | 120 |
| gacacatttg agattccatc ggctcaatca gccggccatg atctcaacaa gatcatggga | 180 |
| atagcactgc gcaacaaggt ggacctgcaa atgagtctag aggctagaca gatgtggaag | 240 |
| gaggatgagt tattccagcc cttctttcac aataccggca gaatggactg cgaacacacg | 300 |
| cctgagggta tcgaggacct gaaaaagtat taccaggcac tgcacgatgc cggtgcgggt | 360 |
| ctggagaaga ctcatgcctg gttggacaac gaggatgaga tcttatccaa gatgccgttg | 420 |
| cttcaacgtg accaaataca aggatggaaa gcaatatgga gtcaagatgg cggctggtta | 480 |
| gctgcggcaa aggccatcaa tgcgatcgga cagttcttga agaacgtgg tgtaaagttc | 540 |
| ggattcggcg gcgctggatc cttcaagcaa ccccttttcg acgatgaagg cacaacttgc | 600 |
| attggcgttg agacggcaga tggtaccaaa tattacgctg acaaggtggt cttagcagct | 660 |
| ggcgcatgga gcccaacccct ggtggacctg gaagatcaat gttgctcgaa ggcttgggtg | 720 |
| tatgctcata ttcagttgac gcctgaagag gccgctgagt ataagggtgt cccagttgtg | 780 |
| tataatggcg aatttggctt cttctttgag cctgatgagt ttggtgtaat aaaggtgtgc | 840 |
| gacgagttcc caggattctc gcgcttcaag gaacatcaac cctatggcgc cccatctccg | 900 |
| aaacggatat cagtaccacg atcgcacgcc aagcatccca cagacactta tccagacgca | 960 |
| tccgaagtca gcatcaaaaa agcaatcgcg acgtttctcc ctcgatttca ggacaaggag | 1020 |
| ctcttcaatc gcgccttgtg ctggtgtaca gacactgcgg acgctgctct cttgatgtgt | 1080 |
| gaacacccca atggaagaa tttcattcta gcgaccggcg acagcggaca ctcattcaaa | 1140 |
| atcttgccta acgtcggaaa atacgtagtc gagttgatag agggccgcct gccggaggaa | 1200 |
| atggcttatc aatggaggtg gcggccagga ggcgatgcac tcaagtctag acgtgcggca | 1260 |
| ccgccaaaag atcttgcaga catgccagga tggaaacatg atccgaaatt gtaa | 1314 |

<210> SEQ ID NO 161
<211> LENGTH: 437
<212> TYPE: PRT
<213> ORGANISM: Coniochaeta sp.

<400> SEQUENCE: 161

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asn Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp

```
            85                  90                  95
Cys Glu His Thr Pro Glu Gly Ile Glu Asp Leu Lys Leu Tyr Gln
            100                 105                 110
Ala Leu His Asp Ala Gly Ala Gly Leu Glu Lys Thr His Ala Trp Leu
            115                 120                 125
Asp Asn Glu Asp Glu Ile Leu Ser Lys Met Pro Leu Leu Gln Arg Asp
        130                 135                 140
Gln Ile Gln Gly Trp Lys Ala Ile Trp Ser Gln Asp Gly Gly Trp Leu
145                 150                 155                 160
Ala Ala Ala Lys Ala Ile Asn Ala Ile Gly Gln Phe Leu Lys Glu Arg
            165                 170                 175
Gly Val Lys Phe Gly Phe Gly Ala Gly Ser Phe Lys Gln Pro Leu
            180                 185                 190
Phe Asp Asp Glu Gly Thr Thr Cys Ile Gly Val Glu Thr Ala Asp Gly
        195                 200                 205
Thr Lys Tyr Tyr Ala Asp Lys Val Val Leu Ala Ala Gly Ala Trp Ser
        210                 215                 220
Pro Thr Leu Val Asp Leu Glu Asp Gln Cys Cys Ser Lys Ala Trp Val
225                 230                 235                 240
Tyr Ala His Ile Gln Leu Thr Pro Glu Glu Ala Ala Glu Tyr Lys Gly
            245                 250                 255
Val Pro Val Val Tyr Asn Gly Glu Phe Gly Phe Phe Glu Pro Asp
            260                 265                 270
Glu Phe Gly Val Ile Lys Val Cys Asp Glu Phe Pro Gly Phe Ser Arg
        275                 280                 285
Phe Lys Glu His Gln Pro Tyr Gly Ala Pro Ser Pro Lys Arg Ile Ser
        290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
            325                 330                 335
Gln Asp Lys Glu Leu Phe Asn Arg Ala Leu Cys Trp Cys Thr Asp Thr
            340                 345                 350
Ala Asp Ala Ala Leu Leu Met Cys Glu His Pro Lys Trp Lys Asn Phe
        355                 360                 365
Ile Leu Ala Thr Gly Asp Ser Gly His Ser Phe Lys Ile Leu Pro Asn
        370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
            405                 410                 415
Arg Arg Ala Ala Pro Pro Lys Asp Leu Ala Asp Met Pro Gly Trp Lys
            420                 425                 430
His Asp Pro Lys Leu
            435

<210> SEQ ID NO 162
<211> LENGTH: 1314
<212> TYPE: DNA
<213> ORGANISM: Coniochaeta sp.

<400> SEQUENCE: 162
atgacgtcga atcgtgcaga tacaagggtg attgtcgtcg gtggcggagg aacgattggt    60
tcctcgacag cgctgcatct tgtgaggagt ggttatgctc ccgcaaatat cacggtcttg   120
```

```
gacacatttg agattccatc ggctcaatca gccggccatg atctcaacaa gatcatggga      180
ataaacctgc gcaacaaggt ggacctgcaa atgagtctag aggctagaca gatgtggaag      240
gaggatgagt tattccagcc cttctttcac aataccggca gaatggactg cgaacacacg      300
cctgagggta tcgaggacct gaaaaagctg taccaggcac tgcacgatgc cggtgcgggt      360
ctggagaaga ctcatgcctg gttggacaac gaggatgaga tcttatccaa gatgccgttg      420
cttcaacgtg accaaataca aggatggaaa gcaatatgga gtcaagatgg cggctggtta      480
gctgcggcaa aggccatcaa tgcgatcgga cagttcttga agaacgtgg tgtaaagttc       540 ggattcggcg cgctggatc cttcaagcaa ccccttttcg acgatgaagg cacaacttgc       600
attggcgttg agacggcaga tggtaccaaa tattacgctg acaaggtggt cttagcagct      660
ggcgcatgga gcccaaccct ggtggacctg aagatcaat gttgctcgaa ggcttgggtg       720
tatgctcata ttcagttgac gcctgaagag gccgctgagt ataagggtgt cccagttgtg      780
tataatggcg aatttggctt cttctttgag cctgatgagt ttggtgtaat aaaggtgtgc      840
gacgagttcc caggattctc gcgcttcaag gaacatcaac cctatgcgc cccatctccg       900 aaacggatat cagtaccacg atcgcacgcc aagcatccca cagacactta tccagacgca      960
tccgaagtca gcatcaaaaa agcaatcgcg acgtttctcc ctcgatttca ggacaaggag     1020
ctcttcaatc gcgccttgtg ctggtgtaca gacactgcgg acgctgctct cttgatgtgt     1080
gaacacccca atggaagaa tttcattcta gcgaccggcg acagcggaca ctcattcaaa     1140
atcttgccta acgtcggaaa atacgtagtc gagttgatag agggccgcct gccggaggaa     1200
atggcttatc aatggaggtg gcggccagga ggcgatgcac tcaagtctag acgtgcggca     1260
ccgccaaaag atcttgcaga catgccagga tggaaacatg atccgaaatt gtaa           1314
```

<210> SEQ ID NO 163
<211> LENGTH: 437
<212> TYPE: PRT
<213> ORGANISM: Coniochaeta sp.

<400> SEQUENCE: 163

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp Leu Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Leu Tyr Gln
                100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175
Gly Val Lys Phe Gly Phe Gly Ala Gly Ser Phe Lys Gln Pro Leu
            180                 185                 190
Phe Asp Asp Glu Gly Thr Thr Cys Ile Gly Val Glu Thr Ala Asp Gly
                195                 200                 205
Thr Lys Tyr Tyr Ala Asp Lys Val Val Leu Ala Ala Gly Ala Trp Ser
210                 215                 220
Pro Thr Leu Val Asp Leu Glu Asp Gln Cys Cys Ser Lys Ala Trp Val
225                 230                 235                 240
Tyr Ala His Ile Gln Leu Thr Pro Glu Glu Ala Glu Tyr Lys Gly
                245                 250                 255
Val Pro Val Val Tyr Asn Gly Glu Phe Gly Phe Phe Glu Pro Asp
            260                 265                 270
Glu Phe Gly Val Ile Lys Val Cys Asp Glu Phe Pro Gly Phe Ser Arg
                275                 280                 285
Phe Lys Glu His Gln Pro Tyr Gly Ala Pro Ser Pro Lys Arg Ile Ser
290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Gln Asp Lys Glu Leu Phe Asn Arg Ala Leu Cys Trp Cys Thr Asp Thr
                340                 345                 350
Ala Asp Ala Ala Leu Leu Met Cys Glu His Pro Lys Trp Lys Asn Phe
                355                 360                 365
Ile Leu Ala Thr Gly Asp Ser Gly His Ser Phe Lys Ile Leu Pro Asn
                370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
                405                 410                 415
Arg Arg Ala Ala Pro Pro Lys Asp Leu Ala Asp Met Pro Gly Trp Lys
                420                 425                 430
His Asp Pro Lys Leu
            435

<210> SEQ ID NO 164
<211> LENGTH: 1314
<212> TYPE: DNA
<213> ORGANISM: Coniochaeta sp.

<400> SEQUENCE: 164
atgacgtcga atcgtgcaga tacaagggtg attgtcgtcg gtggcggagg aacgattggt        60
tcctcgacag cgctgcatct tgtgaggagt ggttatgctc ccgcaaatat cacggtcttg       120
gacacatttg agattccatc ggctcaatca gccggccatg atctcaacaa gatcatggga       180
atagatctgc gcaacaaggt ggacctgcaa atgagtctag aggctagaca gatgtggaag       240
gaggatgagt tattccagcc cttctttcac aataccggca gaatggactg cgaacacacg       300
cctgagggta tcgaggacct gaaaaagctg taccaggcac tgcacgatgc cggtgcgggt       360
ctggagaaga ctcatgcctg gttggacaac gaggatgaga tcttatccaa gatgccgttg       420
cttcaacgtg accaaataca aggatggaaa gcaatatgga gtcaagatgg cggctggtta       480
gctgcggcaa aggccatcaa tgcgatcgga cagttcttga agaacgtgg tgtaaagttc       540

```
ggattcggcg gcgctggatc cttcaagcaa cccctttcg acgatgaagg cacaacttgc    600
attggcgttg agacggcaga tggtaccaaa tattacgctg acaaggtggt cttagcagct    660
ggcgcatgga gcccaaccct ggtggacctg aagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc ccatctccg     900 aaacggatat cagtaccacg atcgcacgcc aagcatccca cagacactta ccagacgca     960 tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca atggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314
```

<210> SEQ ID NO 165
<211> LENGTH: 437
<212> TYPE: PRT
<213> ORGANISM: Coniochaeta sp.

<400> SEQUENCE: 165

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Ala Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240
```

Tyr Ala His Ile Gln Leu Thr Pro Glu Glu Ala Ala Glu Tyr Lys Gly
             245                 250                 255

Val Pro Val Val Tyr Asn Gly Glu Phe Gly Phe Phe Glu Pro Asp
         260                 265                 270

Glu Phe Gly Val Ile Lys Val Cys Asp Glu Phe Pro Gly Phe Ser Arg
         275                 280                 285

Phe Lys Glu His Gln Pro Tyr Gly Ala Pro Ser Pro Lys Arg Ile Ser
         290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                 325                 330                 335

Gln Asp Lys Glu Leu Phe Asn Arg Ala Leu Cys Trp Cys Thr Asp Thr
             340                 345                 350

Ala Asp Ala Ala Leu Leu Met Cys Glu His Pro Lys Trp Lys Asn Phe
             355                 360                 365

Ile Leu Ala Thr Gly Asp Ser Gly His Ser Phe Lys Ile Leu Pro Asn
         370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                 405                 410                 415

Arg Arg Ala Ala Pro Pro Lys Asp Leu Ala Asp Met Pro Gly Trp Lys
             420                 425                 430

His Asp Pro Lys Leu
         435

<210> SEQ ID NO 166
<211> LENGTH: 1314
<212> TYPE: DNA
<213> ORGANISM: Coniochaeta sp.

<400> SEQUENCE: 166
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggccct gaaaaagctg taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc      540 ggattcggcg cgctggatc cttcaagcaa cccctttcg acgatgaagg cacaacttgc       600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttcttgag cctgatgagt ttggtgtaat aaaggtgtgc      840
gacgagttcc caggattctc gcgcttcaag gaacatcaac cctatggcgc ccatctcccg     900
aaacggatat cagtaccacg atcgcacgcc aagcatccca cagacactta tccagacgca     960

-continued

```
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca aatggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 167
<211> LENGTH: 437
<212> TYPE: PRT
<213> ORGANISM: Coniochaeta sp.

<400> SEQUENCE: 167

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
```

|  | 305 |  |  | 310 |  |  |  | 315 |  |  |  | 320 |
|---|---|---|---|---|---|---|---|---|---|---|---|---|

Ser Glu Val Ser Ile Lys Lys Ala Ile Ala Thr Phe Leu Pro Arg Phe
              325                    330                  335

Gln Asp Lys Glu Leu Phe Asn Arg Ala Leu Cys Trp Cys Thr Asp Thr
            340                  345                  350

Ala Asp Ala Ala Leu Leu Met Cys Glu His Pro Lys Trp Lys Asn Phe
        355                  360                  365

Ile Leu Ala Thr Gly Asp Ser Gly His Ser Phe Lys Ile Leu Pro Asn
    370                  375                  380

Val Gly Lys Tyr Val Val Glu Leu Ile Glu Gly Arg Leu Pro Glu Glu
385                  390                  395            400

Met Ala Tyr Gln Trp Arg Trp Arg Pro Gly Gly Asp Ala Leu Lys Ser
            405                  410                  415

Arg Arg Ala Ala Pro Pro Lys Asp Leu Ala Asp Met Pro Gly Trp Lys
        420                  425                  430

His Asp Pro Lys Leu
        435

<210> SEQ ID NO 168
<211> LENGTH: 1314
<212> TYPE: DNA
<213> ORGANISM: Coniochaeta sp.

<400> SEQUENCE: 168

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540
ggattcggcg cgctggatc cttcaagcaa cccctttcg acgatgaagg cacaacttgc       600
attggcgttg agacggcaga tggtaccaaa tattacgctg acaaggtggt cttagcagct     660
ggcgcatgga gcccaacccct ggtggacctg aagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc aggattctc gcgcttcaag gaacatcaac cctatggcgc cccatctccg     900
aaacggatat cagtaccacg atcgcacgcc aagcatccca cagacactta tccgacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 169
<211> LENGTH: 437
<212> TYPE: PRT
<213> ORGANISM: Coniochaeta sp.

<400> SEQUENCE: 169

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Arg Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

```
Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
        420                 425                 430

His Asp Pro Lys Leu
        435
```

<210> SEQ ID NO 170
<211> LENGTH: 1314
<212> TYPE: DNA
<213> ORGANISM: Coniochaeta sp.

<400> SEQUENCE: 170

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagcgcct gaaaaagctg taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt tgtaaagttc     540
ggattcggcg cgctggatc cttcaagcaa cccctttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc ccatctccg     900
aaacggatat cagtaccacg atcgcacgcc aagcatccca cagacactta ccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 171
<211> LENGTH: 437
<212> TYPE: PRT
<213> ORGANISM: Coniochaeta sp.

<400> SEQUENCE: 171

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
```

35                  40                  45
Gln Ser Ala Gly His Asp Leu Asn Lys Ile Met Gly Ile Asp Leu Arg
 50                  55                  60

Asn Lys Val Asp Leu Gln Met Ser Leu Glu Ala Arg Gln Met Trp Lys
 65                  70                  75                  80

Glu Asp Glu Leu Phe Gln Pro Phe Phe His Asn Thr Gly Arg Met Asp
                 85                  90                  95

Cys Glu His Thr Pro Glu Gly Ile Glu Asp Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 172

<211> LENGTH: 1314
<212> TYPE: DNA
<213> ORGANISM: Coniochaeta sp.

<400> SEQUENCE: 172

| | | | | | |
|---|---|---|---|---|---|
| atgacgtcga | atcgtgcaga | tacaagggtg | attgtcgtcg | gtggcggagg | aacgattggt | 60 |
| tcctcgacag | cgctgcatct | tgtgaggagt | ggttatgctc | ccgcaaatat | cacggtcttg | 120 |
| gacacatttg | agattccatc | ggctcaatca | gccggccatg | atctcaacaa | gatcatggga | 180 |
| atagatctgc | gcaacaaggt | ggacctgcaa | atgagtctag | aggctagaca | gatgtggaag | 240 |
| gaggatgagt | tattccagcc | cttctttcac | aataccggca | gaatggactg | cgaacacacg | 300 |
| cctgagggta | tcgaggacct | gaaaaagctg | taccagaaac | tgcacgatgc | cggtgcgggt | 360 |
| ctggagaaga | ctcatgcctg | gttggacaac | gaggatgaga | tcttatccaa | gatgccgttg | 420 |
| cttcaacgtg | accaaataca | aggatggaaa | gcaatatgga | gtcaagatgg | cggctggtta | 480 |
| gctgcggcaa | aggccatcaa | tgcgatcgga | cagttcttga | agaacgtggt | gtaaagttc | 540 |
| ggattcggcg | gcgctggatc | cttcaagcaa | ccccttttcg | acgatgaagg | cacaacttgc | 600 |
| attggcgttg | agacggcaga | tgtaccaaaa | tattacgctg | acaaggtggt | cttagcagct | 660 |
| ggcgcatgga | gcccaaccct | ggtggacctg | aagatcaatg | ttgctcgaa | ggcttgggtg | 720 |
| tatgctcata | ttcagttgac | gcctgaagag | gccgctgagt | ataagggtgt | cccagttgtg | 780 |
| tataatggcg | aatttggctt | cttctttgag | cctgatgagt | ttggtgtaat | aaaggtgtgc | 840 |
| gacgagttcc | caggattctc | gcgcttcaag | gaacatcaac | cctatggcgc | cccatctccg | 900 |
| aaacggatat | cagtaccacg | atcgcacgcc | aagcatccca | cagacactta | tccagacgca | 960 |
| tccgaagtca | gcatcaaaaa | agcaatcgcg | acgtttctcc | ctcgatttca | ggacaaggag | 1020 |
| ctcttcaatc | gcgccttgtg | ctggtgtaca | gacactgcgg | acgctgctct | cttgatgtgt | 1080 |
| gaacacccca | atggaagaa | tttcattcta | gcgaccggcg | acagcggaca | ctcattcaaa | 1140 |
| atcttgccta | acgtcggaaa | atacgtagtc | gagttgatag | agggccgcct | gccggaggaa | 1200 |
| atggcttatc | aatggaggtg | gcggccagga | ggcgatgcac | tcaagtctag | acgtgcggca | 1260 |
| ccgccaaaag | atcttgcaga | catgccagga | tggaaacatg | atccgaaatt | gtaa | 1314 |

<210> SEQ ID NO 173
<211> LENGTH: 437
<212> TYPE: PRT
<213> ORGANISM: Coniochaeta sp.

<400> SEQUENCE: 173

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

```
Arg Leu His Asp Ala Gly Ala Gly Leu Glu Lys Thr His Ala Trp Leu
            115                 120                 125
Asp Asn Glu Asp Glu Ile Leu Ser Lys Met Pro Leu Leu Gln Arg Asp
        130                 135                 140
Gln Ile Gln Gly Trp Lys Ala Ile Trp Ser Gln Asp Gly Trp Leu
145                 150                 155                 160
Ala Ala Ala Lys Ala Ile Asn Ala Ile Gly Gln Phe Leu Lys Glu Arg
                165                 170                 175
Gly Val Lys Phe Gly Phe Gly Ala Gly Ser Phe Lys Gln Pro Leu
            180                 185                 190
Phe Asp Asp Glu Gly Thr Thr Cys Ile Gly Val Glu Thr Ala Asp Gly
            195                 200                 205
Thr Lys Tyr Tyr Ala Asp Lys Val Val Leu Ala Ala Gly Ala Trp Ser
            210                 215                 220
Pro Thr Leu Val Asp Leu Glu Asp Gln Cys Cys Ser Lys Ala Trp Val
225                 230                 235                 240
Tyr Ala His Ile Gln Leu Thr Pro Glu Glu Ala Ala Glu Tyr Lys Gly
                245                 250                 255
Val Pro Val Val Tyr Asn Gly Glu Phe Gly Phe Phe Glu Pro Asp
            260                 265                 270
Glu Phe Gly Val Ile Lys Val Cys Asp Glu Phe Pro Gly Phe Ser Arg
            275                 280                 285
Phe Lys Glu His Gln Pro Tyr Gly Ala Pro Ser Pro Lys Arg Ile Ser
            290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Gln Asp Lys Glu Leu Phe Asn Arg Ala Leu Cys Trp Cys Thr Asp Thr
            340                 345                 350
Ala Asp Ala Ala Leu Leu Met Cys Glu His Pro Lys Trp Lys Asn Phe
            355                 360                 365
Ile Leu Ala Thr Gly Asp Ser Gly His Ser Phe Lys Ile Leu Pro Asn
            370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Asp Ala Leu Lys Ser
                405                 410                 415
Arg Arg Ala Ala Pro Pro Lys Asp Leu Ala Asp Met Pro Gly Trp Lys
            420                 425                 430
His Asp Pro Lys Leu
        435

<210> SEQ ID NO 174
<211> LENGTH: 1314
<212> TYPE: DNA
<213> ORGANISM: Coniochaeta sp.

<400> SEQUENCE: 174
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
```

```
gaggatgagt tattccagcc cttctttcac aataccggca gaatggactg cgaacacacg    300
cctgagggta tcgaggacct gaaaaagctg taccagcgtc tgcacgatgc cggtgcgggt    360
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtggg tgtaaagttc    540
ggattcggcg cgctggatc cttcaagcaa ccccttttcg acgatgaagg cacaacttgc    600
attggcgttg agacggcaga tggtaccaaa tattacgctg acaaggtggt cttagcagct    660
ggcgcatgga cccaaccct ggtggacctg gaagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa          1314
```

<210> SEQ ID NO 175
<211> LENGTH: 437
<212> TYPE: PRT
<213> ORGANISM: Coniochaeta sp.

<400> SEQUENCE: 175

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp Leu Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Lys Leu Lys Lys Leu Tyr Gln
                100                 105                 110

Arg Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190
```

```
Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Ala Ala Glu Tyr Lys Gly
                245                 250                 255

Val Pro Val Val Tyr Asn Gly Glu Phe Gly Phe Phe Glu Pro Asp
                260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 176
<211> LENGTH: 1314
<212> TYPE: DNA
<213> ORGANISM: Coniochaeta sp.

<400> SEQUENCE: 176
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagcgtc tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc     540 ggattcggcg cgctggatc cttcaagcaa cccttttcg acgatgaagg cacaacttgc     600
attggcgttg agacggcaga tggtaccaaa tattacgctg acaaggtggt cttagcagct     660
```

-continued

```
ggcgcatgga gcccaaccct ggtggacctg gaagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca aatggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 177
<211> LENGTH: 437
<212> TYPE: PRT
<213> ORGANISM: Coniochaeta sp.

<400> SEQUENCE: 177

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp Ala Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp

|   |   |   | 260 |   |   |   | 265 |   |   |   | 270 |   |   |
|---|---|---|---|---|---|---|---|---|---|---|---|---|---|

Glu Phe Gly Val Ile Lys Val Cys Asp Glu Phe Pro Gly Phe Ser Arg
                  275                  280                  285

Phe Lys Glu His Gln Pro Tyr Gly Ala Pro Ser Pro Lys Arg Ile Ser
    290                  295                  300

Val Pro Arg Ser His Ala Lys His Pro Thr Asp Thr Tyr Pro Asp Ala
305                  310                  315                  320

Ser Glu Val Ser Ile Lys Lys Ala Ile Ala Thr Phe Leu Pro Arg Phe
                  325                  330                  335

Gln Asp Lys Glu Leu Phe Asn Arg Ala Leu Cys Trp Cys Thr Asp Thr
    340                  345                  350

Ala Asp Ala Ala Leu Leu Met Cys Glu His Pro Lys Trp Lys Asn Phe
              355                  360                  365

Ile Leu Ala Thr Gly Asp Ser Gly His Ser Phe Lys Ile Leu Pro Asn
        370                  375                  380

Val Gly Lys Tyr Val Val Glu Leu Ile Glu Gly Arg Leu Pro Glu Glu
385                  390                  395                  400

Met Ala Tyr Gln Trp Arg Trp Arg Pro Gly Gly Asp Ala Leu Lys Ser
                  405                  410                  415

Arg Arg Ala Ala Pro Pro Lys Asp Leu Ala Asp Met Pro Gly Trp Lys
    420                  425                  430

His Asp Pro Lys Leu
        435

<210> SEQ ID NO 178
<211> LENGTH: 1314
<212> TYPE: DNA
<213> ORGANISM: Coniochaeta sp.

<400> SEQUENCE: 178

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatgcgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatgggga gtcaagatgg cggctggtta     480
gctgcggcaa aggccatcaa tgcgatcgga cagttcttga agaacgtggt gtaaagttc     540 ggattcggcg cgctggatc cttcaagcaa cccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta ccagacgca     960 tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
```

-continued

```
gaacacccca aatggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 179
<211> LENGTH: 437
<212> TYPE: PRT
<213> ORGANISM: Coniochaeta sp.

<400> SEQUENCE: 179

```
Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Glu Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335
```

```
Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 180
<211> LENGTH: 1314
<212> TYPE: DNA
<213> ORGANISM: Coniochaeta sp.

<400> SEQUENCE: 180
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatcatc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc      540 ggattcggcg cgctggatc cttcaagcaa cccctttcg acgatgaagg cacaacttgc       600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc aggattctc gcgcttcaag gaacatcaac cctatggcgc cccatctccg      900
aaacggatat cagtaccacg atcgcacgcc aagcatccca cagacactta ccagacgca     960 tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa         1314

<210> SEQ ID NO 181
<211> LENGTH: 437
<212> TYPE: PRT
<213> ORGANISM: Coniochaeta sp.
```

```
<400> SEQUENCE: 181

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp His Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Lys Gly Ile Glu Lys Leu Lys Lys Leu Tyr Gln
                100                 105                 110

Lys Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
                180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
                260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
                340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415
```

Arg Arg Ala Ala Pro Pro Lys Asp Leu Ala Asp Met Pro Gly Trp Lys
            420                 425                 430

His Asp Pro Lys Leu
        435

<210> SEQ ID NO 182
<211> LENGTH: 1314
<212> TYPE: DNA
<213> ORGANISM: Coniochaeta sp.

<400> SEQUENCE: 182

| | | |
|---|---|---|
| atgacgtcga atcgtgcaga tacaagggtg attgtcgtcg gtggcggagg aacgattggt | 60 |
| tcctcgacag cgctgcatct tgtgaggagt ggttatgctc ccgcaaatat cacggtcttg | 120 |
| gacacatttg agattccatc ggctcaatca gccggccatg atctcaacaa gatcatggga | 180 |
| atagatcatc gcaacaaggt ggacctgcaa atgagtctag aggctagaca gatgtggaag | 240 |
| gaggatgagt tattccagcc cttctttcac aataccggca gaatggactg cgaacacacg | 300 |
| cctaagggta tcgagaaact gaaaaagctg taccagaaac tgcacgatgc cggtgcgggt | 360 |
| ctggagaaga ctcatgcctg gttggacaac gaggatgaga tcttatccaa gatgccgttg | 420 |
| cttcaacgtg accaaataca aggatggaaa gcaatatgga gtcaagatgg cggctggtta | 480 |
| gctgcggcaa aggccatcaa tgcgatcgga cagttcttga agaacgtgg tgtaaagttc | 540 |
| ggattcggcg gcgctggatc cttcaagcaa cccctttcg acgatgaagg cacaacttgc | 600 |
| attggcgttg agacggcaga tggtaccaaa tattacgctg acaaggtggt cttagcagct | 660 |
| ggcgcatgga gcccaaccct ggtggacctg gaagatcaat gttgctcgaa ggcttgggtg | 720 |
| tatgctcata ttcagttgac gcctgaagag gccgctgagt ataagggtgt cccagttgtg | 780 |
| tataatggcg aatttggctt cttctttgag cctgatgagt ttggtgtaat aaaggtgtgc | 840 |
| gacgagttcc caggattctc gcgcttcaag gaacatcaac cctatggcgc cccatctccg | 900 |
| aaacggatat cagtaccacg atcgcacgcc aagcatccca cagacactta ccagacgca | 960 |
| tccgaagtca gcatcaaaaa agcaatcgcg acgtttctcc ctcgatttca ggacaaggag | 1020 |
| ctcttcaatc gcgccttgtg ctggtgtaca gacactgcgg acgctgctct cttgatgtgt | 1080 |
| gaacacccca atggaagaa tttcattcta gcgaccggcg acagcggaca ctcattcaaa | 1140 |
| atcttgccta acgtcggaaa atacgtagtc gagttgatag agggccgcct gccggaggaa | 1200 |
| atggcttatc aatggaggtg gcggccagga ggcgatgcac tcaagtctag acgtgcggca | 1260 |
| ccgccaaaag atcttgcaga catgccagga tggaaacatg atccgaaatt gtaa | 1314 |

<210> SEQ ID NO 183
<211> LENGTH: 437
<212> TYPE: PRT
<213> ORGANISM: Coniochaeta sp.

<400> SEQUENCE: 183

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
 65                  70                  75                  80

Glu Asp Glu Leu Phe Gln Pro Phe Phe His Asn Thr Gly Arg Met Asp
                 85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Lys Ala Pro Pro Lys Asp Leu Ala Asp Met Pro Gly Trp Lys
            420                 425                 430

His Asp Pro Lys Leu
        435

<210> SEQ ID NO 184
<211> LENGTH: 1314
<212> TYPE: DNA
<213> ORGANISM: Coniochaeta sp.

<400> SEQUENCE: 184

```
atgacgtcga atcgtgcaga tacaagggtg attgtcgtcg gtggcggagg aacgattggt    60
tcctcgacag cgctgcatct tgtgaggagt ggttatgctc ccgcaaatat cacggtcttg   120
gacacatttg agattccatc ggctcaatca gccggccatg atctcaacaa gatcatggga   180
atagatcatc gcaacaaggt ggacctgcaa atgagtctag aggctagaca gatgtggaag   240
gaggatgagt tattccagcc cttctttcac aataccggca gaatggactg cgaacacacg   300
cctgagggta tcgagaaact gaaaaagctg taccagaaac tgcacgatgc cggtgcgggt   360
ctggagaaga ctcatgcctg gttggacaac gaggatgaga tcttatccaa gatgccgttg   420
cttcaacgtg accaaataca aggatggaaa gcaatatgga gtcaagatgg cggctggtta   480
gctgcggcaa aggccatcaa tgcgatcgga cagttcttga agaacgtgg tgtaaagttc    540
ggattcggcg cgctggatc cttcaagcaa ccccttttcg acgatgaagg cacaacttgc   600
attggcgttg agacggcaga tggtaccaaa tattacgctg acaaggtggt cttagcagct   660
ggcgcatgga gcccaaccct ggtggacctg aagatcaat gttgctcgaa ggcttgggtg    720
tatgctcata ttcagttgac gcctgaagag gccgctgagt ataagggtgt cccagttgtg   780
tataatggcg aatttggctt cttctttgag cctgatgagt ttggtgtaat aaaggtgtgc   840
gacgagttcc aggattctc gcgcttcaag gaacatcaac cctatggcgc cccatctccg    900
aaacggatat cagtaccacg atcgcacgcc aagcatccca cagacactta tccagacgca   960
tccgaagtca gcatcaaaaa agcaatcgcg acgtttctcc ctcgatttca ggacaaggag  1020
ctcttcaatc gcgccttgtg ctggtgtaca gacactgcgg acgctgctct cttgatgtgt  1080
gaacacccca atggaagaa tttcattcta gcgaccggcg acagcggaca ctcattcaaa   1140
atcttgccta acgtcggaaa atacgtagtc gagttgatag agggccgcct gccggaggaa  1200
atggcttatc aatggaggtg gcggccagga ggcgatgcac tcaagtctag acgtaaggca  1260
ccgccaaaag atcttgcaga catgccagga tggaaacatg atccgaaatt gtaa        1314
```

<210> SEQ ID NO 185
<211> LENGTH: 438
<212> TYPE: PRT
<213> ORGANISM: Aspergillus nidulans

<400> SEQUENCE: 185

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Asp His Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Lys Gly Ile Glu Lys Leu Arg Lys Leu Tyr Gln Lys
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Lys Glu Gln Gly
                165                 170                 175

Val Lys Phe Gly Phe Gly Gly Ala Gly Thr Phe Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Phe Glu Pro Asn
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Ala Pro Lys Pro Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ser Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 186
<211> LENGTH: 1317
<212> TYPE: DNA
<213> ORGANISM: Aspergillus nidulans

<400> SEQUENCE: 186
atgacgcccc gagccaacac caaaatcatt gtcgtcggcg gcggcggcac aatgggctcg    60
tcgacagccc tacacctcct gcgcgccggc tacacgccgt ccaacattac agtgctcgac   120
acgtgcccta tccctccgc acagtctgca ggctacgacc tgaacaaaat catgggcatc   180
gatcatcgca acaagcctga tttacagctc tctcttgagg cgctggacat gtggaaaaat   240
gatcctctct tcaagccgtt tttccacaat gttggaatga tcgacgtctc ttcaacagag   300
aaaggcatcg agaacttcg gaagctgtac cagaaacttc tcgacgcagg cattgggctc   360
gagaagacga atttcatgct ggaaagtgaa gacgagatcc tggctaaagc gccgcatttc   420

```
acgcaggagc agattaaagg ctggaaaggc ctgttctgtg gcgacggcgg ctggctcgct    480
gcagccaaag ccatcaatgc cattgggcag ttcctcaagg aacagggcgt caagtttgga    540
ttcggcggcg ccggcacgtt caaaaagcca ctcttcgccg atgcccacga agacgtgc     600 atcggcgtcg agactgtaga cggcacaaag tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt ataagaacac tcctgttata    780
tacgacggtg actatgggtt tttctttgag ccgaatgaaa acggcatcat aaaagtctgt    840
gacgaattcc ctggcttcac gcatttcaaa atgcaccagc cgtacggctc gccggcgccc    900
aaacccatct ctgtgcctcg ttcccatgcg aagcacccca cagatacata cccgcacgcg    960
tcggaggtca cgatcaaaaa ggctatcaac cggttcctgc cgaggttcaa tgacaaggaa   1020
ctgtttaaca gggccatgtg ctggtgcacc gataccgcgg atagcaatct gcttgtttgt   1080
gagcatccac gctggaaggg gttttatctt gcaacagggg acagtgggca ttcgttcaag   1140
ttgctgccga atattggaaa gcatgttgtc gagttattgg aggagaggct ggaaagtgtg   1200
tttaaggatg cttggaggtg gaggcctggc agtggggatg cattaaaaag tagacgggct   1260
gcgcctgcga aggacctggc ggatatgccg gggtggagga atgaggcaaa gatgtag      1317
```

<210> SEQ ID NO 187
<211> LENGTH: 437
<212> TYPE: PRT
<213> ORGANISM: Phaeosphaeria nodorum

<400> SEQUENCE: 187

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Asp His Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Lys Leu Lys Ser Leu Tyr Gln
            100                 105                 110

Lys Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
```

```
            210                 215                 220
Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
                260                 265                 270

Ile Lys Val Cys Asp Glu Phe Pro Gly Phe Thr Arg Phe Lys Met His
            275                 280                 285

Gln Pro Phe Gly Ala Lys Ala Pro Lys Arg Ile Ser Val Pro Arg Ser
290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ser Ala
                340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
        370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
                420                 425                 430

Pro Arg Ala Asn Leu
            435

<210> SEQ ID NO 188
<211> LENGTH: 1314
<212> TYPE: DNA
<213> ORGANISM: Phaeosphaeria nodorum

<400> SEQUENCE: 188
atggccccgt cgcgtgctaa tacgtcggtc attgtggttg gtggtggtgg tacgattggc    60
tcatctacgg ctctgcatct ggtccgctca ggctataccc cgtcgaacgt gacggttctg   120
gatgcatacc cgattccgag ctctcagagc gctggcaacg acctgaataa atcatgggt    180 gtcgatcatc gtaatccggt ggatctgcag ctggctctgg aagcgcgcca aatgtggaac   240
gaagacgaac tgttcaagaa gttttttccat aacaccggcc gtctggattg cgcgcacggt   300
gaaaaagata ttgccaaact gaagagcctg tatcagaaac tggtggatgc gggtctggac   360
gccacgaacg aatggctgga tagtgaagac gaaatcctga acgtatgcc gctgctgtcc    420 cgcgatcaaa ttaaggctg gaaggcgatc ttttcaaaag acggtggttg gctggcagca   480
gcaaaggcaa ttaatgcagt tggtgaatat ctgcgtgatc agggcgtccg cttcggtttt   540
tacggcgccg ttctttcaa agcaccgctg ctggctgaag cgtctgcat cggtgtcgaa    600 accgtggatg gcacgcgcta ttacgcagac aaagtggttc tggctgcagg tgcatggtcg   660
ccgaccctgg ttgaactgca tgaacagtgt gtgagcaaag cgtgggttta cggccacatt   720
caactgacgc cggaagaagc cgcacgttat aagaacagcc cggtcgtgta caatggcgat   780
gtgggctttt tctttgaacc gaacgaacat ggcgttatca agtctgcga tgaatttccg    840
```

```
ggttttaccc gcttcaagat gcaccagccg tttggtgcca aagcaccgaa gcgtattagt    900
gtgccgcgct cccatgccaa acacccgacc gatacgatcc cggatgcaag tgacgtttcc    960
attcgtcgcg ctatcgcgac ctttatgccg cagttcaaga acaaaaagat gttcaaccaa   1020
gcgatgtgct ggtgtaccga tacgccgac agcgcgctgc tgatttgtga acatccggaa    1080
tggaaaaact tgttctggc gaccggcgat tcaggtcatt cgttcaaact gctgccgaat    1140
atcggcaagc acgttgtcga actgctggag ggtacgctgg cagatgacct ggcacacgca   1200
tggcgttggc gtccgggtag tggtgatgca ctgaaaagcc gtcgctctgc tccggcgaaa   1260
gacctggctg atatgccggg ctggaaccat gacaaaccgc gtgctaatct gtaa         1314
```

<210> SEQ ID NO 189
<211> LENGTH: 443
<212> TYPE: PRT
<213> ORGANISM: Cryptococcus neoformans

<400> SEQUENCE: 189

```
Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Asp Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Lys Leu Arg Lys Leu Tyr Glu
            100                 105                 110

Lys Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285
```

```
Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
                340                 345                 350

Ala Asp Ala Asn Leu Leu Ile Cys Glu His Pro Lys Trp Lys Asn Phe
                355                 360                 365

Ile Leu Ala Thr Gly Asp Ser Gly His Ser Phe Lys Ile Leu Pro Asn
370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
                420                 425                 430

Asn His Asp Glu Pro Ser Asp Asp Asp Met Asp
                435                 440
```

```
<210> SEQ ID NO 190
<211> LENGTH: 1332
<212> TYPE: DNA
<213> ORGANISM: Cryptococcus neoformans

<400> SEQUENCE: 190
atgccgccgt cccgtgcttc aacgaaagtg attgtcattg gtggtggtgg tacgctgggc      60
tcctcaaccg ccctgcatct gctgcgcgcg ggctataccc cgagtaacat accgtgctg     120 gatacgtacc tgatcccgag tgcccagtcc gcaggcaacg acctgaataa aattatgggt     180
attgatatcc gcaatccggt ggataaacaa ctgagcctgg aagcccgtga tatgtggcgc     240
aacgacgaag ttttcaaacc gtacttccat aacaccggtc gtctggactg cgctcacacg     300
ccggaatcaa ttgcgaaact gcgtaaactg tacgaaaaaa tcctgaaagc aggctcaggt     360
ctggaaaaaa cccatcactg gctgtcgacg aagatgaaa tcctggcacg tgcaccgctg     420
ctggaccgta acagattaa aggttggaaa gcaatctata gtgaagatgg cggttggctg     480
gcggccgcaa aagctattaa ctccatcggc caagtcctga agaaaaaagg tgtgaccttc     540
ggctttggta gcgcaggctc ttttaaaaaa ccgctgttcg atgaagacgg cacgaaagcc     600
attggtatcg aaaccgttga tggtacgcag tattttgccg acaaagtggt tctggctgca     660
ggtgcatgga gcccgaccct ggttgatctg gaaggccagt gctgttctaa gcttgggtc     720 tacgcgcaca tgcaactgac gccggaagaa gccgcagaat ataagaatg cccggtcgtg     780 tacaacagcg aactgggctt tttctttgaa ccgaacgaaa aggtgtgat caaagtttgt     840 gatgaattcc cgggctttac ccgtttcaaa cagcatcaac cgtacggtgc tagctctacg     900
aaacacatta gctttccgcg ctctcatgcg aaacacccga ccgatacgat cccggatgaa     960
agtgacgcct ccattcgtcg cgctatctct gcgtttctgc cgcgtttcaa agaaaaagaa    1020
ctgtttaacc gcgcgctgtg ctggtgtacc gatacggctg acgcgaacct gctgatttgt    1080
gaacacccga atggaaaaa ttttatcctg gccaccggcg attcaggtca ttcgttcaaa    1140
attctgccga atatcggcaa acacgttgtc gaactgattg aaggtaccct ggccgaagat    1200
ctggcagaaa gctggcgttg gcgtccgggc agtggtgacc cgctgatctc cgtcgcgct    1260
```

```
gcgccggcgc gcgacctggc ggacctgccg ggctggaacc acgacgaacc gagcgacgat   1320
gacatggact ga                                                       1332
```

<210> SEQ ID NO 191
<211> LENGTH: 440
<212> TYPE: PRT
<213> ORGANISM: Curvularia clavata

<400> SEQUENCE: 191

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Ala Tyr Pro Ile Pro Ser Ser
            35                  40                  45

Gln Ser Ala Gly Asn Asp Leu Asn Lys Ile Met Gly Ile Asp His Arg
50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Lys Leu Arg Gln Leu Tyr Gln
            100                 105                 110

Lys Leu Leu Asp Ala Asn Ala Gly Leu Glu Glu Thr Thr Glu Trp Leu
            115                 120                 125

Asp Ser Glu Asp Glu Ile Leu Lys Lys Met Pro Leu Leu Ser Arg Asp
130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
            195                 200                 205

Tyr Tyr Ala Asp Lys Val Val Leu Ala Ala Gly Ala Trp Ser Pro Thr
210                 215                 220

Leu Val Glu Leu His Glu Gln Cys Val Ser Lys Ala Trp Val Tyr Gly
225                 230                 235                 240

His Ile Gln Leu Thr Pro Glu Glu Ala Ala Glu Tyr Lys Asn Ser Pro
                245                 250                 255

Val Val Tyr Asn Gly Asp Val Gly Phe Phe Phe Glu Pro Asn Glu His
            260                 265                 270

Gly Val Ile Lys Val Cys Asp Glu Phe Pro Gly Phe Thr Arg Phe Lys
            275                 280                 285

Met His Gln Pro Phe Gly Ala Lys Ala Pro Lys Arg Ile Ser Val Pro
290                 295                 300

Arg Ser His Ala Lys His Pro Thr Asp Thr Ile Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Thr Ala Asp
            340                 345                 350
```

Ser Ala Leu Leu Ile Cys Glu His Pro Glu Trp Lys Asn Phe Val Leu
            355                 360                 365

Ala Thr Gly Asp Ser Gly His Ser Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Ser Gly Asp Ala Leu Lys Ser Arg
                405                 410                 415

Arg Ser Ala Pro Ala Lys Asp Leu Ala Asp Met Pro Gly Trp Lys His
            420                 425                 430

Asp Asp Val Val Lys Ser Lys Leu
            435                 440

<210> SEQ ID NO 192
<211> LENGTH: 1323
<212> TYPE: DNA
<213> ORGANISM: Curvularia clavata

<400> SEQUENCE: 192
atggccccgt cgcgtgctaa tacgtcggtc attgtggttg gtggtggtgg tacgattggc    60
tcatctacgg ctctgcatct ggtccgctca ggctataccc cgtcgaacat tacggttctg   120
gatgcatacc cgattccgag ctctcagagc gctggcaacg acctgaataa aatcatgggt   180
atcgatcatc gtaataaggt ggatctgcag ctgtctctgg aagcgcgcca aatgtggcgc   240
gaagacgatc tgttcaagga gtatttccat aacaccggcc gtctggattg cgcgcacggt   300
gaagaaggtc ttgccaaact gcgtcaactg tatcagaaac tgctggatgc gaatgcgggt   360
ctggaagaga cgaccgaatg gctggatagt gaagacgaaa tcctgaaaaa aatgccgctg   420
ctgtcccgcg atcaaattaa aggctggaag gcggtgtatt cacaggacgg tggttggctg   480
gcagcagcaa aggcaattaa tgcaattggt gaatatctgc gtgctcaggg cgtcaaattc   540
ggttttggcg cgccggttc tttcaaacaa ccgctgctgg ctgaaggcgt ctgcatcggt   600
gtcgaaaccg tggatggcac gcgctattac gcagacaaag tggttctggc tgcaggtgca   660
tggtcgccga ccctggttga actgcatgaa cagtgtgtga gcaaagcgtg ggtttacggc   720
cacattcaac tgacgccgga agaagccgca gaatataaga cagcccggt cgtgtacaat   780
ggcgatgtgg gcttttttctt tgaaccgaac gaacatggcg ttatcaaagt ctgcgatgaa   840
tttccgggtt ttacccgctt caagatgcac cagccgtttg gtgccaaagc accgaagcgt   900
attagtgtgc cgcgctccca tgccaaacac ccgaccgata cgatcccgga tgcaagtgaa   960
aaatccattc gtaaagctat cgcgcacctttt ctgccgaagt tcacggagaa agagctgttc  1020
aaccgtcatc tgtgctggtg taccgatacg gccgacagcg cgctgctgat ttgtgaacat  1080
ccggaatgga aaactttgt tctggcgacc ggcgattcag gtcattcgtt caaactgctg  1140
ccgaatatcg gcaagcacgt tgtcgaactg ctggagggta cgctggcaga tgacctggca  1200
cacgcatggc gttggcgtcc gggtagtggt gatgcactga aaagccgtcg ctctgctccg  1260
gcgaaagacc tggctgatat gccgggctgg aaacatgacg atgtggtgaa aagcaaactg  1320
taa                                                                1323

<210> SEQ ID NO 193
<211> LENGTH: 28
<212> TYPE: DNA
<213> ORGANISM: Artificial
<220> FEATURE:
<223> OTHER INFORMATION: primer

```
<400> SEQUENCE: 193
caccttgttg cgatgatcta ttcccatg                                              28

<210> SEQ ID NO 194
<211> LENGTH: 28
<212> TYPE: DNA
<213> ORGANISM: Artificial
<220> FEATURE:
<223> OTHER INFORMATION: primer

<400> SEQUENCE: 194
cgcaacaagg tgaacctgca aatgagtc                                              28

<210> SEQ ID NO 195
<211> LENGTH: 28
<212> TYPE: DNA
<213> ORGANISM: Artificial
<220> FEATURE:
<223> OTHER INFORMATION: primer

<400> SEQUENCE: 195
agagtccgca gtgtctgtac accagcac                                              28

<210> SEQ ID NO 196
<211> LENGTH: 30
<212> TYPE: DNA
<213> ORGANISM: Artificial
<220> FEATURE:
<223> OTHER INFORMATION: primer

<400> SEQUENCE: 196
acactgcgga ctctactctc ttgatgtgtg                                            30

<210> SEQ ID NO 197
<211> LENGTH: 10
<212> TYPE: DNA
<213> ORGANISM: Artificial
<220> FEATURE:
<223> OTHER INFORMATION: primer

<400> SEQUENCE: 197
aaaaaaaaaa                                                                  10

<210> SEQ ID NO 198
<211> LENGTH: 10
<212> TYPE: DNA
<213> ORGANISM: Artificial
<220> FEATURE:
<223> OTHER INFORMATION: primer

<400> SEQUENCE: 198
cccccccccc                                                                  10

<210> SEQ ID NO 199
<211> LENGTH: 434
<212> TYPE: PRT
<213> ORGANISM: Coniochaeta sp. NISL 9330

<400> SEQUENCE: 199

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30
```

Ala Pro Ala Asn Ile Thr Val Leu Asp Thr Phe Pro Ile Pro Ser Ala
                35                  40                  45

Gln Ser Ala Gly His Asp Leu Asn Lys Ile Met Gly Ile Asp His Arg
 50                  55                  60

Asn Lys Val Asn Leu Gln Met Ser Leu Glu Ala Arg Gln Met Trp Lys
 65                  70                  75                  80

Glu Asp Glu Leu Phe Gln Pro Phe His Asn Thr Gly Arg Met Asp
                 85                  90                  95

Cys Glu His Thr Pro Lys Gly Ile Glu Lys Leu Lys Lys Leu Tyr Gln
                100                 105                 110

Lys Leu His Asp Ala Gly Ala Gly Leu Glu Lys Thr His Ala Trp Leu
                115                 120                 125

Asp Asn Glu Asp Ala Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
                180                 185                 190

Phe Asp Asp Glu Gly Thr Thr Cys Ile Gly Val Glu Thr Ala Asp Gly
                195                 200                 205

Thr Lys Tyr Tyr Ala Asp Lys Val Val Leu Ala Ala Gly Ala Trp Ser
                210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Lys Tyr Lys Gly
                245                 250                 255

Cys Pro Val Val Tyr His Gly Glu Phe Gly Phe Phe Glu Pro Asp
                260                 265                 270

Glu Phe Gly Val Ile Lys Val Cys Asp Glu Phe Pro Gly Phe Ser Arg
                275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Lys Asp Lys Pro Leu Phe Asn Arg Ala Leu Cys Trp Cys Thr Asp Thr
                340                 345                 350

Ala Asp Ser Ala Leu Leu Met Cys Glu His Pro Lys Trp Lys Asn Phe
                355                 360                 365

Ile Leu Ala Thr Gly Asp Ser Gly His Ser Phe Lys Ile Leu Pro Asn
                370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp

<210> SEQ ID NO 200

<211> LENGTH: 1305
<212> TYPE: DNA
<213> ORGANISM: Coniochaeta sp. NISL 9330

<400> SEQUENCE: 200

```
atgacctcaa accgtgctga tacccgtgtt attgttgttg gtggtggtgg tacgattggc      60
tcctcgaccg ctctgcatct ggtgcgtagt ggctatgctc cggcgaacat taccgtcctg     120
gatacgtttc cgatcccgag cgcccagtct gcaggccatg atctgaataa aattatgggt     180
atcgaccacc gtaacaaagt taatctgcag atgagcctgg aagcgcgcca aatgtggaaa     240
gaagatgaac tgttccagcc gttttttccat aacaccggcc gtatggactg cgaacacacg    300
ccgaaaggta tcgaaaaact gaaaaaactg taccaaaaac tgcatgatgc cggcgcaggt     360
ctggaaaaaa cccacgcctg gctgataaac gaagacgcaa ttctgagcaa aatgccgctg     420
ctgcagcgtg atcagattca aggttggaaa gccatctggt ctcaagacgg cggttggctg     480
gcagcagcaa aagctattaa tgcgatcggc cagtttctga agaacgcgg cgtgaaattc      540
ggttttggcg gtgcaggttc ttttaaacaa ccgctgttcg atgacgaagg caccacgtgt     600
atcggtgttg aaaccgctga tggcacgaaa tattacgcgg acaaagtggt tctggctgca     660
ggtgcatgga gtccgaccct ggtcgatctg aagaccagt gctgttccaa agcgtgggtg      720
tatgcgcata ttcaactgac gccggaagaa gccgcaaaat ataaaggctg cccggtcgtg     780
taccacggcg aatttggctt tttctttgaa ccggatgaat ttggcgtgat caaagtttgt     840
gacgaatttc cgggttttttc acgtttcaaa gaacatcagc cgtatggtgc gccgtcgccg    900
aaacgtatta gcgttccgcg ctctcatgcc aaacacccga ccgatacgta cccggacgca     960
agtgaagtct ccattaagaa agcgatcgcg acctttctgc gcgtttcaa agataaaccg     1020
ctgtttaatc gcgcactgtg ctggtgtacc gatacggccg acagcgcact gctgatgtgc    1080
gaacatccga aatggaaaaa ctttattctg gcgaccggcg attcaggtca ctcgttcaaa    1140
atcctgccga atgtgggcaa atatgttgtc gaactgattg aaggtcgcct gccggaagaa    1200
atggcttacc agtggcgttg gcgtccgggc ggtgatgccc tgaaaagtcg ccgtgctgct    1260
ccgccgaaag acctggctga tatgccgggc tggaaacatg actaa                    1305
```

<210> SEQ ID NO 201
<211> LENGTH: 30
<212> TYPE: DNA
<213> ORGANISM: Artificial
<220> FEATURE:
<223> OTHER INFORMATION: primer

<400> SEQUENCE: 201

```
gctgtcggcc gtatcggtac accagcacag                                       30
```

<210> SEQ ID NO 202
<211> LENGTH: 30
<212> TYPE: DNA
<213> ORGANISM: Artificial
<220> FEATURE:
<223> OTHER INFORMATION: primer

<400> SEQUENCE: 202

```
atacggccga cagcacactg ctgatgtgcg                                       30
```

<210> SEQ ID NO 203
<211> LENGTH: 434
<212> TYPE: PRT
<213> ORGANISM: Coniochaeta sp.

<400> SEQUENCE: 203

```
Met Thr Ser Asn Arg Ala Asp Thr Arg Val Ile Val Val Gly Gly Gly
 1               5                  10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Pro Ile Pro Ser Ala
        35                  40                  45

Gln Ser Ala Gly His Asp Leu Asn Lys Ile Met Gly Ile Asp His Arg
50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Ala Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Lys Tyr Lys Gly
                245                 250                 255

Cys Pro Val Val Tyr His Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
```

```
                    405                 410                 415
Arg Arg Ala Ala Pro Pro Lys Asp Leu Ala Asp Met Pro Gly Trp Lys
                420                 425                 430
His Asp
```

<210> SEQ ID NO 204
<211> LENGTH: 1305
<212> TYPE: DNA
<213> ORGANISM: Coniochaeta sp.

<400> SEQUENCE: 204

| | | | | |
|---|---|---|---|---|
| atgacctcaa accgtgctga tacccgtgtt attgttgttg gtggtggtgg tacgattggc | 60 |
| tcctcgaccg ctctgcatct ggtgcgtagt ggctatgctc cggcgaacat taccgtcctg | 120 |
| gatacgtttc cgatcccgag cgcccagtct gcaggccatg atctgaataa aattatgggt | 180 |
| atcgaccacc gtaacaaagt taatctgcag atgagcctgg aagcgcgcca aatgtggaaa | 240 |
| gaagatgaac tgttccagcc gttttttccat aacaccggcc gtatggactg cgaacacacg | 300 |
| ccgaaaggta tcgaaaaact gaaaaaactg taccaaaaac tgcatgatgc cggcgcaggt | 360 |
| ctggaaaaaa cccacgcctg gctggataac gaagacgcaa ttctgagcaa aatgccgctg | 420 |
| ctgcagcgtg atcagattca aggttggaaa gccatctggt ctcaagacgg cggttggctg | 480 |
| gcagcagcaa aagctattaa tgcgatcggc cagtttctga agaacgcgg cgtgaaattc | 540 |
| ggttttggcg gtgcaggttc ttttaaacaa ccgctgttcg atgacgaagg caccacgtgt | 600 |
| atcggtgttg aaaccgctga tggcacgaaa tattacgcgg acaaagtggt tctggctgca | 660 |
| ggtgcatgga gtccgaccct ggtcgatctg aagaccagt gctgttccaa agcgtgggtg | 720 |
| tatgcgcata ttcaactgac gccggaagaa ccgcaaaat ataaaggctg cccggtcgtg | 780 |
| taccacggcg aatttggctt tttctttgaa ccggatgaat ttggcgtgat caaagtttgt | 840 |
| gacgaatttc cgggtttttc acgtttcaaa gaacatcagc cgtatggtgc cgtcgccg | 900 |
| aaacgtatta gcgttccgcg ctctcatgcc aaacacccga ccgatacgta cccggacgca | 960 |
| agtgaagtct ccattaagaa agcgatcgcg acctttctgc gcgttttcaa agataaaccg | 1020 |
| ctgtttaatc gcgcactgtg ctggtgtacc gatacggccg acagcacact gctgatgtgc | 1080 |
| gaacatccga aatggaaaaa ctttattctg gcgaccggcg attcaggtca ctcgttcaaa | 1140 |
| atcctgccga atgtgggcaa atatgttgtc gaactgattg aaggtcgcct gccggaagaa | 1200 |
| atggcttacc agtggcgttg gcgtccgggc ggtgatgccc tgaaaagtcg ccgtgctgct | 1260 |
| ccgccgaaag acctggctga tatgccgggc tggaaacatg actaa | 1305 |

<210> SEQ ID NO 205
<211> LENGTH: 27
<212> TYPE: DNA
<213> ORGANISM: Artificial
<220> FEATURE:
<223> OTHER INFORMATION: primer

<400> SEQUENCE: 205
atgatctatt cccatgatct tgttgag    27

<210> SEQ ID NO 206
<211> LENGTH: 30
<212> TYPE: DNA
<213> ORGANISM: Artificial
<220> FEATURE:
<223> OTHER INFORMATION: primer -continued

<400> SEQUENCE: 206
tgggaataga tcatggcaac aaggtgaacc　　　　　　　　　　　　　　　　30

<210> SEQ ID NO 207
<211> LENGTH: 30
<212> TYPE: DNA
<213> ORGANISM: Artificial
<220> FEATURE:
<223> OTHER INFORMATION: primer

<400> SEQUENCE: 207
gtggtcgata cccataattt tattcagatc　　　　　　　　　　　　　　　　30

<210> SEQ ID NO 208
<211> LENGTH: 30
<212> TYPE: DNA
<213> ORGANISM: Artificial
<220> FEATURE:
<223> OTHER INFORMATION: primer

<400> SEQUENCE: 208
tgggtatcga ccacggtaac aaagttaatc　　　　　　　　　　　　　　　　30

<210> SEQ ID NO 209
<211> LENGTH: 437
<212> TYPE: PRT
<213> ORGANISM: Coniochaeta sp.

<400> SEQUENCE: 209

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val

```
              225                 230                 235                 240
Tyr Ala His Ile Gln Leu Thr Pro Glu Glu Ala Glu Tyr Lys Gly
                245                 250                 255
Val Pro Val Tyr Asn Gly Glu Phe Gly Phe Phe Glu Pro Asp
            260                 265                 270
Glu Phe Gly Val Ile Lys Val Cys Asp Glu Phe Pro Gly Phe Ser Arg
            275                 280                 285
Phe Lys Glu His Gln Pro Tyr Gly Ala Pro Ser Pro Lys Arg Ile Ser
        290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Gln Asp Lys Glu Leu Phe Asn Arg Ala Leu Cys Trp Cys Thr Asp Thr
                340                 345                 350
Ala Asp Ser Thr Leu Leu Met Cys Glu His Pro Lys Trp Lys Asn Phe
                355                 360                 365
Ile Leu Ala Thr Gly Asp Ser Gly His Ser Phe Lys Ile Leu Pro Asn
        370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
                405                 410                 415
Arg Arg Ala Ala Pro Pro Lys Asp Leu Ala Asp Met Pro Gly Trp Lys
                420                 425                 430
His Asp Pro Lys Leu
        435

<210> SEQ ID NO 210
<211> LENGTH: 1314
<212> TYPE: DNA
<213> ORGANISM: Coniochaeta sp.

<400> SEQUENCE: 210
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatcatc gcaacaaggt gaacctgcaa atgagtctag aggctagaca gatgtggaag     240
gaggatgagt tattccagcc cttctttcac aataccggca gaatggactg cgaacacacg     300
cctaagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc     540 ggattcggcg cgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc ccatctccg     900
```

```
aaacggatat cagtaccacg atcgcacgcc aagcatccca cagacactta tccagacgca      960
tccgaagtca gcatcaaaaa agcaatcgcg acgtttctcc ctcgatttca ggacaaggag     1020
ctcttcaatc gcgccttgtg ctggtgtaca gacactgcgg actctactct cttgatgtgt     1080
gaacacccca aatggaagaa tttcattcta gcgaccggcg acagcggaca ctcattcaaa     1140
atcttgccta acgtcggaaa atacgtagtc gagttgatag agggccgcct gccggaggaa     1200
atggcttatc aatggaggtg gcggccagga ggcgatgcac tcaagtctag acgtgcggca     1260
ccgccaaaag atcttgcaga catgccagga tggaaacatg atccgaaatt gtaa           1314
```

<210> SEQ ID NO 211
<211> LENGTH: 437
<212> TYPE: PRT
<213> ORGANISM: Coniochaeta sp.

<400> SEQUENCE: 211

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300
```

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
            325                 330                 335

Gln Asp Lys Glu Leu Phe Asn Arg Ala Leu Cys Trp Cys Thr Asp Thr
        340                 345                 350

Ala Asp Ser Thr Leu Leu Met Cys Glu His Pro Lys Trp Lys Asn Phe
    355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
        420                 425                 430

His Asp Pro Lys Leu
        435

<210> SEQ ID NO 212
<211> LENGTH: 1314
<212> TYPE: DNA
<213> ORGANISM: Coniochaeta sp.

<400> SEQUENCE: 212

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatcatg gcaacaaggt gaacctgcaa atgagtctag aggctagaca gatgtggaag     240
gaggatgagt tattccagcc cttctttcac aataccggca gaatggactg cgaacacacg     300
cctaagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc     540
ggattcggcg cgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccgacgca     960
tccgaagtca gcatcaaaaa agcaatcgcg acgtttctcc ctcgatttca ggacaaggag    1020
ctcttcaatc gcgccttgtg ctggtgtaca gacactgcgg actctactct cttgatgtgt    1080
gaacaccca aatggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 213
<211> LENGTH: 434
<212> TYPE: PRT
<213> ORGANISM: Coniochaeta sp.

<400> SEQUENCE: 213

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Pro Ile Pro Ser Ala
            35                  40                  45

Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
            115                 120                 125

Asp Asn Glu Asp Ala Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Lys Tyr Lys Gly
                245                 250                 255

Cys Pro Val Val Tyr His Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
            290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
            370                 375                 380

```
Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp
```

<210> SEQ ID NO 214
<211> LENGTH: 1305
<212> TYPE: DNA
<213> ORGANISM: Coniochaeta sp.

<400> SEQUENCE: 214

```
atgacctcaa accgtgctga tacccgtgtt attgttgttg gtggtggtgg tacgattggc      60
tcctcgaccg ctctgcatct ggtgcgtagt ggctatgctc cggcgaacat taccgtcctg     120
gatacgtttc cgatcccgag cgcccagtct gcaggccatg atctgaataa aatttatggg     180
atcgaccacg gtaacaaagt taatctgcag atgagcctgg aagcgcgcca aatgtggaaa     240
gaagatgaac tgttccagcc gttttttccat aacaccggcc gtatggactg cgaacacacg    300
ccgaaaggta tcgaaaaact gaaaaaactg taccaaaaac tgcatgatgc cggcgcaggt     360
ctggaaaaaa cccacgcctg gctggataac gaagacgcaa ttctgagcaa aatgccgctg     420
ctgcagcgtg atcagattca aggttggaaa gccatctggt ctcaagacgg cggttggctg     480
gcagcagcaa aagctattaa tgcgatcggc cagtttctga agaacgcgg cgtgaaattc      540
ggttttggcg gtgcaggttc ttttaaacaa ccgctgttcg atgacgaagg caccacgtgt     600
atcggtgttg aaaccgctga tgcacgaaa tattacgcgg acaaagtggt tctggctgca     660
ggtgcatgga gtccgaccct ggtcgatctg aagaccagt gctgttccaa agcgtgggtg     720
tatgcgcata ttcaactgac gccggaagaa gccgcaaaat ataaaggctg cccggtcgtg    780
taccacggcg aatttggctt tttctttgaa ccggatgaat ttggcgtgat caaagtttgt    840
gacgaatttc cggttttttc acgtttcaaa gaacatcagc cgtatggtgc gccgtcgccg    900
aaacgtatta gcgttccgcg ctctcatgcc aaacacccga ccgatacgta cccggacgca    960
agtgaagtct ccattaagaa agcgatcgcg acctttctgc gcgtttcaa agataaaccg    1020
ctgtttaatc gcgcactgtg ctggtgtacc gatacggccg acagcacact gctgatgtgc   1080
gaacatccga atggaaaaaa ctttattctg cgcgaccggcg attcaggtca ctcgttcaaa  1140
atcctgccga atgtgggcaa atatgttgtc gaactgattg aaggtcgcct gccggaagaa   1200
atggcttacc agtggcgttg gcgtccgggc ggtgatgccc tgaaaagtcg ccgtgctgct   1260
ccgccgaaag acctggctga tatgccgggc tggaaacatg actaa                  1305
```

<210> SEQ ID NO 215
<211> LENGTH: 30
<212> TYPE: DNA
<213> ORGANISM: Artificial
<220> FEATURE:
<223> OTHER INFORMATION: primer

<400> SEQUENCE: 215
tgggaataga tcatgccaac aaggtgaacc      30

<210> SEQ ID NO 216
<211> LENGTH: 30

```
<212> TYPE: DNA
<213> ORGANISM: Artificial
<220> FEATURE:
<223> OTHER INFORMATION: primer

<400> SEQUENCE: 216
tgggaataga tcatgtcaac aaggtgaacc                              30

<210> SEQ ID NO 217
<211> LENGTH: 30
<212> TYPE: DNA
<213> ORGANISM: Artificial
<220> FEATURE:
<223> OTHER INFORMATION: primer

<400> SEQUENCE: 217
tgggaataga tcatatcaac aaggtgaacc                              30

<210> SEQ ID NO 218
<211> LENGTH: 30
<212> TYPE: DNA
<213> ORGANISM: Artificial
<220> FEATURE:
<223> OTHER INFORMATION: primer

<400> SEQUENCE: 218
tgggaataga tcatctgaac aaggtgaacc                              30

<210> SEQ ID NO 219
<211> LENGTH: 30
<212> TYPE: DNA
<213> ORGANISM: Artificial
<220> FEATURE:
<223> OTHER INFORMATION: primer

<400> SEQUENCE: 219
tgggaataga tcatatgaac aaggtgaacc                              30

<210> SEQ ID NO 220
<211> LENGTH: 30
<212> TYPE: DNA
<213> ORGANISM: Artificial
<220> FEATURE:
<223> OTHER INFORMATION: primer

<400> SEQUENCE: 220
tgggaataga tcatagcaac aaggtgaacc                              30

<210> SEQ ID NO 221
<211> LENGTH: 30
<212> TYPE: DNA
<213> ORGANISM: Artificial
<220> FEATURE:
<223> OTHER INFORMATION: primer

<400> SEQUENCE: 221
tgggaataga tcataccaac aaggtgaacc                              30

<210> SEQ ID NO 222
<211> LENGTH: 30
<212> TYPE: DNA
<213> ORGANISM: Artificial
<220> FEATURE:
<223> OTHER INFORMATION: primer

<400> SEQUENCE: 222
```

```
cttttttcagt ttctcgatac ccttaggcgt                                              30

<210> SEQ ID NO 223
<211> LENGTH: 30
<212> TYPE: DNA
<213> ORGANISM: Artificial
<220> FEATURE:
<223> OTHER INFORMATION: primer

<400> SEQUENCE: 223
agaaactgaa aaagtattac cagaaactgc                                               30

<210> SEQ ID NO 224
<211> LENGTH: 30
<212> TYPE: DNA
<213> ORGANISM: Artificial
<220> FEATURE:
<223> OTHER INFORMATION: primer

<400> SEQUENCE: 224
agaaactgaa aaagttttac cagaaactgc                                               30

<210> SEQ ID NO 225
<211> LENGTH: 30
<212> TYPE: DNA
<213> ORGANISM: Artificial
<220> FEATURE:
<223> OTHER INFORMATION: primer

<400> SEQUENCE: 225
agaaactgaa aaagcattac cagaaactgc                                               30

<210> SEQ ID NO 226
<211> LENGTH: 30
<212> TYPE: DNA
<213> ORGANISM: Artificial
<220> FEATURE:
<223> OTHER INFORMATION: primer

<400> SEQUENCE: 226
ttcgcagtcc attctgccgg tattgtgaaa                                               30

<210> SEQ ID NO 227
<211> LENGTH: 30
<212> TYPE: DNA
<213> ORGANISM: Artificial
<220> FEATURE:
<223> OTHER INFORMATION: primer

<400> SEQUENCE: 227
atggactgcg aaagcacgcc taagggtatc                                               30

<210> SEQ ID NO 228
<211> LENGTH: 30
<212> TYPE: DNA
<213> ORGANISM: Artificial
<220> FEATURE:
<223> OTHER INFORMATION: primer

<400> SEQUENCE: 228
atgatcgaca cccatgattt tattcaggtc                                               30

<210> SEQ ID NO 229
<211> LENGTH: 30
<212> TYPE: DNA
<213> ORGANISM: Artificial
```

```
<220> FEATURE:
<223> OTHER INFORMATION: primer

<400> SEQUENCE: 229
agtaatccgg tggatctgca gctggctctg                                     30

<210> SEQ ID NO 230
<211> LENGTH: 30
<212> TYPE: DNA
<213> ORGANISM: Artificial
<220> FEATURE:
<223> OTHER INFORMATION: primer

<400> SEQUENCE: 230
atcgataccc ataattttat tcaggtcgtt                                     30

<210> SEQ ID NO 231
<211> LENGTH: 30
<212> TYPE: DNA
<213> ORGANISM: Artificial
<220> FEATURE:
<223> OTHER INFORMATION: primer

<400> SEQUENCE: 231
catcgcaata aagttgatct gcaactgagc                                     30

<210> SEQ ID NO 232
<211> LENGTH: 22
<212> TYPE: DNA
<213> ORGANISM: Artificial
<220> FEATURE:
<223> OTHER INFORMATION: primer

<400> SEQUENCE: 232
aattctgttt cctgtgtgaa at                                             22

<210> SEQ ID NO 233
<211> LENGTH: 30
<212> TYPE: DNA
<213> ORGANISM: Artificial
<220> FEATURE:
<223> OTHER INFORMATION: primer

<400> SEQUENCE: 233
aagcttggct gttttggcgg atgagagaag                                     30

<210> SEQ ID NO 234
<211> LENGTH: 35
<212> TYPE: DNA
<213> ORGANISM: Artificial
<220> FEATURE:
<223> OTHER INFORMATION: primer

<400> SEQUENCE: 234
aaaacagcca agctttcagc gtgattccga gtctt                               35

<210> SEQ ID NO 235
<211> LENGTH: 34
<212> TYPE: DNA
<213> ORGANISM: Artificial
<220> FEATURE:
<223> OTHER INFORMATION: primer

<400> SEQUENCE: 235
aggaaacaga attcatgacg accccgcgta aaga                                34
```

<210> SEQ ID NO 236
<211> LENGTH: 30
<212> TYPE: DNA
<213> ORGANISM: Artificial
<220> FEATURE:
<223> OTHER INFORMATION: primer

<400> SEQUENCE: 236
atgatcgata cccataattt tattcaggtc                                   30

<210> SEQ ID NO 237
<211> LENGTH: 30
<212> TYPE: DNA
<213> ORGANISM: Artificial
<220> FEATURE:
<223> OTHER INFORMATION: primer

<400> SEQUENCE: 237
atgaataaag ttgatctgca actgagcctg                                   30

<210> SEQ ID NO 238
<211> LENGTH: 30
<212> TYPE: DNA
<213> ORGANISM: Artificial
<220> FEATURE:
<223> OTHER INFORMATION: primer

<400> SEQUENCE: 238
agcaataaag ttgatctgca actgagcctg                                   30

<210> SEQ ID NO 239
<211> LENGTH: 30
<212> TYPE: DNA
<213> ORGANISM: Artificial
<220> FEATURE:
<223> OTHER INFORMATION: primer

<400> SEQUENCE: 239
accaataaag ttgatctgca actgagcctg                                   30

<210> SEQ ID NO 240
<211> LENGTH: 1323
<212> TYPE: DNA
<213> ORGANISM: Curvularia clavata

<400> SEQUENCE: 240
atggccccga gtcgcgctaa cacgagcgtc attgtggtgg gtggtggtgg cacgattggt      60
tcctcaacgg cactgcatct ggtccgtagc ggctataccc cgtctaacat taccgtgctg     120
gacacgtacc cgatcccgag cgcccagtct gcaggcaacg atctgaataa aattatgggt     180
atccgtctgc gcaacaaagt tgatctgcag ctgtcactgg aagcccgtca aatgtggcgc     240
gaagatgacc tgtttaaaga atacttccat aacaccggcc gtctggattg cgcacacggt     300
gaagaaggtc tggccgacct cgccaggct taccaagcgc tgctggatgc caacgcaggt     360
ctggaagaaa ccacggaatg gctggattca gaagacgaaa ttctgaagaa aatgccgctg     420
ctggatcgtg aacagatcaa aggttggaaa gccgtgtatt cgcaagatgg cggttggctg     480
gcggccgcaa aagccattaa tgcaatcggc gaatacctgc gcgcgcaggg cgttaaattc     540
ggttttggcg gtgctggttc ctttaaacag ccgctgctgg cagaaggcgt ctgcattggt     600
gtcgaaaccg tggatggcac gcgttattac gcggacaaag tggttctggc tgcaggtgca     660
tggagtccgg tgctggttga tctggaagac cagtgtgtgt ccaaagcgtg ggtttatgcg     720

```
catatccaac tgaccccgga agaagccgca gaatataaaa acgtcccggt cgtgtacaat    780
ggcgatgtgg gcttttttctt tgaaccggac gaacatggcg ttattaaagt ctgcgatgaa   840
tttccgggtt ttacccgctt caaacagcac caaccgtatg gcgctaaagc gccgaaacgt   900
atctcagtgc cgcgttcggc tgcaaaacac ccgaccgata cgtacccgga cgcgagtgaa   960
aaatccattc gtaaagccat cgcaacctttt ctgccgaaat tcacggaaaa agaactgttt  1020
aatcgccatc tgtgctggtg taccgatacg gccgacgccg cactgctgat gtgtgaacac  1080
ccggaatgga aaaactttgt tctggcgacc ggcgatagcg gtcatacgtt caaactgctg  1140
ccgaatattg gcaaacacgt tgtcgaactg ctggaaggta ccctggcaga agacctggct  1200
catgcgtggc gttggcgtcc gggtacgggt gatgcactga aatctcgtcg cgctgcgccg  1260
gcgaaagacc tggcggatat gccgggctgg aaacacgacg atgtggtgaa aagcaaactg  1320
taa                                                                 1323
```

<210> SEQ ID NO 241
<211> LENGTH: 30
<212> TYPE: DNA
<213> ORGANISM: Artificial
<220> FEATURE:
<223> OTHER INFORMATION: primer

<400> SEQUENCE: 241
gatacccata attttattca gatcgttgcc                                      30

<210> SEQ ID NO 242
<211> LENGTH: 30
<212> TYPE: DNA
<213> ORGANISM: Artificial
<220> FEATURE:
<223> OTHER INFORMATION: primer

<400> SEQUENCE: 242
gatctgcgca acaaagttga tctgcagctg                                      30

<210> SEQ ID NO 243
<211> LENGTH: 30
<212> TYPE: DNA
<213> ORGANISM: Artificial
<220> FEATURE:
<223> OTHER INFORMATION: primer

<400> SEQUENCE: 243
gatcatcgca acaaagttga tctgcagctg                                      30

<210> SEQ ID NO 244
<211> LENGTH: 30
<212> TYPE: DNA
<213> ORGANISM: Artificial
<220> FEATURE:
<223> OTHER INFORMATION: primer

<400> SEQUENCE: 244
ggccagacct ttttcaccgt gtgcgcaatc                                      30

<210> SEQ ID NO 245
<211> LENGTH: 30
<212> TYPE: DNA
<213> ORGANISM: Artificial
<220> FEATURE:
<223> OTHER INFORMATION: primer

```
<400> SEQUENCE: 245
aaactgcgcc aggcttacca agcgctgctg                                    30

<210> SEQ ID NO 246
<211> LENGTH: 30
<212> TYPE: DNA
<213> ORGANISM: Artificial
<220> FEATURE:
<223> OTHER INFORMATION: primer

<400> SEQUENCE: 246
atgatcgata cccataattt tattcagatc                                    30

<210> SEQ ID NO 247
<211> LENGTH: 30
<212> TYPE: DNA
<213> ORGANISM: Artificial
<220> FEATURE:
<223> OTHER INFORMATION: primer

<400> SEQUENCE: 247
ctcaacaaag ttgatctgca gctgtcactg                                    30

<210> SEQ ID NO 248
<211> LENGTH: 30
<212> TYPE: DNA
<213> ORGANISM: Artificial
<220> FEATURE:
<223> OTHER INFORMATION: primer

<400> SEQUENCE: 248
accaacaaag ttgatctgca gctgtcactg                                    30
```